United States Patent [19]

Fukumi et al.

[11] Patent Number: 5,616,579

[45] Date of Patent: Apr. 1, 1997

[54] ANTI-ULCER PYRIDYLOXY DERIVATIVES, THEIR PREPARATION AND USES

[75] Inventors: Hiroshi Fukumi; Mitsuo Sugiyama; Keiichi Tabata; Koichi Kojima, all of Tokyo, Japan

[73] Assignee: Sankyo Company, Limited, Tokyo, Japan

[21] Appl. No.: 35,081

[22] Filed: Mar. 22, 1993

[30] Foreign Application Priority Data

Mar. 23, 1992 [JP] Japan .................................. 4-65324
Apr. 21, 1992 [JP] Japan .................................. 4-101392
Jul. 2, 1992 [JP] Japan .................................. 4-175707
Dec. 28, 1992 [JP] Japan .................................. 4-349035

[51] Int. Cl.$^6$ .................... C07D 401/00; C07D 409/00; A61K 31/54; A61K 31/505
[52] U.S. Cl. .................... 514/222.5; 514/223.8; 514/226.8; 514/227.8; 514/237.2; 514/241; 514/252; 514/326; 514/332; 514/336; 514/340; 514/341; 514/342; 514/343; 514/318; 544/3; 544/8; 544/55; 544/56; 544/66; 544/67; 544/96; 544/98; 544/124; 544/179; 544/180; 544/238; 544/333; 544/360; 544/405; 546/193; 546/194; 546/268.7; 546/269.1; 546/269.7; 546/271.1; 546/271.4; 546/242.1; 546/272.4; 546/272.7; 546/275.4; 546/276.4; 546/280.1; 546/280.7; 546/282.1; 546/283.4
[58] Field of Search ............................... 54/193; 514/318, 514/326, 222.5, 223.8, 226.8, 227.8, 237.2, 241, 252, 332, 336, 340, 341, 342, 343; 544/3, 8, 55, 56, 66, 67, 96, 98, 124, 179, 180, 238, 333, 360, 405; 546/193, 194, 268.7, 269.1, 269.7, 271.1, 271.4, 272.1, 272.4, 272.7, 275.4, 276.4, 280.1, 280.7, 282.1, 283.4

[56] References Cited

U.S. PATENT DOCUMENTS 5,190,994  3/1993  Clemence et al. ...................... 546/193

FOREIGN PATENT DOCUMENTS 0023578  2/1981  European Pat. Off. .
0214823  3/1987  European Pat. Off. .
0282077  9/1988  European Pat. Off. .
0032422  2/1989  European Pat. Off. .
0404949  1/1991  European Pat. Off. .
1-93247   8/1989  Japan .
4-257581  9/1992  Japan .

*Primary Examiner*—C. Warren Ivy
*Assistant Examiner*—Raymond Covington
*Attorney, Agent, or Firm*—Frishauf, Holtz, Goodman, Langer & Chick, P.C.

[57] ABSTRACT

Compounds of formula (I):

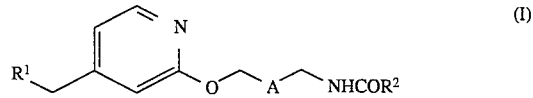

[wherein: $R^1$ is a cyclic amino group, or a dialkylamino group; $R^2$ a group of formula —NHCHR$^3$R$^4$ wherein $R^3$ and $R^4$ are each alkyl aryl or aralkyl, or together form a cycloalkyl group, or $R^2$ is an aromatic heterocyclic group, or a group of formula —B—S(O)$_m$—R$^5$ wherein $R^5$ is a substituted alkyl group, or an aromatic heterocyclic group; B is an alkylene or alkylidene group; m is 0, 1 or 2; A is a group of formula —CH=CH— or —(CH$_2$)$_n$—, where n is 1, 2 or 3]; and salts thereof have valuable anti-ulcer activity.

39 Claims, No Drawings

ANTI-ULCER PYRIDYLOXY DERIVATIVES, THEIR PREPARATION AND USES

BACKGROUND TO THE INVENTION

The present invention relates to a series of new pyridyloxy derivatives which have the ability to inhibit the secretion of gastric juices and which may thus be used for the treatment and prevention of ulcers. The invention also provides methods and compositions using these new compounds for such treatment and prevention and processes for the preparation of these compounds.

Peptic ulcers are said to occur when there is an imbalance between factors which attack the gastro-intestinal mucosa and factors which defend the gastrointestinal mucosa. The gastric juice is among the attacking factors. Accordingly, if its secretion could be inhibited, this would be useful for the prevention and therapy of ulcers.

Among the drugs so far proposed for the inhibition of gastric juice secretion, anticholinergic agents and histamine-$H_2$ receptor antagonists (such as cimetidine) have been widely used clinically and have had considerable success, although they are not free from disadvantages. For example, anticholinergic agents have exhibited a range of side effects, including inhibition of movement of the gastrointestinal tract, thirst, mydriasis and inhibition of sweating. Some of the histamine-$H_2$ receptor antagonists also have undesirable side effects on the central nervous system, and may also have an antagonistic effect on androgens. Moreover, it is thought that the histamine-$H_2$ receptor antagonists may weaken mucosal protecting factors after long-term administration, and recurrence of ulcers after withdrawal of these drugs has also been observed. Since recurrence is thought to be caused by a decrease in the protecting factors, a drug having the ability both to inhibit gastric juice secretion and to potentiate protecting factor activity would be highly desirable.

We have now discovered that a series of pyridyloxy derivatives having a certain specific and limited class of substituents has the desired combination of gastric juice secretion inhibitory activity, anti-ulcer activity and defense factor potentiating activity, and may therefore be used in the treatment and prevention of gastric ulcers.

A number of compounds having anti-ulcer activity and similar structures to the pyridyloxy derivatives of the present invention is known. Examples include Compound A (disclosed, for example, in European Patent Publication No. 404 949 or WO90/00544), Compound B (disclosed, for example, in Japanese Patent Kokai Application No. Hei-1-193247, Japanese Patent Kokai Application No. Sho-63-225371 and European Patent Publication No. 282 077) and Compound C (disclosed, for example, in Japanese Patent Kokai Application No. Hei-4-257581):

Compound A:

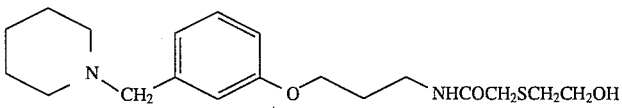

Compound B:

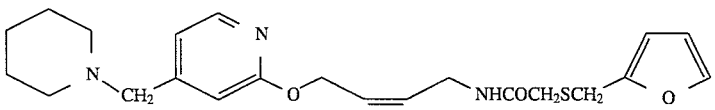

Compound C:

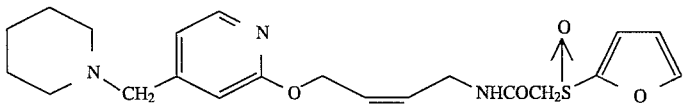

Compound C was disclosed after the priority dates hereof. The compounds of the present invention surprisingly have substantially better activities than these structurally similar and have a combination of gastric juice secretion inhibitory, anti-ulcer and defense factor potentiating activities which these prior compounds do not possess.

BRIEF SUMMARY OF INVENTION

It is, therefore, an object of the present invention to provide a series of new pyridyloxy derivatives.

It is a further, and more specific object of the invention to provide such compounds which may be useful for the treatment and/or prevention of gastric ulcers.

Other objects and advantages of the invention will become apparent as the description proceeds.

The compounds of the present invention are those compounds of formula (I):

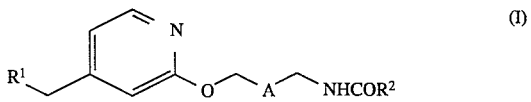

wherein:
$R^1$ represents
    a cyclic amino group having from 3 to 7 ring atoms, of which from 1 to 3 are nitrogen atoms, 0 or 1 is an oxygen atom or a sulfur atom, and the remainder are carbon atoms, or
    a dialkylamino group in which each alkyl group is independently selected from the group consisting of alkyl groups having from 1 to 4 carbon atoms;
$R^2$ represents
    a group of formula —NHCHR$^3$R$^4$, wherein
      $R^3$ and $R^4$ are independently selected from the group consisting of alkyl groups having from 1 to 6 carbon atoms, aryl groups as defined below and aralkyl groups as defined below, or $R^3$ and $R^4$ together with the carbon atom to which they are attached, represent a cycloalkyl group having from 3 to 8 ring carbon atoms, which group is unsubstituted or is substituted by at least one substituent selected from the group consisting of substituents α, an aromatic heterocyclic, group having 5 ring atoms, of which from 1 to 3 are hetero-atoms selected from the group consisting of nitrogen, oxygen and sulfur heteroatoms, said group being unsubstituted or having at least one substituent selected, in the case of substituents on carbon atoms, from the group consisting of substituents α and, in the case of substituents on nitrogen atoms, from the group consisting of substituents β, or a group of formula —B—S(O)$_m$—R$^5$, wherein R$^5$ represents: a substituted alkyl group which has from 1 to 4 carbon atoms and which is substituted by at least one substituent selected from the group consisting of substituents γ; or an aromatic heterocyclic group which has 5 or 6 ring atoms of which from 1 to 4 are hetero-atoms selected from the group consisting of nitrogen, oxygen and sulfur hetero-atoms, said group being unsubstituted or having at least one substituent selected, in the case of substituents on carbon atoms, from the group consisting of substituents α and, in the case of substituents on nitrogen atoms, from the group consisting of substituents ε, B represents an alkylene or alkylidene group having from 1 to 6 carbon atoms, and m is 0, 1 or 2;

A represents a group of formula —CH=CH— or —(CH$_2$)$_n$—, where n is 1, 2 or 3;

said aryl groups are carbocyclic aromatic groups having from 6 to 10 ring carbon atoms which are unsubstituted or which are substituted by at least one substituent selected from the group consisting of substituents ζ;

said aralkyl groups are alkyl groups which have from 1 to 4 carbon atoms and which are substituted by from 3 aryl groups as defined above;

said substituents α are selected from the group consisting of: alkyl groups having from 1 to 4 carbon atoms; alkoxy groups having from 1 to 4 carbon atoms; hydroxy groups; halogen atoms; amino groups; monoalkylamino groups in which the alkyl part has from 1 to 4 carbon atoms; dialkylamino groups in which each alkyl part is independently selected from the group consisting of alkyl groups having from 1 to 4 carbon atoms; alkanoylamino groups having from 1 to 5 carbon atoms; arylcarbonylamino groups in which the aryl part is as defined above; and aryl groups as defined above;

said substituents β are selected from the group consisting of alkyl groups having from 1 to 4 carbon atoms;

said substituents y are selected from the group consisting of: hydroxy groups; alkanoyloxy groups having from 1 to 5 carbon atoms; substituted alkanoyloxy groups which have from 2 to 5 carbon atoms and which are substituted by at least one substituent selected from the group consisting of substituents δ; arylcarbonyloxy groups in which the aryl part is as defined above; and cycloalkylcarbonyloxy groups in which the cycloalkyl part has from 3 to 6 ring carbon atoms and is unsubstituted or is substituted by at least one substituent selected from the group consisting of substituents α;

said substituents δ are selected from the group consisting of: carboxy groups; alkoxycarbonyl groups in which the alkoxy part has from 1 to 4 carbon atoms; aryloxycarbonyl groups in which the aryl part is as defined above; and aryl groups as defined above;

said substituents ε are selected from the group consisting of: alkyl groups having from 1 to 4 carbon atoms; and hydroxyalkyl groups having from 2 to 4 carbon atoms;

said substituents ζ are selected from the group consisting of substituents α, provided that any aryl group in said substituents α is not further substituted by an aryl group;

PROVIDED THAT, when m is 1, R$^5$ represents: said substituted alkyl group having from 1 to 4 carbon atoms; an aromatic heterocyclic group which has 5 ring atoms of which from 2 to 4 are hetero-atoms selected from the group consisting of nitrogen, oxygen and sulfur hetero-atoms, said group being unsubstituted as defined above or an aromatic heterocyclic group which has 6 ring atoms of which from 1 to 4 are hetero-atoms selected from the group consisting of nitrogen, oxygen and sulfur hetero-atoms, said group being unsubstituted as defined above;

and pharmaceutically acceptable salts thereof.

The invention also provides a pharmaceutical composition for the treatment and prophylaxis of ulcerous conditions, which comprises an anti-ulcer compound in admixture with a pharmaceutically acceptable carrier or diluent, wherein the anti-ulcer compound is selected from the group consisting of compounds of formula (I) and pharmaceutically acceptable salts thereof.

The invention still further provides a method for the treatment and prophylaxis of ulcerous conditions, which comprises administering an effective amount of an anti-ulcer compound to a mammal, wherein the anti-ulcer compound is selected from the group consisting of compounds of formula (I) and pharmaceutically acceptable salts thereof.

The present invention also provides processes for preparing these compounds, which are described in greater detail hereafter.

DETAILED DESCRIPTION OF INVENTION

In the compounds of the present invention, where $R^1$ represents a cyclic amino group, this has from 3 to 7 ring atoms, including at least one nitrogen atom. In addition, there may be another 1 or 2 nitrogen atoms and/or an oxygen or sulfur atom. The group is attached to the methylene group forming part of the remainder of the molecule by means of a nitrogen atom. The group preferably has a single nitrogen atom, the remainder of the ring atoms being carbon. Examples of such groups include the 1-aziridinyl, 1-azetidinyl, 1-pyrrolidinyl, piperidino and 1-hexahydroazepinyl groups. Of these we prefer the 1-pyrrolidinyl and piperidino groups, more preferably the piperidino group.

Where $R^1$ represents a dialkylamino group or substituent α, β, ε or ζ represents an alkyl group, this alkyl group may be a straight or branched chain alkyl group having from 1 to 4 carbon atoms, and examples include the methyl, ethyl, propyl, isopropyl, butyl, isobutyl, sec-butyl and t-butyl groups, preferably the methyl, ethyl, propyl, isopropyl, butyl and sec-butyl groups, and most preferably the methyl or ethyl group.

In the case of the dialkylamino group represented by $R^1$, the two alkyl groups may be the same or different although they are preferably the same. Specific examples of dialkylamino groups include the dimethylamino, diethylamino, dipropylamino, diisopropylamino, dibutylamino, dipentylamino, dihexylamino, methylethylamino and methylpropylamino, of which we prefer the dimethylamino, diethylamino and dipropylamino groups, especially the dimethylamino group.

Where $R^2$ represents a group of formula —NHCHR$^3$R$^4$ and $R^3$ and/or $R^4$ represents an alkyl group having from 1 to 6 carbon atoms, this may be a straight or branched chain group having from 1 to 6, preferably from 1 to 4, carbon atoms, and examples include the methyl, ethyl, propyl, isopropyl, butyl, isobutyl, sec-butyl, t-butyl, pentyl, isopentyl, neopentyl, 2-methylbutyl, 1-ethylpropyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, hexyl and isohexyl groups. Of these, we prefer the methyl, ethyl, propyl, isopropyl, butyl, sec-butyl, pentyl and hexyl groups, and most prefer the methyl and ethyl groups.

Where $R^2$ represents a group of formula —NHCHR$^3$R$^4$ and $R^3$ and/or $R^4$ represents an aryl group, this has from 6 to 10, preferably 6 or 10, ring carbon atoms and may be unsubstituted or it may be substituted by one or more of substituents ζ, defined above and exemplified below. Specific examples of the unsubstituted aryl groups include the phenyl and naphthyl (1- or 2- naphthyl) groups, of which the phenyl group is preferred. The aryl ring may optionally have one or more substituents (preferably from 1 to 3 substituents, and more preferably 1 substituent). Examples of such substituents are given in more detail below, but the preferred substituents are alkyl groups having from 1 to 4 carbon atoms, alkoxy groups having from 1 to 4 carbon atoms, and halogen atoms (such as the fluorine, chlorine, bromine or iodine atoms). Preferred substituents are the methyl group, the methoxy group, the fluorine atom and the chlorine atom. The substituents are, in the case of substituted phenyl groups, preferably on the 4-position. Examples of preferred substituted phenyl groups include the 4-methylphenyl, 4-methoxyphenyl, 4-chlorophenyl and 4-fluorophenyl groups.

Where $R^2$ represents a group of formula —NHCHR$^3$R$^4$, and $R^3$ and/or $R^4$ represents an aralkyl group, the aryl part may be as exemplified above and the alkyl part may be any one of those alkyl groups having from 1 to 4 carbon atoms exemplified above. Preferably the aryl and alkyl parts of the aralkyl group together have from 7 to 11 carbon atoms. The aryl part of the aralkyl group may be substituted or unsubstituted, and, if substituted, the substituents are selected from the group consisting of substituents ζ defined above and exemplified below. However, the group is preferably unsubstituted. Examples of such aralkyl groups include the benzyl, phenethyl, 1-phenylethyl, 2-phenylpropyl, 3-phenylpropyl, 4-phenylbutyl and 1- and 2- naphthylmethyl groups, of which the benzyl, phenethyl and 1- and 2- naphthylmethyl groups are preferred, the benzyl group being most preferred.

Where $R^2$ represents a group of formula —NHCHR$^3$R$^4$ and $R^3$ and $R^4$ together with the carbon atom to which they are attached, represent a cycloalkyl group, this has from 3 to 8 ring carbon atoms, and examples include the cyclopropyl, cyclobutyl, cyclopentyl, cyclohexyl, cycloheptyl and cyclooctyl groups, of which the cyclopropyl, cyclobutyl and cyclopentyl groups are preferred, and the cyclopropyl and cyclobutyl groups are most preferred. The cycloalkyl ring may be substituted or unsubstituted, and, if substituted, it preferably has from 1 to 3, more preferably 1, substituents selected from the group consisting of substituents α. Examples of such substituents are given in more detail below, but the preferred substituents are alkyl groups having from 1 to 4 carbon atoms and alkoxy groups having from 1 to 4 carbon atoms. Of these, we prefer the methyl or ethyl group, but the cycloalkyl group is preferably unsubstituted.

Where $R^2$ represents an aromatic heterocyclic group, this has 5 ring atoms, of which from 1 to 3 are hetero-atoms selected from oxygen, nitrogen and sulfur atoms. Where there is one hetero-atom, this may be any of the oxygen, nitrogen and sulfur atoms. Where there are two or three hetero-atoms, we prefer that all three or two should be nitrogen atoms and none or one should be an oxygen or sulfur atom. Examples of such groups include the furyl, thienyl, pyrrolyl, oxazolyl, isoxazolyl, thiazolyl, isothiazolyl, pyrazolyl, imidazolyl, 1,2,3-, 1,2,4-, 1,2,5-, or 1,3,4-oxadiazolyl, 1,2,3-, 1,2,4-, 1,2,5- or 1,3,4thiadiazolyl, and 1,2,3- or 1,2,4-triazolyl groups. Of these, the furyl, thienyl, pyrrolyl, oxazolyl, isoxazolyl, thiazolyl, pyrazolyl, imidazolyl and 1,2,3-thiadiazolyl groups are preferred, and the thienyl, thiazolyl, pyrrolyl, pyrazolyl and 1,2,3-thiadiazolyl groups are more preferred. We particularly prefer the thienyl, pyrrolyl and pyrazolyl groups. These groups may be unsubstituted or they may be substituted by one or more substituents. Where the substituent is on a carbon atom, it may be selected from the group consisting of substituents α, defined above and exemplified below. Where the substituent is on a nitrogen atom, it may be selected from the group consisting of substituents β, defined above and exemplified below. There is no particular limitation on the number of such substituents, except that the number of substitutable positions on 5-membered aromatic heterocyclic groups is 4, and from 1 to 4 such substituents are possible, from 1 to 3 being preferred and 1 or 2 being most preferred.

Examples of substituents α include:

alkyl groups having from 1 to 4 carbon atoms, as exemplified above;

alkoxy groups having from 1 to 4 carbon atoms, such as the methoxy, ethoxy, propoxy, isopropoxy, butoxy and isobutoxy groups, of which the methoxy and ethoxy groups are preferred;

hydroxy groups;

halogen atoms, such as the fluorine, chlorine, bromine and iodine atoms, of which the fluorine and chlorine atoms are preferred;

amino groups;

monoalkylamino groups in which the alkyl part has from 1 to 4 carbon atoms, such as the methylamino, ethylamino, propylamino, isopropylamino, butylamino and isobutylamino groups, preferably the methylamino and ethylamino groups;

dialkylamino groups in which each alkyl part is independently selected from the group consisting of alkyl groups having from 1 to 4 carbon atoms, such as those exemplified above in relation to the dialkylamino groups which may be represented by $R^1$;

alkanoylamino groups having from 1 to 5 carbon atoms, such as the formamido, acetamido, propionamido, butyramido, valerylamino and isovalerylamino groups, preferably the acetamido or propionamido group;

arylcarbonylamino groups in which the aryl part is as defined and exemplified above in relation to the aryl groups which may be represented by $R^3$ and $R^4$ particularly the benzamido group;

and aryl groups as defined and exemplified above in relation to the aryl groups which may be represented by $R^3$ and $R^4$, particularly the phenyl group.

Examples of substituents β are straight or branched chain alkyl groups having from 1 to 4 carbon atoms, and examples include the methyl, ethyl, propyl, isopropyl, butyl, isobutyl, sec-butyl and t-butyl groups, preferably the methyl, ethyl, propyl, isopropyl, butyl and sec-butyl groups, and most preferably the methyl or ethyl group.

Specific examples of such substituted and unsubstituted groups which may be represented by $R^2$ are given hereafter.

Where $R^5$ represents a substituted alkyl group, the alkyl moiety may be a straight or branched chain alkyl group having from 1 to 4 carbon atoms, and examples include the methyl, ethyl, propyl, isopropyl, butyl, isobutyl, sec-butyl and t-butyl groups, preferably the methyl, ethyl, propyl, isopropyl, butyl and sec-butyl groups, more preferably the ethyl or propyl group having a substituent at the 2-position, and most preferably the ethyl group having a substituent at the 2-position. The group is substituted by at least one, and preferably from 1 to 3, more preferably 1, substituent selected from the group consisting of substituents γ.

Examples of substituents γ include:

hydroxy groups;

alkanoyloxy groups having from 1 to 5 carbon atoms, such as the formoxy, acetoxy, propionyloxy, butyryloxy, valeryloxy and isovaleryloxy groups, preferably the acetoxy or propionyloxy group;

substituted alkanoyloxy groups which have from 2 to 5 carbon atoms and which are substituted by at least one substituent selected from the group consisting of substituents δ, such as the acetoxy, propionyloxy, butyryloxy, valeryloxy and isovaleryloxy groups, preferably the acetoxy or propionyloxy group; examples of substituents δ are:

carboxy groups;

alkoxycarbonyl groups in which the alkoxy part has from 1 to 4 carbon atoms, such as the methoxycarbonyl, ethoxycarbonyl, propoxycarbonyl, isopropoxycarbonyl, butoxycarbonyl and isobutoxycarbonyl groups, of which the methoxycarbonyl and ethoxycarbonyl groups are preferred;

aryloxycarbonyl groups in which the aryl part is as defined and exemplified above in relation to the aryl groups which may be represented by $R^3$ and $R^4$, particularly the phenoxycarbonyl group; and aryl groups as defined and exemplified above in relation to the aryl groups which may be represented by $R^3$ and $R^4$, particularly the phenyl group;

especially, propionyloxy groups substituted at the 3-position by a carboxy, alkoxycarbonyl or aryloxycarbonyl group and acetoxy groups substituted by an aryl group;

arylcarbonyloxy groups in which the aryl part is as defined and exemplified above in relation to the aryl groups which may be represented by $R^3$ and $R^4$ particularly the benzoyloxy group;

and cycloalkylcarbonyloxy groups in which the cycloalkyl part has from 3 to 6 ring carbon atoms,, such as the cyclopropylcarbonyloxy, cyclobutylcarbonyloxy, cyclopentylcarbonyloxy and cyclohexylcarbonyloxy groups, which may be substituted or unsubstituted (preferably unsubstituted) and, if substituted, have one or more substituents selected from the group consisting of substituents α, preferably alkyl groups or alkoxy groups, as exemplified above, and more preferably methyl or ethyl groups; the cycloalkylcarbonyloxy group is preferably a cyclopentylcarbonyloxy or cyclohexylcarbonyloxy group.

Where $R^5$ represents an aromatic heterocyclic group, this has 5 or 6 ring atoms, of which from 1 to 4 are hetero-atoms selected from the group consisting of oxygen, nitrogen and sulfur atoms. Where there is only one hetero-atom, this may be any of the oxygen, nitrogen and sulfur atoms. However, where there are two, three or four hetero-atoms, it is preferred that 0 or 1 is an oxygen or sulfur atom and, where there are no oxygen or sulfur atoms, 1, 2, 3 or 4 are nitrogen atoms, or, where there is 1 oxygen or sulfur atom, 0, 1, 2 or 3 are nitrogen atoms. Examples of such groups include the furyl, thienyl, pyrrolyl, oxazolyl, isoxazolyl, thiazolyl, isothiazolyl, pyrazolyl, imidazolyl, 1,2,3-, 1,2,4-, 1,2,5- or 1,3,4-oxadiazolyl, 1,2,3-, 1,2,4-, 1,2,5- or 1,3,4-thiadiazolyl, 1,2,3- or 1,2,4-triazolyl, tetrazolyl, pyridyl, pyrimidinyl, pyridazinyl, pyrazinyl and 1,2,3-, 1,2,4- or 1,3,5-triazinyl groups. Of these, we prefer the imidazolyl, 1,3,4-oxadiazolyl, 1,3,4-thiadiazolyl, 1,2,4-triazolyl, tetrazolyl, pyridyl and pyrimidinyl groups, more preferably the 1,3,4-oxadiazolyl, 1,2,4-triazolyl, tetrazolyl and pyrimidinyl groups and most preferably the 1,3,4-oxadiazolyl, 1,2,4-triazolyl and pyrimidinyl groups. Such groups may be unsubstituted or they may have one or more (preferably from 1 to 3) substituents selected from the group consisting of substituents α, in the case of substituents on carbon atoms, or substituents ε, in the case of substituents on nitrogen atoms. Examples of substituents α have been given above. Examples of substituents ε are as follows:

alkyl groups having from 1 to 4 carbon atoms, such as those exemplified above in relation to substituents β; and hydroxyalkyl groups having from 2 to 4 carbon atoms, such as the 2-hydroxyethyl, 2-hydroxypropyl, 3-hydroxypropyl, 2-hydroxybutyl, 3-hydroxybutyl and 4-hydroxybutyl groups; preferably a 2-hydroxyethyl or 3-hydroxypropyl group.

Specific examples of such substituted and unsubstituted groups which may be represented by $R^5$ are given hereafter.

B can represent an alkylene or alkylidene group having from 1 to 6 carbon atoms. Examples include the methylene, ethylene, trimethylene, propylene, tetramethylene, 2-methyltrimethylene, pentamethylene and hexamethylene groups. Of these, we prefer the methylene, ethylene or trimethylene group, more preferably a methylene or trimethylene group.

Preferably m is 0 or 1, and most preferably m is 0.

Preferably A is a group of formula —CH=CH— or —CH$_2$CH$_2$—, and most preferably A is a group of formula —CH=CH—.

Specific examples of preferred optionally substituted 5-membered aromatic heterocyclic groups containing from 1 to 3 hetero-atoms selected from the group consisting of oxygen, nitrogen and sulfur atoms, which may be represented by $R^2$ include the 2-furyl, 3-furyl, 3-methyl-2-furyl, 4-methyl-2-furyl, 5-methyl-2-furyl, 2-methyl-3-furyl, 4-methyl-3-furyl, 5-methyl-3-furyl, 5-chloro-2ofuryl, 5-chloro-3-furyl, 3-amino-2ofuryl, 5-amino-2-furyl, 3-acetamido-2-furyl, 5-acetamido-2-furyl, 5-phenyl-2-furyl, 5-(4-methylphenyl)-2furyl, 5-(4-chlorophenyl)-2-furyl, 2,4-dimethyl-3-furyl, 2,5-dimethyl-3-furyl, 3-methyl-5-amino-2-furyl, 2-thienyl, 3-thienyl, 3-methyl-2-thienyl, 4-methyl-2-thienyl, 5-methyl-2-thienyl, 2-methyl-3-thienyl, 4-methyl-3-thienyl, 5-methyl-3-thienyl, 5-ethyl-2-thienyl, 4-methoxy-2-thienyl, 4-methoxy-3-thienyl, 4-hydroxy-2-thienyl, 4-hydroxy-3-thienyl, 5-chloro-2-thienyl, 5-chloro-3 -thienyl, 5-bromo-3-thienyl, 3-amino-2-thienyl, 5-amino-2-thienyl, 2-amino-3-thienyl, 4-amino-3-thienyl, 3-acetamido-2-thienyl, 5-acetamido-2-thienyl, 2-acetamido-3-thienyl, 4-acetamido-3-thienyl, 5-phenyl-2-thienyl, 5-(4-methylphenyl)-2-thienyl, 5-(4-chlorophenyl)-2-thienyl, 3,4-dimethyl-2-thienyl, 3,5-dimethyl-2-thienyl, 4,5-dimethyl-2- thienyl, 2,4-dimethyl-3-thienyl, 2,5-dimethyl-3-thienyl, 4,5-dimethyl-3-thienyl, 5-methyl-2-amino-3-thienyl, 4-methyl-5-chloro-3-thienyl, 4,5-dichloro-2-thienyl, 2-amino-5-phenyl-3-thienyl, 2,4,5-trimethyl-3-thienyl, 2,5-dimethyl-4-amino-3-thienyl, 2-pyrrolyl, 3-pyrrolyl, 1-methyl-2-pyrrolyl, 3-methyl-2-pyrrolyl, 4-methyl-2-pyrrolyl, 5-methyl-2-pyrrolyl, 1-methyl-3-pyrrolyl, 2-methyl-3-pyrrolyl, 4-methyl-3-pyrrolyl, 5-methyl-3-pyrrolyl, 4-methoxy-3-pyrrolyl, 4-hydroxy-3-pyrrolyl, 5-chloro-2-pyrrolyl, 5-chloro-3-pyrrolyl, 3-amino-2-pyrrolyl, 4-amino-2-pyrrolyl, 3-acetamido-2-pyrrolyl, 4-acetamido-2-pyrrolyl, 4-phenyl-2-pyrrolyl, 5-phenyl-2-pyrrolyl, 5-phenyl-3-pyrrolyl, 4-(4-methylphenyl)-2-pyrrolyl, 5-(4-methylphenyl)-2-pyrrolyl, 4-(4-methoxy-phenyl)-2-pyrrolyl, 5-(4-methoxyphenyl)-2-pyrrolyl, 4-(4-fluorophenyl)-2-pyrrolyl, 5-(4-fluorophenyl)-2pyrrolyl, 4-(4-chlorophenyl)-2-pyrrolyl, 5-(4-chlorophenyl)-2-pyrrolyl, 5-(4-methylphenyl)-3-pyrrolyl, 5-(4-methoxyphenyl)-3-pyrrolyl, 5-(4-fluorophenyl)-3-pyrrolyl, 5-(4-chlorophenyl)-3-pyrrolyl, 1,3-dimethyl-2-pyrrolyl, 1,4-dimethyl-2-pyrrolyl, 1,5-dimethyl-2-pyrrolyl, 3,4-dimethyl-2-pyrrolyl, 3,5-dimethyl-2-pyrrolyl, 4,5-dimethyl-2-pyrrolyl, 1,5-dimethyl-3-pyrrolyl, 2,4-dimethyl-3-pyrrolyl, 2,5-dimethyl-3-pyrrolyl, 1-methyl-4-hydroxy-3-pyrrolyl, 1-methyl-4-methoxy-3-pyrrolyl, 1-methyl-2-chloro-3-pyrrolyl, 4-methyl-5-chloro-3-pyrrolyl, 1-methyl-5-amino-2-pyrrolyl, 3,4,5-trimethyl-2-pyrrolyl, 1,2,4-trimethyl-3-pyrrolyl, 1,4-dimethyl-5-chloro-3-pyrrolyl, 1,4-dimethyl-5-bromo-3 -pyrrolyl, 3,5-dimethyl-4-amino-2-pyrrolyl, 2-oxazolyl, 4-oxazolyl, 5-oxazolyl, 2-methyl-4-oxazolyl, 5-methyl-2-oxazolyl, 2-methoxy-4-oxazolyl, 2-hydroxy-4-oxazolyl, 2-phenyl-4-oxazolyl, 5-phenyl-2-oxazolyl, 2,5-dimethyl-4-oxazolyl, 2,4-dimethyl-5-oxazolyl, 5-methyl-2-phenyl-4-oxazolyl, 4-methyl-2-phenyl-5-oxazolyl, 3-isoxazolyl, 4-isoxazolyl, 3-methyl-4-isoxazolyl, 4-methyl-3-isoxazolyl, 5-methyl-3-isoxazolyl, 3-methoxy-4-isoxazolyl, 4-methoxy-3-isoxazolyl, 3-hydroxy-4-isoxazolyl, 3-hydroxy-5-isoxazolyl, 4-hydroxy-3-isoxazolyl, 5-amino-4-isoxazolyl, 4-amino-3-isoxazolyl, 4-phenyl-3-isoxazolyl, 5-phenyl-3-isoxazolyl, 4-(4-methylphenyl)-3-isoxazolyl, 5-(4-methylphenyl)-3-isoxazolyl, 4,5-dimethyl-3-isoxazolyl, 5-methyl-4-hydroxy-3-isoxazolyl, 2-thiazolyl, 4-thiazolyl, 5-thiazolyl, 4-methyl-2-thiazolyl, 5-methyl-2-thiazolyl, 2-methyl-4-thiazolyl, 5-methyl-4-thiazolyl, 2-methyl-5-thiazolyl, 4-methyl-5-thiazolyl, 2-methoxy-4-thiazolyl, 2-methoxy-5-thiazolyl, 2-hydroxy-4-thiazolyl, 2-hydroxy-5-thiazolyl, 5-chloro-2-thiazolyl, 2-chloro-4-thiazolyl, 5-chloro-4-thiazolyl, 2-chloro-5-thiazolyl, 4-chloro-5thiazolyl, 2-amino-4-thiazolyl, 5-amino-4-thiazolyl, 2-amino-5-thiazolyl, 2-acetamido-4-thiazolyl, 5-acetamido-4-thiazolyl, 2-acetamido-5-thiazolyl, 2-phenyl-4-thiazolyl, 2-phenyl-5-thiazolyl, 4,5-dimethyl-2-thiazolyl, 2,5-dimethyl-4-thiazolyl, 2,4-dimethyl-5-thiazolyl, 5-methyl-2-hydroxy-4-thiazolyl, 4-methyl-2-hydroxy-5-thiazolyl, 5-methyl-2-chloro-4-thiazolyl, 4-methyl-2-chloro-5-thiazolyl, 2-methyl-4-chloro-5-thiazolyl, 5-methyl-2-amino-4-thiazolyl, 2-methyl-5-amino-4-thiazolyl, 4-methyl-2-amino-5-thiazolyl, 3-isothiazolyl, 4-isothiazolyl, 3-pyrazolyl, 4-pyrazolyl, 1-methyl-4-pyrazolyl, 3-methyl-4-pyrazolyl, 1-methyl-3-pyrazolyl, 4-methyl-3-pyrazolyl, 5-methyl-3-pyrazolyl, 1-methyl-5-pyrazolyl, 1-ethyl-4-pyrazolyl, 1-ethyl-3-pyrazolyl, 5-ethyl-3-pyrazolyl, 1-propyl-4-pyrazolyl, 1-propyl-3-pyrazolyl, 5-propyl-3-pyrazolyl, 1-butyl-4-pyrazolyl, 4-methoxy-3-pyrazolyl, 4-propoxy-3-pyrazolyl, 4-hydroxy-3-pyrazolyl, 4-chloro-3pyrazolyl, 3-chloro-4-pyrazolyl, 4-bromo-3-pyrazolyl, 4-amino-3-pyrazolyl, 5-amino-3-pyrazolyl, 3-amino-4-pyrazolyl, 3-acetamido-4-pyrazolyl, 3-propionylamino-4-pyrazolyl, 4-acetamido-3-pyrazolyl, 5-acetamido-3-pyrazolyl, 5-phenyl-3-pyrazolyl, 1,3-dimethyl-4-pyrazolyl, 1,5-dimethyl-4-pyrazolyl, 3,5-dimethyl-4-pyrazolyl, 1,4-dimethyl-3-pyrazolyl, 1,5-dimethyl-3-pyrazolyl, 4,5-dimethyl-3-pyrazolyl, 1,3-dimethyl-5-pyrazolyl, 1,4-dimethyl-5-pyrazolyl, 1-methyl-4-methoxy-3-pyrazolyl, 5-methyl-4-hydroxy-3-pyrazolyl, 1-methyl-3-chloro-4-pyrazolyl, 1-methyl-5-chloro-4-pyrazolyl, 5-methyl-3-chloro-4-pyrazolyl, 1-methyl-4-chloro-3-pyrazolyl, 5-methyl-4-chloro-3-pyrazolyl, 1-methyl-4-chloro-5-pyrazolyl, 1-methyl-3-amino-4-pyrazolyl, 1-methyl-5-amino-4-pyrazolyl, 5-methyl-3-amino-4-pyrazolyl, 1-methyl-3-acetamido-4-pyrazolyl, 1-methyl-5-acetamido-4-pyrazolyl, 3-methyl-5-acetamido-4-pyrazolyl, 1-methyl-5-amino-3-pyrazolyl, 5-methyl-4-amino-3-pyrazolyl, 4-methyl-5-amino-3-pyrazolyl, 1,3,5-trimethyl-4-pyrazolyl, 1,4,5-trimethyl-3-pyrazolyl, 1,3,4-trimethyl-5-pyrazolyl, 1,3-dimethyl-4-chloro-5-pyrazolyl, 2-imidazolyl, 4-imidazolyl, 1-methyl-2-imidazolyl, 5-methyl-2-imidazolyl, 1-methyl-4-imidazolyl, 2-methyl-4-imidazolyl, 5-methyl-4-imidazolyl, 1,2,3-oxadiazol-4-yl, 1,2,3-oxadiazol-5-yl, 5-methyl-1,2,3-oxadiazol-4-yl, 4-methyl-1,2,3-oxadiazol-5-yl, 1,2,4-oxadiazol-3-yl, 1,2,4-oxadiazol-5-yl, 1,2,5-oxodiazol-3-yl, 4-methyl-1,2,5-oxadiazol-3-yl, 4-phenyl-1,2,5-oxadiazol-3-yl, 4-(4-methylphenyl)-1,2,5-oxadiazol-3-yl, 1,3,4-oxadiazol-2-yl, 1,2,3-thiadiazol-4-yl, 1,2,3-thiadiazol-5-yl, 5-methyl-1,2,3-thiadiazol-4-yl, 5-phenyl-1,2,3-thiadiazol-4-yl, 5-(4-methylphenyl)-1,2,3-thiadiazol-4-yl, 4-methyl-1,2,3-thiadiazol-5-yl, 1,2,4-thiadiazol-3-yl, 1,2,4-thiadiazol-5-yl, 1,2,5-thiadiazol-3-yl, 4-methyl-1,2,5-thiadiazol-3-yl, 1,3,4-thiadiazol-2-yl, 1,2,3-triazol-4-yl, 1-methyl-1,2,3-triazol-4-yl, 5-methyl-1,2,3-triazol-4-yl, 1,5-dimethyl-1,2,3-triazol-4-yl, 1,2,4-triazol-5-yl, 1-methyl-1,2,4-triazol-3-yl and 2-ethyl-4-methyl-1,2,3-triazol-5-yl groups.

Examples of more preferred such groups include: the 2-furyl, 3-furyl, 3-methyl-2-furyl, 4-methyl-2-furyl, 5-methyl-2-furyl, 2- methyl-3-furyl, 4-methyl-3-furyl, 5-methyl-3-furyl, 2- thienyl, 3-thienyl, 3-methyl-2-thienyl, 4-methyl-2- thienyl, 5-methyl-2-thienyl, 2-methyl-3-thienyl, 4-methyl-3-thienyl, 5-methyl-3-thienyl, 5-chloro-2-thienyl, 5-chloro-3-thienyl, 3-amino-2-thienyl, 5-amino-2-thienyl, 2-amino-3-thienyl, 4-amino-3-thienyl, 3-acetamido-2-thienyl, 5-acetamido-2-thienyl, 2-acetamido-3-thienyl, 4-acetamido-3-thienyl, 2-pyrrolyl, 3-pyrrolyl, 1-methyl-2-pyrrolyl, 3-methyl-2-pyrrolyl, 4-methyl-2-pyrrolyl, 5-methyl-2-pyrrolyl, 1-methyl-3-pyrrolyl, 2-methyl-3-pyrrolyl, 4-methyl-3-pyrrolyl, 5-methyl-3-pyrrolyl, 4-methoxy-3-pyrrolyl, 5-chloro-2-pyrrolyl, 5-chloro-3-pyrrolyl, 3-amino-2-pyrrolyl, 4-amino-2-pyrrolyl, 2-oxazolyl, 4-oxazolyl, 5-oxazolyl, 2-methyl-4-oxazolyl, 3-isoxazolyl, 4-isoxazolyl, 3-methyl-4-isoxazolyl, 4-methyl-3-isoxazolyl, 5-methyl-3-isoxazolyl, 2-thiazolyl, 4-thiazolyl, 5-thiazolyl, 4-methyl-2-thiazolyl, 5-methyl-2-thiazolyl, 2-methyl-4-thiazolyl, 5-methyl-4-thiazolyl, 2-methyl-5-thiazolyl, 4-methyl-5-thiazolyl, 2-chloro-4-thiazolyl, 5-chloro-4-thiazolyl, 2-chloro-5-thiazolyl, 4-chloro-5-thiazolyl, 2-amino-4-thiazolyl, 5-amino-4-thiazolyl, 3-pyrazolyl, 4-pyrazolyl, 1-methyl-4-pyrazolyl, 3-methyl-4-pyrazolyl, 1-methyl-3-pyrazolyl, 4-methyl-3-pyrazolyl, 5-methyl-3-pyrazolyl, 1-methyl-5-pyrazolyl, 1-ethyl-4-pyrazolyl, 4-methoxy-3-pyrazolyl, 4-chloro-3-pyrazolyl, 3-chloro-4-pyrazolyl, 4-amino-3-pyrazolyl, 5-amino-3-pyrazolyl, 3-amino-4-pyrazolyl, 3-acetamido-4-pyrazolyl, 2-imidazolyl, 4-imidazolyl, 1-methyl-2-imidazolyl, 5-methyl-2-imidazolyl, 1-methyl-4-imidazolyl, 2-methyl-4-imidazolyl, 5-methyl-4-imidazolyl, 1,2,3-thiadiazol-4-yl, 1,2,3-thiadiazol-5-yl, 5-methyl-1,2,3-thiadiazol-4-yl, 4-methyl-1,2,3-thiadiazol-5-yl, 1,2,4-thiadiazol-3-yl, 1,2,4- thiadiazol-5-yl, 1,2,5-thiadiazol-3-yl, 4-methyl-1,2,5-thiadiazol-3-yl and 1,3,4-thiadiazol-2-yl groups.

Examples of still more preferred such groups include: the 2-furyl, 3-furyl, 2-thienyl, 3-thienyl, 3-methyl-2-thienyl, 4-methyl-2-thienyl, 5-methyl-2-thienyl, 2-methyl-3-thienyl, 4-methyl-3-thienyl, 5-methyl-3-thienyl, 5-chloro-2-thienyl, 5-chloro-3-thienyl, 2-pyrrolyl, 3-pyrrolyl, 1-methyl-2-pyrrolyl, 3-methyl-2-pyrrolyl, 4-methyl-2-pyrrolyl, 5-methyl-2-pyrrolyl, 1-methyl-3-pyrrolyl, 2-methyl-3-pyrrolyl, 4-methyl-3-pyrrolyl, 5-methyl-3-pyrrolyl, 2-oxazolyl, 4-oxazolyl, 5-oxazolyl, 3-isoxazolyl, 4-isoxazolyl, 2-thiazolyl, 4-thiazolyl, 5-thiazolyl, 2-methyl-4-thiazolyl, 5-methyl-4-thiazolyl, 2-methyl-5-thiazolyl, 4-methyl-5-thiazolyl, 3-pyrazolyl, 4-pyrazolyl, 1-methyl-4-pyrazolyl, 3-methyl-4-pyrazolyl, 1-methyl-3-pyrazolyl, 4-methyl -3-pyrazolyl, 5-methyl-3-pyrazolyl, 1-methyl-5-pyrazolyl, 3-chloro-4-pyrazolyl, 4-amino-3-pyrazolyl, 5-amino-3-pyrazolyl, 3-amino-4-pyrazolyl, 2-imidazolyl, 4-imidazolyl, 1,2,3-thiadiazol-4-yl 1,2,3-thiadiazol-5-yl, 1,2,4-thiadiazol-3-yl and 1,2,4-thiadiazol-5-yl.

Examples of the most preferred such groups which may be represented by $R^2$ include: the 2-thienyl, 3-thienyl, 5-methyl-2-thienyl, 5-chloro-3-thienyl, 2-pyrrolyl, 3-pyrrolyl, 1-methyl-2-pyrrolyl, 2-thiazolyl, 4-thiazolyl, 5-thiazolyl, 3-pyrazolyl, 4-pyrazolyl, 1-methyl-4-pyrazolyl, 3-methyl-4-pyrazolyl, 5-methyl-3-pyrazolyl, 3-amino-4-pyrazolyl, 1,2,3-thiadiazol-4-yl groups and 1,2,3-thiadiazol-5-yl groups.

Specific examples of optionally substituted 5- or 6-membered aromatic heterocyclic groups having from 1 to 4 hetero-atoms selected from the group consisting of oxygen, nitrogen and sulfur atoms, which may be represented by $R^5$ include: the 2-furyl, 3-furyl, 3-methyl-2-furyl, 4-methyl-2-furyl, 5-methyl-2-furyl, 2-methyl-3-furyl, 4-methyl-3-furyl, 5-methyl-3-furyl, 5-chloro-2-furyl, 5-chloro-3-furyl, 3-amino-2-furyl, 5-amino-2-furyl, 3-acetamido-2-furyl, 5-acetamido-2-furyl, 5-phenyl-2-furyl, 5-(4-methylphenyl)-2-furyl, 5-(4-chlorophenyl)-2-furyl, 2,4-dimethyl-3-furyl, 2,5-dimethyl-3-furyl, 3-methyl-5-amino-2-furyl, 2-thienyl, 3-thienyl, 3-methyl-2-thienyl, 4-methyl-2-thienyl, 5-methyl-2-thienyl, 2-methyl-3-thienyl, 4-methyl-3-thienyl, 5-methyl-3-thienyl, 5-ethyl-2-thienyl, 4-methoxy-2-thienyl, 4-methoxy-3-thienyl, 4-hydroxy-2-thienyl, 4-hydroxy-3-thienyl, 5-chloro-2-thienyl, 5-chloro-3-thienyl, 5-bromo-3-thienyl, 3-amino-thienyl, 5-amino-2-thienyl, 2-amino-3-thienyl, 4-amino-3-thienyl, 3-acetamido-2-thienyl, 5-acetamido-2-thienyl, 2-acetamido-3-thienyl, 4-acetamido-3-thienyl, 5-phenyl-2-thienyl, 5-(4-methylphenyl)-2-thienyl, 5-(4-chlorophenyl)-2-thienyl, 3,4-dimethyl-2-thienyl, 3,5-dimethyl-2-thienyl, 4,5-dimethyl-2-thienyl, 2,4-dimethyl-3-thienyl, 2,5-dimethyl-3-thienyl, 4,5-dimethyl-3-thienyl, 5-methyl-2-amino-3-thienyl, 4-methyl-5-chloro-3-thienyl, 4,5-dichloro-2-thienyl, 2-amino-5-phenyl-3-thienyl, 2,4,5-trimethyl-3-thienyl, 2,5-dimethyl-4-amino-3-thienyl, 2-pyrrolyl, 3-pyrrolyl, 1-methyl-2-pyrrolyl, 3-methyl-2-pyrrolyl, 4-methyl-2-pyrrolyl, 5-methyl-2-pyrrolyl, 1-methyl-3-pyrrolyl, 2-methyl-3-pyrrolyl, 4-methyl-3-pyrrolyl, 5-methyl-3-pyrrolyl, 4-methoxy-3-pyrrolyl, 4-hydroxy-3-pyrrolyl, 5-chloro-2-pyrrolyl, 5-chloro-3-pyrrolyl, 3-amino-2-pyrrolyl, 4-amino-2-pyrrolyl, 3-acetamido-2-pyrrolyl, 4-acetamido-2-pyrrolyl, 4-phenyl-2-pyrrolyl, 5-phenyl-2-pyrrolyl, 5-phenyl-3-pyrrolyl, 4-(4-methylphenyl)-2-pyrrolyl, 5-(4-methylphenyl)-2-pyrrolyl, 4-(4-methoxyphenyl)-2-pyrrolyl, 5-(4-methoxyphenyl)-2-pyrrolyl, 4-(4-fluorophenyl)-2-pyrrolyl, 5-(4-fluorophenyl)-2-pyrrolyl, 4-(4-chlorophenyl)-2-pyrrolyl, 5-(4-chlorophenyl)-2-pyrrolyl, 5-(4-methylphenyl)-3-pyrrolyl, 5-(4-methoxyphenyl)-3-pyrrolyl, 5-(4-fluorophenyl)-3-pyrrolyl, 5-(4-chlorophenyl)-3-pyrrolyl, 1-(2-hydroxyethyl)-2-pyrrolyl, 1-(3-hydroxypropyl)-2-pyrrolyl, 1-(2-hydroxyethyl)-3-pyrrolyl, 1-(3-hydroxypropyl)-3-pyrrolyl, 1,3-dimethyl-2-pyrrolyl, 1,4-dimethyl-2-pyrrolyl, pyrrolyl, 1,5-dimethyl-2-pyrrolyl, 3,4-dimethyl-2-pyrrolyl, 3,5-dimethyl-2-pyrrolyl, 4,5-dimethyl-2-pyrrolyl, 1,5-dimethyl-3-pyrrolyl, 2,4-dimethyl-3-pyrrolyl, 2,5-dimethyl-3-pyrrolyl, 1-methyl-4-hydroxy-3-pyrrolyl, 1-methyl-4-methoxy-3-pyrrolyl, 1-methyl-2-chloro-3-pyrrolyl, 4-methyl-5-chloro-3-pyrrolyl, 1-methyl-5-amino-2-pyrrolyl, 3,4,5-trimethyl-2-pyrrolyl, 1,2,4-trimethyl-3-pyrrolyl, 1,4-dimethyl-5-chloro-3-pyrrolyl, 1,4-dimethyl-5-bromo-3-pyrrolyl, 3,5-dimethyl-4-amino-2-pyrrolyl, 2-oxazolyl, 4-oxazolyl, 5-oxazolyl, 2-methyl-4-oxazolyl, 5-methyl-2-oxazolyl, 2-methoxy-4-oxazolyl, 2-hydroxy-4-oxazolyl, 2-phenyl-4-oxazolyl, 5-phenyl-2-oxazolyl, 2,5-dimethyl-4-oxazolyl, 2,4-dimethyl-5-oxazolyl, 5-methyl-2-phenyl-4-oxazolyl, 4-methyl-2-phenyl-5-oxazolyl, 3-isoxazolyl, 4-isoxazolyl, 3-methyl-4-isoxazolyl, 4-methyl-3-isoxazolyl, 5-methyl-3-isoxazolyl, 3-methoxy-4-isoxazolyl, 4-methoxy-3-isoxazolyl, 3-hydroxy-4-isoxazolyl, 3-hydroxy-5-isoxazolyl, 4-hydroxy-3-isoxazolyl, 5-amino-4-isoxazolyl, 4-amino-3-isoxazolyl, 4-phenyl-3-isoxazolyl, 5-phenyl-3-isoxazolyl, 4-(4-methylphenyl)-3-isoxazolyl, 5-(4-methylphenyl)-3-isoxazolyl, 4,5-dimethyl-3-isoxazolyl, 5-methyl-4-hydroxy-3-isoxazolyl, 2-thiazolyl, 4-thiazolyl, 5-thiazolyl, 4-methyl-2-thiazolyl, 5-methyl-2-thiazolyl, 2-methyl-4-thiazolyl, 5-methyl-4-thiazolyl, 2-methyl-5-thiazolyl, 4-methyl-5-thiazolyl, 2-methoxy-4-thiazolyl, 2-methoxy-5-thiazolyl, 2-hydroxy-4-thiazolyl, 2-hydroxy-5-thiazolyl, 5-chloro-2-thiazolyl, 2-chloro-4-thiazolyl, 5-chloro-4-thiazolyl, 2-chloro-5-thiazolyl, 4-chloro-5-thiazolyl, 2-amino-4-thiazolyl, 5-amino-4-thiazolyl, 2-amino-5-thiazolyl, 2-acetamido-4-thiazolyl, 5-acetamido-4-thiazolyl, 2-acetamido-5-thiazolyl, 2-phenyl-4-thiazolyl, 2-phenyl-5-thiazolyl, 4,5-dimethyl-2-thiazolyl, 2,5-dimethyl-4-thiazolyl, 2,4-dimethyl-5-thiazolyl, 5-methyl-2-hydroxy-4-thiazolyl, 4-methyl-2-hydroxy-5-thiazolyl, 5-methyl-2-chloro-4-thiazolyl, 4-methyl-2-chloro-5-thiazolyl, 2-methyl-4-chloro-5-thiazolyl, 5-methyl-2-amino-4-thiazolyl, 2-methyl-5-amino-4-thiazolyl, 4-methyl-2-amino-5-thiazolyl, 3-isothiazolyl, 4-isothiazolyl, 3-pyrazolyl, 4-pyrazolyl, 1-methyl-4-pyrazolyl, 3-methyl-4-pyrazolyl, 1-methyl-3-pyrazolyl, 4-methyl-3-pyrazolyl, 5-methyl-3-pyrazolyl, 1-methyl-5-pyrazolyl, 1-ethyl-4-pyrazolyl, 1-ethyl-3-pyrazolyl, 5-ethyl-3-pyrazolyl, 1-propyl-4-pyrazolyl, 1-propyl-3-pyrazolyl, 5-propyl-3-pyrazolyl, 1-butyl-4-pyrazolyl, 4-methoxy-3-pyrazolyl, 4-propoxy-3-pyrazolyl, 4-hydroxy-3-pyrazolyl, 4-chloro-3-pyrazolyl, 3-chloro-4-pyrazolyl, 4-bromo-3-pyrazolyl, 4-amino-3-pyrazolyl, 5-amino-3-pyrazolyl, 3-amino-4-pyrazolyl, 3-acetamido-4-pyrazolyl, 3-propionylamino-4-pyrazolyl, 4-acetamido-3-pyrazo lyl, 5-acetamido-3-pyrazolyl, 5-phenyl-3-pyrazolyl , 1-(2-hydroxyethyl)-3-pyrazolyl, 1-(3-hydroxypropyl)- 3-pyrazolyl, 1-(2-hydroxyethyl)-4-pyrazolyl, 1-(3-hydroxypropyl)-4-pyrazolyl, 1-(2-hydroxyethyl)-5-pyrazolyl, 1-(3-hydroxypropyl)-5-pyrazolyl, 1,3-dimethyl-4-pyrazolyl, 1,5-dimethyl-4-pyrazolyl, 3,5-dimethyl-4-pyrazolyl, 1,4-dimethyl-3-pyrazolyl, 1,5-dimethyl-3-pyrazolyl, 4,5-dimethyl-3-pyrazolyl, 1,3-dimethyl-5-pyrazolyl, 1,4-dimethyl-5-pyrazolyl, 1-methyl-4-methoxy-3-pyrazolyl, 5-methyl-4-hydroxy-3-pyrazolyl, 1-methyl-3-chloro-4-pyrazolyl, 1-methyl-5-chloro-4-pyrazolyl, 5-methyl-3-chloro-4-pyrazolyl, 1-methyl-4-chloro-3-pyrazolyl, 5-methyl-4-chloro-3-pyrazolyl, 1-methyl-4-chloro-5-pyrazolyl, 1-methyl-3-amino-4-pyrazolyl, 1-methyl-5-amino-4-pyrazolyl, 5-methyl-3-amino-4-pyrazolyl, 1-methyl-3-acetamido-4- pyrazolyl, 1-methyl-5-acetamido-4-pyrazolyl, 3-methyl-5-acetamido-4-pyrazolyl, 1-methyl-5-amino-3-pyrazolyl, 5-methyl-4-amino-3-pyrazolyl, 4-methyl-5-amino-3-pyrazolyl, 1,3,5-trimethyl-4-pyrazolyl, 1,4,5-trimethyl-3-pyrazolyl, 1,3,4-trimethyl-5-pyrazolyl, 1,3-dimethyl-4-chloro-5-pyrazolyl, 2-imidazolyl, 4-imidazolyl, 1-methyl-2-imidazolyl, 5-methyl-2-imidazolyl, 1-methyl-4-imidazolyl, 2-methyl-4-imidazolyl, 5-methyl-4-imidazolyl, 1-ethyl-2-imidazolyl, 4-ethyl-2-imidazolyl, 1-(2-hydroxyethyl)-2-imidazolyl, 1-(3-hydroxypropyl)-2-imidazolyl, 4-amino-2-imidazolyl, 2-amino-4-imidazolyl, 5-amino-4-imidazolyl, 4-chloro-2-imidazolyl, 2-chloro-4-imidazolyl, 5-chloro-4-imidazolyl, 1,2,3-oxadiazol-4-yl, 1,2,3-oxadiazol-5-yl, 5-methyl-1,2,3-oxadiazol-4-yl, 4-methyl-1,2,3-oxadiazol-5-yl, 1,2,4-oxadiazol-3-yl, 1,2,4-oxadiazol-5-yl, 1,2,5-oxadiazol-3-yl, 4-methyl-1,2,5-oxadiazol-3-yl, 4-phenyl-1,2,5-oxadiazol-3-yl, 4-(4-methylphenyl)-1,2,5-oxadiazol-3-yl, 1,3,4-oxadiazol-2-yl, 5-methyl-1,3,4-oxadiazol-2-yl, 5-ethyl-1,3,4-oxadiazol-2-yl, 5-phenyl-1,3,4-oxadiazol-2-yl, 5-chloro-1,3,4-oxadiazol-2-yl, 5-amino-1,3,4-oxadiazol-2-yl, 5-acetamido-1,3,4-oxadiazol-2-yl, 1,2,3-thiadiazol-4-yl, 1,2,3-thiadiazol-5-yl, 5-methyl-1,2,3-thiadiazol-4-yl, 5-phenyl-1,2,3-thiadiazol-4-yl, 5-(4-methylphenyl)-1,2,3-thiadiazol-4-yl, 4-methyl-1,2,3-thiadiazol-5-yl, 1,2,4-thiadiazol-3-yl, 1,2,4-thiadiazol-5-yl, 1,2,5-thiadiazol-3-yl, 4-methyl-1,2,5-thiadiazol-3-yl, 1,3,4-thiadiazol-2-yl, 5-methyl-1,3,4-thiadiazol-2-yl, 5-ethyl-1,3,4-thiadiazol-2-yl, 5-phenyl-1,3,4-thiadiazol-2-yl, 5-chloro-1,3,4-thiadiazol-2-yl, 5-amino-1,3,4-thiadiazol-2-yl, 5-acetamido-1,3,4-thiadiazol-2-yl, 1,2,3-triazol-4-yl, 1-methyl-1,2,3-triazol-4-yl, 5-methyl-1,2,3-triazol-4-yl, 1,5-dimethyl-1,2,3-triazol-4-yl, 1,2,4-triazol-3-yl, 1,2,4-triazol-5-yl, 1-methyl-1,2,4-triazol-3-yl, 1-methyl-1,2,4-triazol-5-yl, 5-methyl-1,2,4-triazol-3-yl, 5-ethyl-1,2,4-triazol-3-yl, 5-phenyl-1,2,4-triazol-3-yl, 1-(2-hydroxyethyl)-1,2,4-triazol-3-yl, 1-(3-hydroxypropyl)-1,2,4-triazol-3-yl, 1-(2-hydroxyethyl)-1,2,4-triazol-5-yl, 1-(3-hydroxypropyl)-1,2,4-triazol-5-yl, 5-chloro-1,2,4-triazol-3-yl, 5-amino-1,2,4-triazol-3-yl, 5-acetamido-1,2,4-triazol-3-yl, 1,3-dimethyl-1,2,4-triazol-5-yl, 1,5-dimethyl-1,2,4-triazol-3-yl, 2-ethyl-4-methyl-1,2,3-triazol-5-yl, tetrazol-5-yl, 1-methyltetrazol-5-yl, 2-methyltetrazol-5-yl, 1-ethyltetrazol-5-yl, 2-ethyltetrazol-5-yl, 1-phenyltetrazol-5-yl, 2-phenyltetrazol-5-yl, 1-(2-hydroxyethyl)tetrazol-5-yl, 2-(2-hydroxyethyl)-tetrazol-5-yl, 1-(2-hydroxypropyl) tetrazol-5-yl, 2-(2-hydroxypropyl) tetrazol-5-yl, 1-(3-hydroxypropyl)-tetrazol-5-yl, 2-(3-hydroxypropyl)tetrazol-5-yl, 2-pyridyl, 3-pyridyl, 4-pyridyl, 3-methyl-2-pyridyl, 4-methyl-2-pyridyl, 5-methyl-2-pyridyl, 6-methyl-2-pyridyl, 2-methyl-4-pyridyl, 3-methyl-4-pyridyl, 3-chloro-2-pyridyl, 4-chloro-2-pyridyl, 5-chloro-2-pyridyl, 6-chloro-2-pyridyl, 2-chloro-3-pyridyl, 4-chloro-3-pyridyl, 5-chloro-3-pyridyl, 6-chloro-3-pyridyl, 2-chloro-4-pyridyl, 3-chloro-4-pyridyl, 3-amino-2-pyridyl, 4-amino-2-pyridyl, 5-amino-2-pyridyl, 6-amino-2-pyridyl, 2-amino-3-pyridyl, 4-amino-3-pyridyl, 5-amino-3-pyridyl, 6-amino-3-pyridyl, 2-amino-4-pyridyl, 3-amino-4-pyridyl, 3-hydroxy-2-pyridyl, 4-hydroxy-2-pyridyl, 5-hydroxy-2-pyridyl, 6-hydroxy-2-pyridyl, 2-hydroxy-4-pyridyl, 3-hydroxy-4-pyridyl, 3-phenyl-2-pyridyl, 4-phenyl-2-pyridyl, 5-phenyl-2-pyridyl, 6-phenyl-2-pyridyl, 2-phenyl-4-pyridyl, 3-phenyl-4-pyridyl, 2-pyrimidinyl, 4-pyrimidinyl, 5-pyrimidinyl, 4-methyl-2-pyrimidinyl, 5-methyl-2-pyrimidinyl, 2-methyl-4-pyrimidinyl, 5-methyl-4-pyrimidinyl, 6-methyl-4-pyrimidinyl, 2-methyl-5-pyrimidinyl, 4-methyl-5-pyrimidinyl, 4-phenyl-2-pyrimidinyl, 5-phenyl-2-pyrimidinyl, 2-phenyl-4-pyrimidinyl, 5-phenyl-4-pyrimidinyl, 6-phenyl-4-pyrimidinyl, 2-phenyl-5-pyrimidinyl, 4-phenyl-5-pyrimidinyl, 4-chloro-2-pyrimidinyl, 5-chloro-2-pyrimidinyl, 2-chloro-4-pyrimidinyl, 5-chloro-4-pyrimidinyl, 6-chloro-4-pyrimidinyl, 2-chloro-5-pyrimidinyl, 4-chloro-5-pyrimidinyl, 4-amino-2-pyrimidinyl, 5-amino-2-pyrimidinyl, 2-amino-4-pyrimidinyl, 5-amino-4-pyrimidinyl, 6-amino-4-pyrimidinyl, 2-amino-5-pyrimidinyl, 4-amino-5-pyrimidinyl, 4-acetamido-2-pyrimidinyl, 5-acetamido-2-pyrimidinyl, 2-acetamido-4-pyrimidinyl, 5-acetamido-4-pyrimidinyl, 6-acetamido-4-pyrimidinyl, 2-acetamido-5-pyrimidinyl, 4-acetamido-5-pyrimidinyl, 4,5-dimethyl-2-pyrimidinyl, 4,6-dimethyl-2-pyrimidinyl, 2,5-dimethyl-4-pyrimidinyl, 2,6-dimethyl-4-pyrimidinyl, 2,4-dimethyl-5-pyrimidinyl, 2,6-dimethyl-5-pyrimidinyl, 4-amino-5-hydroxy-2-pyrimidinyl, 4-amino-6-hydroxy-2-pyrimidinyl, 2-amino-5-hydroxy-4-pyrimidinyl, 2-amino-6-hydroxy-4-pyrimidinyl, 2-amino-4-hydroxy-5-pyrimidinyl, 5-amino-2-hydroxy-4-pyrimidinyl, 6-amino-2-hydroxy-4-pyrimidinyl, 4-amino-2-hydroxy-5-pyrimidinyl, 4,5-diamino-2-pyrimidinyl, 4,6-diamino-2-pyrimidinyl, 5-diamino-4-pyrimidinyl, 2,6-diamino-4-pyrimidinyl, 4-diamino-5-pyrimidinyl, 2,6-diamino-5-pyrimidinyl, 3-pyridazinyl, 4-pyridazinyl, 4-methyl-3-pyridazinyl, 5-methyl-3-pyridazinyl, 6-methyl-3-pyridazinyl, 3-methyl-4-pyridazinyl, 5-methyl-4-pyridazinyl, 6-methyl-4-pyridazinyl, 4-chloro-3-pyridazinyl, 5-chloro-3-pyridazinyl, 6-chloro-3-pyridazinyl, 3-chloro-4-pyridazinyl, 5-chloro-4-pyridazinyl, 6-chloro-4-pyridazinyl, 4-hydroxy-3-pyridazinyl, 5-hydroxy-3-pyridazinyl, 6-hydroxy-3-pyridazinyl, 3-hydroxy-4-pyridazinyl, 5-hydroxy-4-pyridazinyl, 6-hydroxy-4-pyridazinyl, 4-amino-3-pyridazinyl, 5-amino-3-pyridazinyl, 6-amino-3-pyridazinyl, 3-amino-4-pyridazinyl, 5-amino-4-pyridazinyl, 6-amino-4-pyridazinyl, 2-pyrazinyl, 3-amino-2-pyrazinyl, 5-amino-2-pyrazinyl, 6-amino-2-pyrazinyl, 3-hydroxy-2-pyrazinyl, 5-hydroxy-2-pyrazinyl, 6-hydroxy-2-pyrazinyl, 3,5-dihydroxy-2-pyrazinyl, 3,6-dihydroxy-2-pyrazinyl, 1,2,3-triazin-4-yl, 1,2,3-triazin-5-yl, 5-methyl-1,2,3-triazin-4-yl, 6-methyl-1,2,3-triazin-4-yl, 4-methyl-1,2,3-triazin-5-yl, 1,2,4-triazin-3-yl, 1,2,4-triazin-5-yl, 1,2,4-triazin-6-yl, 5-methyl-1,2,4triazin-3-yl, 6-methyl-1,2,4-triazin-3-yl, 3-methyl-1,2,4-triazin-5-yl, 6-methyl-1,2,4-triazin-5-yl, 3-methyl-1,2,4-triazin-6-yl, 5-methyl-1,2,4-triazin-6-yl, 1,3,5-triazin-2-yl and 4-methyl-1,3,5-triazin-2-yl groups.

Examples of preferred such groups include: the 2-furyl, 3-furyl, 3-methyl-2-furyl, 4-methyl-2-furyl, 5-methyl-2-furyl, 2-methyl-3-furyl, 4-methyl-3-furyl, 5-methyl-3-furyl, 2-thienyl, 3-thienyl, 3-methyl-2-thienyl, 4-methyl-2-thienyl, 5-methyl-2-thienyl, 2-methyl-3-thienyl, 4-methyl-3-thienyl, 5-methyl-3-thienyl, 5-ethyl-2-thienyl, 4-methoxy-2-thienyl, 4-methoxy-3-thienyl, 3-amino-2-thienyl, 5-amino-2-thienyl, 2-amino-3-thienyl, 4-amino-3-thienyl, 2-pyrrolyl, 3-pyrrolyl, 1-methyl-2-pyrrolyl, 3-methyl-2-pyrrolyl, 4-methyl-2-pyrrolyl, 5-methyl-2-pyrrolyl, 1-methyl-3-pyrrolyl, 2-methyl-3-pyrrolyl, 4-methyl-3-pyrrolyl, 5-methyl-3-pyrrolyl, 4-methoxy-3-pyrrolyl, 4-hydroxy-3-pyrrolyl, 5-chloro-2-pyrrolyl, 5-chloro-3-pyrrolyl, 3-amino-2-pyrrolyl, 4-amino-2-pyrrolyl, 3-acetamido-2-pyrrolyl, 4-acetamido-2-pyrrolyl, 4-phenyl-2-pyrrolyl, 5-phenyl-2-pyrrolyl, 5-phenyl-3-pyrrolyl, 4-(4-methylphenyl)-2-pyrrolyl, 5-(4-methylphenyl)-2-pyrrolyl, 4-(4-methoxyphenyl)-2-pyrrolyl, 5-(4-methoxyphenyl)-2-pyrrolyl, 4-(4-chlorophenyl)-2-pyrrolyl, 5-(4-chlorophenyl)-2-pyrrolyl, 5-(4-methylphenyl)-3-pyrrolyl, 1-(2-hydroxyethyl)-2-pyrrolyl, 1-(3-hydroxypropyl)-2-pyrrolyl, 1-(2-hydroxyethyl)-3-pyrrolyl, 1-(3-hydroxypropyl)-3-pyrrolyl, 1,3-dimethyl-2-pyrrolyl, 1,4-dimethyl-2-pyrrolyl, 1,5-dimethyl-2-pyrrolyl, 3,4-dimethyl-2-pyrrolyl, 4,5-dimethyl-2-pyrrolyl, 1,5-dimethyl-3-pyrrolyl, 2,4-dimethyl-3-pyrrolyl, 2,5-dimethyl-3- pyrrolyl, 2-oxazolyl, 4-oxazolyl, 5-oxazolyl, 2-methyl-4-oxazolyl, 5-methyl-2-oxazolyl, 2-methoxy-4-oxazolyl, 2-hydroxy-4-oxazolyl, 3-isoxazolyl, 4-isoxazolyl, 3-methyl-4-isoxazolyl, 4-methyl-3-isoxazolyl, 5-methyl-3-isoxazolyl, 4-isoxazolyl, 2-thiazolyl, 4-thiazolyl, 5othiazolyl, 4-methyl-2-thiazolyl, 5-methyl-2-thiazolyl, 2-methyl-4-thiazolyl, 5-methyl-4-thiazolyl, 2-methyl-5-thiazolyl, 4-methyl-5-thiazolyl, 2-methoxy-4-thiazolyl, 2-methoxy-5-thiazolyl, 2-hydroxy-4-thiazolyl, 2-hydroxy-5-thiazolyl, 5-chloro-2-thiazolyl, 2-chloro-4-thiazolyl, 5-chloro-4-thiazolyl, 2-chloro-5-thiazolyl, 4-chloro-5-thiazolyl, 2-amino-4-thiazolyl, 5-amino-4-thiazolyl, 2-amino-5-thiazolyl, 2-acetamido-4-thiazolyl, 5-acetamido-4-thiazolyl, 2-acetamido-5-thiazolyl, 3-isothiazolyl, 4-isothiazolyl, 3-pyrazolyl, 4-pyrazolyl, 1-methyl-4-pyrazolyl, 3-methyl-4-pyrazolyl, 1-methyl-3-pyrazolyl, 4-methyl-3-pyrazolyl, 5-methyl-3-pyrazolyl, 1-methyl-5-pyrazolyl, 1-ethyl-4-pyrazolyl, 1-ethyl-3-pyrazolyl, 5-ethyl-3-pyrazolyl, 1-propyl-4-pyrazolyl, 1-propyl-3-pyrazolyl, 5-propyl-3-pyrazolyl, 1-butyl-4-pyrazolyl, 4-methoxy-3-pyrazolyl, 4-chloro-3-pyrazolyl, 3-chloro-4-pyrazolyl, 4-bromo-3-pyrazolyl, 4-amino-3-pyrazolyl, 5-amino-3-pyrazolyl, 3-amino-4-pyrazolyl, 3-acetamido-4-pyrazolyl, 3-propionylamino-4-pyrazolyl, 4-acetamido-3-pyrazolyl, 5oacetamido-3-pyrazolyl, 5-phenyl-3-pyrazolyl, 1-(2-hydroxyethyl)-3-pyrazolyl, 1-(3-hydroxypropyl)-3-pyrazolyl, 1-(2-hydroxyethyl)-4-pyrazolyl, 1-(3-hydroxypropyl)-4-pyrazolyl, 1-(2-hydroxyethyl)-5-pyrazolyl, 1-(3-hydroxypropyl)-5-pyrazolyl, 1,3-dimethyl-4-pyrazolyl, 1,5-dimethyl-4-pyrazolyl, 3,5-dimethyl-4-pyrazolyl, 1,4-dimethyl-3-pyrazolyl, 1,5-dimethyl-3-pyrazolyl, 4,5-dimethyl-3-pyrazolyl, 1,3-dimethyl-5-pyrazolyl, 1,4-dimethyl-5-pyrazolyl, 1-methyl-3-amino-4-pyrazolyl, 1-methyl-5-amino-4-pyrazolyl, 5-methyl-3-amino-4-pyrazolyl, 1-methyl-3-acetamido-4-pyrazolyl, 1-methyl-5-acetamido-4-pyrazolyl, 3-methyl-5-acetamido-4-pyrazolyl, 1-methyl-5-amino-3-pyrazolyl, 5-methyl-4-amino-3-pyrazolyl, 4-methyl-5-amino-3-pyrazolyl, 2-imidazolyl, 4-imidazolyl, 1-methyl-2-imidazolyl, 5-methyl-2-imidazolyl, 1-methyl-4-imidazolyl, 2-methyl-4-imidazolyl, 5-methyl-4-imidazolyl, 1-ethyl-2-imidazolyl, 4-ethyl-2-imidazolyl, 1-(2-hydroxyethyl)-2-imidazolyl, 1-(3-hydroxypropyl)-2-imidazolyl, 4-amino-2-imidazolyl, 2-amino-4-imidazolyl, 5-amino-4-imidazolyl, 4-chloro-2-imidazoly, 2-chloro-4-imidazolyl, 5-chloro-4-imidazolyl, 1,2,3-oxadiazol-4-yl, 1,2,3-oxadiazol-5-yl, 5-methyl-1,2,3-oxadiazol-4-yl, 4-methyl-1,2,3-oxadiazol-5-yl, 1,2,4-oxadiazol-3-yl, 1,2,4-oxadiazol-5-yl, 1,2,5-oxadiazol-3-yl, 4-methyl-1,2,5-oxadiazol-3-yl, 4-phenyl-1,2,5-oxadiazol-3-yl, 1,3,4-oxadiazol-2-yl, 5-methyl-1,3,4-oxadiazol-2-yl, 5-ethyl-1,3,4-oxadiazol-2-yl, 5-phenyl-1,3,4-oxadiazol-2-yl, 5-chloro-1,3,4-oxadiazol-2-yl, 5-amino-1,3,4-oxadiazol-2-yl, 5-acetamido-1,3,4-oxadiazol-2-yl, 1,2,3-thiadiazol-4-yl, 1,2,3-thiadiazol-5-yl, 5-methyl-1,2,3-thiadiazol-4-yl, 5-phenyl-1,2,3-thiadiazol-4-yl, 4-methyl-1,2,3-thiadiazol-5-yl, 1,2,4-thiadiazol-3-yl, 1,2,4-thiadiazol-5-yl, 1,2,5-thiadiazol-3-yl, 4-methyl-1,2,5-thiadiazol-3-yl, 1,3,4-thiadiazol-2-yl, 5-methyl-1,3,4-thiadiazol-2-yl, 5-ethyl-1,3,4-thiadiazol-2-yl, 5-phenyl-1,3,4-thiadiazol-2-yl, 5-chloro-1,3,4-thiadiazol-2-yl, 5-amino-1,3,4-thiadiazol-2-yl, 5-acetamido-1,3,4-thiadiazol-2-yl, 1,2,3-triazol-4-yl, 1-methyl-1,2,3-triazol-4-yl, 5-methyl-1,2,3-triazol-4-yl, 1,5-dimethyl-1,2,3-triazol-4-yl, 1,2,4-triazol-3-yl, 1,2,4-triazol-5-yl, 1-methyl-1,2,4-triazol-3-yl, 1-methyl-1,2,4-triazol-5-yl, 5-methyl-1,2,4-triazol-3-yl, 5-ethyl-1,2,4-triazol-3-yl, 5-phenyl-1,2,4-triazol-3-yl, 1-(2-hydroxyethyl)-1,2,4-triazol-3-yl, 1-(3-hydroxypropyl)-1,2,4-triazol-3-yl, 1-(2-hydroxyethyl)-1,2,4-triazol-5-yl, 1-(3-hydroxypropyl)-1,2,4-triazol-5-yl, 5-chloro-1,2,4-triazol-3-yl, 5-amino-1,2,4-triazol-3-yl, 5-acetamido-1,2,4-triazol-3-yl, 1,3-dimethyl-1,2,4-triazol-5-yl, 1,5-dimethyl-1,2,4-triazol-3-yl, tetrazol-5-yl, 1-methyltetrazol-5-yl, 2-methyltetrazol-5-yl, 1-ethyltetrazol-5-yl, 2-ethyltetrazol-5-yl, 1-phenyltetrazol-5-yl, 2-phenyltetrazol-5-yl, 1- (2-hydroxyethyl)tetrazol-5-yl, 2-(2-hydroxyethyl) tetrazol -5 -yl, 1-(2-hydroxypropyl) tetrazol-5 -yl, 2- ( 2 - hydroxypropyl ) tet razol - 5 - yl, 1 - ( 3 - hydroxypropyl)- tetrazol-5 -yl, 2-(3 -hydroxypropyl ) tetrazol - 5 -yl, 2-pyridyl, 3-pyridyl, 4-pyridyl, 3-methyl-2-pyridyl, 4-methyl-2-pyridyl, 5-methyl-2-pyridyl, 6-methyl-2-pyridyl, 2-methyl-4-pyridyl, 3-methyl-4-pyridyl, 3-chloro-2-pyridyl, 4-chloro-2-pyridyl, 5-chloro-2-pyridyl, 6-chloro-2-pyridyl, 2-chloro-4-pyridyl, 3-chloro-4-pyridyl, 3-amino-2-pyridyl, 4-amino-2-pyridyl, 5-amino-2-pyridyl, 6-amino-2-pyridyl, 2-amino4-pyridyl, 3-amino-4-pyridyl, 3-hydroxy-2-pyridyl, 4-hydroxy-2-pyridyl, 5-hydroxy-2-pyridyl, 6-hydroxy2-pyridyl, 2-hydroxy-4-pyridyl, 3-hydroxy-4-pyridyl, 3-phenyl-2-pyridyl, 4-phenyl-2-pyridyl, 5-phenyl-2pyridyl, 6-phenyl-2-pyridyl, 2-phenyl-4-pyridyl, 3-phenyl-4-pyridyl, 2-pyrimidinyl, 4-pyrimidinyl, 5-pyrimidinyl, 4-methyl-2-pyrimidinyl, 5-methyl-2pyrimidinyl, 2-methyl-4-pyrimidinyl, 5 -methyl-4-pyrimidinyl, 6-methyl-4-pyrimidinyl, 4 -phenyl-2-pyrimidinyl, 5-phenyl-2-pyrimidinyl, 2 -phenyl-4-pyrimidinyl, 5-phenyl-4-pyrimidinyl, 6 -phenyl-4-pyrimidinyl, 4-chloro-2-pyrimidinyl, 5 -chloro-2-pyrimidinyl, 2-chloro-4-pyrimidinyl, 5 -chloro-4-pyrimidinyl, 6-chloro-4-pyrimidinyl, 4-amino-2-pyrimidinyl, 5-amino-2-pyrimidinyt, 2-amino-4-pyrimidinyl, 5-amino-4-pyrimidinyl, 6-amino-4-pyrimidinyl, 4-acetamido-2-pyrimidinyl, 5-acetamido-2-pyrimidinyl, 2-acetamido-4-pyrimidinyl, 5-acetamido-4-pyrimidinyl, 6-acetamido-4-pyrimidinyl, 4,5-dimethyl-2-pyrimidinyl, 4,6-dimethyl-2-pyrimidinyl, 2,5-dimethyl-4-pyrimidinyl, 2,6-dimethyl-4-pyrimidinyl, 4-amino-5-hydroxy-2-pyrimidinyl, 4-amino-6-hydroxy-2-pyrimidinyl, 2-amino-5-hydroxy-4-pyrimidinyl, 2-amino-6-hydroxypyrimidinyl, 5-amino-2-hydroxy-4-pyrimidinyl, 6-amino-2-hydroxy-4-pyrimidinyl, 4,5-diamino-2-pyrimidinyl, 4,6-diamino-2-pyrimidinyl, 2,5-diamino-4-pyrimidinyl, 2,6-diamino-4-pyrimidinyl , 3-pyridazinyl, 4-pyridazinyl, 4-methyl-3-pyridazinyl, 5 -methyl-3-pyridazinyl, 6-methyl-3-pyridazinyl, 3 -methyl-4-pyridazinyl, 5-methyl-4-pyridazinyl, 6 -methyl-4-pyridazinyl, 4-chloro-3-pyridazinyl, 5 -chloro-3-pyridazinyl, 6-chloro-3-pyridazinyl, 3 -chloro-4-pyridazinyl, 5-chloro-4-pyridazinyl, 6 -chloro-4-pyridazinyl, 4-hydroxy-3-pyridazinyl, 5-hydroxy-3-pyridazinyl, 6-hydroxy-3-pyridazinyl, 3-hydroxy-4-pyridazinyl, 5-hydroxy-4-pyridazinyl, 6-hydroxy-4-pyridazinyl, 4- amino-3-pyridazinyl, 5-amino-3-pyridazinyl, 6-amino-3-pyridazinyl, 3-amino-4-pyridazinyl, 5-amino-4-pyridazinyl, 6-amino-4-pyridazinyl, 2-pyrazinyl, 3-methyl-2-pyrazinyl, 5-methyl-2-pyrazinyl, 6-methyl-2-pyrazinyl, 3-amino-2-pyrazinyl, 5-amino-2-pyrazinyl, 6-amino-2-pyrazinyl, 3-hydroxy-2-pyrazinyl, 5-hydroxy-2-pyrazinyl, 6-hydroxy-2-pyrazinyl, 3,5-dihydroxy-2-pyrazinyl, 3,6-dihydroxy-2-pyrazinyl, 1,2,3-triazin-4-yl, 1,2,3-triazin-5-yl, 5-methyl-1,2,3-triazin-4-yl, 6-methyl-1,2,3-triazin-4-yl, 4-methyl-1,2,3-triazin-5-yl, 1,2,4-triazin-3-yl, 1,2,4-triazin-5-yl, 1,2,4-triazin-6-yl, 5-methyl-1,2,4-triazin-3-yl, 6-methyl-1,2,4-triazin-3-yl, 3-methyl-1,2,4-triazin-5-yl, 6-methyl-1,2,4-triazin-5-yl, 3-methyl-1,2,4-triazin-6-yl, 5-methyl-1,2,4-triazin-6-yl, 1,3,5-triazin-2-yl and 4-methyl-1,3,5-triazin-2-yl groups.

Examples of more preferred such groups include: the 2-imidazolyl, 4-imidazolyl, 1-methyl-2-imidazolyl, 5-methyl-2-imidazolyl, 1-methyl-4-imidazolyl, 2-methyl-4-imidazolyl, 5-methyl-4-imidazolyl, 4-chloro-2-imidazolyl, 2-chloro-4-imidazolyl, 5-chloro-4-imidazolyl, 1,3,4-oxadiazol-2-yl, 5-methyl-1,3,4-oxadiazol-2-yl, 5-ethyl-1,3,4-oxadiazol-2-yl, 5-chloro-1,3,4-oxadiazol-2-yl, 5-amino-1,3,4-oxadiazol-2-yl, 5-acetamido-1,3,4-oxadiazol-2-yl, 1,3,4-thiadiazol-2-yl, 5-methyl-1,3,4-thiadiazol-2-yl, 5-ethyl-1,3,4-thiadiazol-2-yl, 5-chloro-1,3,4-thiadiazol-2-yl, 5-amino-1,3,4-thiadiazol-2-yl, 5-acetamido-1,3,4-thiadiazol-2-yl, 1,2,4-triazol-3-yl, 1,2,4-triazol-5-yl, 1-methyl-1,2,4-triazol-3-yl, 1-methyl-1,2,4-triazol-5-yl, 5-methyl-1,2,4-triazol-3-yl, 5-ethyl-1,2,4-triazol-3-yl, 5-phenyl-1,2,4-triazol-3-yl, 5-chloro-1,2,4-triazol-3-yl, 5-amino-1,2,4-triazol-3-yl, 5-acetamido-1,2,4triazol-3-yl, tetrazol-5-yl, 1-methyltetrazol-5-yl, 1-ethyltetrazol-5-yl, 2-pyridyl, 3-pyridyl, 4-pyridyl, 3-methyl-2-pyridyl, 4-methyl-2-pyridyl, 5-methyl-2-pyridyl, 6-methyl-2-pyridyl, 2-methyl-4-pyridyl, 3-methyl-4-pyridyl, 3-chloro-2-pyridyl, 4-chloro-2-pyridyl, 5-chloro-2-pyridyl, 6-chloro-2-pyridyl, 2-chloro-4-pyridyl, 3-chloro-4-pyridyl, 3-amino-2-pyridyl, 4-amino-2-pyridyl, 5-amino-2-pyridyl, 6-amino-2-pyridyl, 2-amino-4-pyridyl, 3-amino-4-pyridyl, 3-hydroxy-2-pyridyl, 4-hydroxy-2-pyridyl, 5-hydroxy-2-pyridyl, 6-hydroxy-2-pyridyl, 2-hydroxy-4-pyridyl, 3-hydroxy-4-pyridyl, 2-pyrimidinyl, 4-pyrimidinyl, 5-pyrimidinyl, 4-methyl-2-pyrimidinyl, 5-methyl-2-pyrimidinyl, 2-methyl-4-pyrimidinyl, 5-methyl-4-pyrimidinyl, 6-methyl-4-pyrimidinyl, 4-chloro-2-pyrimidinyl, 5-chloro-2-pyrimidinyl, 2-chloro-4-pyrimidinyl, 5-chloro-4-pyrimidinyl, 6-chloro-4-pyrimidinyl, 4-amino-2-pyrimidinyl, 5-amino-2-pyrimidinyl, 2-amino-4-pyrimidinyl, 5-amino-4-pyrimidinyl, 6-amino-4-pyrimidinyl, 4-acetamido-2-pyrimidinyl, 5-acetamido-2-pyrimidinyl, 2-acetamido-4-pyrimidinyl, 5-acetamido-4-pyrimidinyl, 6-acetamido-4-pyrimidinyl, 4-amino-5-hydroxy-2-pyrimidinyl, 4-amino-6-hydroxy-2-pyrimidinyl, 2-amino-5-hydroxy-4-pyrimidinyl, 2-amino-6-hydroxy-4-pyrimidinyl, 5-amino-2-hydroxy-4-pyrimidinyl, 6-amino-2-hydroxy-4-pyrimidinyl, 4,5-diamino-2-pyrimidinyl, 4,6-diamino-2-pyrimidinyl, 2,5-diamino-4-pyrimidinyl and 2,6-diamino-4-pyrimidinyl groups.

Examples of still more preferred such groups include: the 2-imidazolyl, 4-imidazolyl, 1,3,4-oxadiazol-2-yl, 5-methyl-1,3,4-oxadiazol-2-yl, 1,3,4-thiadiazol-2-yl, 5-methyl-1,3,4-thiadiazol-2-yl, 1,2,4-triazol-3-yl, 1,2,4-triazol-5-yl, 1-methyl-1,2,4-triazol-3-yl, 1-methyl-1,2,4-triazol-5-yl, 5-methyl-1,2,4-triazol-3-yl, tetrazol-5-yl, 1-methyltetrazol-5-yl, 2-pyridyl, 3-pyridyl, 4-pyridyl, 3-methyl-2-pyridyl, 4-methyl-2-pyridyl, 5-methyl-2-pyridyl, 6-methyl-2-pyridyl, 2-methyl-4-pyridyl, 3-methyl-4-pyridyl, 3-amino-2-pyridyl, 4-amino-2-pyridyl, 5-amino-2-pyridyl, 6-amino-2-pyridyl, 2-amino-4-pyridyl, 3-amino-4-pyridyl, 3-hydroxy-2-pyridyl, 4-hydroxy-2-pyridyl, 5-hydroxy-2-pyridyl, 6-hydroxy-2-pyridyl, 2-hydroxy-4opyridyl, 3-hydroxy-4-pyridyl, 2-pyrimidinyl, 4-pyrimidinyl, 5-pyrimidinyl, 4-methyl-2-pyrimidinyl, 5-methyl-2-pyrimidinyl, 2-methyl-4-pyrimidinyl, 5-methyl-4-pyrimidinyl, 6-methyl-4-pyrimidinyl, 4-amin-2-pyrimidinyl, 5-amino-2-pyrimidinyl, 2-amino-4-pyrimidinyl, 5-amino-4-pyrimidinyl, 6-amino-4-pyrimidinyl, 4-amino-5-hydroxy-2-pyrimidinyl, 4-amino-6-hydroxy-2-pyrimidinyl, 2-amino-5-hydroxy-4-pyrimidinyl 2-amino-6-hydroxy-4opyrimidinyl, 5-amino-2ohydroxy-4-pyrimidinyl and 6-amino-2-hydroxy-4-pyrimidinyl groups.

Examples of the most preferred such groups include: the 1,3,4-oxadiazol-2-yl, 5-methyl-1,3,4-oxadiazol-2-yl, 1,3,4-thiadiazol-2-yl, 1,2,4-triazol-3-yl, 1,2,4-triazol-5-yl, 1-methyl-1,2,4-triazol-3-yl, 1-methyl-1,2,4-triazol-5-yl, 5-methyl-1,2,4-triazol-3-yl, 2-pyridyl, 3-pyridyl, 4-pyridyl, 2-pyrimidinyl, 4-pyrimidinyl, 4-methyl-2-pyrimidinyl, 5-methyl-2-pyrimidinyl, 2-methyl-4-pyrimidinyl, 5-methyl-4-pyrimidinyl and 6-methyl-4-pyrimidinyl groups.

The compounds of the present invention can form salts. Where the compound contains a carboxy group, it can form a salt with a cation. Examples of such salts include: salts with an alkali metal, such as sodium, potassium or lithium; salts with an alkaline earth metal, such as barium or calcium; salts with another metal, such as magnesium or aluminum; ammonium salts; organic base salts, such as a salt with triethylamine, diisopropylamine, cyclohexylamine or dicyclohexylamine; and salts with a basic amino acid, such as lysine or arginine. Also, since the compounds of the present invention necessarily contain basic groups in their molecules, they can form acid addition salts. Examples of such acid addition salts include: salts with mineral acids, especially hydrohalic acids (such as hydrofluoric acid, hydrobromic acid, hydroiodic acid or hydrochloric acid), nitric acid, perchloric acid, carbonic acid, sulfuric acid or phosphoric acid; salts with lower alkylsulfonic acids, such as methanesulfonic acid, trifluoromethanesulfonic acid or ethanesulfonic acid; salts with arylsulfonic acids, such as benzenesulfonic acid or p-toluenesulfonic acid; salts with organic carboxylic acids, such as acetic acid, fumaric acid, tartaric acid, oxalic acid, maleic acid, malic acid, succinic acid, benzoic acid, mandelic acid, ascorbic acid, lactic acid, gluconic acid, citric acid or 2-(4-hydroxybenzoyl)benzoic acid; and salts with amino acids, such as glutamic acid or aspartic acid.

The compounds of the present invention may contain several asymmetric carbon atoms in their molecules, and can thus form optical isomers. Although these are all represented herein by a single molecular formula, the present invention includes both the individual, isolated isomers and mixtures, including racemates thereof. Where stereospecific synthesis techniques are employed or optically active compounds are employed as starting materials, individual isomers may be prepared directly; on the other hand, if a mixture of isomers is prepared, the individual isomers may be obtained by conventional resolution techniques.

Of the compounds of the present invention, we prefer those wherein $R^1$ represents a cyclic amino group having from 3 to 7 ring atoms, of which 1 is a nitrogen atom and the remainder are carbon atoms, or said dialkylamino group, more preferably those wherein $R^1$ represents a cyclic amino group having 5 or 6 ring atoms, of which 1 is a nitrogen atom and the remainder are carbon atoms, or said dialkylamino group, especially those wherein $R^1$ represents a 1-pyrrolidinyl, piperidino, dimethylamino or diethylamino group.

Another preferred class of compounds of the present invention are those wherein $R^2$ represents a group of formula —NHCHR$^3$R$^4$ wherein $R^3$ and $R^4$ are independently selected from the group consisting of:

alkyl groups having from 1 to 4 carbon atoms, phenyl groups which are unsubstituted or have at least one substituent selected from the group consisting of substituents ζ, defined above, and benzyl and phenethyl groups; or $R^3$ and $R^4$ together with the carbon atom to which they are attached, represent a cycloalkyl group having from 3 to 6 ring carbon atoms, An alternative preferred class of compounds of the present invention are those wherein $R^2$ represents an aromatic heterocyclic group having 5 ring atoms, of which 1 is a hetero-atom selected from the group consisting of nitrogen, oxygen and sulfur hetero-atoms, there are 0, 1 or 2 additional nitrogen hetero-atoms, and the remaining ring atoms are carbon atoms, said group being unsubstituted or having at least one substituent selected, in the case of substituents on carbon atoms, from the group consisting of substituents α and, in the case of substituents on nitrogen atoms, from the group consisting of substituents β, as defined above, and particularly those wherein said aromatic heterocyclic group is selected from the group consisting of furyl, thienyl, pyrrolyl, oxazolyl, isoxazolyl, thiazolyl, isothiazolyl, pyrazolyl, imidazolyl, oxadiazolyl and thiadiazolyl groups, which are unsubstituted or are substituted as defined above.

A further alternative preferred class of compounds of the present invention are those wherein $R^2$ represents a group of formula —B—S(O)$_m$—R$^5$, wherein:

B represents an alkylene or alkylidene group having from 1 to 3 carbon atoms;

m is 0, 1 or 2; and $R^5$ represents: a substituted alkyl group which has from 2 to 4 carbon atoms and which is substituted at its 2-position by at least one substituent selected from the group consisting of substituents γ; or an aromatic heterocyclic group which has 5 or 6 ring atoms of which 1 is a hetero-atom selected from the group consisting of nitrogen, oxygen and sulfur hetero-atoms, there are 0, 1, 2 or 3 additional nitrogen hetero-atoms, and the remaining ring atoms are carbon atoms, said group being unsubstituted or having at least one substituent selected, in the case of substituents on carbon atoms, from the group consisting of substituents α and, in the case of substituents on nitrogen atoms, from the group consisting of substituents ε, as defined above.

We also especially prefer those compounds of the present invention wherein A represents a group of formula —CH═CH— or —(CH$_2$)$_n$—, where n is 1 or 2.

A more preferred class of compounds of the present invention are those wherein:

$R^1$ represents a 1-pyrrolidinyl, piperidino, dimethylamino or diethylamino group;

$R^2$ represents a group of formula —NHCHR$^3$R$^4$ wherein
$R^3$ and $R^4$ are independently selected from the group consisting of alkyl groups having from 1 to 4 carbon atoms, benzyl groups, phenethyl groups and phenyl groups which are unsubstituted or which are substituted by at least one substituent selected from the group consisting of methyl, methoxy, fluorine atoms and chlorine atoms, or $R^3$ and $R^4$ together with the carbon atom to which they are attached, represent a cycloalkyl group having from 3 to 6 ring carbon atoms, a furyl, thienyl, pyrrolyl, oxazolyl, isoxazolyl, thiazolyl, pyrazolyl, imidazolyl or thiadiazolyl group, which is unsubstituted or is substituted by at least one substituent selected, in the case of substituents on carbon atoms, from the group consisting of substituents α$^1$ and, in the case of substituents on nitrogen atoms, from the group consisting of methyl and ethyl groups, or a group of formula —B—S(O)$_m$—R$^5$, wherein
$R^5$ represents: a substituted ethyl or propyl group which is substituted at its 2-position by at least one substituent selected from the group consisting of substituents γ$^1$; or an imidazolyl, 1,2,4-triazolyl, 1,3,4-oxadiazolyl, 1,3,4-thiadiazolyl, tetrazolyl, pyridyl or pyrimidinyl group which is unsubstituted or has at least one substituent selected, in the case of substituents on carbon atoms, from the group consisting of substituents α$^1$ and, in the case of substituents on nitrogen atoms, from the group consisting of substituents ε$^1$, B represents an alkylene or alkylidene group having from 1 to 3 carbon atoms, and m is 0, 1 or 2;

A represents a group of formula —CH═CH— or —(CH$_2$)$_n$—, where n is 1 or 2;

said substituents α$^1$ are selected from the group consisting of: methyl groups, ethyl groups, methoxy groups, ethoxy groups, hydroxy groups, chlorine atoms, amino groups; methylamino groups, ethylamino groups, dimethylamino groups, diethylamino groups, alkanoylamino groups having from 1 to 3 carbon atoms, phenyl groups, and substituted phenyl groups in which the substituent is selected from the group consisting of methyl groups, methoxy groups, chlorine atoms and fluorine atoms;

said substituents γ$^1$ are selected from the group consisting of: hydroxy groups; alkanoyloxy groups having from 1 to 5 carbon atoms; substituted alkanoyloxy groups which have 3 or 4 carbon atoms and which are substituted by at least one substituent selected from the group consisting of carboxy, methoxycarbonyl and ethoxycarbonyl groups; phenylacetoxy groups; benzoyloxy groups; and cycloalkylcarbonyloxy groups in which the cycloalkyl part has from 3 to 6 ring carbon atoms;

said substituents ε$^1$ are selected from the group consisting of: methyl groups, ethyl groups, and hydroxyalkyl groups having from 2 to 4 carbon atoms.

Still more preferred compounds of the present invention are those compounds of formula (I) and salts thereof, wherein:

$R^1$ represents a 1-pyrrolidinyl or piperidino group;

$R^2$ represents a group of formula —NHCHR$^3$R$^4$ wherein
$R^3$ and $R^4$ are independently selected from the group consisting of methyl, ethyl, phenyl and benzyl groups, or $R^3$ and $R^4$, together with the carbon atom to which they are attached, represent a cycloalkyl group having from 3 to 5 ring carbon atoms, a furyl, thienyl, pyrrolyl, oxazolyl, isoxazolyl, thiazolyl, pyrazolyl or 1,2,3-thiadiazolyl group, which is unsubstituted or is substituted by at least one substituent selected, in the case of substituents on carbon atoms, from the group consisting of substituents α$^2$ and, in the case of substituents on nitrogen atoms, from the group consisting of methyl and ethyl groups, or a group of formula —B—S(O)$_m$—R$^5$, wherein
$R^5$ represents: a substituted ethyl or propyl group which is substituted at its 2-position by at least one substituent selected from the group consisting of substituents γ$^2$; or a 1,2,4-triazolyl, 1,3,4-oxadiazolyl or pyrimidinyl group which is unsubstituted or has at least one substituent selected, in the case of substituents on carbon atoms, from the group consisting of substituents α$^3$ and, in the case of substituents on nitrogen atoms, from the group consisting of methyl and ethyl groups, B represents an alkylene or alkylidene group having from 1 to 3 carbon atoms, and m is 0 or 1;

A represents a group of formula —CH═CH— or —(CH$_2$)$_2$—;

said substituents α$^2$ are selected from the group consisting of: methyl groups, ethyl groups, methoxy groups, ethoxy groups, hydroxy groups, chlorine atoms, amino groups, acetamido groups and phenyl groups;

said substituents α$^3$ are selected from the group consisting of: methyl groups, ethyl groups, methoxy groups, ethoxy groups, hydroxy groups, chlorine atoms, amino groups, and acetamido groups;

said substituents $\gamma^2$ are selected from the group consisting of: hydroxy groups; acetoxy groups; propionyloxy groups; substituted alkanoyloxy groups which have 3 or 4 carbon atoms and which are substituted by at least one substituent selected from the group consisting of carboxy, methoxycarbonyl and ethoxycarbonyl groups; phenylacetoxy groups; benzoyloxy groups; and cycloalkylcarbonyloxy groups in which the cycloalkyl part has from 3 to 6 ring carbon atoms.

Yet more preferred compounds of the present invention are those compounds of formula (I) and salts thereof, wherein:

$R^1$ represents a piperidino group;

$R^2$ represents a group of formula $-NHCHR^3R^4$ wherein
$R^3$ and $R^4$ are independently selected from the group consisting of methyl, ethyl, phenyl and benzyl groups, or
$R^3$ and $R^4$ together with the carbon atom to which they are attached, represent a cycloalkyl group having 3 or 4 ring carbon atoms, a thienyl, pyrrolyl, thiazolyl, pyrazolyl or 1,2,3-thiadiazolyl group, which is unsubstituted or is substituted by at least one substituent selected, in the case of substituents on carbon atoms, from the group consisting of substituents $\alpha^4$ and, in the case of substituents on nitrogen atoms, from methyl groups, or a group of formula $-B-S(O)_m-R^5$, wherein
B represents a methylene group and $R^5$ represents: a substituted ethyl or propyl group which is substituted at its 2-position by at least one substituent selected from the group consisting of substituents $\gamma^3$; or
B represents a trimethylene group and $R^5$ represents: a 1,2,4-triazolyl, 1,3,4-oxadiazolyl or pyrimidinyl group which is unsubstituted or has at least one substituent selected, in the case of substituents on carbon atoms, from the group consisting of methyl, hydroxy and amino groups, and, in the case of substituents on nitrogen atoms, from methyl groups, and m is 0;

A represents a group of formula $-CH=CH-$;

said substituents $\alpha^4$ are selected from the group consisting of: methyl groups, methoxy groups, hydroxy groups, chlorine atoms and amino groups; said substituents $\gamma^3$ are selected from the group consisting of: hydroxy groups; acetoxy groups; propionyloxy groups; substituted propionoyloxy groups which are substituted by at least one substituent selected from the group consisting of carboxy, methoxycarbonyl and ethoxycarbonyl groups; benzoyloxy groups; and cycloalkylcarbonyloxy groups in which the cycloalkyl part has 5 or 6 ring carbon atoms.

The most preferred compounds of the present invention are those compounds of formula (I) and salts thereof, wherein:

$R^1$ represents a piperidino group;

$R^2$ represents:

a pyrazolyl group, which is unsubstituted or is substituted on a carbon atom by at least one amino substituent, or a group of formula $-B-S(O)_m-R^5$, wherein
B represents a methylene group and $R^5$ represents: a substituted ethyl group which is substituted at its 2-position by at least one substituent selected from the group consisting of substituents hydroxy, acetoxy, propionyloxy, benzoyloxy, cyclopentylcarbonyloxy and cyclohexylcarbonyloxy groups; or B represents a trimethylene group and $R^5$ represents: a 2-pyrimidinyl group;

and m is 0;

A represents a group of formula $-CH=CH-$.

Examples of specific preferred compounds of the present invention are those compounds of formula (I-1), in which the substituents are as defined in Table 1, and those compounds of formula (I-1), in which the substituents are as defined in Tables 2 and 3.

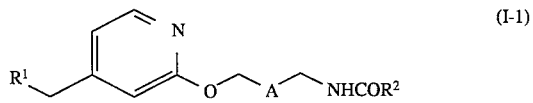

(I-1)

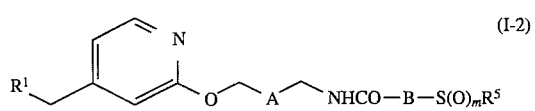

(I-2)

In the Tables, the following abbreviations are used:

| | |
|---|---|
| Ac | acetyl |
| Aze | azetidino |
| Azi | aziridino |
| Boz | benzoyl |
| Bu | butyl |
| cBu | cyclobutyl |
| iBu | isobutyl |
| sBu | sec-butyl |
| Byr | butyryl |
| iByr | isobutyryl |
| Bz | benzyl |
| Et | ethyl |
| Etc | ethoxycarbonyl |
| Fo | formyl |
| Fur | furyl |
| Hp | heptyl |
| cHp | cycloheptyl |
| Hx | hexyl |
| cHx | cyclohexyl |
| iHx | isohexyl |
| Imidazo | imidazolyl |
| Isoxazo | isoxazolyl |
| Isothiazo | isothiazolyl |
| Me | methyl |
| Mec | methoxycarbonyl |
| Naph | naphthyl |
| cOc | cyclooctyl |
| Oxazo | oxazolyl |
| Oxadiazo | oxadiazolyl |
| Ph | phenyl |
| Phc | phenoxycarbonyl |
| Pip | piperidino |
| Piv | pivaloyl |
| Pn | pentyl |
| cPn | cyclopentyl |
| iPn | isopentyl |
| nPn | neopentyl |
| Pr | propyl |
| cPr | cyclopropyl |
| iPr | isopropyl |
| Prc | propoxycarbonyl |
| Prn | propionyl |
| Pyl | pyrrolyl |
| Pymz | pyrimidinyl |
| Pyr | 1-pyrrolidinyl |
| Pyrazo | pyrazolyl |
| Pyz | pyridyl |
| Tetrazo | tetrazolyl |
| Thi | thienyl |
| Thiazo | thiazolyl |
| Thiadiazo | thiadiazolyl |
| Triazo | triazolyl |
| Val | valeryl |
| iVal | isovaleryl. |

TABLE 1

| Cpd. No. | R¹ | A | R² |
|---|---|---|---|
| 1-1 | Pip | CH=CH | 2-Fur |
| 1-2 | Pip | CH=CH | 3-Fur |
| 1-3 | Pip | CH=CH | 4-Me-2-Fur |
| 1-4 | Pip | CH=CH | 5-Me-2-Fur |
| 1-5 | Pip | CH=CH | 2-Me-3-Fur |
| 1-6 | Pip | CH=CH | 5-Me-3-Fur |
| 1-7 | Pip | CH=CH | 5-Cl-2-Fur |
| 1-8 | Pip | CH=CH | 5-Cl-3-Fur |
| 1-9 | Pip | CH=CH | 5-NH$_2$-2-Fur |
| 1-10 | Pip | CH=CH | 5-AcNH-2-Fur |
| 1-11 | Pip | CH=CH | 5-Ph-2-Fur |
| 1-12 | Pip | CH=CH | 5-(4-MePh)-2-Fur |
| 1-13 | Pip | CH=CH | 5-(4-ClPh)-2-Fur |
| 1-14 | Pip | CH=CH | 3-Me-5-NH$_2$-2-Fur |
| 1-15 | Pip | CH=CH | 2,4-diMe-3-Fur |
| 1-16 | Pip | CH=CH | 2-Thi |
| 1-17 | Pip | CH=CH | 3-Thi |
| 1-18 | Pip | CH=CH | 3-Me-2-Thi |
| 1-19 | Pip | CH=CH | 5-Me-2-Thi |
| 1-20 | Pip | CH=CH | 2-Me-3-Thi |
| 1-21 | Pip | CH=CH | 4-Me-3-Thi |
| 1-22 | Pip | CH=CH | 5-Me-3-Thi |
| 1-23 | Pip | CH=CH | 4-MeO-2-Thi |
| 1-24 | Pip | CH=CH | 4-MeO-3-Thi |
| 1-25 | Pip | CH=CH | 4-HO-2-Thi |
| 1-26 | Pip | CH=CH | 4-HO-3-Thi |
| 1-27 | Pip | CH=CH | 5-Et-2-Thi |
| 1-28 | Pip | CH=CH | 5-Cl-2-Thi |
| 1-29 | Pip | CH=CH | 5-Cl-3-Thi |
| 1-30 | Pip | CH=CH | 5-Br-3-Thi |
| 1-31 | Pip | CH=CH | 3-NH$_2$-2-Thi |
| 1-32 | Pip | CH=CH | 5-NH$_2$-2-Thi |
| 1-33 | Pip | CH=CH | 2-NH$_2$-3-Thi |
| 1-34 | Pip | CH=CH | 4-NH$_2$-3-Thi |
| 1-35 | Pip | CH=CH | 3-AcNH-2-Thi |
| 1-36 | Pip | CH=CH | 4-AcNH-3-Thi |
| 1-37 | Pip | CH=CH | 5-Ph-2-Thi |
| 1-38 | Pip | CH=CH | 4,5-diMe-2-Thi |
| 1-39 | Pip | CH=CH | 3,5-diMe-2-Thi |
| 1-40 | Pip | CH=CH | 2,5-diMe-3-Thi |
| 1-41 | Pip | CH=CH | 4,5-diMe-3-Thi |
| 1-42 | Pip | CH=CH | 4,5-diCl-2-Thi |
| 1-43 | Pip | CH=CH | 2-NH$_2$-5-Ph-3-Thi |
| 1-44 | Pip | CH=CH | 4-NH$_2$-2,5-diMe-3-Thi |
| 1-45 | Pip | CH=CH | 2-Pyl |
| 1-46 | Pip | CH=CH | 3-Pyl |
| 1-47 | Pip | CH=CH | 1-Me-2-Pyl |
| 1-48 | Pip | CH=CH | 3-Me-2-Pyl |
| 1-49 | Pip | CH=CH | 4-Me-2-Pyl |
| 1-50 | Pip | CH=CH | 2-Me-3-Pyl |
| 1-51 | Pip | CH=CH | 5-Me-3-Pyl |
| 1-52 | Pip | CH=CH | 3-NH$_2$-2-Pyl |
| 1-53 | Pip | CH=CH | 4-NH$_2$-2-Pyl |
| 1-54 | Pip | CH=CH | 3-AcNH-2-Pyl |
| 1-55 | Pip | CH=CH | 5-Cl-2-Pyl |
| 1-56 | Pip | CH=CH | 5-Cl-3-Pyl |
| 1-57 | Pip | CH=CH | 4-Ph-2-Pyl |
| 1-58 | Pip | CH=CH | 5-Ph-3-Pyl |
| 1-59 | Pip | CH=CH | 1-Me-4-MeO-3-Pyl |
| 1-60 | Pip | CH=CH | 1-Me-4-HO-3-Pyl |
| 1-61 | Pip | CH=CH | 3,5-diMe-2-Pyl |
| 1-62 | Pip | CH=CH | 4,5-diMe-2-Pyl |
| 1-63 | Pip | CH=CH | 1,3-diMe-2-Pyl |
| 1-64 | Pip | CH=CH | 5-NH$_2$-1-Me-2-Pyl |
| 1-65 | Pip | CH=CH | 4-NH$_2$-3,5-diMe-2-Pyl |
| 1-66 | Pip | CH=CH | 5-Br-1,4-diMe-3-Pyl |
| 1-67 | Pip | CH=CH | 4-Oxazo |
| 1-68 | Pip | CH=CH | 5-Oxazo |
| 1-69 | Pip | CH=CH | 2-Oxazo |
| 1-70 | Pip | CH=CH | 2-Me-4-Oxazo |
| 1-71 | Pip | CH=CH | 2-Ph-4-Oxazo |
| 1-72 | Pip | CH=CH | 5-Ph-2-Oxazo |
| 1-73 | Pip | CH=CH | 2-HO-4-Oxazo |
| 1-74 | Pip | CH=CH | 2,5-diMe-4-Oxazo |
| 1-75 | Pip | CH=CH | 4-Me-2-Ph-5-Oxazo |
| 1-76 | Pip | CH=CH | 3-Isoxazo |
| 1-77 | Pip | CH=CH | 4-Isoxazo |
| 1-78 | Pip | CH=CH | 4-Me-3-Isoxazo |
| 1-79 | Pip | CH=CH | 5-Me-3-Isoxazo |
| 1-80 | Pip | CH=CH | 3-Me-4-Isoxazo |
| 1-81 | Pip | CH=CH | 4-MeO-3-Isoxazo |
| 1-82 | Pip | CH=CH | 4-HO-3-Isoxazo |
| 1-83 | Pip | CH=CH | 3-HO-4-Isoxazo |
| 1-84 | Pip | CH=CH | 3-HO-5-Isoxazo |
| 1-85 | Pip | CH=CH | 4-NH$_2$-3-Isoxazo |
| 1-86 | Pip | CH=CH | 5-NH$_2$-4-Isoxazo |
| 1-87 | Pip | CH=CH | 5-Ph-3-Isoxazo |
| 1-88 | Pip | CH=CH | 4-Ph-3-Isoxazo |
| 1-89 | Pip | CH=CH | 4,5-diMe-3-Isoxazo |
| 1-90 | Pip | CH=CH | 4-HO-5-Me-3-Isoxazo |
| 1-91 | Pip | CH=CH | 2-Thiazo |
| 1-92 | Pip | CH=CH | 4-Thiazo |
| 1-93 | Pip | CH=CH | 5-Thiazo |
| 1-94 | Pip | CH=CH | 4-Me-2-Thiazo |
| 1-95 | Pip | CH=CH | 2-Me-4-Thiazo |
| 1-96 | Pip | CH=CH | 2-Me-5-Thiazo |
| 1-97 | Pip | CH=CH | 2-MeO-4-Thiazo |
| 1-98 | Pip | CH=CH | 2-MeO-5-Thiazo |
| 1-99 | Pip | CH=CH | 2-HO-4-Thiazo |
| 1-100 | Pip | CH=CH | 2-HO-5-Thiazo |
| 1-101 | Pip | CH=CH | 2-Cl-5-Thiazo |
| 1-102 | Pip | CH=CH | 5-Cl-2-Thiazo |
| 1-103 | Pip | CH=CH | 2-NH$_2$-4-Thiazo |
| 1-104 | Pip | CH=CH | 2-NH$_2$-5-Thiazo |
| 1-105 | Pip | CH=CH | 5-NH$_2$-4-Thiazo |
| 1-106 | Pip | CH=CH | 2-AcNH-4-Thiazo |
| 1-107 | Pip | CH=CH | 5-AcNH-4-Thiazo |
| 1-108 | Pip | CH=CH | 2-Ph-4-Thiazo |
| 1-109 | Pip | CH=CH | 4,5-diMe-2-Thiazo |
| 1-110 | Pip | CH=CH | 2-HO-5-Me-4-Thiazo |
| 1-111 | Pip | CH=CH | 5-NH$_2$-2-Me-4-Thiazo |
| 1-112 | Pip | CH=CH | 2-Cl-4-Me-5-Thiazo |
| 1-113 | Pip | CH=CH | 3-Isothiazo |
| 1-114 | Pip | CH=CH | 4-Isothiazo |
| 1-115 | Pip | CH=CH | 3-Pyrazo |
| 1-116 | Pip | CH=CH | 4-Pyrazo |
| 1-117 | Pip | CH=CH | 1-Me-3-Pyrazo |
| 1-118 | Pip | CH=CH | 1-Et-3-Pyrazo |
| 1-119 | Pip | CH=CH | 1-Pr-3-Pyrazo |
| 1-120 | Pip | CH=CH | 1-Me-4-Pyrazo |
| 1-121 | Pip | CH=CH | 1-Et-4-Pyrazo |
| 1-122 | Pip | CH=CH | 1-Pr-4-Pyrazo |
| 1-123 | Pip | CH=CH | 1-Bu-4-Pyrazo |
| 1-124 | Pip | CH=CH | 4-Me-3-Pyrazo |
| 1-125 | Pip | CH=CH | 5-Me-3-Pyrazo |
| 1-126 | Pip | CH=CH | 5-Et-3-Pyrazo |
| 1-127 | Pip | CH=CH | 5-Pr-3-Pyrazo |
| 1-128 | Pip | CH=CH | 5-Me-4-Pyrazo |
| 1-129 | Pip | CH=CH | 4-MeO-3-Pyrazo |
| 1-130 | Pip | CH=CH | 4-PrO-3-Pyrazo |
| 1-131 | Pip | CH=CH | 4-HO-3-Pyrazo |
| 1-132 | Pip | CH=CH | 4-Cl-3-Pyrazo |
| 1-133 | Pip | CH=CH | 4-Br-3-Pyrazo |
| 1-134 | Pip | CH=CH | 3-Cl-4-Pyrazo |
| 1-135 | Pip | CH=CH | 4-NH$_2$-3-Pyrazo |
| 1-136 | Pip | CH=CH | 5-NH$_2$-3-Pyrazo |
| 1-137 | Pip | CH=CH | 3-NH$_2$-4-Pyrazo |
| 1-138 | Pip | CH=CH | 4-AcNH-3-Pyrazo |
| 1-139 | Pip | CH=CH | 5-AcNH-3-Pyrazo |
| 1-140 | Pip | CH=CH | 3-AcNH-4-Pyrazo |
| 1-141 | Pip | CH=CH | 3-EtCONH-4-Pyrazo |
| 1-142 | Pip | CH=CH | 5-Ph-3-Pyrazo |
| 1-143 | Pip | CH=CH | 1,5-diMe-3-Pyrazo |
| 1-144 | Pip | CH=CH | 1,4-diMe-3-Pyrazo |
| 1-145 | Pip | CH=CH | 4,5-diMe-3-Pyrazo |
| 1-146 | Pip | CH=CH | 3-Me-4-Pyrazo |
| 1-147 | Pip | CH=CH | 3,5-diMe-4-Pyrazo |
| 1-148 | Pip | CH=CH | 1,5-diMe-4-Pyrazo |
| 1-149 | Pip | CH=CH | 1,3-diMe-4-Pyrazo |
| 1-150 | Pip | CH=CH | 1,3-diMe-5-Pyrazo |
| 1-151 | Pip | CH=CH | 3-Cl-5-Me-4-Pyrazo |
| 1-152 | Pip | CH=CH | 3-Cl-1-Me-4-Pyrazo |

TABLE 1-continued

| Cpd. No. | R¹ | A | R² |
|---|---|---|---|
| 1-153 | Pip | CH=CH | 5-Cl-1-Me-4-Pyrazo |
| 1-154 | Pip | CH=CH | 4-Cl-1-Me-3-Pyrazo |
| 1-155 | Pip | CH=CH | 4-Cl-5-Me-3-Pyrazo |
| 1-156 | Pip | CH=CH | 4-Cl-1-Me-3-Pyrazo |
| 1-157 | Pip | CH=CH | 3-NH₂-5-Me-4-Pyrazo |
| 1-158 | Pip | CH=CH | 3-NH₂-1-Me-4-Pyrazo |
| 1-159 | Pip | CH=CH | 5-NH₂-1-Me-4-Pyrazo |
| 1-160 | Pip | CH=CH | 5-NH₂-4-Me-3-Pyrazo |
| 1-161 | Pip | CH=CH | 5-NH₂-1-Me-3-Pyrazo |
| 1-162 | Pip | CH=CH | 5-AcNH-1-Me-4-Pyrazo |
| 1-163 | Pip | CH=CH | 4-NH₂-5-Me-3-Pyrazo |
| 1-164 | Pip | CH=CH | 4-HO-5-Me-3-Pyrazo |
| 1-165 | Pip | CH=CH | 5-AcNH-3-Me-4-Pyrazo |
| 1-166 | Pip | CH=CH | 1,3,5-triMe-4-Pyrazo |
| 1-167 | Pip | CH=CH | 1,3,4-triMe-5-Pyrazo |
| 1-168 | Pip | CH=CH | 4-Cl-1,3-diMe-5-Pyrazo |
| 1-169 | Pip | CH=CH | 2-Imidazo |
| 1-170 | Pip | CH=CH | 4-Imidazo |
| 1-171 | Pip | CH=CH | 2-Me-4-Imidazo |
| 1-172 | Pip | CH=CH | 1-Me-4-Imidazo |
| 1-173 | Pip | CH=CH | 5-Me-4-Imidazo |
| 1-174 | Pip | CH=CH | 5-Me-2-Imidazo |
| 1-175 | Pip | CH=CH | 1-Me-2-Imidazo |
| 1-176 | Pip | CH=CH | 1,2,3-Oxadiazo-5-yl |
| 1-177 | Pip | CH=CH | 1,3,4-Oxadiazo-2-yl |
| 1-178 | Pip | CH=CH | 1,2,3-Oxadiazo-4-yl |
| 1-179 | Pip | CH=CH | 1,2,4-Oxadiazo-5-yl |
| 1-180 | Pip | CH=CH | 1,2,4-Oxadiazo-3-yl |
| 1-181 | Pip | CH=CH | 1,2,5-Oxadiazo-3-yl |
| 1-182 | Pip | CH=CH | 5-Me-1,2,3-Oxadiazo-4-yl |
| 1-183 | Pip | CH=CH | 4-Me-1,2,5-Oxadiazo-3-yl |
| 1-184 | Pip | CH=CH | 4-Ph-1,2,5-Oxadiazo-3-yl |
| 1-185 | Pip | CH=CH | 1,2,3-Thiadiazo-4-yl |
| 1-186 | Pip | CH=CH | 1,2,3-Thiadiazo-5-yl |
| 1-187 | Pip | CH=CH | 1,3,4-Thiadiazo-2-yl |
| 1-188 | Pip | CH=CH | 1,2,4-Thiadiazo-3-yl |
| 1-189 | Pip | CH=CH | 1,2,4-Thiadiazo-5-yl |
| 1-190 | Pip | CH=CH | 1,2,5-Thiadiazo-3-yl |
| 1-191 | Pip | CH=CH | 4-Me-1,2,3-Thiadiazo-5-yl |
| 1-192 | Pip | CH=CH | 5-Me-1,2,3-Thiadiazo-4-yl |
| 1-193 | Pip | CH=CH | 4-Me-1,2,5-Thiadiazo-3-yl |
| 1-194 | Pip | CH=CH | 5-Ph-1,2,3-Thiadiazo-4-yl |
| 1-195 | Pyr | CH=CH | 2-Fur |
| 1-196 | Pyr | CH=CH | 3-Fur |
| 1-197 | Pyr | CH=CH | 4-Me-2-Fur |
| 1-198 | Pyr | CH=CH | 2-Me-3-Fur |
| 1-199 | Pyr | CH=CH | 2,4-diMe-3-Fur |
| 1-200 | Pyr | CH=CH | 2-Thi |
| 1-201 | Pyr | CH=CH | 3-Thi |
| 1-202 | Pyr | CH=CH | 3-Me-2-Thi |
| 1-203 | Pyr | CH=CH | 2-Me-3-Thi |
| 1-204 | Pyr | CH=CH | 4-Me-3-Thi |
| 1-205 | Pyr | CH=CH | 4-MeO-3-Thi |
| 1-206 | Pyr | CH=CH | 4-HO-2-Thi |
| 1-207 | Pyr | CH=CH | 5-Cl-3-Thi |
| 1-208 | Pyr | CH=CH | 3-NH₂-2-Thi |
| 1-209 | Pyr | CH=CH | 2-NH₂-3-Thi |
| 1-210 | Pyr | CH=CH | 3-AcNH-2-Thi |
| 1-211 | Pyr | CH=CH | 5-Ph-2-Thi |
| 1-212 | Pyr | CH=CH | 4,5-diMe-2-Thi |
| 1-213 | Pyr | CH=CH | 2,5-diMe-3-Thi |
| 1-214 | Pyr | CH=CH | 4,5-diCl-2-Thi |
| 1-215 | Pyr | CH=CH | 4-NH₂-2,5-diMe-3-Thi |
| 1-216 | Pyr | CH=CH | 2-Pyl |
| 1-217 | Pyr | CH=CH | 3-Pyl |
| 1-218 | Pyr | CH=CH | 1-Me-2-Pyl |
| 1-219 | Pyr | CH=CH | 3-Me-2-Pyl |
| 1-220 | Pyr | CH=CH | 4-Me-2-Pyl |
| 1-221 | Pyr | CH=CH | 2-Me-3-Pyl |
| 1-222 | Pyr | CH=CH | 1-Me-4-MeO-3-Pyl |
| 1-223 | Pyr | CH=CH | 3,5-diMe-2-Pyl |
| 1-224 | Pyr | CH=CH | 1,3-diMe-2-Pyl |
| 1-225 | Pyr | CH=CH | 4-Oxazo |
| 1-226 | Pyr | CH=CH | 5-Oxazo |
| 1-227 | Pyr | CH=CH | 2-Oxazo |
| 1-228 | Pyr | CH=CH | 2-Me-4-Oxazo |
| 1-229 | Pyr | CH=CH | 5-Ph-2-Oxazo |
| 1-230 | Pyr | CH=CH | 2,5-diMe-4-Oxazo |
| 1-231 | Pyr | CH=CH | 3-Isoxazo |
| 1-232 | Pyr | CH=CH | 4-Isoxazo |
| 1-233 | Pyr | CH=CH | 5-Me-3-Isoxazo |
| 1-234 | Pyr | CH=CH | 3-Me-4-Isoxazo |
| 1-235 | Pyr | CH=CH | 4-MeO-3-Isoxazo |
| 1-236 | Pyr | CH=CH | 4-HO-3-Isoxazo |
| 1-237 | Pyr | CH=CH | 3-HO-5-Isoxazo |
| 1-238 | Pyr | CH=CH | 5-HO-4-Isoxazo |
| 1-239 | Pyr | CH=CH | 4-NH₂-3-Isoxazo |
| 1-240 | Pyr | CH=CH | 5-Ph-3-Isoxazo |
| 1-241 | Pyr | CH=CH | 4,5-diMe-3-Isoxazo |
| 1-242 | Pyr | CH=CH | 4-HO-5-Me-3-Isoxazo |
| 1-243 | Pyr | CH=CH | 2-Thiazo |
| 1-244 | Pyr | CH=CH | 4-Thiazo |
| 1-245 | Pyr | CH=CH | 5-Thiazo |
| 1-246 | Pyr | CH=CH | 4-Me-2-Thiazo |
| 1-247 | Pyr | CH=CH | 2-Me-5-Thiazo |
| 1-248 | Pyr | CH=CH | 2-MeO-4-Thiazo |
| 1-249 | Pyr | CH=CH | 2-MeO-5-Thiazo |
| 1-250 | Pyr | CH=CH | 2-HO-5-Thiazo |
| 1-251 | Pyr | CH=CH | 5-Cl-2-Thiazo |
| 1-252 | Pyr | CH=CH | 2-NH₂-4-Thiazo |
| 1-253 | Pyr | CH=CH | 2-AcNH-4-Thiazo |
| 1-254 | Pyr | CH=CH | 4,5-diMe-2-Thiazo |
| 1-255 | Pyr | CH=CH | 2-HO-5-Me-4-Thiazo |
| 1-256 | Pyr | CH=CH | 5-NH₂-2-Me-4-Thiazo |
| 1-257 | Pyr | CH=CH | 3-Isothiazo |
| 1-258 | Pyr | CH=CH | 4-Isothiazo |
| 1-259 | Pyr | CH=CH | 3-Pyrazo |
| 1-260 | Pyr | CH=CH | 4-Pyrazo |
| 1-261 | Pyr | CH=CH | 1-Me-3-Pyrazo |
| 1-262 | Pyr | CH=CH | 1-Et-3-Pyrazo |
| 1-263 | Pyr | CH=CH | 1-Me-4-Pyrazo |
| 1-264 | Pyr | CH=CH | 1-Et-4-Pyrazo |
| 1-265 | Pyr | CH=CH | 4-Me-3-Pyrazo |
| 1-266 | Pyr | CH=CH | 5-Me-3-Pyrazo |
| 1-267 | Pyr | CH=CH | 5-Me-4-Pyrazo |
| 1-268 | Pyr | CH=CH | 4-MeO-3-Pyrazo |
| 1-269 | Pyr | CH=CH | 4-HO-3-Pyrazo |
| 1-270 | Pyr | CH=CH | 4-Cl-3-Pyrazo |
| 1-271 | Pyr | CH=CH | 4-NH₂-3-Pyrazo |
| 1-272 | Pyr | CH=CH | 5-NH₂-3-Pyrazo |
| 1-273 | Pyr | CH=CH | 3-NH₂-4-Pyrazo |
| 1-274 | Pyr | CH=CH | 4-AcNH-3-Pyrazo |
| 1-275 | Pyr | CH=CH | 5-Ph-3-Pyrazo |
| 1-276 | Pyr | CH=CH | 1,5-diMe-3-Pyrazo |
| 1-277 | Pyr | CH=CH | 1,4-diMe-3-Pyrazo |
| 1-278 | Pyr | CH=CH | 3,5-diMe-4-Pyrazo |
| 1-279 | Pyr | CH=CH | 1,5-diMe-4-Pyrazo |
| 1-280 | Pyr | CH=CH | 1,3-diMe-4-Pyrazo |
| 1-281 | Pyr | CH=CH | 1,3-diMe-5-Pyrazo |
| 1-282 | Pyr | CH=CH | 3-Cl-5-Me-4-Pyrazo |
| 1-283 | Pyr | CH=CH | 3-Cl-1-Me-4-Pyrazo |
| 1-284 | Pyr | CH=CH | 4-Cl-5-Me-3-Pyrazo |
| 1-285 | Pyr | CH=CH | 4-Cl-1-Me-3-Pyrazo |
| 1-286 | Pyr | CH=CH | 3-NH₂-5-Me-4-Pyrazo |
| 1-287 | Pyr | CH=CH | 3-NH₂-1-Me-4-Pyrazo |
| 1-288 | Pyr | CH=CH | 5-NH₂-1-Me-4-Pyrazo |
| 1-289 | Pyr | CH=CH | 5-NH₂-4-Me-3-Pyrazo |
| 1-290 | Pyr | CH=CH | 5-NH₂-1-Me-3-Pyrazo |
| 1-291 | Pyr | CH=CH | 5-NH₂-3-Me-3-Pyrazo |
| 1-292 | Pyr | CH=CH | 4-NH₂-5-Me-3-Pyrazo |
| 1-293 | Pyr | CH=CH | 4-HO-5-Me-3-Pyrazo |
| 1-294 | Pyr | CH=CH | 1,3,5-triMe-4-Pyrazo |
| 1-295 | Pyr | CH=CH | 1,3,4-triMe-5-Pyrazo |
| 1-296 | Pyr | CH=CH | 4-Cl-1,3-diMe-5-Pyrazo |
| 1-297 | Pyr | CH=CH | 2-Imidazo |
| 1-298 | Pyr | CH=CH | 4-Imidazo |
| 1-299 | Pyr | CH=CH | 1-Me-4-Imidazo |
| 1-300 | Pyr | CH=CH | 5-Me-4-Imidazo |
| 1-301 | Pyr | CH=CH | 5-Me-2-Imidazo |
| 1-302 | Pyr | CH=CH | 1-Me-2-Imidazo |
| 1-303 | Pyr | CH=CH | 1,2,3-Oxadiazo-5-yl |
| 1-304 | Pyr | CH=CH | 1,2,4-Oxadiazo-5-yl |

TABLE 1-continued

| Cpd. No. | R¹ | A | R² |
|---|---|---|---|
| 1-305 | Pyr | CH=CH | 1,2,5-Oxadiazo-3-yl |
| 1-306 | Pyr | CH=CH | 5-Me-1,2,3-Oxadiazo-4-yl |
| 1-307 | Pyr | CH=CH | 1,2,3-Thiadiazo-4-yl |
| 1-308 | Pyr | CH=CH | 1,2,4-Thiadiazo-2-yl |
| 1-309 | Pyr | CH=CH | 1,2,5-Thiadiazo-3-yl |
| 1-310 | Pyr | CH=CH | 4-Me-1,2,3-Thiadiazo-5-yl |
| 1-311 | Pyr | CH=CH | 5-Ph-1,2,3-Thiadiazo-4-yl |
| 1-312 | NMe₂ | CH=CH | 2-Fur |
| 1-313 | NMe₂ | CH=CH | 3-Fur |
| 1-314 | NMe₂ | CH=CH | 4-Me-2-Fur |
| 1-315 | NMe₂ | CH=CH | 2,4-diMe-3-Fur |
| 1-316 | NMe₂ | CH=CH | 2-Thi |
| 1-317 | NMe₂ | CH=CH | 3-Thi |
| 1-318 | NMe₂ | CH=CH | 3-Me-2-Thi |
| 1-319 | NMe₂ | CH=CH | 2-Me-3-Thi |
| 1-320 | NMe₂ | CH=CH | 4,5-diMe-2-Thi |
| 1-321 | NMe₂ | CH=CH | 2-Pyl |
| 1-322 | NMe₂ | CH=CH | 3-Pyl |
| 1-323 | NMe₂ | CH=CH | 1-Me-2-Pyl |
| 1-324 | NMe₂ | CH=CH | 4-Me-2-Pyl |
| 1-325 | NMe₂ | CH=CH | 2-Me-3-Pyl |
| 1-326 | NMe₂ | CH=CH | 3,5-diMe-2-Pyl |
| 1-327 | NMe₂ | CH=CH | 1,3-diMe-2-Pyl |
| 1-328 | NMe₂ | CH=CH | 4-Oxazo |
| 1-329 | NMe₂ | CH=CH | 5-Oxazo |
| 1-330 | NMe₂ | CH=CH | 2-Oxazo |
| 1-331 | NMe₂ | CH=CH | 2-Me-4-Oxazo |
| 1-332 | NMe₂ | CH=CH | 2,5-diMe-4-Oxazo |
| 1-333 | NMe₂ | CH=CH | 3-Isoxazo |
| 1-334 | NMe₂ | CH=CH | 4-Isoxazo |
| 1-335 | NMe₂ | CH=CH | 5-Me-3-Isoxazo |
| 1-336 | NMe₂ | CH=CH | 4-MeO-3-Isoxazo |
| 1-337 | NMe₂ | CH=CH | 4-HO-3-Isoxazo |
| 1-338 | NMe₂ | CH=CH | 4,5-diMe-3-Isoxazo |
| 1-339 | NMe₂ | CH=CH | 4-HO-5-Me-3-Isoxzo |
| 1-340 | NMe₂ | CH=CH | 2-Thiazo |
| 1-341 | NMe₂ | CH=CH | 4-Thiazo |
| 1-342 | NMe₂ | CH=CH | 5-Thiazo |
| 1-343 | NMe₂ | CH=CH | 4-Me-2-Thiazo |
| 1-344 | NMe₂ | CH=CH | 2-Me-5-Thiazo |
| 1-345 | NMe₂ | CH=CH | 2-MeO-4-Thiazo |
| 1-346 | NMe₂ | CH=CH | 4,5-diMe-2-Thiazo |
| 1-347 | NMe₂ | CH=CH | 3-Isothiazo |
| 1-348 | NMe₂ | CH=CH | 4-Isothiazo |
| 1-349 | NMe₂ | CH=CH | 3-Pyrazo |
| 1-350 | NMe₂ | CH=CH | 4-Pyrazo |
| 1-351 | NMe₂ | CH=CH | 1-Me-3-Pyrazo |
| 1-352 | NMe₂ | CH=CH | 1-Me-4-Pyrazo |
| 1-353 | NMe₂ | CH=CH | 4-Me-3-Pyrazo |
| 1-354 | NMe₂ | CH=CH | 5-Me-3-Pyrazo |
| 1-355 | NMe₂ | CH=CH | 5-Me-4-Pyrazo |
| 1-356 | NMe₂ | CH=CH | 4-MeO-3-Pyrazo |
| 1-357 | NMe₂ | CH=CH | 4-HO-3-Pyrazo |
| 1-358 | NMe₂ | CH=CH | 3,5-diMe-4-Pyrazo |
| 1-359 | NMe₂ | CH=CH | 1,3,5-triMe-4-Pyrazo |
| 1-360 | NMe₂ | CH=CH | 1,3,4-triMe-5-Pyrazo |
| 1-361 | NMe₂ | CH=CH | 2-Imidazo |
| 1-362 | NMe₂ | CH=CH | 4-Imidazo |
| 1-363 | NMe₂ | CH=CH | 5-Me-4-Imidazo |
| 1-364 | Azi | CH=CH | 2-Fur |
| 1-365 | Azi | CH=CH | 3-Fur |
| 1-366 | Azi | CH=CH | 4-Me-2-Fur |
| 1-367 | Azi | CH=CH | 2-Thi |
| 1-368 | Azi | CH=CH | 3-Thi |
| 1-369 | Azi | CH=CH | 5-Me-2-Thi |
| 1-370 | Azi | CH=CH | 2-Pyl |
| 1-371 | Azi | CH=CH | 3-Pyl |
| 1-372 | Azi | CH=CH | 1-Me-2-Pyl |
| 1-373 | Azi | CH=CH | 4-Me-2-Pyl |
| 1-374 | Azi | CH=CH | 4-Oxazo |
| 1-375 | Azi | CH=CH | 5-Oxazo |
| 1-376 | Azi | CH=CH | 2-Oxazo |
| 1-377 | Azi | CH=CH | 3-Isoxazo |
| 1-378 | Azi | CH=CH | 4-Isoxazo |
| 1-379 | Azi | CH=CH | 4-HO-3-Isoxazo |
| 1-380 | Azi | CH=CH | 2-Thiazo |
| 1-381 | Azi | CH=CH | 4-Thiazo |
| 1-382 | Azi | CH=CH | 5-Thiazo |
| 1-383 | Azi | CH=CH | 2-Me-5-Thiazo |
| 1-384 | Azi | CH=CH | 3-Pyrazo |
| 1-385 | Azi | CH=CH | 4-Pyrazo |
| 1-386 | Azi | CH=CH | 1-Me-3-Pyrazo |
| 1-387 | Azi | CH=CH | 4-Me-3-Pyrazo |
| 1-388 | Azi | CH=CH | 5-Me-4-Pyrazo |
| 1-389 | Azi | CH=CH | 4-NH₂-3-Pyrazo |
| 1-390 | Azi | CH=CH | 3-NH₂-4-Pyrazo |
| 1-391 | Azi | CH=CH | 3,5-diMe-4-Pyrazo |
| 1-392 | Azi | CH=CH | 1,3,5-triMe-4-Pyrazo |
| 1-393 | Azi | CH=CH | 2-Imidazo |
| 1-394 | Azi | CH=CH | 4-Imidazo |
| 1-395 | Azi | CH=CH | 5-Me-4-Imidazo |
| 1-396 | Aze | CH=CH | 2-Fur |
| 1-397 | Aze | CH=CH | 3-Fur |
| 1-398 | Aze | CH=CH | 4-Me-2-Fur |
| 1-399 | Aze | CH=CH | 2-Thi |
| 1-400 | Aze | CH=CH | 3-Thi |
| 1-401 | Aze | CH=CH | 5-Me-2-Thi |
| 1-402 | Aze | CH=CH | 2-Pyl |
| 1-403 | Aze | CH=CH | 3-Pyl |
| 1-404 | Aze | CH=CH | 1-Me-2-Pyl |
| 1-405 | Aze | CH=CH | 4-Me-2-Pyl |
| 1-406 | Aze | CH=CH | 4-Oxazo |
| 1-407 | Aze | CH=CH | 5-Oxazo |
| 1-408 | Aze | CH=CH | 2-Oxazo |
| 1-409 | Aze | CH=CH | 3-Isoxazo |
| 1-410 | Aze | CH=CH | 4-Isoxazo |
| 1-411 | Aze | CH=CH | 4-HO-3-Isoxazo |
| 1-412 | Aze | CH=CH | 2-Thiazo |
| 1-413 | Aze | CH=CH | 4-Thiazo |
| 1-414 | Aze | CH=CH | 5-Thiazo |
| 1-415 | Aze | CH=CH | 2-Me-5-Thiazo |
| 1-416 | Aze | CH=CH | 3-Pyrazo |
| 1-417 | Aze | CH=CH | 4-Pyrazo |
| 1-418 | Aze | CH=CH | 1-Me-3-Pyrazo |
| 1-419 | Aze | CH=CH | 4-Me-3-Pyrazo |
| 1-420 | Aze | CH=CH | 5-Me-4-Pyrazo |
| 1-421 | Aze | CH=CH | 4-NH2 -3-Pyrazo |
| 1-422 | Aze | CH=CH | 3-NH2 -4-Pyrazo |
| 1-423 | Aze | CH=CH | 3,5-diMe-4-Pyrazo |
| 1-424 | Aze | CH=CH | 1,3,5-triMe-4-Pyrazo |
| 1-425 | Aze | CH=CH | 2-Imidazo |
| 1-426 | Aze | CH=CH | 4-Imidazo |
| 1-427 | Aze | CH=CH | 5-Me-4-Imidazo |
| 1-428 | Pip | CH=CH | 1,2,3-Triazo-4-yl |
| 1-429 | Pip | CH=CH | 1-Me-1,2,3-Triazo-4-yl |
| 1-430 | Pip | CH=CH | 5-Me-1,2,3-Triazo-4-yl |
| 1-431 | Pip | CH=CH | 1,5-diMe-1,2,3-Triazo-4-yl |
| 1-432 | Pip | CH=CH | 1,2,4-Triazo-5-yl |
| 1-433 | Pip | CH=CH | 1-Me-1,2,5-Triazo-3-yl |
| 1-434 | Pyr | CH=CH | 1,2,3-Triazo-4-yl |
| 1-435 | Pyr | CH=CH | 1,2,4-Triazo-5-yl |
| 1-436 | NMe₂ | CH=CH | 1,2,3-Triazo-4-yl |
| 1-437 | NMe₂ | CH=CH | 1,2,4-Triazo-5-yl |
| 1-438 | Pip | (CH₂)₃ | 2-Fur |
| 1-439 | Pip | (CH₂)₃ | 3-Fur |
| 1-440 | Pip | (CH₂)₃ | 4-Me-2-Fur |
| 1-441 | Pip | (CH₂)₃ | 2-Thi |
| 1-442 | Pip | (CH₂)₃ | 3-Thi |
| 1-443 | Pip | (CH₂)₃ | 5-Me-2-Thi |
| 1-444 | Pip | (CH₂)₃ | 2-Pyl |
| 1-445 | Pip | (CH₂)₃ | 3-Pyl |
| 1-446 | Pip | (CH₂)₃ | 1-Me-2-Pyl |
| 1-447 | Pip | (CH₂)₃ | 4-Me-2-Pyl |
| 1-448 | Pip | (CH₂)₃ | 3,5-diMe-2-Pyl |
| 1-449 | Pip | (CH₂)₃ | 4-Oxazo |
| 1-450 | Pip | (CH₂)₃ | 5-Oxazo |
| 1-451 | Pip | (CH₂)₃ | 2-Oxazo |
| 1-452 | Pip | (CH₂)₃ | 2-Me-4-Oxazo |
| 1-453 | Pip | (CH₂)₃ | 3-Isoxazo |
| 1-454 | Pip | (CH₂)₃ | 4-Isoxazo |
| 1-455 | Pip | (CH₂)₃ | 5-Me-3-Isoxazo |
| 1-456 | Pip | (CH₂)₃ | 4-HO-3-Isoxazo |

TABLE 1-continued

| Cpd. No. | R¹ | A | R² |
|---|---|---|---|
| 1-457 | Pip | (CH₂)₃ | 2-Thiazo |
| 1-458 | Pip | (CH₂)₃ | 4-Thiazo |
| 1-459 | Pip | (CH₂)₃ | 5-Thiazo |
| 1-460 | Pip | (CH₂)₃ | 2-Me-5-Thiazo |
| 1-461 | Pip | (CH₂)₃ | 3-Pyrazo |
| 1-462 | Pip | (CH₂)₃ | 4-Pyrazo |
| 1-463 | Pip | (CH₂)₃ | 1-M.e-3-Pyrazo |
| 1-464 | Pip | (CH₂)₃ | 1-Me-4-Pyrazo |
| 1-465 | Pip | (CH₂)₃ | 4-Me-3-Pyrazo |
| 1-466 | Pip | (CH₂)₃ | 5-Me-3-Pyrazo |
| 1-467 | Pip | (CH₂)₃ | 5-Me-4-Pyrazo |
| 1-468 | Pip | (CH₂)₃ | 4-NH₂-3-Pyrazo |
| 1-469 | Pip | (CH₂)₃ | 5-NH₂-3-Pyrazo |
| 1-470 | Pip | (CH₂)₃ | 3-NH₂-4-Pyrazo |
| 1-471 | Pip | (CH₂)₃ | 3,5-diMe-4-Pyrazo |
| 1-472 | Pip | (CH₂)₃ | 1,3,5-triMe-4-Pyrazo |
| 1-473 | Pip | (CH₂)₃ | 2-Imidazo |
| 1-474 | Pip | (CH₂)₃ | 4-Imidazo |
| 1-475 | Pip | (CH₂)₃ | 5-Me-4-Imidazo |
| 1-476 | Pip | CH₂CH₂ | 2-Fur |
| 1-477 | Pip | CH₂CH₂ | 3-Fur |
| 1-478 | Pip | CH₂CH₂ | 4-Me-2-Fur |
| 1-479 | Pip | CH₂CH₂ | 5-Me-2-Fur |
| 1-480 | Pip | CH₂CH₂ | 2-Me-3-Fur |
| 1-481 | Pip | CH₂CH₂ | 5-Me-3-Fur |
| 1-482 | Pip | CH₂CH₂ | 5-Cl-2-Fur |
| 1-483 | Pip | CH₂CH₂ | 5-Cl-3-Fur |
| 1-484 | Pip | CH₂CH₂ | 5-NH₂-2-Fur |
| 1-485 | Pip | CH₂CH₂ | 5-AcNH-2-Fur |
| 1-486 | Pip | CH₂CH₂ | 5-Ph-2-Fur |
| 1-487 | Pip | CH₂CH₂ | 5-(4-MePh)-2-Fur |
| 1-488 | Pip | CH₂CH₂ | 5-(4-ClPh)-2-Fur |
| 1-489 | Pip | CH₂CH₂ | 3-Me-5-NH₂-2-Fur |
| 1-490 | Pip | CH₂CH₂ | 2,4-diMe-3-Fur |
| 1-491 | Pip | CH₂CH₂ | 2-Thi |
| 1-492 | Pip | CH₂CH₂ | 3-Thi |
| 1-493 | Pip | CH₂CH₂ | 3-Me-2-Thi |
| 1-494 | Pip | CH₂CH₂ | 5-Me-2-Thi |
| 1-495 | Pip | CH₂CH₂ | 2-Me-3-Thi |
| 1-496 | Pip | CH₂CH₂ | 4-Me-3-Thi |
| 1-497 | Pip | CH₂CH₂ | 5-Me-3-Thi |
| 1-498 | Pip | CH₂CH₂ | 4-MeO-2-Thi |
| 1-499 | Pip | CH₂CH₂ | 4-MeO-3-Thi |
| 1-500 | Pip | CH₂CH₂ | 4-HO-2-Thi |
| 1-501 | Pip | CH₂CH₂ | 4-HO-3-Thi |
| 1-502 | Pip | CH₂CH₂ | 5-Et-2-Thi |
| 1-503 | Pip | CH₂CH₂ | 5-Cl-2-Thi |
| 1-504 | Pip | CH₂CH₂ | 5-Cl-3-Thi |
| 1-505 | Pip | CH₂CH₂ | 5-Br-3-Thi |
| 1-506 | Pip | CH₂CH₂ | 3-NH₂-2-Thi |
| 1-507 | Pip | CH₂CH₂ | 5-NH₂-2-Thi |
| 1-508 | Pip | CH₂CH₂ | 2-NH₂-3-Thi |
| 1-509 | Pip | CH₂CH₂ | 4-NH₂-3-Thi |
| 1-510 | Pip | CH₂CH₂ | 3-AcNH-2-Thi |
| 1-511 | Pip | CH₂CH₂ | 4-AcNH-3-Thi |
| 1-512 | Pip | CH₂CH₂ | 5-Ph-2-Thi |
| 1-513 | Pip | CH₂CH₂ | 4,5-diMe-2-Thi |
| 1-514 | Pip | CH₂CH₂ | 3,5-diMe-2-Thi |
| 1-515 | Pip | CH₂CH₂ | 2,5-diMe-3-Thi |
| 1-516 | Pip | CH₂CH₂ | 4,5-diMe-3-Thi |
| 1-517 | Pip | CH₂CH₂ | 4,5-diCl-2-Thi |
| 1-518 | Pip | CH₂CH₂ | 2-NH₂-5-Ph-3-Thi |
| 1-519 | Pip | CH₂CH₂ | 4-NH₂-2,5-diMe-3-Thi |
| 1-520 | Pip | CH₂CH₂ | 2-Pyl |
| 1-521 | Pip | CH₂CH₂ | 3-Pyl |
| 1-522 | Pip | CH₂CH₂ | 1-Me-2-Pyl |
| 1-523 | Pip | CH₂CH₂ | 3-Me-2-Pyl |
| 1-524 | Pip | CH₂CH₂ | 4-Me-2-Pyl |
| 1-525 | Pip | CH₂CH₂ | 2-Me-3-Pyl |
| 1-526 | Pip | CH₂CH₂ | 5-Me-3-Pyl |
| 1-527 | Pip | CH₂CH₂ | 3-NH₂-2-Pyl |
| 1-528 | Pip | CH₂CH₂ | 4-NH₂-2-Pyl |
| 1-529 | Pip | CH₂CH₂ | 3-AcNH-2-Pyl |
| 1-530 | Pip | CH₂CH₂ | 5-Cl-2-Pyl |
| 1-531 | Pip | CH₂CH₂ | 5-Cl-3-Pyl |
| 1-532 | Pip | CH₂CH₂ | 4-Ph-2-Pyl |
| 1-533 | Pip | CH₂CH₂ | 5-Ph-3-Pyl |
| 1-534 | Pip | CH₂CH₂ | 1-Me-4-MeO-3-pyl |
| 1-535 | Pip | CH₂CH₂ | 1-Me-4-HO-3-Pyl |
| 1-536 | Pip | CH₂CH₂ | 3,5-diMe-2-Pyl |
| 1-537 | Pip | CH₂CH₂ | 4,5-diMe-2-Pyl |
| 1-538 | Pip | CH₂CH₂ | 1,3-diMe-2-Pyl |
| 1-539 | Pip | CH₂CH₂ | 5-NH₂-1-Me-2-Pyl |
| 1-540 | Pip | CH₂CH₂ | 4-NH₂-3,5-diMe-2-Pyl |
| 1-541 | Pip | CH₂CH₂ | 5-Br-1,4-diMe-3-Pyl |
| 1-542 | Pip | CH₂CH₂ | 4-Oxazo |
| 1-543 | Pip | CH₂CH₂ | 5-Oxazo |
| 1-544 | Pip | CH₂CH₂ | 2-Oxazo |
| 1-545 | Pip | CH₂CH₂ | 2-Me-4-Oxazo |
| 1-546 | Pip | CH₂CH₂ | 2-Ph-4-Oxazo |
| 1-547 | Pip | CH₂CH₂ | 5-Ph-2-Oxazo |
| 1-548 | Pip | CH₂CH₂ | 2-HO-4-Oxazo |
| 1-549 | Pip | CH₂CH₂ | 2,5-diMe-4-Oxazo |
| 1-550 | Pip | CH₂CH₂ | 4-Me-2-Ph-5-Oxazo |
| 1-551 | Pip | CH₂CH₂ | 3-Isoxazo |
| 1-552 | Pip | CH₂CH₂ | 4-Isoxazo |
| 1-553 | Pip | CH₂CH₂ | 4-Me-3-Isoxazo |
| 1-554 | Pip | CH₂CH₂ | 5-Me-3-Isoxazo |
| 1-555 | Pip | CH₂CH₂ | 3-Me-4-Isoxazo |
| 1-556 | Pip | CH₂CH₂ | 4-MeO-3-Isoxazo |
| 1-557 | Pip | CH₂CH₂ | 4-HO-3-Isoxazo |
| 1-558 | Pip | CH₂CH₂ | 3-HO-4-Isoxazo |
| 1-559 | Pip | CH₂CH₂ | 3-HO-5-Isoxazo |
| 1-560 | Pip | CH₂CH₂ | 4-NH₂-3-Isoxazo |
| 1-561 | Pip | CH₂CH₂ | 5-NH₂-4-Isoxazo |
| 1-562 | Pip | CH₂CH₂ | 5-Ph-3-Isoxazo |
| 1-563 | Pip | CH₂CH₂ | 4-Ph-3-Isoxazo |
| 1-564 | Pip | CH₂CH₂ | 4,5-diMe-3-Isoxazo |
| 1-565 | Pip | CH₂CH₂ | 4-HO-5-Me-3-Isoxazo |
| 1-566 | Pip | CH₂CH₂ | 2-Thiazo |
| 1-567 | Pip | CH₂CH₂ | 4-Thiazo |
| 1-568 | Pip | CH₂CH₂ | 5-Thiazo |
| 1-569 | Pip | CH₂CH₂ | 4-Me-2-Thiazo |
| 1-570 | Pip | CH₂CH₂ | 2-Me-4-Thiazo |
| 1-571 | Pip | CH₂CH₂ | 2-Me-5-Thiazo |
| 1-572 | Pip | CH₂CH₂ | 2-MeO-4-Thiazo |
| 1-573 | Pip | CH₂CH₂ | 2-MeO-5-Thiazo |
| 1-574 | Pip | CH₂CH₂ | 2-HO-4-Thiazo |
| 1-575 | Pip | CH₂CH₂ | 2-HO-5-Thiazo |
| 1-576 | Pip | CH₂CH₂ | 2-Cl-5-Thiazo |
| 1-577 | Pip | CH₂CH₂ | 5-Cl-2-Thiazo |
| 1-578 | Pip | CH₂CH₂ | 2-NH 4-Thiazo |
| 1-579 | Pip | CH₂CH₂ | 2-NH₂-5-Thiazo |
| 1-580 | Pip | CH₂CH₂ | 5-NH₂-4-Thiazo |
| 1-581 | Pip | CH₂CH₂ | 2-AcNH-4-Thiazo |
| 1-582 | Pip | CH₂CH₂ | 5-AcNH-4-Thiazo |
| 1-583 | Pip | CH₂CH₂ | 2-Ph-4-Thiazo |
| 1-584 | Pip | CH₂CH₂ | 4,5-diMe-2-Thiazo |
| 1-585 | Pip | CH₂CH₂ | 2-HO-5-Me-4-Thiazo |
| 1-586 | Pip | CH₂CH₂ | 5-NH₂-2-Me-4-Thiazo |
| 1-587 | Pip | CH₂CH₂ | 2-Cl-4-Me-5-Thiazo |
| 1-588 | Pip | CH₂CH₂ | 3-Isothiazo |
| 1-589 | Pip | CH₂CH₂ | 4-Isothiazo |
| 1-590 | Pip | CH₂CH₂ | 3-Pyrazo |
| 1-591 | Pip | CH₂CH₂ | 4-Pyrazo |
| 1-592 | Pip | CH₂CH₂ | 1-Me-3-Pyrazo |
| 1-593 | Pip | CH₂CH₂ | 1-Et-3-Pyrazo |
| 1-594 | Pip | CH₂CH₂ | 1-Pr-3-Pyrazo |
| 1-595 | Pip | CH₂CH₂ | 1-Me-4-Pyrazo |
| 1-596 | Pip | CH₂CH₂ | 1-Et-4-Pyrazo |
| 1-597 | Pip | CH₂CH₂ | 1-Pr-4-Pyrazo |
| 1-598 | Pip | CH₂CH₂ | 1-Bu-4-Pyrazo |
| 1-599 | Pip | CH₂CH₂ | 4-Me-3-Pyrazo |
| 1-600 | Pip | CH₂CH₂ | 5-Me-3-Pyrazo |
| 1-601 | Pip | CH₂CH₂ | 5-Et-3-Pyrazo |
| 1-602 | Pip | CH₂CH₂ | 5-Pr-3-Pyrazo |
| 1-603 | Pip | CH₂CH₂ | 5-Me-4-Pyrazo |
| 1-604 | Pip | CH₂CH₂ | 4-MeO-3-Pyrazo |
| 1-605 | Pip | CH₂CH₂ | 4-PrO-3-Pyrazo |
| 1-606 | Pip | CH₂CH₂ | 4-HO-3-Pyrazo |
| 1-607 | Pip | CH₂CH₂ | 4-Cl-3-Pyrazo |
| 1-608 | Pip | CH₂CH₂ | 4-Br-3-Pyrazo |

TABLE 1-continued

| Cpd. No. | R¹ | A | R² |
| --- | --- | --- | --- |
| 1-609 | Pip | CH₂CH₂ | 3-Cl-4-Pyrazo |
| 1-610 | Pip | CH₂CH₂ | 4-NH₂-3-Pyrazo |
| 1-611 | Pip | CH₂CH₂ | 5-NH₂-3-Pyrazo |
| 1-612 | Pip | CH₂CH₂ | 3-NH₂-4-Pyrazo |
| 1-613 | Pip | CH₂CH₂ | 4-AcNH-3-Pyrazo |
| 1-614 | Pip | CH₂CH₂ | 5-AcNH-3-Pyrazo |
| 1-615 | Pip | CH₂CH₂ | 3-AcNH-4-Pyrazo |
| 1-616 | Pip | CH₂CH₂ | 3-EtCONH-4-Pyrazo |
| 1-617 | Pip | CH₂CH₂ | 5-Ph-3-Pyrazo |
| 1-618 | Pip | CH₂CH₂ | 1,5-diMe-3-Pyrazo |
| 1-619 | Pip | CH₂CH₂ | 1,4-diMe-3-Pyrazo |
| 1-620 | Pip | CH₂CH₂ | 4,5-diMe-3-Pyrazo |
| 1-621 | Pip | CH₂CH₂ | 3-Me-4-Pyrazo |
| 1-622 | Pip | CH₂CH₂ | 3,5-diMe-4-Pyrazo |
| 1-623 | Pip | CH₂CH₂ | 1,5-diMe-4-Pyrazo |
| 1-624 | Pip | CH₂CH₂ | 1,3-diMe-4-Pyrazo |
| 1-625 | Pip | CH₂CH₂ | 1,3-diMe-5-Pyrazo |
| 1-626 | Pip | CH₂CH₂ | 3-Cl-5-Me-4-Pyrazo |
| 1-627 | Pip | CH₂CH₂ | 3-Cl-1-Me-4-Pyrazo |
| 1-628 | Pip | CH₂CH₂ | 5-Cl-1-Me-4-Pyrazo |
| 1-629 | Pip | CH₂CH₂ | 4-Cl-1-Me-3-Pyrazo |
| 1-630 | Pip | CH₂CH₂ | 4-Cl-5-Me-3-Pyrazo |
| 1-631 | Pip | CH₂CH₂ | 4-Cl-1-Me-3-Pyrazo |
| 1-632 | Pip | CH₂CH₂ | 3-NH₂-5-Me-4-Pyrazo |
| 1-633 | Pip | CH₂CH₂ | 3-NH₂-1-Me-4-Pyrazo |
| 1-634 | Pip | CH₂CH₂ | 5-NH₂-1-Me-4-Pyrazo |
| 1-635 | Pip | CH₂CH₂ | 5-NH₂-4-Me-3-Pyrazo |
| 1-636 | Pip | CH₂CH₂ | 5-NH₂-1-Me-3-Pyrazo |
| 1-637 | Pip | CH₂CH₂ | 5-AcNH-1-Me-4-Pyrazo |
| 1-638 | Pip | CH₂CH₂ | 4-NH₂-5-Me-3-Pyrazo |
| 1-639 | Pip | CH₂CH₂ | 4-HO-5-Me-3-Pyrazo |
| 1-640 | Pip | CH₂CH₂ | 5-AcNH-3-Me-4-Pyrazo |
| 1-641 | Pip | CH₂CH₂ | 1,3,5-triMe-4-Pyrazo |
| 1-642 | Pip | CH₂CH₂ | 1,3,4-triMe-5-Pyrazo |
| 1-643 | Pip | CH₂CH₂ | 4-Cl-1,3-diMe-5-Pyrazo |
| 1-644 | Pip | CH₂CH₂ | 2-Imidazo |
| 1-645 | Pip | CH₂CH₂ | 4-Imidazo |
| 1-646 | Pip | CH₂CH₂ | 2-Me-4-Imidazo |
| 1-647 | Pip | CH₂CH₂ | 1-Me-4-Imidazo |
| 1-648 | Pip | CH₂CH₂ | 5-Me-4-Imidazo |
| 1-649 | Pip | CH₂CH₂ | 5-Me-2-Imidazo |
| 1-650 | Pip | CH₂CH₂ | 1-Me-2-Imidazo |
| 1-651 | Pip | CH₂CH₂ | 1,2,3-Oxadiazo-5-yl |
| 1-652 | Pip | CH₂CH₂ | 1,3,4-Oxadiazo-2-yl |
| 1-653 | Pip | CH₂CH₂ | 1,2,3-Oxadiazo-4-yl |
| 1-654 | Pip | CH₂CH₂ | 1,2,4-Oxadiazo-5-yl |
| 1-655 | Pip | CH₂CH₂ | 1,2,4-Oxadiazo-3-yl |
| 1-656 | Pip | CH₂CH₂ | 1,2,5-Oxadiazo-3-yl |
| 1-657 | Pip | CH₂CH₂ | 5-Me-1,2,3-Oxadiazo-4-yl |
| 1-658 | Pip | CH₂CH₂ | 4-Me-1,2,5-Oxadiazo-3-yl |
| 1-659 | Pip | CH₂CH₂ | 4-Ph-1,2,5-Oxadiazo-3-yl |
| 1-660 | Pip | CH₂CH₂ | 1,2,3-Thiadiazo-4-yl |
| 1-661 | Pip | CH₂CH₂ | 1,2,3-Thiadiazo-5-yl |
| 1-662 | Pip | CH₂CH₂ | 1,3,4-Thiadiazo-2-yl |
| 1-663 | Pip | CH₂CH₂ | 1,2,4-Thiadiazo-3-yl |
| 1-664 | Pip | CH₂CH₂ | 1,2,4-Thiadiazo-5-yl |
| 1-665 | Pip | CH₂CH₂ | 1,2,5-Thiadiazo-3-yl |
| 1-666 | Pip | CH₂CH₂ | 4-Me-1,2,3-Thiadiazo-5-yl |
| 1-667 | Pip | CH₂CH₂ | 5-Me-1,2,3-Thiadiazo-4-yl |
| 1-668 | Pip | CH₂CH₂ | 4-Me-1,2,5-Thiadiazo-3-yl |
| 1-669 | Pip | CH₂CH₂ | 5-Ph-1,2,3-Thiadiazo-4-yl |
| 1-670 | Pyr | CH₂CH₂ | 2-Fur |
| 1-671 | Pyr | CH₂CH₂ | 3-Fur |
| 1-672 | Pyr | CH₂CH₂ | 4-Me-2-Fur |
| 1-673 | Pyr | CH₂CH₂ | 2-Me-3-Fur |
| 1-674 | Pyr | CH₂CH₂ | 2,4-diMe-3-Fur |
| 1-675 | Pyr | CH₂CH₂ | 2-Thi |
| 1-676 | Pyr | CH₂CH₂ | 3-Thi |
| 1-677 | Pyr | CH₂CH₂ | 3-Me-2-Thi |
| 1-678 | Pyr | CH₂CH₂ | 2-Me-3-Thi |
| 1-679 | Pyr | CH₂CH₂ | 4-Me-3-Thi |
| 1-680 | Pyr | CH₂CH₂ | 4-MeO-3-Thi |
| 1-681 | Pyr | CH₂CH₂ | 4-HO-2-Thi |
| 1-682 | Pyr | CH₂CH₂ | 5-Cl-3-Thi |
| 1-683 | Pyr | CH₂CH₂ | 3-NH₂-2-Thi |
| 1-684 | Pyr | CH₂CH₂ | 2-NH₂-3-Thi |
| 1-685 | Pyr | CH₂CH₂ | 3-AcNH-2-Thi |
| 1-686 | Pyr | CH₂CH₂ | 5-Ph-2-Thi |
| 1-687 | Pyr | CH₂CH₂ | 4,5-diMe-2-Thi |
| 1-688 | Pyr | CH₂CH₂ | 2,5-diMe-3-Thi |
| 1-689 | Pyr | CH₂CH₂ | 4,5-diCl-2-Thi |
| 1-690 | Pyr | CH₂CH₂ | 4-NH₂-2,5-diMe-3-Thi |
| 1-691 | Pyr | CH₂CH₂ | 2-Pyl |
| 1-692 | Pyr | CH₂CH₂ | 3-Pyl |
| 1-693 | Pyr | CH₂CH₂ | 1-Me-2-Pyl |
| 1-694 | Pyr | CH₂CH₂ | 3-Me-2-Pyl |
| 1-695 | Pyr | CH₂CH₂ | 4-Me-2-Pyl |
| 1-696 | Pyr | CH₂CH₂ | 2-Me-3-Pyl |
| 1-697 | Pyr | CH₂CH₂ | 1-Me-4-MeO-3-Pyl |
| 1-698 | Pyr | CH₂CH₂ | 1-Me-4-HO-3-Pyl |
| 1-699 | Pyr | CH₂CH₂ | 3,5-diMe-2-Pyl |
| 1-700 | Pyr | CH₂CH₂ | 1,3-diMe-2-Pyl |
| 1-701 | Pyr | CH₂CH₂ | 4-Oxazo |
| 1-702 | Pyr | CH₂CH₂ | 5-Oxazo |
| 1-703 | Pyr | CH₂CH₂ | 2-Oxazo |
| 1-704 | Pyr | CH₂CH₂ | 2-Me-4-Oxazo |
| 1-705 | Pyr | CH₂CH₂ | 5-Ph-2-Oxazo |
| 1-706 | Pyr | CH₂CH₂ | 2,5-d.iMe-4-Oxazo |
| 1-707 | Pyr | CH₂CH₂ | 3-Isoxazo |
| 1-708 | Pyr | CH₂CH₂ | 4-Isoxazo |
| 1-709 | Pyr | CH₂CH₂ | 5-Me-3-Isoxazo |
| 1-710 | Pyr | CH₂CH₂ | 3-Me-4-Isoxazo |
| 1-711 | Pyr | CH₂CH₂ | 4-MeO-3-Isoxazo |
| 1-712 | Pyr | CH₂CH₂ | 4-HO-3-Isoxazo |
| 1-713 | Pyr | CH₂CH₂ | 3-HO-5-Isoxazo |
| 1-714 | Pyr | CH₂CH₂ | 5-HO-4-Isoxazo |
| 1-715 | Pyr | CH₂CH₂ | 4-NH₂-3-Isoxazo |
| 1-716 | Pyr | CH₂CH₂ | 5-Ph-3-Isoxazo |
| 1-717 | Pyr | CH₂CH₂ | 4,5-diMe-3-Isoxazo |
| 1-718 | Pyr | CH₂CH₂ | 4-HO-5-Me-3-Isoxazo |
| 1-719 | Pyr | CH₂CH₂ | 2-Thiazo |
| 1-720 | Pyr | CH₂CH₂ | 4-Thiazo |
| 1-721 | Pyr | CH₂CH₂ | 5-Thiazo |
| 1-722 | Pyr | CH₂CH₂ | 4-Me-2-Thiazo |
| 1-723 | Pyr | CH₂CH₂ | 2-Me-5-Thiazo |
| 1-724 | Pyr | CH₂CH₂ | 2-MeO-4-Thiazo |
| 1-725 | Pyr | CH₂CH₂ | 2-MeO-5-Thiazo |
| 1-726 | Pyr | CH₂CH₂ | 2-HO-5-Thiazo |
| 1-727 | Pyr | CH₂CH₂ | 5-Cl-2-Thiazo |
| 1-728 | Pyr | CH₂CH₂ | 2-NH₂-4-Thiazo |
| 1-729 | Pyr | CH₂CH₂ | 2-AcNH-4-Thiazo |
| 1-730 | Pyr | CH₂CH₂ | 4,5-diMe-2-Thiazo |
| 1-731 | Pyr | CH₂CH₂ | 2-HO-5-Me-4-Thiazo |
| 1-732 | Pyr | CH₂CH₂ | 5-NH₂-2-Me-4-Thiazo |
| 1-733 | Pyr | CH₂CH₂ | 3-Isothiazo |
| 1-734 | Pyr | CH₂CH₂ | 4-Isothiazo |
| 1-735 | Pyr | CH₂CH₂ | 3-Pyrazo |
| 1-736 | Pyr | CH₂CH₂ | 4-Pyrazo |
| 1-737 | Pyr | CH₂CH₂ | 1-Me-3-Pyrazo |
| 1-738 | Pyr | CH₂CH₂ | 1-Et-3-Pyrazo |
| 1-739 | Pyr | CH₂CH₂ | 1-Me-4-Pyrazo |
| 1-740 | Pyr | CH₂CH₂ | 1-Et-4-Pyrazo |
| 1-741 | Pyr | CH₂CH₂ | 4-Me-3-Pyrazo |
| 1-742 | Pyr | CH₂CH₂ | 5-Me-3-Pyrazo |
| 1-743 | Pyr | CH₂CH₂ | 5-Me-4-Pyrazo |
| 1-744 | Pyr | CH₂CH₂ | 4-MeO-3-Pyrazo |
| 1-745 | Pyr | CH₂CH₂ | 4-HO-3-Pyrazo |
| 1-746 | Pyr | CH₂CH₂ | 4-Cl-3-Pyrazo |
| 1-747 | Pyr | CH₂CH₂ | 4-NH₂-3-Pyrazo |
| 1-748 | Pyr | CH₂CH₂ | 5-NH₂-3-Pyrazo |
| 1-749 | Pyr | CH₂CH₂ | 3-NH₂-4-Pyrazo |
| 1-750 | Pyr | CH₂CH₂ | 4-AcNH-3-Pyrazo |
| 1-751 | Pyr | CH₂CH₂ | 5-Ph-3-Pyrazo |
| 1-752 | Pyr | CH₂CH₂ | 1,5-diMe-3-Pyrazo |
| 1-753 | Pyr | CH₂CH₂ | 1,4-diMe-3-Pyrazo |
| 1-754 | Pyr | CH₂CH₂ | 3,5-diMe-4-Pyrazo |
| 1-755 | Pyr | CH₂CH₂ | 1,5-diMe-4-Pyrazo |
| 1-756 | Pyr | CH₂CH₂ | 1,3-diMe-4-Pyrazo |
| 1-757 | Pyr | CH₂CH₂ | 1,3-diMe-5-Pyrazo |
| 1-758 | Pyr | CH₂CH₂ | 3-Cl-5-Me-4-Pyrazo |
| 1-759 | Pyr | CH₂CH₂ | 3-Cl-1-Me-4-Pyrazo |
| 1-760 | Pyr | CH₂CH₂ | 4-Cl-5-Me-3-Pyrazo |

TABLE 1-continued

| Cpd. No. | R¹ | A | R² |
|---|---|---|---|
| 1-761 | Pyr | CH₂CH₂ | 4-Cl-1-Me-3-Pyrazo |
| 1-762 | Pyr | CH₂CH₂ | 3-NH₂-5-Me-4-Pyrazo |
| 1-763 | Pyr | CH₂CH₂ | 3-NH₂-1-Me-4-Pyrazo |
| 1-764 | Pyr | CH₂CH₂ | 5-NH₂-1-Me-4-Pyrazo |
| 1-765 | Pyr | CH₂CH₂ | 5-NH₂-4-Me-3-Pyrazo |
| 1-766 | Pyr | CH₂CH₂ | 5-NH₂-1-Me-3-Pyrazo |
| 1-767 | Pyr | CH₂CH₂ | 5-NH₂-3-Me-4-Pyrazo |
| 1-768 | Pyr | CH₂CH₂ | 4-NH₂-5-Me-3-Pyrazo |
| 1-769 | Pyr | CH₂CH₂ | 4-HO-5-Me-3-Pyrazo |
| 1-770 | Pyr | CH₂CH₂ | 1,3,5-triMe-4-Pyrazo |
| 1-771 | Pyr | CH₂CH₂ | 1,3,4-triMe-5-Pyrazo |
| 1-772 | Pyr | CH₂CH₂ | 4-Cl-1,3-diMe-5-Pyrazo |
| 1-773 | Pyr | CH₂CH₂ | 2-Imidazo |
| 1-774 | Pyr | CH₂CH₂ | 4-Imidazo |
| 1-775 | Pyr | CH₂CH₂ | 1-Me-4-Imidazo |
| 1-776 | Pyr | CH₂CH₂ | 5-Me-4-Imidazo |
| 1-777 | Pyr | CH₂CH₂ | 5-Me-2-Imidazo |
| 1-778 | Pyr | CH₂CH₂ | 1-Me-2-Imidazo |
| 1-779 | Pyr | CH₂CH₂ | 1,2,3-Oxadiazo-5-yl |
| 1-780 | Pyr | CH₂CH₂ | 1,2,4-Oxadiazo-5-yl |
| 1-781 | Pyr | CH₂CH₂ | 1,2,5-Oxadiazo-3-yl |
| 1-782 | Pyr | CH₂CH₂ | 5-Me-1,2,3-Oxadiazo-4-yl |
| 1-783 | Pyr | CH₂CH₂ | 1,2,3-Thiadiazo-4-yl |
| 1-784 | Pyr | CH₂CH₂ | 1,2,4-Thiadiazo-3-yl |
| 1-785 | Pyr | CH₂CH₂ | 1,2,5-Thiadiazo-3-yl |
| 1-786 | Pyr | CH₂CH₂ | 4-Me-1,2,3-Thiadiazo-5-yl |
| 1-787 | Pyr | CH₂CH₂ | 5-Ph-1,2,3-Thiadiaio-4-yl |
| 1-788 | NMe₂ | CH₂CH₂ | 2-Fur |
| 1-789 | NMe₂ | CH₂CH₂ | 3-Fur |
| 1-790 | NMe₂ | CH₂CH₂ | 4-Me-2-Fur |
| 1-791 | NMe₂ | CH₂CH₂ | 2,4-diMe-3-Fur |
| 1-792 | NMe₂ | CH₂CH₂ | 2-Thi |
| 1-793 | NMe₂ | CH₂CH₂ | 3-Thi |
| 1-794 | NMe₂ | CH₂CH₂ | 3-Me-2-Thi |
| 1-795 | NMe₂ | CH₂CH₂ | 2-Me-3-Thi |
| 1-796 | NMe₂ | CH₂CH₂ | 4-MeO-3-Thi |
| 1-797 | NMe₂ | CH₂CH₂ | 4,5-diMe-2-Thi |
| 1-798 | NMe₂ | CH₂CH₂ | 2-Pyl |
| 1-799 | NMe₂ | CH₂CH₂ | 3-Pyl |
| 1-800 | NMe₂ | CH₂CH₂ | 1-Me-2-Pyl |
| 1-801 | NMe₂ | CH₂CH₂ | 4-Me-2-Pyl |
| 1-802 | NMe₂ | CH₂CH₂ | 2-Me-3-Pyl |
| 1-803 | NMe₂ | CH₂CH₂ | 3,5-diMe-2-Pyl |
| 1-804 | NMe₂ | CH₂CH₂ | 1,3-diMe-2-Pyl |
| 1-805 | NMe₂ | CH₂CH₂ | 4-Oxazo |
| 1-806 | NMe₂ | CH₂CH₂ | 5-Oxazo |
| 1-807 | NMe₂ | CH₂CH₂ | 2-Oxazo |
| 1-808 | NMe₂ | CH₂CH₂ | 2-Me-4-Oxazo |
| 1-809 | NMe₂ | CH₂CH₂ | 2,5-diMe-4-Oxazo |
| 1-810 | NMe₂ | CH₂CH₂ | 3-Isoxazo |
| 1-811 | NMe₂ | CH₂CH₂ | 4-Isoxazo |
| 1-812 | NMe₂ | CH₂CH₂ | 5-Me-3-Isoxazo |
| 1-813 | NMe₂ | CH₂CH₂ | 4-MeO-3-Isoxazo |
| 1-814 | NMe₂ | CH₂CH₂ | 4-HO-3-Isoxazo |
| 1-815 | NMe₂ | CH₂CH₂ | 4,5-diMe-3-Isoxazo |
| 1-816 | NMe₂ | CH₂CH₂ | 4-HO-5-Me-3-Isoxazo |
| 1-817 | NMe₂ | CH₂CH₂ | 2-Thiazo |
| 1-818 | NMe₂ | CH₂CH₂ | 4-Thiazo |
| 1-819 | NMe₂ | CH₂CH₂ | 5-Thiazo |
| 1-820 | NMe₂ | CH₂CH₂ | 4-Me-2-Thiazo |
| 1-821 | NMe₂ | CH₂CH₂ | 2-Me-5-Thiazo |
| 1-822 | NMe₂ | CH₂CH₂ | 2-MeO-4-Thiazo |
| 1-823 | NMe₂ | CH₂CH₂ | 4,5-diMe-2-Thiazo |
| 1-824 | NMe₂ | CH₂CH₂ | 3-Isothiazo |
| 1-825 | NMe₂ | CH₂CH₂ | 4-Isothiazo |
| 1-826 | NMe₂ | CH₂CH₂ | 3-Pyrazo |
| 1-827 | NMe₂ | CH₂CH₂ | 4-Pyrazo |
| 1-828 | NMe₂ | CH₂CH₂ | 1-Me-3-Pyrazo |
| 1-829 | NMe₂ | CH₂CH₂ | 1-Me-4-Pyrazo |
| 1-830 | NMe₂ | CH₂CH₂ | 4-Me-3-Pyrazo |
| 1-831 | NMe₂ | CH₂CH₂ | 5-Me-3-Pyrazo |
| 1-832 | NMe₂ | CH₂CH₂ | 5-Me-4-Pyrazo |
| 1-833 | NMe₂ | CH₂CH₂ | 4-MeO-3-Pyrazo |
| 1-834 | NMe₂ | CH₂CH₂ | 4-HO-3-Pyrazo |
| 1-835 | NMe₂ | CH₂CH₂ | 3,5-diMe-4-Pyrazo |
| 1-836 | NMe₂ | CH₂CH₂ | 1,3,5-triMe-4-Pyrazo |
| 1-837 | NMe₂ | CH₂CH₂ | 1,3,4-triMe-5-Pyrazo |
| 1-838 | NMe₂ | CH₂CH₂ | 2-Imidazo |
| 1-839 | NMe₂ | CH₂CH₂ | 4-Imidazo |
| 1-840 | NMe | CH₂CH₂ | 5-Me-4-Imidazo |
| 1-841 | Azi | CH₂CH₂ | 2-Fur |
| 1-842 | Azi | CH₂CH₂ | 3-Fur |
| 1-843 | Azi | CH₂CH₂ | 4-Me-2-Fur |
| 1-844 | Azi | CH₂CH₂ | 2-Thi |
| 1-845 | Azi | CH₂CH₂ | 3-Thi |
| 1-846 | Azi | CH₂CH₂ | 5-Me-2-Thi |
| 1-847 | Azi | CH₂CH₂ | 2-Pyl |
| 1-848 | Azi | CH₂CH₂ | 3-Pyl |
| 1-849 | Azi | CH₂CH₂ | 1-Me-2-Pyl |
| 1-850 | Azi | CH₂CH₂ | 4-Me-2-Pyl |
| 1-851 | Azi | CH₂CH₂ | 4-Oxazo |
| 1-852 | Azi | CH₂CH₂ | 5-Oxazo |
| 1-853 | Azi | CH₂CH₂ | 2-Oxazo |
| 1-854 | Azi | CH₂CH₂ | 3-Isoxazo |
| 1-855 | Azi | CH₂CH₂ | 4-Isoxazo |
| 1-856 | Azi | CH₂CH₂ | 4-HO-3-Isoxazo |
| 1-857 | Azi | CH₂CH₂ | 2-Thiazo |
| 1-858 | Azi | CH₂CH₂ | 4-Thiazo |
| 1-859 | Azi | CH₂CH₂ | 5-Thiazo |
| 1-860 | Azi | CH₂CH₂ | 2-Me-5-Thiazo |
| 1-861 | Azi | CH₂CH₂ | 3-Pyrazo |
| 1-862 | Azi | CH₂CH₂ | 4-Pyrazo |
| 1-863 | Azi | CH₂CH₂ | 1-Me-3-Pyrazo |
| 1-864 | Azi | CH₂CH₂ | 4-Me-3-Pyrazo |
| 1-865 | Azi | CH₂CH₂ | 5-Me-4-Pyrazo |
| 1-866 | Azi | CH₂CH₂ | 4-NH₂-3-Pyrazo |
| 1-867 | Azi | CH₂CH₂ | 3-NH₂-4-Pyrazo |
| 1-868 | Azi | CH₂CH₂ | 3,5-diMe-4-Pyrazo |
| 1-869 | Azi | CH₂CH₂ | 1,3,5-triMe-4-Pyrazo |
| 1-870 | Azi | CH₂CH₂ | 2-Imidazo |
| 1-871 | Azi | CH₂CH₂ | 4-Imidazo |
| 1-872 | Azi | CH₂CH₂ | 5-Me-4-Imidazo |
| 1-873 | Aze | CH₂CH₂ | 2-Fur |
| 1-874 | Aze | CH₂CH₂ | 3-Fur |
| 1-875 | Aze | CH₂CH₂ | 4-Me-2-Fur |
| 1-876 | Aze | CH₂CH₂ | 2-Thi |
| 1-877 | Aze | CH₂CH₂ | 3-Thi |
| 1-878 | Aze | CH₂CH₂ | 5-Me-2-Thi |
| 1-879 | Aze | CH₂CH₂ | 2-Pyl |
| 1-880 | Aze | CH₂CH₂ | 3-Pyl |
| 1-881 | Aze | CH₂CH₂ | 1-Me-2-Pyl |
| 1-882 | Aze | CH₂CH₂ | 4-Me-2-Pyl |
| 1-883 | Aze | CH₂CH₂ | 4-Oxazo |
| 1-884 | Aze | CH₂CH₂ | 5-Oxazo |
| 1-885 | Aze | CH₂CH₂ | 2-Oxazo |
| 1-886 | Aze | CH₂CH₂ | 3-Isoxazo |
| 1-887 | Aze | CH₂CH₂ | 4-Isoxazo |
| 1-888 | Aze | CH₂CH₂ | 4-HO-3-Isoxazo |
| 1-889 | Aze | CH₂CH₂ | 2-Thiazo |
| 1-890 | Aze | CH₂CH₂ | 4-Thiazo |
| 1-891 | Aze | CH₂CH₂ | 5-Thiazo |
| 1-892 | Aze | CH₂CH₂ | 2-Me-5-Thiazo |
| 1-893 | Aze | CH₂CH₂ | 3-Pyrazo |
| 1-894 | Aze | CH₂CH₂ | 4-Pyrazo |
| 1-895 | Aze | CH₂CH₂ | 1-Me-3-Pyrazo |
| 1-896 | Aze | CH₂CH₂ | 4-Me-3-Pyrazo |
| 1-897 | Aze | CH₂CH₂ | 5-Me-4-Pyrazo |
| 1-898 | Aze | CH₂CH₂ | 4-NH₂-3-Pyrazo |
| 1-899 | Aze | CH₂CH₂ | 3-NH₂-4-Pyrazo |
| 1-900 | Aze | CH₂CH₂ | 3,5-diMe-4-Pyrazo |
| 1-901 | Aze | CH₂CH₂ | 1,3,5-triMe-4-Pyrazo |
| 1-902 | Aze | CH₂CH₂ | 2-Imidazo |
| 1-903 | Aze | CH₂CH₂ | 4-Imidazo |
| 1-904 | Aze | CH₂CH₂ | 5-Me-4-Imidazo |
| 1-905 | Pip | CH₂CH₂ | 1,2,3-Triazo-4-yl |
| 1-906 | Pip | CH₂CH₂ | 1-Me-1,2,3-Triazo-4-yl |
| 1-907 | Pip | CH₂CH₂ | 5-Me-1,2,3-Triazo-4-yl |
| 1-908 | Pip | CH₂CH₂ | 1,5-diMe-1,2,3-Triazo-4-yl |
| 1-909 | Pip | CH₂CH₂ | 1,2,4-Triazo-5-yl |
| 1-910 | Pip | CH₂CH₂ | 1-Me-1,2,5-Triazo-3-yl |
| 1-911 | Pyr | CH₂CH₂ | 1,2,3-Triazo-4-yl |
| 1-912 | Pyr | CH₂CH₂ | 1,2,4-Triazo-5-yl |

TABLE 1-continued

| Cpd. No. | R¹ | A | R² |
|---|---|---|---|
| 1-913 | NMe₂ | CH₂CH₂ | 1,2,3-Triazo-4-yl |
| 1-914 | NMe₂ | CH₂CH₂ | 1,2,4-Triazo-5-yl |
| 1-915 | Pip | CH₂ | 1,2,3-Triazo-4-yl |
| 1-916 | Pip | CH₂ | 2-Fur |
| 1-917 | Pip | CH₂ | 3-Fur |
| 1-918 | Pip | CH₂ | 4-Me-2-Fur |
| 1-919 | Pip | CH₂ | 2,4-diMe-3-Fur |
| 1-920 | Pip | CH₂ | 2-Thi |
| 1-921 | Pip | CH₂ | 3-Thi |
| 1-922 | Pip | CH₂ | 3-Me-2-Thi |
| 1-923 | Pip | CH₂ | 2-Me-3-Thi |
| 1-924 | Pip | CH₂ | 4-MeO-3-Thi |
| 1-925 | Pip | CH₂ | 4,5-diMe-2-Thi |
| 1-926 | Pip | CH₂ | 2-Pyl |
| 1-927 | Pip | CH₂ | 3-Pyl |
| 1-928 | Pip | CH₂ | 1-Me-2-Pyl |
| 1-929 | Pip | CH₂ | 4-Me-2-Pyl |
| 1-930 | Pip | CH₂ | 2-Me-3-Pyl |
| 1-931 | Pip | CH₂ | 3,5-diMe-2-Pyl |
| 1-932 | Pip | CH₂ | 1,3-diMe-2-Pyl |
| 1-933 | Pip | CH₂ | 5-NH₂-1-Me-2-Pyl |
| 1-934 | Pip | CH₂ | 4-Oxazo |
| 1-935 | Pip | CH₂ | 5-Oxazo |
| 1-936 | Pip | CH₂ | 2-Oxazo |
| 1-937 | Pip | CH₂ | 2-Me-4-Oxazo |
| 1-938 | Pip | CH₂ | 2,5-diMe-4-Oxazo |
| 1-939 | Pip | CH₂ | 3-Isoxazo |
| 1-940 | Pip | CH₂ | 4-Isoxazo |
| 1-941 | Pip | CH₂ | 5-Me-3-Isoxazo |
| 1-942 | Pip | CH₂ | 4,5-diMe-3-Isoxazo |
| 1-943 | Pip | CH₂ | 2-Thiazo |
| 1-944 | Pip | CH₂ | 4-Thiazo |
| 1-945 | Pip | CH₂ | 5-Thiazo |
| 1-946 | Pip | CH₂ | 2-Me-5-Thiazo |
| 1-947 | Pip | CH₂ | 4,5-diMe-2-Thiazo |
| 1-948 | Pip | CH₂ | 3-Isothiazo |
| 1-949 | Pip | CH₂ | 4-Isothiazo |
| 1-950 | Pip | CH₂ | 3-Pyrazo |
| 1-951 | Pip | CH₂ | 4-Pyrazo |
| 1-952 | Pip | CH₂ | 1-Me-3-Pyrazo |
| 1-953 | Pip | CH₂ | 1-Me-4-Pyrazo |
| 1-954 | Pip | CH₂ | 4-Me-3-Pyrazo |
| 1-955 | Pip | CH₂ | 5-Me-3-Pyrazo |
| 1-956 | Pip | CH₂ | 5-Me-4-Pyrazo |
| 1-957 | Pip | CH₂ | 4-MeO-3-Pyrazo |
| 1-958 | Pip | CH₂ | 4-HO-3-Pyrazo |
| 1-959 | Pip | CH₂ | 4-Cl-3-Pyrazo |
| 1-960 | Pip | CH₂ | 4-NH₂-3-Pyrazo |
| 1-961 | Pip | CH₂ | 5-NH₂-3-Pyrazo |
| 1-962 | Pip | CH₂ | 3-NH₂-4-Pyrazo |
| 1-963 | Pip | CH₂ | 5-Ph-3-Pyrazo |
| 1-964 | Pip | CH₂ | 3,5-diMe-4-Pyrazo |
| 1-965 | Pip | CH₂ | 3-NH₂-5-Me-4-Pyrazo |
| 1-966 | Pip | CH₂ | 5-NH₂-4-Me-3-Pyrazo |
| 1-967 | Pip | CH₂ | 5-NH₂-3-Me-3-Pyrazo |
| 1-968 | Pip | CH₂ | 4-NH₂-5-Me-3-Pyrazo |
| 1-969 | Pip | CH₂ | 1,3,5-triMe-4-Pyrazo |
| 1-970 | Pip | CH₂ | 1,3,4-triMe-5-Pyrazo |
| 1-971 | Pip | CH₂ | 2-Imidazo |
| 1-972 | Pip | CH₂ | 4-Imidazo |
| 1-973 | Pip | CH₂ | 5-Me-4-Imidazo |
| 1-974 | Pip | CH=CH | NHiPr |
| 1-975 | Pip | CH=CH | NHsBu |
| 1-976 | Pip | CH=CH | NH(1-MeBu) |
| 1-977 | Pip | CH=CH | NH(1,2-diMePr) |
| 1-978 | Pip | CH=CH | NH(1-MePn) |
| 1-979 | Pip | CH=CH | NH(1,3-diMeBu) |
| 1-980 | Pip | CH=CH | NH(1,2-diMeBu) |
| 1-981 | Pip | CH=CH | NH(1-MeHx) |
| 1-982 | Pip | CH=CH | NH(1,4-diMePn) |
| 1-983 | Pip | CH=CH | NH(1-MeHp) |
| 1-984 | Pip | CH=CH | NH(1,5-diMeHx) |
| 1-985 | Pip | CH=CH | NH(1-EtPr) |
| 1-986 | Pip | CH=CH | NH(1-EtBu) |
| 1-987 | Pip | CH=CH | NH(1-Et-2-MePr) |
| 1-988 | Pip | CH=CH | NH(1-EtPn) |
| 1-989 | Pip | CH=CH | NH(1-Et-3-MeBu) |
| 1-990 | Pip | CH=CH | NH(1-EtHx) |
| 1-991 | Pip | CH=CH | NH(1-EtHp) |
| 1-992 | Pip | CH=CH | NH(1-PrBu) |
| 1-993 | Pip | CH=CH | NH(1-iPrBu) |
| 1-994 | Pip | CH=CH | NH(1-PrPn) |
| 1-995 | Pip | CH=CH | NH(1-PrHx) |
| 1-996 | Pip | CH=CH | NH(1-PrHp) |
| 1-997 | Pip | CH=CH | NH(1-BuPn) |
| 1-998 | Pip | CH=CH | NH(1-PnHx) |
| 1-999 | Pip | CH=CH | NH(1-HxHp) |
| 1-1000 | Pip | CH=CH | NH(1-PhEt) |
| 1-1001 | Pip | CH=CH | NH(1-NaPhEt) |
| 1-1002 | Pip | CH=CH | NH(1-PhPr) |
| 1-1003 | Pip | CH=CH | NH(1-PhBu) |
| 1-1004 | Pip | CH=CH | NHCHPh₂ |
| 1-1005 | Pip | CH=CH | NHCHPh(4-MePh) |
| 1-1006 | Pip | CH=CH | NHCHPh(4-MeOPh) |
| 1-1007 | Pip | CH=CH | NHCHPh(4-FPh) |
| 1-1008 | Pip | CH=CH | NHCHPh(4-ClPh) |
| 1-1009 | Pip | CH=CH | NH(1-Me-2-PhEt) |
| 1-1010 | Pip | CH=CH | NH(1-Me-3-PhPr) |
| 1-1011 | Pip | CH=CH | NH(1-Et-2-PhEt) |
| 1-1012 | Pip | CH=CH | NH[1-Me-2-(4-MePh)Et] |
| 1-1013 | Pip | CH=CH | NH[1-Me-2-(4-MeOPh)Et] |
| 1-1014 | Pip | CH=CH | NH[1-Me-2-(4-FPh)Et] |
| 1-1015 | Pip | CH=CH | NH[1-Me-2-(4-ClPh)Et] |
| 1-1016 | Pip | CH=CH | NH(1,2-diPhEt) |
| 1-1017 | Pip | CH=CH | NH(1-Bz-2-PhEt) |
| 1-1018 | Pip | CH=CH | NHcPr |
| 1-1019 | Pip | CH=CH | NHcBu |
| 1-1020 | Pip | CH=CH | NHcPn |
| 1-1021 | Pip | CH=CH | NHcHx |
| 1-1022 | Pip | CH=CH | NHcHp |
| 1-1023 | Pip | CH=CH | NHcOc |
| 1-1024 | Pyr | CH=CH | NHiPr |
| 1-1025 | Pyr | CH=CH | NHsBu |
| 1-1026 | Pyr | CH=CH | NH(1-MeBu) |
| 1-1027 | Pyr | CH=CH | NH(1-MePn) |
| 1-1028 | Pyr | CH=CH | NH(1-MeHx) |
| 1-1029 | Pyr | CH=CH | NH(1-MeHp) |
| 1-1030 | Pyr | CH=CH | NH(1-EtPr) |
| 1-1031 | Pyr | CH=CH | NH(1-EtBu) |
| 1-1032 | Pyr | CH=CH | NH(1-EtPn) |
| 1-1033 | Pyr | CH=CH | NH(1-PrBu) |
| 1-1034 | Pyr | CH=CH | NH(1-BuPn) |
| 1-1035 | Pyr | CH=CH | NH(1-PhEt) |
| 1-1036 | Pyr | CH=CH | NH(1-NaPhEt) |
| 1-1037 | Pyr | CH=CH | NH(1-PhPr) |
| 1-1038 | Pyr | CH=CH | NHCHPh₂ |
| 1-1039 | Pyr | CH=CH | NHCHPh(4-MePh) |
| 1-1040 | Pyr | CH=CH | NHCHPh(4-MeoPh) |
| 1-1041 | Pyr | CH=CH | NHCHPh(4-FPh) |
| 1-1042 | Pyr | CH=CH | NHCHPh(4-ClPh) |
| 1-1043 | Pyr | CH=CH | NH(1-Me-2-PhEt) |
| 1-1044 | Pyr | CH=CH | NH[1-Me-2-(4-MePh)Et] |
| 1-1045 | Pyr | CH=CH | NH[1-Me-2-(4-MeOPh)Et] |
| 1-1046 | Pyr | CH=CH | NH[1-Me-2-(4-FPh)Et] |
| 1-1047 | Pyr | CH=CH | NH(1-Bz-2-PhEt) |
| 1-1048 | Pyr | CH=CH | NHcPr |
| 1-1049 | Pyr | CH=CH | NHcBu |
| 1-1050 | Pyr | CH=CH | NHcPn |
| 1-1051 | Pyr | CH=CH | NHcHx |
| 1-1052 | Pyr | CH=CH | NHcHp |
| 1-1053 | Pyr | CH=CH | NHcOc |
| 1-1054 | NMe₂ | CH=CH | NHiPr |
| 1-1055 | NMe₂ | CH=CH | NHsBu |
| 1-1056 | NMe₂ | CH=CH | NH(1-MeBu) |
| 1-1057 | NMe₂ | CH=CH | NH(1-MePn) |
| 1-1058 | NMe₂ | CH=CH | NH(1-MeHx) |
| 1-1059 | NMe₂ | CH=CH | NH(1-MeHp) |
| 1-1060 | NMe₂ | CH=CH | NH(1-EtPr) |
| 1-1061 | NMe₂ | CH=CH | NH(1-EtBu) |
| 1-1062 | NMe₂ | CH=CH | NH(1-EtPn) |
| 1-1063 | NMe₂ | CH=CH | NH(1-PrBu) |
| 1-1064 | NMe₂ | CH=CH | NH(1-BuPn) |

TABLE 1-continued

| Cpd. No. | R¹ | A | R² |
|---|---|---|---|
| 1-1065 | NMe₂ | CH=CH | NH(1-PhEt) |
| 1-1066 | NMe₂ | CH=CH | NH(1-NaPhEt) |
| 1-1067 | NMe₂ | CH=CH | NH(1-PhPr) |
| 1-1068 | NMe₂ | CH=CH | NHCHPh₂ |
| 1-1069 | NMe₂ | CH=CH | NHCHPh(4-MePh) |
| 1-1070 | NMe₂ | CH=CH | NHCHPh(4-MeOPh) |
| 1-1071 | NMe₂ | CH=CH | NHCHPh(4-FPh) |
| 1-1072 | NMe₂ | CH=CH | NHCHPh(4-ClPh) |
| 1-1073 | NMe₂ | CH=CH | NH(1-Me-2-PhEt) |
| 1-1074 | NMe₂ | CH=CH | NH[1-Me-2-(4-MePh)Et] |
| 1-1075 | NMe₂ | CH=CH | NH[1-Me-2-(4-MeOPh)Et] |
| 1-1076 | NMe₂ | CH=CH | NH[1-Me-2-(4-FPh)Et] |
| 1-1077 | NMe₂ | CH=CH | NH(1-Bz-2-PhEt) |
| 1-1078 | NMe₂ | CH=CH | NHcPr |
| 1-1079 | NMe₂ | CH=CH | NHcBu |
| 1-1080 | NMe₂ | CH=CH | NHcPn |
| 1-1081 | NMe₂ | CH=CH | NHcHx |
| 1-1082 | NMe₂ | CH=CH | NHcHp |
| 1-1083 | NMe₂ | CH=CH | NHcOc |
| 1-1084 | Aze | CH=CH | NHiPr |
| 1-1085 | Aze | CH=CH | NHsBu |
| 1-1086 | Aze | CH=CH | NH(1-MeBu) |
| 1-1087 | Aze | CH=CH | NH(1-MePn) |
| 1-1088 | Aze | CH=CH | NH(1-MeHx) |
| 1-1089 | Aze | CH=CH | NH(1-MeHp) |
| 1-1090 | Aze | CH=CH | NH(1-EtPr) |
| 1-1091 | Aze | CH=CH | NH(1-EtBu) |
| 1-1092 | Aze | CH=CH | NH(1-EtPn) |
| 1-1093 | Aze | CH=CH | NH(1,2-diMePr) |
| 1-1094 | Aze | CH=CH | NH(1-PhEt) |
| 1-1095 | Aze | CH=CH | NHCHPh₂ |
| 1-1096 | Aze | CH=CH | NH(1-Me-2-PhEt) |
| 1-1097 | Aze | CH=CH | NH(1,2-diPhEt) |
| 1-1098 | Aze | CH=CH | NHcPr |
| 1-1099 | Aze | CH=CH | NHcBu |
| 1-1100 | Aze | CH=CH | NHcPn |
| 1-1101 | Aze | CH=CH | NHcHx |
| 1-1102 | Aze | CH=CH | NHcHp |
| 1-1103 | Aze | CH=CH | NHcOc |
| 1-1104 | Azi | CH=CH | NHiPr |
| 1-1105 | Azi | CH=CH | NHsBu |
| 1-1106 | Azi | CH=CH | NH(1-MeBu) |
| 1-1107 | Azi | CH=CH | NH(1-MePn) |
| 1-1108 | Azi | CH=CH | NH(1-MeHx) |
| 1-1109 | Azi | CH=CH | NH(1-MeHp) |
| 1-1110 | Azi | CH=CH | NH(1-EtPr) |
| 1-1111 | Azi | CH=CH | NH(1-EtBu) |
| 1-1112 | Azi | CH=CH | NH(1-EtPn) |
| 1-1113 | Azi | CH=CH | NH(1,2-diMePr) |
| 1-1114 | Azi | CH=CH | NH(1-PhEt) |
| 1-1115 | Azi | CH=CH | NHCHPh 2 |
| 1-1116 | Azi | CH=CH | NH(1-Me-2-PhEt) |
| 1-1117 | Azi | CH=CH | NH(1,2-diPhEt) |
| 1-1118 | Azi | CH=CH | NHcPr |
| 1-1119 | Azi | CH=CH | NHcBu |
| 1-1120 | Azi | CH=CH | NHcPn |
| 1-1121 | Azi | CH=CH | NHcHx |
| 1-1122 | Azi | CH=CH | NHcHp |
| 1-1123 | Azi | CH=CH | NHcOc |
| 1-1124 | Pip | CH₂CH₂ | NHiPr |
| 1-1125 | Pip | CH₂CH₂ | NHsBu |
| 1-1126 | Pip | CH₂CH₂ | NH(1-MeBu) |
| 1-1127 | Pip | CH₂CH₂ | NH(1,2-diMePr) |
| 1-1128 | Pip | CH₂CH₂ | NH(1-MePn) |
| 1-1129 | Pip | CH₂CH₂ | NH(1,3-diMeBu) |
| 1-1130 | Pip | CH₂CH₂ | NH(1,2-diMeBu) |
| 1-1131 | Pip | CH₂CH₂ | NH(1-MeHx) |
| 1-1132 | Pip | CH₂CH₂ | NH(1,4-diMePn) |
| 1-1133 | Pip | CH₂CH₂ | NH(1-MeHp) |
| 1-1134 | Pip | CH₂CH₂ | NH(1,5-diMeHx) |
| 1-1135 | Pip | CH₂CH₂ | NH(1-EtPr) |
| 1-1136 | Pip | CH₂CH₂ | NH(1-EtBu) |
| 1-1137 | Pip | CH₂CH₂ | NH(1-Et-2-MePr) |
| 1-1138 | Pip | CH₂CH₂ | NH(1-EtPn) |
| 1-1139 | Pip | CH₂CH₂ | NH(1-Et-3-MeBu) |
| 1-1140 | Pip | CH₂CH₂ | NH(1-EtHx) |
| 1-1141 | Pip | CH₂CH₂ | NH(1-EtHp) |
| 1-1142 | Pip | CH₂CH₂ | NH(1-PrBu) |
| 1-1143 | Pip | CH₂CH₂ | NH(1-iPrBu) |
| 1-1144 | Pip | CH₂CH₂ | NH(1-PrPn) |
| 1-1145 | Pip | CH₂CH₂ | NH(1-PrHx) |
| 1-1146 | Pip | CH₂CH₂ | NH(1-PrHp) |
| 1-1147 | Pip | CH₂CH₂ | NH(1-BuPn) |
| 1-1148 | Pip | CH₂CH₂ | NH(1-PnHx) |
| 1-1149 | Pip | CH₂CH₂ | NH(1-HxHp) |
| 1-1150 | Pip | CH₂CH₂ | NH(1-PhEt) |
| 1-1151 | Pip | CH₂CH₂ | NH(1-NaPhEt) |
| 1-1152 | Pip | CH₂CH₂ | NH(1-PhPr) |
| 1-1153 | Pip | CH₂CH₂ | NH(1-PhBu) |
| 1-1154 | Pip | CH₂CH₂ | NHCHPh₂ |
| 1-1155 | Pip | CH₂CH₂ | NHCHPh(4-MePh) |
| 1-1156 | Pip | CH₂CH₂ | NHCHPh(4-MeOPh) |
| 1-1157 | Pip | CH₂CH₂ | NHCHPh(4-FPh) |
| 1-1158 | Pip | CH₂CH₂ | NHCHPh(4-ClPh) |
| 1-1159 | Pip | CH₂CH₂ | NH(1-Me-2-PhEt) |
| 1-1160 | Pip | CH₂CH₂ | NH(1-Me-3-PhPr) |
| 1-1161 | Pip | CH₂CH₂ | NH(1-Et-2-PhEt) |
| 1-1162 | Pip | CH₂CH₂ | NH[1-Me-2-(4-MePh)Et] |
| 1-1163 | Pip | CH₂CH₂ | NH[1-Me-2-(4-MeOPh)Et] |
| 1-1164 | Pip | CH₂CH₂ | NH[1-Me-2-(4-FPh)Et] |
| 1-1165 | Pip | CH₂CH₂ | NH[1-Me-2-(4-ClPh)Et] |
| 1-1166 | Pip | CH₂CH₂ | NH(1,2-diPhEt) |
| 1-1167 | Pip | CH₂CH₂ | NH(1-Bz-2-PhEt) |
| 1-1168 | Pip | CH₂CH₂ | NHcPr |
| 1-1169 | Pip | CH₂CH₂ | NHcBu |
| 1-1170 | Pip | CH₂CH₂ | NHcPn |
| 1-1171 | Pip | CH₂CH₂ | NHcHx |
| 1-1172 | Pip | CH₂CH₂ | NHcHp |
| 1-1173 | Pip | CH₂CH₂ | NHcOc |
| 1-1174 | Pyr | CH₂CH₂ | NHiPr |
| 1-1175 | Pyr | CH₂CH₂ | NHsBu |
| 1-1176 | Pyr | CH₂CH₂ | NH(1-MeBu) |
| 1-1177 | Pyr | CH₂CH₂ | NH(1-MePn) |
| 1-1178 | Pyr | CH₂CH₂ | NH(1-MeHx) |
| 1-1179 | Pyr | CH₂CH₂ | NH(1-MeHp) |
| 1-1180 | Pyr | CH₂CH₂ | NH(1-EtPr) |
| 1-1181 | Pyr | CH₂CH₂ | NH(1-EtBu) |
| 1-1182 | Pyr | CH₂CH₂ | NH(1-EtPn) |
| 1-1183 | Pyr | CH₂CH₂ | NH(1-PrBu) |
| 1-1184 | Pyr | CH₂CH₂ | NH(1-BuPn) |
| 1-1185 | Pyr | CH₂CH₂ | NH(1-PhEt) |
| 1-1186 | Pyr | CH₂CH₂ | NH(1-NaPhEt) |
| 1-1187 | Pyr | CH₂CH₂ | NH(1-PhPr) |
| 1-1188 | Pyr | CH₂CH₂ | NHCHPh₂ |
| 1-1189 | Pyr | CH₂CH₂ | NHCHPh(4-MePh) |
| 1-1190 | Pyr | CH₂CH₂ | NHCHPh(4-MeOPh) |
| 1-1191 | Pyr | CH₂CH₂ | NHCHPh(4-FPh) |
| 1-1192 | Pyr | CH₂CH₂ | NHCHPh(4-ClPh) |
| 1-1193 | Pyr | CH₂CH₂ | NH(1-Me-2-PhEt) |
| 1-1194 | Pyr | CH₂CH₂ | NH[1-Me-2-(4-MePh)Et] |
| 1-1195 | Pyr | CH₂CH₂ | NH[1-Me-2-(4-MeOPh)Et] |
| 1-1196 | Pyr | CH₂CH₂ | NH[1-Me-2-(4-FPh)Et] |
| 1-1197 | Pyr | CH₂CH₂ | NH(1-Bz-2-PhEt) |
| 1-1198 | Pyr | CH₂CH₂ | NHcPr |
| 1-1199 | Pyr | CH₂CH₂ | NHcBu |
| 1-1200 | Pyr | CH₂CH₂ | NHcPn |
| 1-1201 | Pyr | CH₂CH₂ | NHcHx |
| 1-1202 | Pyr | CH₂CH₂ | NHcHp |
| 1-1203 | Pyr | CH₂CH₂ | NHcOc |
| 1-1204 | NMe₂ | CH₂CH₂ | NHiPr |
| 1-1205 | NMe₂ | CH₂CH₂ | NHsBu |
| 1-1206 | NMe₂ | CH₂CH₂ | NH(1-MeBu) |
| 1-1207 | NMe₂ | CH₂CH₂ | NH(1-MePn) |
| 1-1208 | NMe₂ | CH₂CH₂ | NH(1-MeHx) |
| 1-1209 | NMe₂ | CH₂CH₂ | NH(1-MeHp) |
| 1-1210 | NMe₂ | CH₂CH₂ | NH(1-EtPr) |
| 1-1211 | NMe₂ | CH₂CH₂ | NH(1-EtBu) |
| 1-1212 | NMe₂ | CH₂CH₂ | NH(1-EtPn) |
| 1-1213 | NMe₂ | CH₂CH₂ | NH(1-PrBu) |
| 1-1214 | NMe₂ | CH₂CH₂ | NH(1-BuPn) |
| 1-1215 | NMe₂ | CH₂CH₂ | NH(1-PhEt) |
| 1-1216 | NMe₂ | CH₂CH₂ | NH(1-NaPhEt) |

TABLE 1-continued

| Cpd. No. | R¹ | A | R² |
|---|---|---|---|
| 1-1217 | NMe₂ | CH₂CH₂ | NH(1-PhPr) |
| 1-1218 | NMe₂ | CH₂CH₂ | NHCHPh₂ |
| 1-1219 | NMe₂ | CH₂CH₂ | NHCHPh(4-MePh) |
| 1-1220 | NMe₂ | CH₂CH₂ | NHCHPh(4-MeOPh) |
| 1-1221 | NMe₂ | CH₂CH₂ | NHCHPh(4-FPh) |
| 1-1222 | NMe₂ | CH₂CH₂ | NHCHPh(4-ClPh) |
| 1-1223 | NMe₂ | CH₂CH₂ | NH(1-Me-2-PhEt) |
| 1-1224 | NMe₂ | CH₂CH₂ | NH[1-Me-2-(4-MePh)Et] |
| 1-1225 | NMe₂ | CH₂CH₂ | NH[1-Me-2-(4-MeOPh)Et] |
| 1-1226 | NMe₂ | CH₂CH₂ | NH[1-Me-2-(4-FPh)Et] |
| 1-1227 | NMe₂ | CH₂CH₂ | NH(1-Bz-2-PhEt) |
| 1-1228 | NMe₂ | CH₂CH₂ | NHcPr |
| 1-1229 | NMe₂ | CH₂CH₂ | NHcBu |
| 1-1230 | NMe₂ | CH₂CH₂ | NHcPn |
| 1-1231 | NMe₂ | CH₂CH₂ | NHcHx |
| 1-1232 | NMe₂ | CH₂CH₂ | NHcHp |
| 1-1233 | NMe₂ | CH₂CH₂ | NHcOc |
| 1-1234 | Aze | CH₂CH₂ | NHiPr |
| 1-1235 | Aze | CH₂CH₂ | NHsBu |
| 1-1236 | Aze | CH₂CH₂ | NH(1-MeBu) |
| 1-1237 | Aze | CH₂CH₂ | NH(1-MePn) |
| 1-1238 | Aze | CH₂CH₂ | NH(1-MeHx) |
| 1-1239 | Aze | CH₂CH₂ | NH(1-MeHp) |
| 1-1240 | Aze | CH₂CH₂ | NH(1-EtPr) |
| 1-1241 | Aze | CH₂CH₂ | NH(1-EtBu) |
| 1-1242 | Aze | CH₂CH₂ | NH(1-EtPn) |
| 1-1243 | Aze | CH₂CH₂ | NH(1,2-diMePr) |
| 1-1244 | Aze | CH₂CH₂ | NH(1-PhEt) |
| 1-1245 | Aze | CH₂CH₂ | NHCHPh₂ |
| 1-1246 | Aze | CH₂CH₂ | NH(1-Me-2-PhEt) |
| 1-1247 | Aze | CH₂CH₂ | NH(1,2-diPhEt) |
| 1-1248 | Aze | CH₂CH₂ | NHcPr |
| 1-1249 | Aze | CH₂CH₂ | NHcBu |
| 1-1250 | Aze | CH₂CH₂ | NHcPn |
| 1-1251 | Aze | CH₂CH₂ | NHcHx |
| 1-1252 | Aze | CH₂CH₂ | NHcHp |
| 1-1253 | Aze | CH₂CH₂ | NHcOc |
| 1-1254 | Azi | CH₂CH₂ | NHiPr |
| 1-1255 | Azi | CH₂CH₂ | NHsBu |
| 1-1256 | Azi | CH₂CH₂ | NH(1-MeBu) |
| 1-1257 | Azi | CH₂CH₂ | NH(1-MePn) |
| 1-1258 | Azi | CH₂CH₂ | NH(1-MeHx) |
| 1-1259 | Azi | CH₂CH₂ | NH(1-MeHp) |
| 1-1260 | Azi | CH₂CH₂ | NH(1-EtPr) |
| 1-1261 | Azi | CH₂CH₂ | NH(1-EtBu) |
| 1-1262 | Azi | CH₂CH₂ | NH(1-EtPn) |
| 1-1263 | Azi | CH₂CH₂ | NH(1,2-diMePr) |
| 1-1264 | Azi | CH₂CH₂ | NH(1-PhEt) |
| 1-1265 | Azi | CH₂CH₂ | NHCHPh₂ |
| 1-1266 | Azi | CH₂CH₂ | NH(1-Me-2-PhEt) |
| 1-1267 | Azi | CH₂CH₂ | NH(1,2-diPhEt) |
| 1-1268 | Azi | CH₂CH₂ | NHcPr |
| 1-1269 | Azi | CH₂CH₂ | NHcBu |
| 1-1270 | Azi | CH₂CH₂ | NHcPn |
| 1-1271 | Azi | CH₂CH₂ | NHcHx |
| 1-1272 | Azi | CH₂CH₂ | NHcHp |
| 1-1273 | Azi | CH₂CH₂ | NHcOc |
| 1-1274 | Pip | CH₂ | NHiPr |
| 1-1275 | Pip | CH₂ | NHsBu |
| 1-1276 | Pip | CH₂ | NH(1-MeBu) |
| 1-1277 | Pip | CH₂ | NH(1,2-diMePr) |
| 1-1278 | Pip | CH₂ | NH(1-MePn) |
| 1-1279 | Pip | CH₂ | NH(1,3-diMeBu) |
| 1-1280 | Pip | CH₂ | NH(1,2-diMeBu) |
| 1-1281 | Pip | CH₂ | NH(1-MeHx) |
| 1-1282 | Pip | CH₂ | NH(1,4-diMePn) |
| 1-1283 | Pip | CH₂ | NH(1-MeHp) |
| 1-1284 | Pip | CH₂ | NH(1,5-diMeHx) |
| 1-1285 | Pip | CH₂ | NH(1-EtPr) |
| 1-1286 | Pip | CH₂ | NH(1-EtBu) |
| 1-1287 | Pip | CH₂ | NH.(1-Et-2-MePr) |
| 1-1288 | Pip | CH₂ | NH(1-EtPn) |
| 1-1289 | Pip | CH₂ | NH(1-Et-3-MeBu) |
| 1-1290 | Pip | CH₂ | NH(1-EtHx) |
| 1-1291 | Pip | CH₂ | NH(1-EtHp) |
| 1-1292 | Pip | CH₂ | NH(1-PrBu) |
| 1-1293 | Pip | CH₂ | NH(1-iPrBu) |
| 1-1294 | Pip | CH₂ | NH(1-PrPn) |
| 1-1295 | Pip | CH₂ | NH(1-PrHx) |
| 1-1296 | Pip | CH₂ | NH(1-PrHp) |
| 1-1297 | Pip | CH₂ | NH(1-BuPn) |
| 1-1298 | Pip | CH₂ | NH(1-PnHx) |
| 1-1299 | Pip | CH₂ | NH(1-HxHp) |
| 1-1300 | Pip | CH₂ | NH(1-PhEt) |
| 1-1301 | Pip | CH₂ | NH(1-NaPhEt) |
| 1-1302 | Pip | CH₂ | NH(1-PhPr) |
| 1-1303 | Pip | CH₂ | NH(1-PhBu) |
| 1-1304 | Pip | CH₂ | NHCHPh₂ |
| 1-1305 | Pip | CH₂ | NHCHPh(4-MePh) |
| 1-1306 | Pip | CH₂ | NHCHPh(4-MeOPh) |
| 1-1307 | Pip | CH₂ | NHCHPh(4-FPh) |
| 1-1308 | Pip | CH₂ | NHCHPh(4-ClPh) |
| 1-1309 | Pip | CH₂ | NH(1-Me-2-PhEt) |
| 1-1310 | Pip | CH₂ | NH(1-Me-3-PhPr) |
| 1-1311 | Pip | CH₂ | NH(1-Et-2-PhEt) |
| 1-1312 | Pip | CH₂ | NH[1-Me-2-(4-MePh)Et] |
| 1-1313 | Pip | CH₂ | NH[1-Me-2-(4-MeOPh)Et] |
| 1-1314 | Pip | CH₂ | NH[1-Me-2-(4-FPh)Et] |
| 1-1315 | Pip | CH₂ | NH[1-Me-2-(4-ClPh)Et] |
| 1-1316 | Pip | CH₂ | NH(1,2-diPhEt) |
| 1-1317 | Pip | CH₂ | NH(1-Bz-2-PhEt) |
| 1-1318 | Pip | CH₂ | NHcPr |
| 1-1319 | Pip | CH₂ | NHcBu |
| 1-1320 | Pip | CH₂ | NHcPn |
| 1-1321 | Pip | CH₂ | NHcHx |
| 1-1322 | Pip | CH₂ | NHcHp |
| 1-1323 | Pip | CH₂ | NHcOc |
| 1-1324 | Pip | (CH₂)₃ | NHiPr |
| 1-1325 | Pip | (CH₂)₃ | NHsBu |
| 1-1326 | Pip | (CH₂)₃ | NH(1-MeBu) |
| 1-1327 | Pip | (CH₂)₃ | NH(1-MePn) |
| 1-1328 | Pip | (CH₂)₃ | NH(1-MeHx) |
| 1-1329 | Pip | (CH₂)₃ | NH(1-MeHp) |
| 1-1330 | Pip | (CH₂)₃ | NH(1-EtPr) |
| 1-1331 | Pip | (CH₂)₃ | NH(1-EtBu) |
| 1-1332 | Pip | (CH₂)₃ | NH(1-EtPn) |
| 1-1333 | Pip | (CH₂)₃ | NH(1-PrBu) |
| 1-1334 | Pip | (CH₂)₃ | NH(1-BuPn) |
| 1-1335 | Pip | (CH₂)₃ | NH(1-PhEt) |
| 1-1336 | Pip | (CH₂)₃ | NH(1-NaPhEt) |
| 1-1337 | Pip | (CH₂)₃ | NH(1-PhPr) |
| 1-1338 | Pip | (CH₂)₃ | NHCHPh₂ |
| 1-1339 | Pip | (CH₂)₃ | NHCHPh(4-MePh) |
| 1-1340 | Pip | (CH₂)₃ | NHCHPh(4-MeOPh) |
| 1-1341 | Pip | (CH₂)₃ | NHCHPh(4-FPh) |
| 1-1342 | Pip | (CH₂)₃ | NHCHPh(4-ClPh) |
| 1-1343 | Pip | (CH₂)₃ | NH(1-Me-2-PhEt) |
| 1-1344 | Pip | (CH₂)₃ | NH[1-Me-2-(4-MePh)Et] |
| 1-1345 | Pip | (CH₂)₃ | NH[1-Me-2-(4-MeOPh)Et] |
| 1-1346 | Pip | (CH₂)₃ | NH[1-Me-2-(4-FPh)Et] |
| 1-1347 | Pip | (CH₂)₃ | NH(1-Bz-2-PhEt) |
| 1-1348 | Pip | (CH₂)₃ | NHcPr |
| 1-1349 | Pip | (CH₂)₃ | NHcBu |
| 1-1350 | Pip | (CH₂)₃ | NHcPn |
| 1-1351 | Pip | (CH₂)₃ | NHcHx |
| 1-1352 | Pip | (CH₂)₃ | NHcHp |
| 1-1353 | Pip | (CH₂)₃ | NHcOc |

TABLE 2

| Cpd. No. | R¹ | A | B | m | R⁵ |
|---|---|---|---|---|---|
| 2-1 | Pip | CH=CH | CH₂ | 0 | CH₂OH |
| 2-2 | Pip | CH=CH | CH₂ | 0 | 2-HOEt |
| 2-3 | Pip | CH=CH | CH₂ | 0 | 2-FoOEt |
| 2-4 | Pip | CH=CH | CH₂ | 0 | 2-AcOEt |
| 2-5 | Pip | CH=CH | CH₂ | 0 | 2-PrnOEt |
| 2-6 | Pip | CH=CH | CH₂ | 0 | 2-ByrOEt |
| 2-7 | Pip | CH=CH | CH₂ | 0 | 2-iByrOEt |
| 2-8 | Pip | CH=CH | CH₂ | 0 | 2-ValOEt |
| 2-9 | Pip | CH=CH | CH₂ | 0 | 2-iValOEt |
| 2-10 | Pip | CH=CH | CH₂ | 0 | 2-(PhAcO)Et |
| 2-11 | Pip | CH=CH | CH₂ | 0 | 2-(HOOC.AcO)Et |
| 2-12 | Pip | CH=CH | CH₂ | 0 | 2-(3-HOOC.PrnO)Et |
| 2-13 | Pip | CH=CH | CH₂ | 0 | 2-(3-Mec.PrnO)Et |
| 2-14 | Pip | CH=CH | CH₂ | 0 | 2-(3-Etc.PrnO)Et |
| 2-15 | Pip | CH=CH | CH₂ | 0 | 2-(3-Prc.PrnO)Et |
| 2-16 | Pip | CH=CH | CH₂ | 0 | 2-(3-Phc.PrnO)Et |
| 2-17 | Pip | CH=CH | CH₂ | 0 | 2-[3-(4-MePhcO)PrnO]Et |
| 2-18 | Pip | CH=CH | CH₂ | 0 | 2-(3-PhPrnO)Et |
| 2-19 | Pip | CH=CH | CH₂ | 0 | 2-(3-PhPrnO)Et |
| 2-20 | Pip | CH=CH | CH₂ | 0 | 2-BozOEt |
| 2-21 | Pip | CH=CH | CH₂ | 0 | 2-(4-MeBozO)Et |
| 2-22 | Pip | CH=CH | CH₂ | 0 | 2-(4-MeOBozO)Et |
| 2-23 | Pip | CH=CH | CH₂ | 0 | 2-(4-FBozO)Et |
| 2-24 | Pip | CH=CH | CH₂ | 0 | 2-(4-ClBozO)Et |
| 2-25 | Pip | CH=CH | CH₂ | 0 | 2-(cPrCOO)Et |
| 2-26 | Pip | CH=CH | CH₂ | 0 | 2-(cBuCOO)Et |
| 2-27 | Pip | CH=CH | CH₂ | 0 | 2-(cPnCOO)Et |
| 2-28 | Pip | CH=CH | CH₂ | 0 | 2-(cHxCOO)Et |
| 2-29 | Pip | CH=CH | CH₂ | 0 | 2-HOPr |
| 2-30 | Pip | CH=CH | CH₂ | 0 | 2-FoOPr |
| 2-31 | Pip | CH=CH | CH₂ | 0 | 2-AcOPr |
| 2-32 | Pip | CH=CH | CH₂ | 0 | 2-PrnOPr |
| 2-33 | Pip | CH=CH | CH₂ | 0 | 2-(3-HOOC.PrnO)Pr |
| 2-34 | Pip | CH=CH | CH₂ | 0 | 2-(3-Mec.PrnO)Pr |
| 2-35 | Pip | CH=CH | CH₂ | 0 | 2-(3-Etc.PrnO)Pr |
| 2-36 | Pip | CH=CH | CH₂ | 0 | 2-(3-Phc.PrnO)Et |
| 2-37 | Pip | CH=CH | CH₂ | 0 | 2-[3-(4-MePhcO)PrnO]Et |
| 2-38 | Pip | CH=CH | CH₂ | 0 | 2-(PhAcO)Pr |
| 2-39 | Pip | CH=CH | CH₂ | 0 | 2-BozOPr |
| 2-40 | Pip | CH=CH | CH₂ | 0 | 2-(cPnCOO)Pr |
| 2-41 | Pip | CH=CH | CH₂ | 0 | 2-(cHxCOO)Pr |
| 2-42 | Pip | CH=CH | CH₂ | 0 | 3-HOPr |
| 2-43 | Pip | CH=CH | CH₂ | 0 | 3-FoOPr |
| 2-44 | Pip | CH=CH | CH₂ | 0 | 3-AcOPr |
| 2-45 | Pip | CH=CH | CH₂ | 0 | 3-PrnOPr |
| 2-46 | Pip | CH=CH | CH₂ | 0 | 3-(3-HOOC.PrnO)Pr |
| 2-47 | Pip | CH=CH | CH₂ | 0 | 3-(3-Mec.PrnO)Pr |
| 2-48 | Pip | CH=CH | CH₂ | 0 | 3-(3-Etc.PrnO)Pr |
| 2-49 | Pip | CH=CH | CH₂ | 0 | 3-BozOPr |
| 2-50 | Pip | CH=CH | CH₂ | 0 | 3-(cPnCOO)Pr |
| 2-51 | Pip | CH=CH | CH₂ | 0 | 3-(cHxCOO)Pr |
| 2-52 | Pip | CH=CH | CH₂ | 0 | 2-HOBu |
| 2-53 | Pip | CH=CH | CH₂ | 0 | 2-AcOBu |
| 2-54 | Pip | CH=CH | CH₂ | 0 | 2-(3-HOOC.PrnO)Bu |
| 2-55 | Pip | CH=CH | CH₂ | 0 | 2-BozOBu |
| 2-56 | Pip | CH=CH | CH₂ | 0 | 2-(cHxCOO)Bu |
| 2-57 | Pip | CH=CH | CH₂CH₂ | 0 | 2-HOEt |
| 2-58 | Pip | CH=CH | CH₂CH₂ | 0 | 2-FoOEt |
| 2-59 | Pip | CH=CH | CH₂CH₂ | 0 | 2-AcOEt |
| 2-60 | Pip | CH=CH | CH₂CH₂ | 0 | 2-PrnOEt |
| 2-61 | Pip | CH=CH | CH₂CH₂ | 0 | 2-ValOEt |
| 2-62 | Pip | CH=CH | CH₂CH₂ | 0 | 2-(PhAcO)Et |
| 2-63 | Pip | CH=CH | CH₂CH₂ | 0 | 2-(3-HOOC.PrnO)Et |
| 2-64 | Pip | CH=CH | CH₂CH₂ | 0 | 2-(3-Mec.Prno)Et |
| 2-65 | Pip | CH=CH | CH₂CH₂ | 0 | 2-(3-Etc.PrnO)Et |
| 2-66 | Pip | CH=CH | CH₂CH₂ | 0 | 2-(3-PhPrnO)Et |
| 2-67 | Pip | CH=CH | CH₂CH₂ | 0 | 2-BozOEt |
| 2-68 | Pip | CH=CH | CH₂CH₂ | 0 | 2-(4-MeBozO)Et |
| 2-69 | Pip | CH=CH | CH₂CH₂ | 0 | 2-(4-FBozO)Et |
| 2-70 | Pip | CH=CH | CH₂CH₂ | 0 | 2-(4-ClBozO)Et |
| 2-71 | Pip | CH=CH | CH₂CH₂ | 0 | 2-(cPrCOO)Et |
| 2-72 | Pip | CH=CH | CH₂CH₂ | 0 | 2-(cBuCOO)Et |
| 2-73 | Pip | CH=CH | CH₂CH₂ | 0 | 2-(cPnCOO)Et |
| 2-74 | Pip | CH=CH | CH₂CH₂ | 0 | 2-(cHxCOO)Et |
| 2-75 | Pip | CH=CH | CH₂CH₂ | 0 | 2-HOPr |
| 2-76 | Pip | CH=CH | CH₂CH₂ | 0 | 2-FoOPr |

TABLE 2-continued

| Cpd. No. | R¹ | A | B | m | R⁵ |
|---|---|---|---|---|---|
| 2-77 | Pip | CH=CH | CH₂CH₂ | 0 | 2-AcOPr |
| 2-78 | Pip | CH=CH | CH₂CH₂ | 0 | 2-PrnOPr |
| 2-79 | Pip | CH=CH | CH₂CH₂ | 0 | 2-(3-HOOC.PrnO)Pr |
| 2-80 | Pip | CH=CH | CH₂CH₂ | 0 | 2-(3-Mec.Prno)Pr |
| 2-81 | Pip | CH=CH | CH₂CH₂ | 0 | 2-BozOPr |
| 2-82 | Pip | CH=CH | CH₂CH₂ | 0 | 2-(cPnCOO)Pr |
| 2-83 | Pip | CH=CH | CH₂CH₂ | 0 | 2-(cHxCOO)Pr |
| 2-84 | Pip | CH=CH | CH₂CH₂ | 0 | 3-HOPr |
| 2-85 | Pip | CH=CH | CH₂CH₂ | 0 | 3-AcOPr |
| 2-86 | Pip | CH=CH | CH₂CH₂ | 0 | 3-PrnOPr |
| 2-87 | Pip | CH=CH | CH₂CH₂ | 0 | 3-(3-HOOC.PrnO)Pr |
| 2-88 | Pip | CH=CH | CH₂CH₂ | 0 | 3-BozOPr |
| 2-89 | Pip | CH=CH | CH₂CH₂ | 0 | 3-(cPnCOO)Pr |
| 2-90 | Pip | CH=CH | CH₂CH₂ | 0 | 3-(cHxCOO)Pr |
| 2-91 | Pip | CH=CH | CH₂CH₂ | 0 | 2-HOBu |
| 2-92 | Pip | CH=CH | CH₂CH₂ | 0 | 2-AcOBu |
| 2-93 | Pip | CH=CH | CH₂CH₂ | 0 | 2-(3-HOOC.PrnO)Bu |
| 2-94 | Pip | CH=CH | CH₂CH₂ | 0 | 2-BozOBu |
| 2-95 | Pip | CH=CH | CH₂CH₂ | 0 | 2-(cHxCOO)Bu |
| 2-96 | Pip | CH=CH | (CH₂)₃ | 0 | 2-HOEt |
| 2-97 | Pip | CH=CH | (CH₂)₃ | 0 | 2-FoOEt |
| 2-98 | Pip | CH=CH | (CH₂)₃ | 0 | 2-AcOEt |
| 2-99 | Pip | CH=CH | (CH₂)₃ | 0 | 2-PrnOEt |
| 2-100 | Pip | CH=CH | (CH₂)₃ | 0 | 2-ByrOEt |
| 2-101 | Pip | CH=CH | (CH₂)₃ | 0 | 2-iByrOEt |
| 2-102 | Pip | CH=CH | (CH₂)₃ | 0 | 2-ValOEt |
| 2-103 | Pip | CH=CH | (CH₂)₃ | 0 | 2-(3-HOOC.PrnO)Et |
| 2-104 | Pip | CH=CH | (CH₂)₃ | 0 | 2-(3-Mec.PrnO)Et |
| 2-105 | Pip | CH=CH | (CH₂)₃ | 0 | 2-(3-Etc.PrnO)Et |
| 2-106 | Pip | CH=CH | (CH₂)₃ | 0 | 2-(PhAcO)Et |
| 2-107 | Pip | CH=CH | (CH₂)₃ | 0 | 2-BozOEt |
| 2-108 | Pip | CH=CH | (CH₂)₃ | 0 | 2-(4-MeBozO)Et |
| 2-109 | Pip | CH=CH | (CH₂)₃ | 0 | 2-(4-MeOBozO)Et |
| 2-110 | Pip | CH=CH | (CH₂)₃ | 0 | 2-(4-FBozO)Et |
| 2-111 | Pip | CH=CH | (CH₂)₃ | 0 | 2-(4-ClBozO)Et |
| 2-112 | Pip | CH=CH | (CH₂)₃ | 0 | 2-(cPrCOO)Et |
| 2-113 | Pip | CH=CH | (CH₂)₃ | 0 | 2-(cBuCOO)Et |
| 2-114 | Pip | CH=CH | (CH₂)₃ | 0 | 2-(cPnCOO)Et |
| 2-115 | Pip | CH=CH | (CH₂)₃ | 0 | 2-(cHxCOO)Et |
| 2-116 | Pip | CH=CH | (CH₂)₃ | 0 | 2-HOPr |
| 2-117 | Pip | CH=CH | (CH₂)₃ | 0 | 2-AcOPr |
| 2-118 | Pip | CH=CH | (CH₂)₃ | 0 | 2-PrnOPr |
| 2-119 | Pip | CH=CH | (CH₂)₃ | 0 | 2-(3-HOOC.PrnO)Pr |
| 2-120 | Pip | CH=CH | (CH₂)₃ | 0 | 2-(3-Etc.PrnO)Pr |
| 2-121 | Pip | CH=CH | (CH₂)₃ | 0 | 2-BozOPr |
| 2-122 | Pip | CH=CH | (CH₂)₃ | 0 | 2-(cHxCOO)Pr |
| 2-123 | Pip | CH=CH | (CH₂)₃ | 0 | 3-HOPr |
| 2-124 | Pip | CH=CH | (CH₂)₃ | 0 | 3-AcOPr |
| 2-125 | Pip | CH=CH | (CH₂)₃ | 0 | 3-(3-HOOC.PrnO)Pr |
| 2-126 | Pip | CH=CH | (CH₂)₃ | 0 | 3-(3-Mec.PrnO)Pr |
| 2-127 | Pip | CH=CH | (CH₂)₃ | 0 | 3-BozOPr |
| 2-128 | Pip | CH=CH | (CH₂)₃ | 0 | 3-(cHxCOO)Pr |
| 2-129 | Pip | CH=CH | (CH₂)₃ | 0 | 2-HOBu |
| 2-130 | Pip | CH=CH | (CH₂)₃ | 0 | 2-AcOBu |
| 2-131 | Pip | CH=CH | (CH₂)₃ | 0 | 2-(3-HOOC.PrnO)Bu |
| 2-132 | Pip | CH=CH | (CH₂)₃ | 0 | 2-BozOBu |
| 2-133 | Pip | CH=CH | (CH₂)₃ | 0 | 2-(cHxCOO)Bu |
| 2-134 | Pip | CH=CH | (CH₂)₄ | 0 | 2-HOEt |
| 2-135 | Pip | CH=CH | (CH₂)₄ | 0 | 2-FoOEt |
| 2-136 | Pip | CH=CH | (CH₂)₄ | 0 | 2-AcOEt |
| 2-137 | Pip | CH=CH | (CH₂)₄ | 0 | 2-PrnOEt |
| 2-138 | Pip | CH=CH | (CH₂)₄ | 0 | 2-(3-HOOC.PrnO)Et |
| 2-139 | Pip | CH=CH | (CH₂)₄ | 0 | 2-(3-Mec.PrnO)Et |
| 2-140 | Pip | CH=CH | (CH₂)₄ | 0 | 2-BozOEt |
| 2-141 | Pip | CH=CH | (CH₂)₄ | 0 | 2-(cHxCOO)Et |
| 2-142 | Pip | CH=CH | (CH₂)₄ | 0 | 2-HOPr |
| 2-143 | Pip | CH=CH | (CH₂)₄ | 0 | 2-AcOPr |
| 2-144 | Pip | CH=CH | (CH₂)₄ | 0 | 2-(3-HOOC.PrnO)Pr |
| 2-145 | Pip | CH=CH | (CH₂)₄ | 0 | 2-BozOPr |
| 2-146 | Pip | CH=CH | (CH₂)₄ | 0 | 2-(cHxCOO)Pr |
| 2-147 | Pip | CH=CH | (CH₂)₄ | 0 | 3-HOPr |
| 2-148 | Pip | CH=CH | (CH₂)₄ | 0 | 3-AcOPr |
| 2-149 | Pip | CH=CH | (CH₂)₄ | 0 | 3-(3-HOOC.PrnO)Pr |
| 2-150 | Pip | CH=CH | (CH₂)₄ | 0 | 3-BozOPr |
| 2-151 | Pip | CH=CH | (CH₂)₄ | 0 | 3-(cHxCOO)Pr |
| 2-152 | Pip | CH=CH | (CH₂)₄ | 0 | 2-HOBu |

TABLE 2-continued

| Cpd. No. | R¹ | A | B | m | R⁵ |
|---|---|---|---|---|---|
| 2-153 | Pip | CH=CH | (CH₂)₄ | 0 | 2-AcOBu |
| 2-154 | Pip | CH=CH | (CH₂)₄ | 0 | 2-(3-HOOC.PrnO)Bu |
| 2-155 | Pip | CH=CH | (CH₂)₄ | 0 | 2-(cHxCOO)Bu |
| 2-156 | Pip | CH=CH | CH₂CH(Me)CH₂ | 0 | 2-HOEt |
| 2-157 | Pip | CH=CH | CH₂CH(Me)CH₂ | 0 | 2-AcOEt |
| 2-158 | Pip | CH=CH | CH₂CH(Me)CH₂ | 0 | 2-(3-HOOC.PrnO)Et |
| 2-159 | Pip | CH=CH | CH₂CH(Me)CH₂ | 0 | 2-BozOEt |
| 2-160 | Pip | CH=CH | CH₂CH(Me)CH₂ | 0 | 2-(cHxCOO)Et |
| 2-161 | Pip | CH=CH | CH₂CH(Me)CH₂ | 0 | 2-HOPr |
| 2-162 | Pip | CH=CH | CH₂CH(Me)CH₂ | 0 | 2-AcOPr |
| 2-163 | Pip | CH=CH | CH₂CH(Me)CH₂ | 0 | 2-BozOPr |
| 2-164 | Pip | CH=CH | CH₂CH(Me)CH₂ | 0 | 2-(cHxCOO)Pr |
| 2-165 | Pip | CH=CH | CH₂CH(Me)CH₂ | 0 | 3-HOPr |
| 2-166 | Pip | CH=CH | CH₂CH(Me)CH₂ | 0 | 3-AcOPr |
| 2-167 | Pip | CH=CH | CH₂CH(Me)CH₂ | 0 | 3-(3-HOOC.PrnO)Pr |
| 2-168 | Pip | CH=CH | CH₂CH(Me)CH₂ | 0 | 3-BozOPr |
| 2-169 | Pip | CH=CH | CH₂CH(Me)CH₂ | 0 | 3-(cHxCOO)Pr |
| 2-170 | Pip | CH=CH | CH₂CH(Me)CH₂ | 0 | 2-HOBu |
| 2-171 | Pip | CH=CH | CH₂CH(Me)CH₂ | 0 | 2-AcOBu |
| 2-172 | Pip | CH=CH | CH₂CH(Me)CH₂ | 0 | 2-(3-Etc.PrnO)Bu |
| 2-173 | Pip | CH=CH | CH₂CH(Me)CH₂ | 0 | 2-(cHxCOO)Bu |
| 2-174 | Pip | CH=CH | (CH₂)₅ | 0 | 2-HOEt |
| 2-175 | Pip | CH=CH | (CH₂)₅ | 0 | 2-AcOEt |
| 2-176 | Pip | CH=CH | (CH₂)₅ | 0 | 2-(3-HOOC.PrnO)Et |
| 2-177 | Pip | CH=CH | (CH₂)₅ | 0 | 2-BozOEt |
| 2-178 | Pip | CH=CH | (CH₂)₅ | 0 | 2-(cHxCOO)Et |
| 2-179 | Pip | CH=CH | (CH₂)₅ | 0 | 2-HOPr |
| 2-180 | Pip | CH=CH | (CH₂)₅ | 0 | 2-AcOPr |
| 2-181 | Pip | CH=CH | (CH₂)₅ | 0 | 2-(3-HOOC.PrnO)Pr |
| 2-182 | Pip | CH=CH | (CH₂)₅ | 0 | 2-BozOPr |
| 2-183 | Pip | CH=CH | (CH₂)₅ | 0 | 2-(cHxCOO)Pr |
| 2-184 | Pip | CH=CH | (CH₂)₅ | 0 | 3-HOPr |
| 2-185 | Pip | CH=CH | (CH₂)₅ | 0 | 3-AcOPr |
| 2-186 | Pip | CH=CH | (CH₂)₅ | 0 | 3-(3-HOOC.PrnO)Pr |
| 2-187 | Pip | CH=CH | (CH₂)₅ | 0 | 3-BozOPr |
| 2-188 | Pip | CH=CH | (CH₂)₅ | 0 | 3-(cHxCOO)Pr |
| 2-189 | Pip | CH=CH | (CH₂)₅ | 0 | 2-HOBu |
| 2-190 | Pip | CH=CH | (CH₂)₅ | 0 | 2-AcOBu |
| 2-191 | Pip | CH=CH | (CH₂)₅ | 0 | 2-(3-HOOC.PrnO)Bu |
| 2-192 | Pip | CH=CH | (CH₂)₅ | 0 | 2-(cHxCOO)Bu |
| 2-193 | Pip | CH=CH | (CH₂)₆ | 0 | 2-HOEt |
| 2-194 | Pip | CH=CH | (CH₂)₆ | 0 | 2-AcOEt |
| 2-195 | Pip | CH=CH | (CH₂)₆ | 0 | 2-(3-HOOC.PrnO)Et |
| 2-196 | Pip | CH=CH | (CH₂)₆ | 0 | 2-(cHxCOO)Et |
| 2-197 | Pip | CH=CH | (CH₂)₆ | 0 | 2-HOPr |
| 2-198 | Pip | CH=CH | (CH₂)₆ | 0 | 2-AcOPr |
| 2-199 | Pip | CH=CH | (CH₂)₆ | 0 | 2-(3-HOOC.PrnO)Pr |
| 2-200 | Pip | CH=CH | (CH₂)₆ | 0 | 2-(cHxCOO)Pr |
| 2-201 | Pip | CH=CH | (CH₂)₆ | 0 | 3-HOPr |
| 2-202 | Pip | CH=CH | (CH₂)₆ | 0 | 3-AcOPr |
| 2-203 | Pip | CH=CH | (CH₂)₆ | 0 | 3-(3-HOOC.PrnO)Pr |
| 2-204 | Pip | CH=CH | (CH₂)₆ | 0 | 3-(cHxCOO)Pr |
| 2-205 | Pip | CH=CH | (CH₂)₆ | 0 | 2-HOBu |
| 2-206 | Pip | CH=CH | (CH₂)₆ | 0 | 2-AcOBu |
| 2-207 | Pip | CH=CH | (CH₂)₆ | 0 | 2-(3-HOOC.PrnO)Bu |
| 2-208 | Pip | CH=CH | (CH₂)₆ | 0 | 2-(cHxCOO)Bu |
| 2-209 | Pyr | CH=CH | CH₂ | 0 | 2-HOEt |
| 2-210 | Pyr | CH=CH | CH₂ | 0 | 2-FoOEt |
| 2-211 | Pyr | CH=CH | CH₂ | 0 | 2-AcOEt |
| 2-212 | Pyr | CH=CH | CH₂ | 0 | 2-PrnOEt |
| 2-213 | Pyr | CH=CH | CH₂ | 0 | 2-(3-HOOC.PrnO)Et |
| 2-214 | Pyr | CH=CH | CH₂ | 0 | 2-(3-Mec.PrnO)Et |
| 2-215 | Pyr | CH=CH | CH₂ | 0 | 2-(3-Etc.PrnO)Et |
| 2-216 | Pyr | CH=CH | CH₂ | 0 | 2-BozOEt |
| 2-217 | Pyr | CH=CH | CH₂ | 0 | 2-(cPnCOO)Et |
| 2-218 | Pyr | CH=CH | CH₂ | 0 | 2-(cHxCOO)Et |
| 2-219 | Pyr | CH=CH | CH₂ | 0 | 2-HOPr |
| 2-220 | Pyr | CH=CH | CH₂ | 0 | 2-AcOPr |
| 2-221 | Pyr | CH=CH | CH₂ | 0 | 2-(3-HOOC.PrnO)Pr |
| 2-222 | Pyr | CH=CH | CH₂ | 0 | 2-BozOPr |
| 2-223 | Pyr | CH=CH | CH₂ | 0 | 2-(cHxCOO)Pr |
| 2-224 | Pyr | CH=CH | CH₂ | 0 | 3-HOPr |
| 2-225 | Pyr | CH=CH | CH₂ | 0 | 3-FoOPr |
| 2-226 | Pyr | CH=CH | CH₂ | 0 | 3-AcOPr |
| 2-227 | Pyr | CH=CH | CH₂ | 0 | 3-(3-HOOC.PrnO)Pr |
| 2-228 | Pyr | CH=CH | CH₂ | 0 | 3-(3-Mec.PrnO)Pr |

TABLE 2-continued

| Cpd. No. | R¹ | A | B | m | R⁵ |
|---|---|---|---|---|---|
| 2-229 | Pyr | CH=CH | CH₂ | 0 | 3-BozOPr |
| 2-230 | Pyr | CH=CH | CH₂ | 0 | 3-(cHxCOO)Pr |
| 2-231 | Pyr | CH=CH | CH₂ | 0 | 2-HOBu |
| 2-232 | Pyr | CH=CH | CH₂ | 0 | 2-AcOBu |
| 2-233 | Pyr | CH=CH | CH₂CH₂ | 0 | 2-HOEt |
| 2-234 | Pyr | CH=CH | CH₂CH₂ | 0 | 2-AcOEt |
| 2-235 | Pyr | CH=CH | CH₂CH₂ | 0 | 2-(3-HOOC.PrnO)Et |
| 2-236 | Pyr | CH=CH | CH₂CH₂ | 0 | 2-(3-Mec.PrnO)Et |
| 2-237 | Pyr | CH=CH | CH₂CH₂ | 0 | 2-BozOEt |
| 2-238 | Pyr | CH=CH | CH₂CH₂ | 0 | 2-(cPnCOO)Et |
| 2-239 | Pyr | CH=CH | CH₂CH₂ | 0 | 2-(cHxCOO)Et |
| 2-240 | Pyr | CH=CH | CH₂CH₂ | 0 | 2-HOPr |
| 2-241 | Pyr | CH=CH | CH₂CH₂ | 0 | 2-AcOPr |
| 2-242 | Pyr | CH=CH | CH₂CH₂ | 0 | 2-(3-HOOC.PrnO)Pr |
| 2-243 | Pyr | CH=CH | CH₂CH₂ | 0 | 2-(cHxCOO)Pr |
| 2-244 | Pyr | CH=CH | CH₂CH₂ | 0 | 3-HOPr |
| 2-245 | Pyr | CH=CH | CH₂CH₂ | 0 | 3-AcOPr |
| 2-246 | Pyr | CH=CH | CH₂CH₂ | 0 | 3-(cHxCOO)Pr |
| 2-247 | Pyr | CH=CH | CH₂CH₂ | 0 | 2-HOBu |
| 2-248 | Pyr | CH=CH | CH₂CH₂ | 0 | 2-AcOBu |
| 2-249 | Pyr | CH=CH | (CH₂)₃ | 0 | 2-HOEt |
| 2-250 | Pyr | CH=CH | (CH₂)₃ | 0 | 2-AcOEt |
| 2-251 | Pyr | CH=CH | (CH₂)₃ | 0 | 2-PrnOEt |
| 2-252 | Pyr | CH=CH | (CH₂)₃ | 0 | 2-(3-HOOC.PrnO)Et |
| 2-253 | Pyr | CH=CH | (CH₂)₃ | 0 | 2-BozOEt |
| 2-254 | Pyr | CH=CH | (CH₂)₃ | 0 | 2-(cPnCOO)Et |
| 2-255 | Pyr | CH=CH | (CH₂)₃ | 0 | 2-(cHxCOO)Et |
| 2-256 | Pyr | CH=CH | (CH₂)₃ | 0 | 2-HOPr |
| 2-257 | Pyr | CH=CH | (CH₂)₃ | 0 | 2-AcOPr |
| 2-258 | Pyr | CH=CH | (CH₂)₃ | 0 | 2-BozOPr |
| 2-259 | Pyr | CH=CH | (CH₂)₃ | 0 | 3-HOPr |
| 2-260 | Pyr | CH=CH | (CH₂)₃ | 0 | 3-AcOPr |
| 2-261 | Pyr | CH=CH | (CH₂)₃ | 0 | 3-(3-HOOC.PrnO)Pr |
| 2-262 | Pyr | CH=CH | (CH₂)₃ | 0 | 2-HOBu |
| 2-263 | Pyr | CH=CH | (CH₂)₃ | 0 | 2-AcOBu |
| 2-264 | Pyr | CH=CH | (CH₂)₄ | 0 | 2-HOEt |
| 2-265 | Pyr | CH=CH | (CH₂)₄ | 0 | 2-AcOEt |
| 2-266 | Pyr | CH=CH | (CH₂)₄ | 0 | 2-(3-HOOC.PrnO)Et |
| 2-267 | Pyr | CH=CH | (CH₂)₄ | 0 | 2-(cHxCOO)Et |
| 2-268 | Pyr | CH=CH | (CH₂)₄ | 0 | 2-HOPr |
| 2-269 | Pyr | CH=CH | (CH₂)₄ | 0 | 2-AcOPr |
| 2-270 | Pyr | CH=CH | (CH₂)₄ | 0 | 3-HOPr |
| 2-271 | Pyr | CH=CH | (CH₂)₄ | 0 | 3-AcOPr |
| 2-272 | Pyr | CH=CH | (CH₂)₄ | 0 | 2-HOBu |
| 2-273 | Pyr | CH=CH | (CH₂)₄ | 0 | 2-AcOBu |
| 2-274 | Pyr | CH=CH | CH₂CH(Me)CH₂ | 0 | 2-HOEt |
| 2-275 | Pyr | CH=CH | CH₂CH(Me)CH₂ | 0 | 2-AcOEt |
| 2-276 | Pyr | CH=CH | CH₂CH(Me)CH₂ | 0 | 2-HOPr |
| 2-277 | Pye | CH=CH | CH₂CH(Me)CH₂ | 0 | 2-AcOPr |
| 2-278 | Pyr | CH=CH | CH₂CH(Me)CH₂ | 0 | 3-HOPr |
| 2-279 | Pyr | CH=CH | CH₂CH(Me)CH₂ | 0 | 3-AcOPr |
| 2-280 | Pyr | CH=CH | CH₂CH(Me)CH₂ | 0 | 2-HOBu |
| 2-281 | Pyr | CH=CH | CH₂CH(Me)CH₂ | 0 | 2-AcOBu |
| 2-282 | Pyr | CH=CH | (CH₂)₅ | 0 | 2-HOEt |
| 2-283 | Pyr | CH=CH | (CH₂)₅ | 0 | 2-AcOEt |
| 2-284 | Pyr | CH=CH | (CH₂)₅ | 0 | 2-HOPr |
| 2-285 | Pyr | CH=CH | (CH₂)₅ | 0 | 2-AcOPr |
| 2-286 | Pyr | CH=CH | (CH₂)₅ | 0 | 2-(cHxCOO)Pr |
| 2-287 | Pyr | CH=CH | (CH₂)₅ | 0 | 3-HOPr |
| 2-288 | Pyr | CH=CH | (CH₂)₅ | 0 | 3-AcOPr |
| 2-289 | Pyr | CH=CH | (CH₂)₅ | 0 | 2-AcOBu |
| 2-290 | Pyr | CH=CH | (CH₂)₆ | 0 | 2-HOEt |
| 2-291 | Pyr | CH=CH | (CH₂)₆ | 0 | 2-AcOEt |
| 2-292 | Pyr | CH=CH | (CH₂)₆ | 0 | 2-HOPr |
| 2-293 | Pyr | CH=CH | (CH₂)₆ | 0 | 2-AcOPr |
| 2-294 | Pyr | CH=CH | (CH₂)₆ | 0 | 3-HOPr |
| 2-295 | Pyr | CH=CH | (CH₂)₆ | 0 | 3-AcOPr |
| 2-296 | Pyr | CH=CH | (CH₂)₆ | 0 | 2-AcOBu |
| 2-297 | NMe₂ | CH=CH | CH₂ | 0 | 2-HOEt |
| 2-298 | NMe₂ | CH=CH | CH₂ | 0 | 2-AcOEt |
| 2-299 | NMe₂ | CH=CH | CH₂ | 0 | 2-PrnOEt |
| 2-300 | NMe₂ | CH=CH | CH₂ | 0 | 2-(3-HOOC.PrnO)Et |
| 2-301 | NMe₂ | CH=CH | CH₂ | 0 | 2-(3-Mec.PrnO)Et |
| 2-302 | NMe₂ | CH=CH | CH₂ | 0 | 2-BozOEt |
| 2-303 | NMe₂ | CH=CH | CH₂ | 0 | 2-(cHxCOO)Et |
| 2-304 | NMe₂ | CH=CH | CH₂ | 0 | 2-HOPr |

TABLE 2-continued

| Cpd. No. | R¹ | A | B | m | R⁵ |
|---|---|---|---|---|---|
| 2-305 | NMe₂ | CH=CH | CH₂ | 0 | 2-(cHxCOO)Pr |
| 2-306 | NMe₂ | CH=CH | CH₂ | 0 | 3-HOPr |
| 2-307 | NMe₂ | CH=CH | CH₂ | 0 | 3-AcOPr |
| 2-308 | NMe₂ | CH=CH | CH₂ | 0 | 2-HOBu |
| 2-309 | NMe₂ | CH=CH | CH₂ | 0 | 2-AcOBu |
| 2-310 | NMe₂ | CH=CH | CH₂CH₂ | 0 | 2-HOEt |
| 2-311 | NMe₂ | CH=CH | CH₂CH₂ | 0 | 2-AcOEt |
| 2-312 | NMe₂ | CH=CH | CH₂CH₂ | 0 | 3-HOPr |
| 2-313 | NMe₂ | CH=CH | CH₂CH₂ | 0 | 3-AcOPr |
| 2-314 | NMe₂ | CH=CH | (CH₂)₃ | 0 | 2-HOEt |
| 2-315 | NMe₂ | CH=CH | (CH₂)₃ | 0 | 2-AcOEt |
| 2-316 | NMe₂ | CH=CH | (CH₂)₃ | 0 | 2-PrnOEt |
| 2-317 | NMe₂ | CH=CH | (CH₂)₃ | 0 | 2-(3-HOOC.PrnO)Et |
| 2-318 | NMe₂ | CH=CH | (CH₂)₃ | 0 | 2-BozOEt |
| 2-319 | NMe₂ | CH=CH | (CH₂)₃ | 0 | 2-(cHxCOO)Et |
| 2-320 | NMe₂ | CH=CH | (CH₂)₃ | 0 | 2-(cPnCOO)Pr |
| 2-321 | NMe₂ | CH=CH | (CH₂)₃ | 0 | 2-(cHxCOO)Pr |
| 2-322 | NMe₂ | CH=CH | (CH₂)₃ | 0 | 3-HOPr |
| 2-323 | NMe₂ | CH=CH | (CH₂)₃ | 0 | 3-AcOPr |
| 2-324 | NMe₂ | CH=CH | (CH₂)₃ | 0 | 2-HOBu |
| 2-325 | NMe₂ | CH=CH | (CH₂)₃ | 0 | 2-AcOBu |
| 2-326 | NMe₂ | CH=CH | (CH₂)₄ | 0 | 2-HOEt |
| 2-327 | NMe₂ | CH=CH | (CH₂)₄ | 0 | 2-AcOEt |
| 2-328 | NMe₂ | CH=CH | (CH₂)₄ | 0 | 3-HOPr |
| 2-329 | NMe₂ | CH=CH | (CH₂)₄ | 0 | 3-AcOPr |
| 2-330 | NMe₂ | CH=CH | (CH₂)₄ | 0 | 2-AcOBu |
| 2-331 | NMe₂ | CH=CH | CH₂CH(Me)CH₂ | 0 | 2-HOEt |
| 2-332 | NMe₂ | CH=CH | CH₂CH(Me)CH₂ | 0 | 2-AcOEt |
| 2-333 | NMe₂ | CH=CH | CH₂CH(Me)CH₂ | 0 | 2-HOPr |
| 2-334 | NMe₂ | CH=CH | CH₂CH(Me)CH₂ | 0 | 2-AcOPr |
| 2-335 | NMe₂ | CH=CH | CH₂CH(Me)CH₂ | 0 | 3-AcOPr |
| 2-336 | NMe₂ | CH=CH | CH₂CH(Me)CH₂ | 0 | 2-AcOBu |
| 2-337 | NMe₂ | CH=CH | (CH₂)₅ | 0 | 2-HOEt |
| 2-338 | NMe₂ | CH=CH | (CH₂)₅ | 0 | 2-AcOEt |
| 2-339 | NMe₂ | CH=CH | (CH₂)₅ | 0 | 3-HOPr |
| 2-340 | NMe₂ | CH=CH | (CH₂)₅ | 0 | 3-AcOPr |
| 2-341 | NMe₂ | CH=CH | (CH₂)₆ | 0 | 2-HOEt |
| 2-342 | NMe₂ | CH=CH | (CH₂)₆ | 0 | 2-AcOEt |
| 2-343 | NMe₂ | CH=CH | (CH₂)₆ | 0 | 3-HOPr |
| 2-344 | NMe₂ | CH=CH | (CH₂)₆ | 0 | 3-AcOPr |
| 2-345 | NEt₂ | CH=CH | CH₂ | 0 | 2-HOEt |
| 2-346 | NEt₂ | CH=CH | CH₂ | 0 | 2-AcOEt |
| 2-347 | NEt₂ | CH=CH | CH₂ | 0 | 2-PrnOEt |
| 2-348 | NEt₂ | CH=CH | CH₂ | 0 | 2-(3-HOOC.PrnO)Et |
| 2-349 | NEt₂ | CH=CH | CH₂ | 0 | 2-BozOEt |
| 2-350 | NEt₂ | CH=CH | CH₂ | 0 | 2-(cHxCOO)Et |
| 2-351 | NEt₂ | CH=CH | CH₂ | 0 | 3-HOPr |
| 2-352 | NEt₂ | CH=CH | CH₂ | 0 | 3-AcOPr |
| 2-353 | NEt₂ | CH=CH | CH₂ | 0 | 3-(3-HOOC.PrnO)Pr |
| 2-354 | NEt₂ | CH=CH | CH₂ | 0 | 3-BozOPr |
| 2-355 | NEt₂ | CH=CH | CH₂ | 0 | 3-(cHxCOO)Pr |
| 2-356 | NEt₂ | CH=CH | CH₂ | 0 | 2-AcOBu |
| 2-357 | NEt₂ | CH=CH | CH₂CH₂ | 0 | 2-HOEt |
| 2-358 | NEt₂ | CH=CH | CH₂CH₂ | 0 | 2-AcOEt |
| 2-359 | NEt₂ | CH=CH | CH₂CH₂ | 0 | 3-AcOPr |
| 2-360 | NEt₂ | CH=CH | CH₂CH₂ | 0 | 3-BozOPr |
| 2-361 | NEt₂ | CH=CH | CH₂CH₂ | 0 | 2-AcOBu |
| 2-362 | NEt₂ | CH=CH | (CH₂)₃ | 0 | 2-HOEt |
| 2-363 | NEt₂ | CH=CH | (CH₂)₃ | 0 | 2-AcOEt |
| 2-364 | NEt₂ | CH=CH | (CH₂)₃ | 0 | 3-HOPr |
| 2-365 | NEt₂ | CH=CH | (CH₂)₃ | 0 | 3-AcOPr |
| 2-366 | NEt₂ | CH=CH | (CH₂)₃ | 0 | 2-AcOBu |
| 2-367 | NEt₂ | CH=CH | (CH₂)₄ | 0 | 2-HOEt |
| 2-368 | NEt₂ | CH=CH | (CH₂)₄ | 0 | 2-AcOEt |
| 2-369 | NEt₂ | CH=CH | (CH₂)₄ | 0 | 3-HOPr |
| 2-370 | NEt₂ | CH=CH | (CH₂)₄ | 0 | 3-AcOPr |
| 2-371 | NEt₂ | CH=CH | (CH₂)₄ | 0 | 2-AcOBu |
| 2-372 | NEt₂ | CH=CH | CH₂CH(Me)CH₂ | 0 | 2-HOEt |
| 2-373 | NEt₂ | CH=CH | CH₂CH(Me)CH₂ | 0 | 2-AcOEt |
| 2-374 | NEt₂ | CH=CH | CH₂CH(Me)CH₂ | 0 | 2-HOPr |
| 2-375 | NEt₂ | CH=CH | CH₂CH(Me)CH₂ | 0 | 2-AcOPr |
| 2-376 | NEt₂ | CH=CH | CH₂CH(Me)CH₂ | 0 | 3-HOPr |
| 2-377 | NEt₂ | CH=CH | CH₂CH(Me)CH₂ | 0 | 3-AcOPr |
| 2-378 | NEt₂ | CH=CH | (CH₂)₅ | 0 | 2-HOEt |
| 2-379 | NEt₂ | CH=CH | (CH₂)₅ | 0 | 2-AcOEt |
| 2-380 | NEt₂ | CH=CH | (CH₂)₅ | 0 | 3-HOPr |

TABLE 2-continued

| Cpd. No. | R¹ | A | B | m | R⁵ |
|---|---|---|---|---|---|
| 2-381 | NEt₂ | CH=CH | (CH₂)₅ | 0 | 3-AcOPr |
| 2-382 | NEt₂ | CH=CH | (CH₂)₅ | 0 | 2-AcOBu |
| 2-383 | NEt₂ | CH=CH | (CH₂)₆ | 0 | 2-HOEt |
| 2-384 | NEt₂ | CH=CH | (CH₂)₆ | 0 | 2-AcOEt |
| 2-385 | NEt₂ | CH=CH | (HC2)₆ | 0 | 3-HOPr |
| 2-386 | NEt₂ | CH=CH | (CH₂)₆ | 0 | 3-AcOPr |
| 2-387 | NEt₂ | CH=CH | (CH₂)₆ | 0 | 2-AcOBu |
| 2-388 | Azi | CH=CH | CH₂ | 0 | 2-AcOEt |
| 2-389 | Aze | CH=CH | CH₂ | 0 | 2-AcOEt |
| 2-390 | Pip | CH=CH | CH₂ | 1 | 2-HOEt |
| 2-391 | Pip | CH=CH | CH₂ | 1 | 2-AcOEt |
| 2-392 | Pip | CH=CH | CH₂ | 1 | 2-PrnOEt |
| 2-393 | Pip | CH=CH | CH₂ | 1 | 2-(3-HOOC.PrnO)Et |
| 2-394 | Pip | CH=CH | CH₂ | 1 | 2-(3-Mec.PrnO)Et |
| 2-395 | Pip | CH=CH | CH₂ | 1 | 2-BozOEt |
| 2-396 | Pip | CH=CH | CH₂ | 1 | 2-(cHxCOO)Et |
| 2-397 | Pip | CH=CH | CH₂ | 1 | 2-HOPr |
| 2-398 | Pip | CH=CH | CH₂ | 1 | 2-FoOPr |
| 2-399 | Pip | CH=CH | CH₂ | 1 | 2-AcOPr |
| 2-400 | Pip | CH=CH | CH₂ | 1 | 2-(3-HOOC.PrnO)Pr |
| 2-401 | Pip | CH=CH | CH₂ | 1 | 2-(cHxCOO)Pr |
| 2-402 | Pip | CH=CH | CH₂ | 1 | 3-HOPr |
| 2-403 | Pip | CH=CH | CH₂ | 1 | 3-AcOPr |
| 2-404 | Pip | CH=CH | CH₂ | 1 | 3-(3-HOOC.PrnO)Pr |
| 2-405 | Pip | CH=CH | CH₂ | 1 | 3-BozOPr |
| 2-406 | Pip | CH=CH | CH₂ | 1 | 3-(cHxCOO)Pr |
| 2-407 | Pip | CH=CH | CH₂ | 1 | 2-HOBu |
| 2-408 | Pip | CH=CH | CH₂ | 1 | 2-AcOBu |
| 2-409 | Pip | CH=CH | CH₂CH₂ | 1 | 2-HOEt |
| 2-410 | Pip | CH=CH | CH₂CH₂ | 1 | 2-AcOEt |
| 2-411 | Pip | CH=CH | CH₂CH₂ | 1 | 2-(3-HOOC.PrnO)Et |
| 2-412 | Pip | CH=CH | CH₂CH₂ | 1 | 2-BozOEt |
| 2-413 | Pip | CH=CH | CH₂CH₂ | 1 | 2-(cHxCOO)Et |
| 2-414 | Pip | CH=CH | CH₂CH₂ | 1 | 3-HOPr |
| 2-415 | Pip | CH=CH | CH₂CH₂ | 1 | 3-AcOPr |
| 2-416 | Pip | CH=CH | CH₂CH₂ | 1 | 2-HOBu |
| 2-417 | Pip | CH=CH | CH₂CH₂ | 1 | 2-AcOBu |
| 2-418 | Pip | CH=CH | (CH₂)₃ | 1 | 2-HOEt |
| 2-419 | Pip | CH=CH | (CH₂)₃ | 1 | 2-AcOEt |
| 2-420 | Pip | CH=CH | (CH₂)₃ | 1 | 2-PrnOE.t |
| 2-421 | Pip | CH=CH | (CH₂)₃ | 1 | 2-(3-HOOC.PrnO)Et |
| 2-422 | Pip | CH=CH | (CH₂)₃ | 1 | 2-BozOEt |
| 2-423 | Pip | CH=CH | (CH₂)₃ | 1 | 2-(cHxCOO)Et |
| 2-424 | Pip | CH=CH | (CH₂)₃ | 1 | 2-HOPr |
| 2-425 | Pip | CH=CH | (CH₂)₃ | 1 | 2-AcOPr |
| 2-426 | Pip | CH=CH | (CH₂)₃ | 1 | 2-(3-HOOC.PrnO)Pr |
| 2-427 | Pip | CH=CH | (CH₂)₃ | 1 | 2-(cPnCOO)Pr |
| 2-428 | Pip | CH=CH | (CH₂)₃ | 1 | 2-(cHxCOO)Pr |
| 2-429 | Pip | CH=CH | (CH₂)₃ | 1 | 3-HOPr |
| 2-430 | Pip | CH=CH | (CH₂)₃ | 1 | 3-AcOPr |
| 2-431 | Pip | CH=CH | (CH₂)₃ | 1 | 2-HOBu |
| 2-432 | Pip | CH=CH | (CH₂)₃ | 1 | 2-AcOBu |
| 2-433 | Pip | CH=CH | (CH₂)₄ | 1 | 2-HOEt |
| 2-434 | Pip | CH=CH | (CH₂)₄ | 1 | 2-AcOEt |
| 2-435 | Pip | CH=CH | (CH₂)₄ | 1 | 2-(cHxCOO)Et |
| 2-436 | Pip | CH=CH | (CH₂)₄ | 1 | 2-HOPr |
| 2-437 | Pip | CH=CH | (CH₂)₄ | 1 | 2-AcOPr |
| 2-438 | Pip | CH=CH | (CH₂)₄ | 1 | 3-HOPr |
| 2-439 | Pip | CH=CH | (CH₂)₄ | 1 | 3-AcOPr |
| 2-440 | Pip | CH=CH | (CH₂)₄ | 1 | 2-AcOBu |
| 2-441 | Pip | CH=CH | CH₂CH(Me)CH₂ | 1 | 2-HOEt |
| 2-442 | Pip | CH=CH | CH₂CH(Me)CH₂ | 1 | 2-AcOEt |
| 2-443 | Pip | CH=CH | CH₂CH(Me)CH₂ | 1 | 2-HOPr |
| 2-444 | Pip | CH=CH | CH₂CH(Me)CH₂ | 1 | 2-AcOPr |
| 2-445 | Pip | CH=CH | CH₂CH(Me)CH₂ | 1 | 3-AcOPr |
| 2-446 | Pip | CH=CH | CH₂CH(Me)CH₂ | 1 | 2-AcOBu |
| 2-447 | Pip | CH=CH | (CH₂)₅ | 1 | 2-HOEt |
| 2-448 | Pip | CH=CH | (CH₂)₅ | 1 | 2-AcOEt |
| 2-449 | Pip | CH=CH | (CH₂)₅ | 1 | 2-HOPr |
| 2-450 | Pip | CH=CH | (CH₂)₅ | 1 | 2-AcOPr |
| 2-451 | Pip | CH=CH | (CH₂)₅ | 1 | 3-HOPr |
| 2-452 | Pip | CH=CH | (CH₂)₅ | 1 | 3-AcOPr |
| 2-453 | Pip | CH=CH | (CH₂)₅ | 1 | 2-AcOBu |
| 2-454 | Pip | CH=CH | (CH₂)₆ | 1 | 2-HOEt |
| 2-455 | Pip | CH=CH | (CH₂)₆ | 1 | 2-AcOEt |
| 2-456 | Pip | CH=CH | (CH₂)₆ | 1 | 2-HOPr |

TABLE 2-continued

| Cpd. No. | R¹ | A | B | m | R⁵ |
|---|---|---|---|---|---|
| 2-457 | Pip | CH=CH | (CH$_2$)$_6$ | 1 | 2-AcOPr |
| 2-458 | Pip | CH=CH | (CH$_2$)$_6$ | 1 | 3-HOPr |
| 2-459 | Pip | CH=CH | (CH$_2$)$_6$ | 1 | 3-AcOPr |
| 2-460 | Pip | CH=CH | CH$_2$ | 2 | 2-HOEt |
| 2-461 | Pip | CH=CH | CH$_2$ | 2 | 2-AcOEt |
| 2-462 | Pip | CH=CH | CH$_2$ | 2 | 2-PrnOEt |
| 2-463 | Pip | CH=CH | CH$_2$ | 2 | 2-(3-HOOC.PrnO)Et |
| 2-464 | Pip | CH=CH | CH$_2$ | 2 | 2-BozOEt |
| 2-465 | Pip | CH=CH | CH$_2$ | 2 | 2-(cHxCOO)Et |
| 2-466 | Pip | CH=CH | CH$_2$ | 2 | 3-HOPr |
| 2-467 | Pip | CH=CH | CH$_2$ | 2 | 3-AcOPr |
| 2-468 | Pip | CH=CH | CH$_2$ | 2 | 3-(3-HOOC.PrnO)Pr |
| 2-469 | Pip | CH=CH | CH$_2$ | 2 | 3-BozOPr |
| 2-470 | Pip | CH=CH | CH$_2$ | 2 | 3-(cHxCOO)Pr |
| 2-471 | Pip | CH=CH | CH$_2$ | 2 | 2-AcOBu |
| 2-472 | Pip | CH=CH | CH$_2$CH$_2$ | 2 | 2-HOEt |
| 2-473 | Pip | CH=CH | CH$_2$CH$_2$ | 2 | 2-AcOEt |
| 2-474 | Pip | CH=CH | CH$_2$CH$_2$ | 2 | 3-AcOPr |
| 2-475 | Pip | CH=CH | CH$_2$CH$_2$ | 2 | 3-BozOPr |
| 2-476 | Pip | CH=CH | CH$_2$CH$_2$ | 2 | 2-AcOBu |
| 2-477 | Pip | CH=CH | (CH$_2$)$_3$ | 2 | 2-HOEt |
| 2-478 | Pip | CH=CH | (CH$_2$)$_3$ | 2 | 2-AcOEt |
| 2-479 | Pip | CH=CH | (CH$_2$)$_3$ | 2 | 3-HOPr |
| 2-480 | Pip | CH=CH | (CH$_2$)$_3$ | 2 | 3-AcOPr |
| 2-481 | Pip | CH=CH | (CH$_2$)$_3$ | 2 | 2-AcOBu |
| 2-482 | Pip | CH=CH | (CH$_2$)$_4$ | 2 | 2-HOEt |
| 2-483 | Pip | CH=CH | (CH$_2$)$_4$ | 2 | 2-AcOEt |
| 2-484 | Pip | CH=CH | (CH$_2$)$_4$ | 2 | 3-HOPr |
| 2-485 | Pip | CH=CH | (CH$_2$)$_4$ | 2 | 3-AcOPr |
| 2-486 | Pip | CH=CH | (CH$_2$)$_4$ | 2 | 2-AcOBu |
| 2-487 | Pip | CH=CH | CH$_2$CH(Me)CH$_2$ | 2 | 2-HOEt |
| 2-488 | Pip | CH=CH | CH$_2$CH(Me)CH$_2$ | 2 | 2-AcOEt |
| 2-489 | Pip | CH=CH | CH$_2$CH(Me)CH$_2$ | 2 | 2-HOPr |
| 2-490 | Pip | CH=CH | CH$_2$CH(Me)CH$_2$ | 2 | 2-AcOPr |
| 2-491 | Pip | CH=CH | CH$_2$CH(Me)CH$_2$ | 2 | 3-HOPr |
| 2-492 | Pip | CH=CH | CH$_2$CH(Me)CH$_2$ | 2 | 3-AcOPr |
| 2-493 | Pip | CH=CH | (CH$_2$)$_5$ | 2 | 2-HOEt |
| 2-494 | Pip | CH=CH | (CH$_2$)$_5$ | 2 | 2-AcOEt |
| 2-495 | Pip | CH=CH | (CH$_2$)$_5$ | 2 | 3-HOPr |
| 2-496 | Pip | CH=CH | (CH$_2$)$_5$ | 2 | 3-AcOPr |
| 2-497 | Pip | CH=CH | (CH$_2$)$_5$ | 2 | 2-AcOBu |
| 2-498 | Pip | CH=CH | (CH$_2$)$_6$ | 2 | 2-HOEt |
| 2-499 | Pip | CH=CH | (CH$_2$)$_6$ | 2 | 2-AcOEt |
| 2-500 | Pip | CH=CH | (CH$_2$)$_6$ | 2 | 3-HOPr |
| 2-501 | Pip | CH=CH | (CH$_2$)$_6$ | 2 | 3-AcOPr |
| 2-502 | Pip | CH=CH | (CH$_2$)$_6$ | 2 | 2-AcOBu |
| 2-503 | Pyr | CH=CH | (CH$_2$)$_6$ | 1 | 2-AcOEt |
| 2-504 | Pyr | CH=CH | CH$_2$ | 1 | 2-AcOEt |
| 2-505 | Pip | CH$_2$CH$_2$ | CH$_2$ | 0 | CH$_2$OH |
| 2-506 | Pip | CH$_2$CH$_2$ | CH$_2$ | 0 | 2-HOEt |
| 2-507 | Pip | CH$_2$CH$_2$ | CH$_2$ | 0 | 2-FoOEt |
| 2-508 | Pip | CH$_2$CH$_2$ | CH$_2$ | 0 | 2-AcOEt |
| 2-509 | Pip | CH$_2$CH$_2$ | CH$_2$ | 0 | 2-PrnOEt |
| 2-510 | Pip | CH$_2$CH$_2$ | CH$_2$ | 0 | 2-ByrOEt |
| 2-511 | Pip | CH$_2$CH$_2$ | CH$_2$ | 0 | 2-iByrOEt |
| 2-512 | Pip | CH$_2$CH$_2$ | CH$_2$ | 0 | 2-ValOEt |
| 2-513 | Pip | CH$_2$CH$_2$ | CH$_2$ | 0 | 2-iValOEt |
| 2-514 | Pip | CH$_2$CH$_2$ | CH$_2$ | 0 | 2-(PhAcO)Et |
| 2-515 | Pip | CH$_2$CH$_2$ | CH$_2$ | 0 | 2-(HOOC.AcO)Et |
| 2-516 | Pip | CH$_2$CH$_2$ | CH$_2$ | 0 | 2-(3-HOOC.PrnO)Et |
| 2-517 | Pip | CH$_2$CH$_2$ | CH$_2$ | 0 | 2-(3-Mec.PrnO)Et |
| 2-518 | Pip | CH$_2$CH$_2$ | CH$_2$ | 0 | 2-(3-Etc.PrnO)Et |
| 2-519 | Pip | CH$_2$CH$_2$ | CH$_2$ | 0 | 2-(3-Prc.PrnO)Et |
| 2-520 | Pip | CH$_2$CH$_2$ | CH$_2$ | 0 | 2-(3-Phc.PrnO)Et |
| 2-521 | Pip | CH$_2$CH$_2$ | CH$_2$ | 0 | 2-[3-(4-MePhcO)PrnO]Et |
| 2-522 | Pip | CH$_2$CH$_2$ | CH$_2$ | 0 | 2-(3-PhPrnO)Et |
| 2-523 | Pip | CH$_2$CH$_2$ | CH$_2$ | 0 | 2-(3-PhPrnO)Et |
| 2-524 | Pip | CH$_2$CH$_2$ | CH$_2$ | 0 | 2-BozOEt |
| 2-525 | Pip | CH$_2$CH$_2$ | CH$_2$ | 0 | 2-(4-MeBozO)Et |
| 2-526 | Pip | CH$_2$CH$_2$ | CH$_2$ | 0 | 2-(4-MeOBozO)Et |
| 2-527 | Pip | CH$_2$CH$_2$ | CH$_2$ | 0 | 2-(4-FBozO)Et |
| 2-528 | Pip | CH$_2$CH$_2$ | CH$_2$ | 0 | 2-(4-ClBozo)Et |
| 2-529 | Pip | CH$_2$CH$_2$ | CH$_2$ | 0 | 2-(cPrCOO)Et |
| 2-530 | Pip | CH$_2$CH$_2$ | CH$_2$ | 0 | 2-(cBuCOO)Et |
| 2-531 | Pip | CH$_2$CH$_2$ | CH$_2$ | 0 | 2-(cPnCOO)Et |
| 2-532 | Pip | CH$_2$CH$_2$ | CH$_2$ | 0 | 2-(cHxCOO)Et |

TABLE 2-continued

| Cpd. No. | R¹ | A | B | m | R⁵ |
|---|---|---|---|---|---|
| 2-533 | Pip | CH₂CH₂ | CH₂ | 0 | 2-HOPr |
| 2-534 | Pip | CH₂CH₂ | CH₂ | 0 | 2-FoOPr |
| 2-535 | Pip | CH₂CH₂ | CH₂ | 0 | 2-AcOPr |
| 2-536 | Pip | CH₂CH₂ | CH₂ | 0 | 2-PrnOPr |
| 2-537 | Pip | CH₂CH₂ | CH₂ | 0 | 2-(3-HOOC.PrnO)Pr |
| 2-538 | Pip | CH₂CH₂ | CH₂ | 0 | 2-(3-Mec.PrnO)Pr |
| 2-539 | Pip | CH₂CH₂ | CH₂ | 0 | 2-(3-Etc.PrnO)Pr |
| 2-540 | Pip | CH₂CH₂ | CH₂ | 0 | 2-(3-Phc.PrnO)Et |
| 2-541 | Pip | CH₂CH₂ | CH₂ | 0 | 2-[3-(4-MePhcO)PrnO]Et |
| 2-542 | Pip | CH₂CH₂ | CH₂ | 0 | 2-(PhAcO)Pr |
| 2-543 | Pip | CH₂CH₂ | CH₂ | 0 | 2-BozOPr |
| 2-544 | Pip | CH₂CH₂ | CH₂ | 0 | 2-(cPnCOO)Pr |
| 2-545 | Pip | CH₂CH₂ | CH₂ | 0 | 2-(cHxCOO)Pr |
| 2-546 | Pip | CH₂CH₂ | CH₂ | 0 | 3-HOPr |
| 2-547 | Pip | CH₂CH₂ | CH₂ | 0 | 3-FoOPr |
| 2-548 | Pip | CH₂CH₂ | CH₂ | 0 | 3-AcOPr |
| 2-549 | Pip | CH₂CH₂ | CH₂ | 0 | 3-PrnOPr |
| 2-550 | Pip | CH₂CH₂ | CH₂ | 0 | 3-(3-HOOC.PrnO)Pr |
| 2-551 | Pip | CH₂CH₂ | CH₂ | 0 | 3-(3-Mec.PrnO)Pr |
| 2-552 | Pip | CH₂CH₂ | CH₂ | 0 | 3-(3-Etc.PrnO)Pr |
| 2-553 | Pip | CH₂CH₂ | CH₂ | 0 | 3-BozOPr |
| 2-554 | Pip | CH₂CH₂ | CH₂ | 0 | 3-(cPnCOO)Pr |
| 2-555 | Pip | CH₂CH₂ | CH₂ | 0 | 3-(cHxCOO)Pr |
| 2-556 | Pip | CH₂CH₂ | CH₂ | 0 | 2-HOBu |
| 2-557 | Pip | CH₂CH₂ | CH₂ | 0 | 2-AcOBu |
| 2-558 | Pip | CH₂CH₂ | CH₂ | 0 | 2-(3-HOOC.PrnO)Bu |
| 2-559 | Pip | CH₂CH₂ | CH₂ | 0 | 2-BozOBu |
| 2-560 | Pip | CH₂CH₂ | CH₂ | 0 | 2-(cHxCOO)Bu |
| 2-561 | Pip | CH₂CH₂ | CH₂CH₂ | 0 | 2-HOEt |
| 2-562 | Pip | CH₂CH₂ | CH₂CH₂ | 0 | 2-FoOEt |
| 2-563 | Pip | CH₂CH₂ | CH₂CH₂ | 0 | 2-AcOEt |
| 2-564 | Pip | CH₂CH₂ | CH₂CH₂ | 0 | 2-PrnOEt |
| 2-565 | Pip | CH₂CH₂ | CH₂CH₂ | 0 | 2-ValOEt |
| 2-566 | Pip | CH₂CH₂ | CH₂CH₂ | 0 | 2-(PhAcO)Et |
| 2-567 | Pip | CH₂CH₂ | CH₂CH₂ | 0 | 2-(3-HOOC.PrnO)Et |
| 2-568 | Pip | CH₂CH₂ | CH₂CH₂ | 0 | 2-(3-Mec.PrnO)Et |
| 2-569 | Pip | CH₂CH₂ | CH₂CH₂ | 0 | 2-(3-Etc.PrnO)Et |
| 2-570 | Pip | CH₂CH₂ | CH₂CH₂ | 0 | 2-(3-PhPrnO)Et |
| 2-571 | Pip | CH₂CH₂ | CH₂CH₂ | 0 | 2-BozOEt |
| 2-572 | Pip | CH₂CH₂ | CH₂CH₂ | 0 | 2-(4-MeBozO)Et |
| 2-573 | Pip | CH₂CH₂ | CH₂CH₂ | 0 | 2-(4-FBozO)Et |
| 2-574 | Pip | CH₂CH₂ | CH₂CH₂ | 0 | 2-(4-ClBozO)Et |
| 2-575 | Pip | CH₂CH₂ | CH₂CH₂ | 0 | 2-(cPrCOO)Et |
| 2-576 | Pip | CH₂CH₂ | CH₂CH₂ | 0 | 2-(cBuCOO)Et |
| 2-577 | Pip | CH₂CH₂ | CH₂CH₂ | 0 | 2-(cPnCOO)Et |
| 2-578 | Pip | CH₂CH₂ | CH₂CH₂ | 0 | 2-(cHxCOO)Et |
| 2-579 | Pip | CH₂CH₂ | CH₂CH₂ | 0 | 2-HOPr |
| 2-580 | Pip | CH₂CH₂ | CH₂CH₂ | 0 | 2-FoOPr |
| 2-581 | Pip | CH₂CH₂ | CH₂CH₂ | 0 | 2-AcOPr |
| 2-582 | Pip | CH₂CH₂ | CH₂CH₂ | 0 | 2-PrnOPr |
| 2-583 | Pip | CH₂CH₂ | CH₂CH₂ | 0 | 2-(3-HOOC.PrnO)Pr |
| 2-584 | Pip | CH₂CH₂ | CH₂CH₂ | 0 | 2-(3-Mec.PrnO)Pr |
| 2-585 | Pip | CH₂CH₂ | CH₂CH₂ | 0 | 2-BozOPr |
| 2-586 | Pip | CH₂CH₂ | CH₂CH₂ | 0 | 2-(cPnCOO)Pr |
| 2-587 | Pip | CH₂CH₂ | CH₂CH₂ | 0 | 2-(cHxCOO)Pr |
| 2-588 | Pip | CH₂CH₂ | CH₂CH₂ | 0 | 3-HOPr |
| 2-589 | Pip | CH₂CH₂ | CH₂CH₂ | 0 | 3-AcOPr |
| 2-590 | Pip | CH₂CH₂ | CH₂CH₂ | 0 | 3-PrnOPr |
| 2-591 | Pip | CH₂CH₂ | CH₂CH₂ | 0 | 3-(3-HOOC.PrnO)Pr |
| 2-592 | Pip | CH₂CH₂ | CH₂CH₂ | 0 | 3-BozOPr |
| 2-593 | Pip | CH₂CH₂ | CH₂CH₂ | 0 | 3-(cPnCOO)Pr |
| 2-594 | Pip | CH₂CH₂ | CH₂CH₂ | 0 | 3-(cHxCOO)Pr |
| 2-595 | Pip | CH₂CH₂ | CH₂CH₂ | 0 | 2-HOBu |
| 2-596 | Pip | CH₂CH₂ | CH₂CH₂ | 0 | 2-AcOBu |
| 2-597 | Pip | CH₂CH₂ | CH₂CH₂ | 0 | 2-(3-HOOC.PrnO)Bu |
| 2-598 | Pip | CH₂CH₂ | CH₂CH₂ | 0 | 2-BozOBu |
| 2-599 | Pip | CH₂CH₂ | CH₂CH₂ | 0 | 2-(cHxCOO)Bu |
| 2-600 | Pip | CH₂CH₂ | (CH₂)₃ | 0 | 2-HOEt |
| 2-601 | Pip | CH₂CH₂ | (CH₂)₃ | 0 | 2-FoOEt |
| 2-602 | Pip | CH₂CH₂ | (CH₂)₃ | 0 | 2-AcOEt |
| 2-603 | Pip | CH₂CH₂ | (CH₂)₃ | 0 | 2-PrnOEt |
| 2-604 | Pip | CH₂CH₂ | (CH₂)₃ | 0 | 2-ByrOEt |
| 2-605 | Pip | CH₂CH₂ | (CH₂)₃ | 0 | 2-iByrOEt |
| 2-606 | Pip | CH₂CH₂ | (CH₂)₃ | 0 | 2-ValOEt |
| 2-607 | Pip | CH₂CH₂ | (CH₂)₃ | 0 | 2-(3-HOOC.PrnO)Et |
| 2-608 | Pip | CH₂CH₂ | (CH₂)₃ | 0 | 2-(3-Mec.PrnO)Et |

TABLE 2-continued

| Cpd. No. | R¹ | A | B | m | R⁵ |
|---|---|---|---|---|---|
| 2-609 | Pip | CH₂CH₂ | (CH₂)₃ | 0 | 2-(3-Etc.PrnO)Et |
| 2-610 | Pip | CH₂CH₂ | (CH₂)₃ | 0 | 2-(PhAcO)Et |
| 2-611 | Pip | CH₂CH₂ | (CH₂)₃ | 0 | 2-BozOEt |
| 2-612 | Pip | CH₂CH₂ | (CH₂)₃ | 0 | 2-(4-MeBozO)Et |
| 2-613 | Pip | CH₂CH₂ | (CH₂)₃ | 0 | 2-(4-MeOBozO)Et |
| 2-614 | Pip | CH₂CH₂ | (CH₂)₃ | 0 | 2-(4-FBozO)Et |
| 2-615 | Pip | CH₂CH₂ | (CH₂)₃ | 0 | 2-(4-ClBozO)Et |
| 2-616 | Pip | CH₂CH₂ | (CH₂)₃ | 0 | 2-(cPrCOO)Et |
| 2-617 | Pip | CH₂CH₂ | (CH₂)₃ | 0 | 2-(cBuCOO)Et |
| 2-618 | Pip | CH₂CH₂ | (CH₂)₃ | 0 | 2-(cPnCOO)Et |
| 2-619 | Pip | CH₂CH₂ | (CH₂)₃ | 0 | 2-(cHxCOO)Et |
| 2-620 | Pip | CH₂CH₂ | (CH₂)₃ | 0 | 2-HOPr |
| 2-621 | Pip | CH₂CH₂ | (CH₂)₃ | 0 | 2-AcOPr |
| 2-622 | Pip | CH₂CH₂ | (CH₂)₃ | 0 | 2-PrnOPr |
| 2-623 | Pip | CH₂CH₂ | (CH₂)₃ | 0 | 2-(3-HOOC.PrnO)Pr |
| 2-624 | Pip | CH₂CH₂ | (CH₂)₃ | 0 | 2-(3-Etc.PrnO)Pr |
| 2-625 | Pip | CH₂CH₂ | (CH₂)₃ | 0 | 2-BozOPr |
| 2-626 | Pip | CH₂CH₂ | (CH₂)₃ | 0 | 2-(cHxCOO)Pr |
| 2-627 | Pip | CH₂CH₂ | (CH₂)₃ | 0 | 3-HOPr |
| 2-628 | Pip | CH₂CH₂ | (CH₂)₃ | 0 | 3-AcOPr |
| 2-629 | Pip | CH₂CH₂ | (CH₂)₃ | 0 | 3-(3-HOOC.PrnO)Pr |
| 2-630 | Pip | CH₂CH₂ | (CH₂)₃ | 0 | 3-(3-Mec.PrnO)Pr |
| 2-631 | Pip | CH₂CH₂ | (CH₂)₃ | 0 | 3-BozOPr |
| 2-632 | Pip | CH₂CH₂ | (CH₂)₃ | 0 | 3-(cHxCOO)Pr |
| 2-633 | Pip | CH₂CH₂ | (CH₂)₃ | 0 | 2-HOBu |
| 2-634 | Pip | CH₂CH₂ | (CH₂)₃ | 0 | 2-AcOBu |
| 2-635 | Pip | CH₂CH₂ | (CH₂)₃ | 0 | 2-(3-HOOC.PrnO)Bu |
| 2-636 | Pip | CH₂CH₂ | (CH₂)₃ | 0 | 2-BozOBu |
| 2-637 | Pip | CH₂CH₂ | (CH₂)₃ | 0 | 2-(cHxCOO)Bu |
| 2-638 | Pip | CH₂CH₂ | (CH₂)₄ | 0 | 2-HOEt |
| 2-639 | Pip | CH₂CH₂ | (CH₂)₄ | 0 | 2-FoOEt |
| 2-640 | Pip | CH₂CH₂ | (CH₂)₄ | 0 | 2-ACOEt |
| 2-641 | Pip | CH₂CH₂ | (CH₂)₄ | 0 | 2-PrnOEt |
| 2-642 | Pip | CH₂CH₂ | (CH₂)₄ | 0 | 2-(3-HOOC.PrnO)Et |
| 2-643 | Pip | CH₂CH₂ | (CH₂)₄ | 0 | 2-(3-Mec.PrnO)Et |
| 2-644 | Pip | CH₂CH₂ | (CH₂)₄ | 0 | 2-BozOEt |
| 2-645 | Pip | CH₂CH₂ | (CH₂)₄ | 0 | 2-(cHxCOO)Et |
| 2-646 | Pip | CH₂CH₂ | (CH₂)₄ | 0 | 2-HOPr |
| 2-647 | Pip | CH₂CH₂ | (CH₂)₄ | 0 | 2-AcOPr |
| 2-648 | Pip | CH₂CH₂ | (CH₂)₄ | 0 | 2-(3-HOOC.PrnO)Pr |
| 2-649 | Pip | CH₂CH₂ | (CH₂)₄ | 0 | 2-BozOPr |
| 2-650 | Pip | CH₂CH₂ | (CH₂)₄ | 0 | 2-(cHxCOO)Pr |
| 2-651 | Pip | CH₂CH₂ | (CH₂)₄ | 0 | 3-HOPr |
| 2-652 | Pip | CH₂CH₂ | (CH₂)₄ | 0 | 3-AcOPr |
| 2-653 | Pip | CH₂CH₂ | (CH₂)₄ | 0 | 3-(3-HOOC.PrnO)Pr |
| 2-654 | Pip | CH₂CH₂ | (CH₂)₄ | 0 | 3-BozOPr |
| 2-655 | Pip | CH₂CH₂ | (CH₂)₄ | 0 | 3-(cHxCOO)Pr |
| 2-656 | Pip | CH₂CH₂ | (CH₂)₄ | 0 | 2-HOBu |
| 2-657 | Pip | CH₂CH₂ | (CH₂)₄ | 0 | 2-AcOBu |
| 2-658 | Pip | CH₂CH₂ | (CH₂)₄ | 0 | 2-(3-HOOC.PrnO)Bu |
| 2-659 | Pip | CH₂CH₂ | (CH₂)₄ | 0 | 2-(cHxCOO)Bu |
| 2-660 | Pip | CH₂CH₂ | CH₂CH(Me)CH₂ | 0 | 2-HOEt |
| 2-661 | Pip | CH₂CH₂ | CH₂CH(Me)CH₂ | 0 | 2-AcOEt |
| 2-662 | Pip | CH₂CH₂ | CH₂CH(Me)CH₂ | 0 | 2-(3-HOOC.PrnO)Et |
| 2-663 | Pip | CH₂CH₂ | CH₂CH(Me)CH₂ | 0 | 2-BozOEt |
| 2-664 | Pip | CH₂CH₂ | CH₂CH(Me)CH₂ | 0 | 2-(cHxCOO)Et |
| 2-665 | Pip | CH₂CH₂ | CH₂CH(Me)CH₂ | 0 | 2-HOPr |
| 2-666 | Pip | CH₂CH₂ | CH₂CH(Me)CH₂ | 0 | 2-AcOPr |
| 2-667 | Pip | CH₂CH₂ | CH₂CH(Me)CH₂ | 0 | 2-BozOPr |
| 2-668 | Pip | CH₂CH₂ | CH₂CH(Me)CH₂ | 0 | 2-(cHxCOO)Pr |
| 2-669 | Pip | CH₂CH₂ | CH₂CH(Me)CH₂ | 0 | 3-HOPr |
| 2-670 | Pip | CH₂CH₂ | CH₂CH(Me)CH₂ | 0 | 3-AcOPr |
| 2-671 | Pip | CH₂CH₂ | CH₂CH(Me)CH₂ | 0 | 3-(3-HOOC.PrnO)Pr |
| 2-672 | Pip | CH₂CH₂ | CH₂CH(Me)CH₂ | 0 | 3-BozOPr |
| 2-673 | Pip | CH₂CH₂ | CH₂CH(Me)CH₂ | 0 | 3-(cHxCOO)Pr |
| 2-674 | Pip | CH₂CH₂ | CH₂CH(Me)CH₂ | 0 | 2-HOBu |
| 2-675 | Pip | CH₂CH₂ | CH₂CH(Me)CH₂ | 0 | 2-AcOBu |
| 2-676 | Pip | CH₂CH₂ | CH₂CH(Me)CH₂ | 0 | 2-(3-Etc.PrnO)Bu |
| 2-677 | Pip | CH₂CH₂ | CH₂CH(Me)CH₂ | 0 | 2-(cHxCOO)Bu |
| 2-678 | Pip | CH₂CH₂ | (CH₂)₅ | 0 | 2-HOEt |
| 2-679 | Pip | CH₂CH₂ | (CH₂)₅ | 0 | 2-AcOEt |
| 2-680 | Pip | CH₂CH₂ | (CH₂)₅ | 0 | 2-(3-HOOC.PrnO)Et |
| 2-681 | Pip | CH₂CH₂ | (CH₂)₅ | 0 | 2-BozOEt |
| 2-682 | Pip | CH₂CH₂ | (CH₂)₅ | 0 | 2-(cHxCOO)Et |
| 2-683 | Pip | CH₂CH₂ | (CH₂)₅ | 0 | 2-HOPr |
| 2-684 | Pip | CH₂CH₂ | (CH₂)₅ | 0 | 2-AcOPr |

TABLE 2-continued

| Cpd. No. | R¹ | A | B | m | R⁵ |
|---|---|---|---|---|---|
| 2-685 | Pip | CH₂CH₂ | (CH₂)₅ | 0 | 2-(3-HOOC.PrnO)Pr |
| 2-686 | Pip | CH₂CH₂ | (CH₂)₅ | 0 | 2-BozOPr |
| 2-687 | Pip | CH₂CH₂ | (CH₂)₅ | 0 | 2-(cHxCOO)Pr |
| 2-688 | Pip | CH₂CH₂ | (CH₂)₅ | 0 | 3-HOPr |
| 2-689 | Pip | CH₂CH₂ | (CH₂)₅ | 0 | 3-AcOPr |
| 2-690 | Pip | CH₂CH₂ | (CH₂)₅ | 0 | 3-(3-HOOC.PrnO)pr |
| 2-691 | Pip | CH₂CH₂ | (CH₂)₅ | 0 | 3-BozOPr |
| 2-692 | Pip | CH₂CH₂ | (CH₂)₅ | 0 | 3-(cHxCOO)Pr |
| 2-693 | Pip | CH₂CH₂ | (CH₂)₅ | 0 | 2-HOBu |
| 2-694 | Pip | CH₂CH₂ | (CH₂)₅ | 0 | 2-AcOBu |
| 2-695 | Pip | CH₂CH₂ | (CH₂)₅ | 0 | 2-(3-HOOC.PrnO)Bu |
| 2-696 | Pip | CH₂CH₂ | (CH₂)₅ | 0 | 2-(cHxCOO)Bu |
| 2-697 | Pip | CH₂CH₂ | (CH₂)₆ | 0 | 2-HOEt |
| 2-698 | Pip | CH₂CH₂ | (CH₂)₆ | 0 | 2-AcOEt |
| 2-699 | Pip | CH₂CH₂ | (CH₂)₆ | 0 | 2-(3-HOOC.PrnO)Et |
| 2-700 | Pip | CH₂CH₂ | (CH₂)₆ | 0 | 2-(cHxCOO)Et |
| 2-701 | Pip | CH₂CH₂ | (CH₂)₆ | 0 | 2-HOPr |
| 2-702 | Pip | CH₂CH₂ | (CH₂)₆ | 0 | 2-AcOPr |
| 2-703 | Pip | CH₂CH₂ | (CH₂)₆ | 0 | 2-(3-HOOC.PrnO)Pr |
| 2-704 | Pip | CH₂CH₂ | (CH₂)₆ | 0 | 2-(cHxCOO)Pr |
| 2-705 | Pip | CH₂CH₂ | (CH₂)₆ | 0 | 3-HOPr |
| 2-706 | Pip | CH₂CH₂ | (CH₂)₆ | 0 | 3-AcOPr |
| 2-707 | Pip | CH₂CH₂ | (CH₂)₆ | 0 | 3-(3-HOOC.PrnO)Pr |
| 2-708 | Pip | CH₂CH₂ | (CH₂)₆ | 0 | 3-(cHxCOO)Pr |
| 2-709 | Pip | CH₂CH₂ | (CH₂)₆ | 0 | 2-HOBu |
| 2-710 | Pip | CH₂CH₂ | (CH₂)₆ | 0 | 2-AcOBu |
| 2-711 | Pip | CH₂CH₂ | (CH₂)₆ | 0 | 2-(3-HOOC.PrnO)Bu |
| 2-712 | Pip | CH₂CH₂ | (CH₂)₆ | 0 | 2-(cHxCOO)Bu |
| 2-713 | Pyr | CH₂CH₂ | CH₂ | 0 | 2-HOEt |
| 2-714 | Pyr | CH₂CH₂ | CH₂ | 0 | 2-FoOEt |
| 2-715 | Pyr | CH₂CH₂ | CH₂ | 0 | 2-AcOEt |
| 2-716 | Pyr | CH₂CH₂ | CH₂ | 0 | 2-PrnOEt |
| 2-717 | Pyr | CH₂CH₂ | CH₂ | 0 | 2-(3-HOOC.PrnO)Et |
| 2-718 | Pyr | CH₂CH₂ | CH₂ | 0 | 2-(3-Mec.PrnO)Et |
| 2-719 | Pyr | CH₂CH₂ | CH₂ | 0 | 2-(3-Etc.PrnO)Et |
| 2-720 | Pyr | CH₂CH₂ | CH₂ | 0 | 2-BozOEt |
| 2-721 | Pyr | CH₂CH₂ | CH₂ | 0 | 2-(cPnCOO)Et |
| 2-722 | Pyr | CH₂CH₂ | CH₂ | 0 | 2-(cHxCOO)Et |
| 2-723 | Pyr | CH₂CH₂ | CH₂ | 0 | 2-HOPr |
| 2-724 | Pyr | CH₂CH₂ | CH₂ | 0 | 2-AcOPr |
| 2-725 | Pyr | CH₂CH₂ | CH₂ | 0 | 2-(3-HOOC.PrnO)Pr |
| 2-726 | Pyr | CH₂CH₂ | CH₂ | 0 | 2-BozOPr |
| 2-727 | Pyr | CH₂CH₂ | CH₂ | 0 | 2-(cHxCOO)Pr |
| 2-728 | Pyr | CH₂CH₂ | CH₂ | 0 | 3-HOPr |
| 2-729 | Pyr | CH₂CH₂ | CH₂ | 0 | 3-FoOPr |
| 2-730 | Pyr | CH₂CH₂ | CH₂ | 0 | 3-AcOPr |
| 2-731 | Pyr | CH₂CH₂ | CH₂ | 0 | 3-(3-HOOC.PrnO)Pr |
| 2-732 | Pyr | CH₂CH₂ | CH₂ | 0 | 3-(3-Mec.PrnO)Pr |
| 2-733 | Pyr | CH₂CH₂ | CH₂ | 0 | 3-BozOPr |
| 2-734 | Pyr | CH₂CH₂ | CH₂ | 0 | 3-(cHxCOO)Pr |
| 2-735 | Pyr | CH₂CH₂ | CH₂ | 0 | 2-HOBu |
| 2-736 | Pyr | CH₂CH₂ | CH₂ | 0 | 2-AcOBu |
| 2-737 | Pyr | CH₂CH₂ | CH₂CH₂ | 0 | 2-HOEt |
| 2-738 | Pyr | CH₂CH₂ | CH₂CH₂ | 0 | 2-AcOEt |
| 2-739 | Pyr | CH₂CH₂ | CH₂CH₂ | 0 | 2-(3-HOOC.PrnO)Et |
| 2-740 | Pyr | CH₂CH₂ | CH₂CH₂ | 0 | 2-(3-Mec.PrnO)Et |
| 2-741 | Pyr | CH₂CH₂ | CH₂CH₂ | 0 | 2-BozOEt |
| 2-742 | Pyr | CH₂CH₂ | CH₂CH₂ | 0 | 2-(cPnCOO)Et |
| 2-743 | Pyr | CH₂CH₂ | CH₂CH₂ | 0 | 2-(cHxCOO)Et |
| 2-744 | Pyr | CH₂CH₂ | CH₂CH₂ | 0 | 2-HOPr |
| 2-745 | Pyr | CH₂CH₂ | CH₂CH₂ | 0 | 2-AcOPr |
| 2-746 | Pyr | CH₂CH₂ | CH₂CH₂ | 0 | 2-(3-HOOC.PrnO)Pr |
| 2-747 | Pyr | CH₂CH₂ | CH₂CH₂ | 0 | 2-(cHxCOO)Pr |
| 2-748 | Pyr | CH₂CH₂ | CH₂CH₂ | 0 | 3-HOPr |
| 2-749 | Pyr | CH₂CH₂ | CH₂CH₂ | 0 | 3-AcOPr |
| 2-750 | Pyr | CH₂CH₂ | CH₂CH₂ | 0 | 3-(cHxCOO)Pr |
| 2-751 | Pyr | CH₂CH₂ | CH₂CH₂ | 0 | 2-HOBu |
| 2-752 | Pyr | CH₂CH₂ | CH₂CH₂ | 0 | 2-AcOBu |
| 2-753 | Pyr | CH₂CH₂ | (CH₂)₃ | 0 | 2-HOEt |
| 2-754 | Pyr | CH₂CH₂ | (CH₂)₃ | 0 | 2-AcOEt |
| 2-755 | Pyr | CH₂CH₂ | (CH₂)₃ | 0 | 2-PrnOEt |
| 2-756 | Pyr | CH₂CH₂ | (CH₂)₃ | 0 | 2-(3-HOOC.PrnO)Et |
| 2-757 | Pyr | CH₂CH₂ | (CH₂)₃ | 0 | 2-BozOEt |
| 2-758 | Pyr | CH₂CH₂ | (CH₂)₃ | 0 | 2-(cPnCOO)Et |
| 2-759 | Pyr | CH₂CH₂ | (CH₂)₃ | 0 | 2-(cHxCOO)Et |
| 2-760 | Pyr | CH₂CH₂ | (CH₂)₃ | 0 | 2-HOPr |

TABLE 2-continued

| Cpd. No. | R¹ | A | B | m | R⁵ |
|---|---|---|---|---|---|
| 2-761 | Pyr | CH₂CH₂ | (CH₂)₃ | 0 | 2-AcOPr |
| 2-762 | Pyr | CH₂CH₂ | (CH₂)₃ | 0 | 2-BozOPr |
| 2-763 | Pyr | CH₂CH₂ | (CH₂)₃ | 0 | 3-HOPr |
| 2-764 | Pyr | CH₂CH₂ | (CH₂)₃ | 0 | 3-AcOPr |
| 2-765 | Pyr | CH₂CH₂ | (CH₂)₃ | 0 | 3-(3-HOOC.PrnO)Pr |
| 2-766 | Pyr | CH₂CH₂ | (CH₂)₃ | 0 | 2-HOBu |
| 2-767 | Pyr | CH₂CH₂ | (CH₂)₃ | 0 | 2-AcOBu |
| 2-768 | Pyr | CH₂CH₂ | (CH₂)₄ | 0 | 2-HOEt |
| 2-769 | Pyr | CH₂CH₂ | (CH₂)₄ | 0 | 2-AcOEt |
| 2-770 | Pyr | CH₂CH₂ | (CH₂)₄ | 0 | 2-(3-HOOC.PrnO)Et |
| 2-771 | Pyr | CH₂CH₂ | (CH₂)₄ | 0 | 2-(cHxCOO)Et |
| 2-772 | Pyr | CH₂CH₂ | (CH₂)₄ | 0 | 2-HOPr |
| 2-773 | Pyr | CH₂CH₂ | (CH₂)₄ | 0 | 2-AcOPr |
| 2-774 | Pyr | CH₂CH₂ | (CH₂)₄ | 0 | 3-HOPr |
| 2-775 | Pyr | CH₂CH₂ | (CH₂)₄ | 0 | 3-AcOPr |
| 2-776 | Pyr | CH₂CH₂ | (CH₂)₄ | 0 | 2-HOBu |
| 2-777 | Pyr | CH₂CH₂ | (CH₂)₄ | 0 | 2-AcOBu |
| 2-778 | Pyr | CH₂CH₂ | CH₂CH(Me)CH₂ | 0 | 2-HOEt |
| 2-779 | Pyr | CH₂CH₂ | CH₂CH(Me)CH₂ | 0 | 2-AcOEt |
| 2-780 | Pyr | CH₂CH₂ | CH₂CH(Me)CH₂ | 0 | 2-HOPr |
| 2-781 | Pyr | CH₂CH₂ | CH₂CH(Me)CH₂ | 0 | 2-AcOPr |
| 2-782 | Pyr | CH₂CH₂ | CH₂CH(Me)CH₂ | 0 | 3-HOPr |
| 2-783 | Pyr | CH₂CH₂ | CH₂CH(Me)CH₂ | 0 | 3-AcOPr |
| 2-784 | Pyr | CH₂CH₂ | CH₂CH(Me)CH₂ | 0 | 2-HOBu |
| 2-785 | Pyr | CH₂CH₂ | CH₂CH(Me)CH₂ | 0 | 2-AcOBu |
| 2-786 | Pyr | CH₂CH₂ | (CH₂)₅ | 0 | 2-HOEt |
| 2-787 | Pyr | CH₂CH₂ | (CH₂)₅ | 0 | 2-AcOEt |
| 2-788 | Pyr | CH₂CH₂ | (CH₂)₅ | 0 | 2-HOPr |
| 2-789 | Pyr | CH₂CH₂ | (CH₂)₅ | 0 | 2-AcOPr |
| 2-790 | Pyr | CH₂CH₂ | (CH₂)₅ | 0 | 2-(cHxCOO)Pr |
| 2-791 | Pyr | CH₂CH₂ | (CH₂)₅ | 0 | 3-HOPr |
| 2-792 | Pyr | CH₂CH₂ | (CH₂)₅ | 0 | 3-AcOPr |
| 2-793 | Pyr | CH₂CH₂ | (CH₂)₅ | 0 | 2-AcOBu |
| 2-794 | Pyr | CH₂CH₂ | (CH₂)₆ | 0 | 2-HOEt |
| 2-795 | Pyr | CH₂CH₂ | (CH₂)₆ | 0 | 2-AcOEt |
| 2-796 | Pyr | CH₂CH₂ | (CH₂)₆ | 0 | 2-HOPr |
| 2-797 | Pyr | CH₂CH₂ | (CH₂)₆ | 0 | 2-AcOPr |
| 2-798 | Pyr | CH₂CH₂ | (CH₂)₆ | 0 | 3-HOPr |
| 2-799 | Pyr | CH₂CH₂ | (CH₂)₆ | 0 | 3-AcOPr |
| 2-800 | Pyr | CH₂CH₂ | (CH₂)₆ | 0 | 2-AcOBu |
| 2-801 | NMe₂ | CH₂CH₂ | CH₂ | 0 | 2-HOEt |
| 2-802 | NMe₂ | CH₂CH₂ | CH₂ | 0 | 2-AcOEt |
| 2-803 | NMe₂ | CH₂CH₂ | CH₂ | 0 | 2-PrnOEt |
| 2-804 | NMe₂ | CH₂CH₂ | CH₂ | 0 | 2-(3-HOOC.PrnO)Et |
| 2-805 | NMe₂ | CH₂CH₂ | CH₂ | 0 | 2-(3-Mec.PrnO)Et |
| 2-806 | NMe₂ | CH₂CH₂ | CH₂ | 0 | 2-BozOEt |
| 2-807 | NMe₂ | CH₂CH₂ | CH₂ | 0 | 2-(cHxCOO)Et |
| 2-808 | NMe₂ | CH₂CH₂ | CH₂ | 0 | 2-HOPr |
| 2-809 | NMe₂ | CH₂CH₂ | CH₂ | 0 | 2-(cHxCOO)Pr |
| 2-810 | NMe₂ | CH₂CH₂ | CH₂ | 0 | 3-HOPr |
| 2-811 | NMe₂ | CH₂CH₂ | CH₂ | 0 | 3-AcOPr |
| 2-812 | NMe₂ | CH₂CH₂ | CH₂ | 0 | 2-HOBu |
| 2-813 | NMe₂ | CH₂CH₂ | CH₂ | 0 | 2-AcOBu |
| 2-814 | NMe₂ | CH₂CH₂ | CH₂CH₂ | 0 | 2-HOEt |
| 2-815 | NMe₂ | CH₂CH₂ | CH₂CH₂ | 0 | 2-AcOEt |
| 2-816 | NMe₂ | CH₂CH₂ | CH₂CH₂ | 0 | 3-HOPr |
| 2-817 | NMe₂ | CH₂CH₂ | CH₂CH₂ | 0 | 3-AcOPr |
| 2-818 | NMe₂ | CH₂CH₂ | (CH₂)₃ | 0 | 2-HOEt |
| 2-819 | NMe₂ | CH₂CH₂ | (CH₂)₃ | 0 | 2-AcOEt |
| 2-820 | NMe₂ | CH₂CH₂ | (CH₂)₃ | 0 | 2-PrnOEt |
| 2-821 | NMe₂ | CH₂CH₂ | (CH₂)₃ | 0 | 2-(3-HOOC.PrnO)Et |
| 2-822 | NMe₂ | CH₂CH₂ | (CH₂)₃ | 0 | 2-BozOEt |
| 2-823 | NMe₂ | CH₂CH₂ | (CH₂)₃ | 0 | 2-(cHxCOO)Et |
| 2-824 | NMe₂ | CH₂CH₂ | (CH₂)₃ | 0 | 2-(cPnCOO)Pr |
| 2-825 | NMe₂ | CH₂CH₂ | (CH₂)₃ | 0 | 2-(cHxCOO)Pr |
| 2-826 | NMe₂ | CH₂CH₂ | (CH₂)₃ | 0 | 3-HOPr |
| 2-827 | NMe₂ | CH₂CH₂ | (CH₂)₃ | 0 | 3-AcOPr |
| 2-828 | NMe₂ | CH₂CH₂ | (CH₂)₃ | 0 | 2-HOBu |
| 2-829 | NMe₂ | CH₂CH₂ | (CH₂)₃ | 0 | 2-AcOBu |
| 2-830 | NMe₂ | CH₂CH₂ | (CH₂)₄ | 0 | 2-HOEt |
| 2-831 | NMe₂ | CH₂CH₂ | (CH₂)₄ | 0 | 2-AcOEt |
| 2-832 | NMe₂ | CH₂CH₂ | (CH₂)₄ | 0 | 3-HOPr |
| 2-833 | NMe₂ | CH₂CH₂ | (CH₂)₄ | 0 | 3-AcOPr |
| 2-834 | NMe₂ | CH₂CH₂ | (CH₂)₄ | 0 | 2-AcOBu |
| 2-835 | NMe₂ | CH₂CH₂ | CH₂CH(Me)CH₂ | 0 | 2-HOEt |
| 2-836 | NMe₂ | CH₂CH₂ | CH₂CH(Me)CH₂ | 0 | 2-AcOEt |

TABLE 2-continued

| Cpd. No. | R¹ | A | B | m | R⁵ |
|---|---|---|---|---|---|
| 2-837 | NMe₂ | CH₂CH₂ | CH₂CH(Me)CH₂ | 0 | 2-HOPr |
| 2-838 | NMe₂ | CH₂CH₂ | CH₂CH(Me)CH₂ | 0 | 2-AcOPr |
| 2-839 | NMe₂ | CH₂CH₂ | CH₂CH(Me)CH₂ | 0 | 3-AcOPr |
| 2-840 | NMe₂ | CH₂CH₂ | CH₂CH(Me)CH₂ | 0 | 2-AcOBu |
| 2-841 | NMe₂ | CH₂CH₂ | (CH₂)₅ | 0 | 2-HOEt |
| 2-842 | NMe₂ | CH₂CH₂ | (CH₂)₅ | 0 | 2-AcOPr |
| 2-843 | NMe₂ | CH₂CH₂ | (CH₂)₅ | 0 | 3-HOPr |
| 2-844 | NMe₂ | CH₂CH₂ | (CH₂)₅ | 0 | 3-AcOPr |
| 2-845 | NMe₂ | CH₂CH₂ | (CH₂)₆ | 0 | 2-HOEt |
| 2-846 | NMe₂ | CH₂CH₂ | (CH₂)₆ | 0 | 2-AcOEt |
| 2-847 | NMe₂ | CH₂CH₂ | (CH₂)₆ | 0 | 3-HOPr |
| 2-848 | NMe₂ | CH₂CH₂ | (CH₂)₆ | 0 | 3-AcOPr |
| 2-849 | Azi | CH₂CH₂ | CH₂ | 0 | 2-AcOEt |
| 2-850 | Aze | CH₂CH₂ | CH₂ | 0 | 2-AcOEt |
| 2-851 | Pip | (CH₂)₃ | CH₂ | 0 | CH₂OH |
| 2-852 | Pip | (CH₂)₃ | CH₂ | 0 | 2-HOEt |
| 2-853 | Pip | (CH₂)₃ | CH₂ | 0 | 2-FoOEt |
| 2-854 | Pip | (CH₂)₃ | CH₂ | 0 | 2-AcOEt |
| 2-855 | Pip | (CH₂)₃ | CH₂ | 0 | 2-PrnOEt |
| 2-856 | Pip | (CH₂)₃ | CH₂ | 0 | 2-ByrOEt |
| 2-857 | Pip | (CH₂)₃ | CH₂ | 0 | 2-iByrOEt |
| 2-858 | Pip | (CH₂)₃ | CH₂ | 0 | 2-ValOEt |
| 2-859 | Pip | (CH₂)₃ | CH₂ | 0 | 2-iValOEt |
| 2-860 | Pip | (CH₂)₃ | CH₂ | 0 | 2-(PhAcO)Et |
| 2-861 | Pip | (CH₂)₃ | CH₂ | 0 | 2-(HOOC.AcO)Et |
| 2-862 | Pip | (CH₂)₃ | CH₂ | 0 | 2-(3-Hooc.prnO)Et |
| 2-863 | Pip | (CH₂)₃ | CH₂ | 0 | 2-(3-Mec.PrnO)Et |
| 2-864 | Pip | (CH₂)₃ | CH₂ | 0 | 2-(3-Etc.PrnO)Et |
| 2-865 | Pip | (CH₂)₃ | CH₂ | 0 | 2-(3-Prc.PrnO)Et |
| 2-866 | Pip | (CH₂)₃ | CH₂ | 0 | 2-(3-Phc.PrnO)Et |
| 2-867 | Pip | (CH₂)₃ | CH₂ | 0 | 2-[3-(4-MePhcO)PrnO]Et |
| 2-868 | Pip | (CH₂)₃ | CH₂ | 0 | 2-(3-PhPrnO)Et |
| 2-869 | Pip | (CH₂)₃ | CH₂ | 0 | 2-(3-PhPrnO)Et |
| 2-870 | Pip | (CH₂)₃ | CH₂ | 0 | 2-BozOEt |
| 2-871 | Pip | (CH₂)₃ | CH₂ | 0 | 2-(4-MeBozO)Et |
| 2-872 | Pip | (CH₂)₃ | CH₂ | 0 | 2-(4-MeOBozo)Et |
| 2-873 | Pip | (CH₂)₃ | CH₂ | 0 | 2-(4-FBozO)Et |
| 2-874 | Pip | (CH₂)₃ | CH₂ | 0 | 2-(4-ClBozO)Et |
| 2-875 | Pip | (CH₂)₃ | CH₂ | 0 | 2-(cPrCOO)Et |
| 2-876 | Pip | (CH₂)₃ | CH₂ | 0 | 2-(cBuCOO)Et |
| 2-877 | Pip | (CH₂)₃ | CH₂ | 0 | 2-(cPnCOO)Et |
| 2-878 | Pip | (CH₂)₃ | CH₂ | 0 | 2-(cHxCoo)Et |
| 2-879 | Pip | (CH₂)₃ | CH₂ | 0 | 2-HOPr |
| 2-880 | Pip | (CH₂)₃ | CH₂ | 0 | 2-FoOPr |
| 2-881 | Pip | (CH₂)₃ | CH₂ | 0 | 2-AcOPr |
| 2-882 | Pip | (CH₂)₃ | CH₂ | 0 | 2-PrnOPr |
| 2-883 | Pip | (CH₂)₃ | CH₂ | 0 | 2-(3-HOOC.PrnO)Pr |
| 2-884 | Pip | (CH₂)₃ | CH₂ | 0 | 2-(3-Mec.PrnO)Pr |
| 2-885 | Pip | (CH₂)₃ | CH₂ | 0 | 2-(3-Etc.PrnO)Pr |
| 2-886 | Pip | (CH₂)₃ | CH₂ | 0 | 2-(3-Phc.PrnO)Et |
| 2-887 | Pip | (CH₂)₃ | CH₂ | 0 | 2-[3-(4-MePhcO)PrnO]Et |
| 2-888 | Pip | (CH₂)₃ | CH₂ | 0 | 2-(PhAcO)Pr |
| 2-889 | Pip | (CH₂)₃ | CH₂ | 0 | 2-BozOPr |
| 2-890 | Pip | (CH₂)₃ | CH₂ | 0 | 2-(cPnCOO)Pr |
| 2-891 | Pip | (CH₂)₃ | CH₂ | 0 | 2-(cHxCOO)Pr |
| 2-892 | Pip | (CH₂)₃ | CH₂ | 0 | 3-HOPr |
| 2-893 | Pip | (CH₂)₃ | CH₂ | 0 | 3-FoOPr |
| 2-894 | Pip | (CH₂)₃ | CH₂ | 0 | 3-AcOPr |
| 2-895 | Pip | (CH₂)₃ | CH₂ | 0 | 3-PrnOPr |
| 2-896 | Pip | (CH₂)₃ | CH₂ | 0 | 3-(3-HOOC.PrnO)Pr |
| 2-897 | Pip | (CH₂)₃ | CH₂ | 0 | 3-(3-Mec.PrnO)Pr |
| 2-898 | Pip | (CH₂)₃ | CH₂ | 0 | 3-(3-Etc.PrnO)Pr |
| 2-899 | Pip | (CH₂)₃ | CH₂ | 0 | 3-BozOPr |
| 2-900 | Pip | (CH₂)₃ | CH₂ | 0 | 3-(cPnCOO)Pr |
| 2-901 | Pip | (CH₂)₃ | CH₂ | 0 | 3-(cHxCOO)Pr |
| 2-902 | Pip | (CH₂)₃ | CH₂ | 0 | 2-HOBu |
| 2-903 | Pip | (CH₂)₃ | CH₂ | 0 | 2-AcOBu |
| 2-904 | Pip | (CH₂)₃ | CH₂ | 0 | 2-(3-HOOC.PrnO)Bu |
| 2-905 | Pip | (CH₂)₃ | CH₂ | 0 | 2-BozOBu |
| 2-906 | Pip | (CH₂)₃ | CH₂ | 0 | 2-(cHxCOO)Bu |
| 2-907 | Pip | (CH₂)₃ | CH₂CH₂ | 0 | 2-HOEt |
| 2-908 | Pip | (CH₂)₃ | CH₂CH₂ | 0 | 2-FoOEt |
| 2-909 | Pip | (CH₂)₃ | CH₂CH₂ | 0 | 2-AcOEt |
| 2-910 | Pip | (CH₂)₃ | CH₂CH₂ | 0 | 2-PrnOEt |
| 2-911 | Pip | (CH₂)₃ | CH₂CH₂ | 0 | 2-ValOEt |
| 2-912 | Pip | (CH₂)₃ | CH₂CH₂ | 0 | 2-(PhAcO)Et |

TABLE 2-continued

| Cpd. No. | R¹ | A | B | m | R⁵ |
|---|---|---|---|---|---|
| 2-913 | Pip | (CH₂)₃ | CH₂CH₂ | 0 | 2-(3-HOOC.PrnO)Et |
| 2-914 | Pip | (CH₂)₃ | CH₂CH₂ | 0 | 2-(3-Mec.PrnO)Et |
| 2-915 | Pip | (CH₂)₃ | CH₂CH₂ | 0 | 2-(3-Etc.PrnO)Et |
| 2-916 | Pip | (CH₂)₃ | CH₂CH₂ | 0 | 2-(3-PhPrnO)Et |
| 2-917 | Pip | (CH₂)₃ | CH₂CH₂ | 0 | 2-BozOEt |
| 2-918 | Pip | (CH₂)₃ | CH₂CH₂ | 0 | 2-(4-MeBozO)Et |
| 2-919 | Pip | (CH₂)₃ | CH₂CH₂ | 0 | 2-(4-FBozO)Et |
| 2-920 | Pip | (CH₂)₃ | CH₂CH₂ | 0 | 2-(4-ClBozO)Et |
| 2-921 | Pip | (CH₂)₃ | CH₂CH₂ | 0 | 2-(cPrCOO)Et |
| 2-922 | Pip | (CH₂)₃ | CH₂CH₂ | 0 | 2-(cBuCOO)Et |
| 2-923 | Pip | (CH₂)₃ | CH₂CH₂ | 0 | 2-(cPnCOO)Et |
| 2-924 | Pip | (CH₂)₃ | CH₂CH₂ | 0 | 2-(cHxCOO)Et |
| 2-925 | Pip | (CH₂)₃ | CH₂CH₂ | 0 | 2-HOPr |
| 2-926 | Pip | (CH₂)₃ | CH₂CH₂ | 0 | 2-FoOPr |
| 2-927 | Pip | (CH₂)₃ | CH₂CH₂ | 0 | 2-AcOPr |
| 2-928 | Pip | (CH₂)₃ | CH₂CH₂ | 0 | 2-PrnOPr |
| 2-929 | Pip | (CH₂)₃ | CH₂CH₂ | 0 | 2-(3-HOOC.PrnO)Pr |
| 2-930 | Pip | (CH₂)₃ | CH₂CH₂ | 0 | 2-(3-Mec.PrnO)Pr |
| 2-931 | Pip | (CH₂)₃ | CH₂CH₂ | 0 | 2-BozOPr |
| 2-932 | Pip | (CH₂)₃ | CH₂CH₂ | 0 | 2-(cPnCOO)Pr |
| 2-933 | Pip | (CH₂)₃ | CH₂CH₂ | 0 | 2-(cHxCOO)Pr |
| 2-934 | Pip | (CH₂)₃ | CH₂CH₂ | 0 | 3-HOPr |
| 2-935 | Pip | (CH₂)₃ | CH₂CH₂ | 0 | 3-AcOPr |
| 2-936 | Pip | (CH₂)₃ | CH₂CH₂ | 0 | 3-PrnOPr |
| 2-937 | Pip | (CH₂)₃ | CH₂CH₂ | 0 | 3-(3-HOOC.PrnO)Pr |
| 2-938 | Pip | (CH₂)₃ | CH₂CH₂ | 0 | 3-BozOPr |
| 2-939 | Pip | (CH₂)₃ | CH₂CH₂ | 0 | 3-(cPnCOO)Pr |
| 2-940 | Pip | (CH₂)₃ | CH₂CH₂ | 0 | 3-(cHxCOO)Pr |
| 2-941 | Pip | (CH₂)₃ | CH₂CH₂ | 0 | 2-HOBu |
| 2-942 | Pip | (CH₂)₃ | CH₂CH₂ | 0 | 2-AcOBu |
| 2-943 | Pip | (CH₂)₃ | CH₂CH₂ | 0 | 2-(3-HOOC.PrnO)Bu |
| 2-944 | Pip | (CH₂)₃ | CH₂CH₂ | 0 | 2-BozOBu |
| 2-945 | Pip | (CH₂)₃ | CH₂CH₂ | 0 | 2-(cHxCOO)Bu |
| 2-946 | Pip | (CH₂)₃ | (CH₂)₃ | 0 | 2-HOEt |
| 2-947 | Pip | (CH₂)₃ | (CH₂)₃ | 0 | 2-FoOEt |
| 2-948 | Pip | (CH₂)₃ | (CH₂)₃ | 0 | 2-AcOEt |
| 2-949 | Pip | (CH₂)₃ | (CH₂)₃ | 0 | 2-PrnOEt |
| 2-950 | Pip | (CH₂)₃ | (CH₂)₃ | 0 | 2-ByrOEt |
| 2-951 | Pip | (CH₂)₃ | (CH₂)₃ | 0 | 2-iByrOEt |
| 2-952 | Pip | (CH₂)₃ | (CH₂)₃ | 0 | 2-ValOEt |
| 2-953 | Pip | (CH₂)₃ | (CH₂)₃ | 0 | 2-(3-HOOC.PrnO)Et |
| 2-954 | Pip | (CH₂)₃ | (CH₂)₃ | 0 | 2-(3-Mec.PrnO)Et |
| 2-955 | Pip | (CH₂)₃ | (CH₂)₃ | 0 | 2-(3-Etc.PrnO)Et |
| 2-956 | Pip | (CH₂)₃ | (CH₂)₃ | 0 | 2-(PhAcO)Et |
| 2-957 | Pip | (CH₂)₃ | (CH₂)₃ | 0 | 2-BozOEt |
| 2-958 | Pip | (CH₂)₃ | (CH₂)₃ | 0 | 2-(4-Bozo)Et |
| 2-959 | Pip | (CH₂)₃ | (CH₂)₃ | 0 | 2-(4-MeOBozO)Et |
| 2-960 | Pip | (CH₂)₃ | (CH₂)₃ | 0 | 2-(4-FBozO)Et |
| 2-961 | Pip | (CH₂)₃ | (CH₂)₃ | 0 | 2-(4-ClBozO)Et |
| 2-962 | Pip | (CH₂)₃ | (CH₂)₃ | 0 | 2-(cPrCOO)Et |
| 2-963 | Pip | (CH₂)₃ | (CH₂)₃ | 0 | 2-(cBuCOO)Et |
| 2-964 | Pip | (CH₂)₃ | (CH₂)₃ | 0 | 2-(cPnCOO)Et |
| 2-965 | Pip | (CH₂)₃ | (CH₂)₃ | 0 | 2-(cHxCOO)Et |
| 2-966 | Pip | (CH₂)₃ | (CH₂)₃ | 0 | 2-HOPr |
| 2-967 | Pip | (CH₂)₃ | (CH₂)₃ | 0 | 2-AcOPr |
| 2-968 | Pip | (CH₂)₃ | (CH₂)₃ | 0 | 2-PrnOPr |
| 2-969 | Pip | (CH₂)₃ | (CH₂)₃ | 0 | 2-(3-HOOC.PrnO)Pr |
| 2-970 | Pip | (CH₂)₃ | (CH₂)₃ | 0 | 2-(3-Etc.PrnO)Pr |
| 2-971 | Pip | (CH₂)₃ | (CH₂)₃ | 0 | 2-BozOPr |
| 2-972 | Pip | (CH₂)₃ | (CH₂)₃ | 0 | 2-(cHxCOO)Pr |
| 2-973 | Pip | (CH₂)₃ | (CH₂)₃ | 0 | 3-HOPr |
| 2-974 | Pip | (CH₂)₃ | (CH₂)₃ | 0 | 3-AcOPr |
| 2-975 | Pip | (CH₂)₃ | (CH₂)₃ | 0 | 3-(3-HOOC.PrnO)Pr |
| 2-976 | Pip | (CH₂)₃ | (CH₂)₃ | 0 | 3-(3-Mec.PrnO)Pr |
| 2-977 | Pip | (CH₂)₃ | (CH₂)₃ | 0 | 3-BozOPr |
| 2-978 | Pip | (CH₂)₃ | (CH₂)₃ | 0 | 3-(cHxCOO)Pr |
| 2-979 | Pip | (CH₂)₃ | (CH₂)₃ | 0 | 2-HOBu |
| 2-980 | Pip | (CH₂)₃ | (CH₂)₃ | 0 | 2-AcOBu |
| 2-981 | Pip | (CH₂)₃ | (CH₂)₃ | 0 | 2-(3-HOOC.PrnO)Bu |
| 2-982 | Pip | (CH₂)₃ | (CH₂)₃ | 0 | 2-BozOBu |
| 2-983 | Pip | (CH₂)₃ | (CH₂)₃ | 0 | 2-(cHxCOO)Bu |
| 2-984 | Pip | (CH₂)₃ | (CH₂)₄ | 0 | 2-HOEt |
| 2-985 | Pip | (CH₂)₃ | (CH₂)₄ | 0 | 2-FoOEt |
| 2-986 | Pip | (CH₂)₃ | (CH₂)₄ | 0 | 2-AcOEt |
| 2-987 | Pip | (CH₂)₃ | (CH₂)₄ | 0 | 2-PrnOEt |
| 2-988 | Pip | (CH₂)₃ | (CH₂)₄ | 0 | 2-(3-HOOC.PrnO)Et |

TABLE 2-continued

| Cpd. No. | R¹ | A | B | m | R⁵ |
|---|---|---|---|---|---|
| 2-989 | Pip | (CH₂)₃ | (CH₂)₄ | 0 | 2-(3-Mec.PrnO)Et |
| 2-990 | Pip | (CH₂)₃ | (CH₂)₄ | 0 | 2-BozOEt |
| 2-991 | Pip | (CH₂)₃ | (CH₂)₄ | 0 | 2-(cHxCOO)Et |
| 2-992 | Pip | (CH₂)₃ | (CH₂)₄ | 0 | 2-HOPr |
| 2-993 | Pip | (CH₂)₃ | (CH₂)₄ | 0 | 2-AcOPr |
| 2-994 | Pip | (CH₂)₃ | (CH₂)₄ | 0 | 2-(3-HOOC.PrnO)Pr |
| 2-995 | Pip | (CH₂)₃ | (CH₂)₄ | 0 | 2-BozOPr |
| 2-996 | Pip | (CH₂)₃ | (CH₂)₄ | 0 | 2-(cHxCOO)Pr |
| 2-997 | Pip | (CH₂)₃ | (CH₂)₄ | 0 | 3-HOPr |
| 2-998 | Pip | (CH₂)₃ | (CH₂)₄ | 0 | 3-AcOPr |
| 2-999 | Pip | (CH₂)₃ | (CH₂)₄ | 0 | 3-(3-HOOC.PrnO)Pr |
| 2-1000 | Pip | (CH₂)₃ | (CH₂)₄ | 0 | 3-BozOPr |
| 2-1001 | Pip | (CH₂)₃ | (CH₂)₄ | 0 | 3-(cHxCOO)Pr |
| 2-1002 | Pip | (CH₂)₃ | (CH₂)₄ | 0 | 2-HOBu |
| 2-1003 | Pip | (CH₂)₃ | (CH₂)₄ | 0 | 2-AcOBu |
| 2-1004 | Pip | (CH₂)₃ | (CH₂)₄ | 0 | 2-(3-HOOC.PrnO)Bu |
| 2-1005 | Pip | (CH₂)₃ | (CH₂)₄ | 0 | 2-(cHxCOO)Bu |
| 2-1006 | Pip | (CH₂)₃ | CH₂CH(Me)CH₂ | 0 | 2-HOEt |
| 2-1007 | Pip | (CH₂)₃ | CH₂CH(Me)CH₂ | 0 | 2-AcOEt |
| 2-1008 | Pip | (CH₂)₃ | CH₂CH(Me)CH₂ | 0 | 2-(3-HOOC.PrnO)Et |
| 2-1009 | Pip | (CH₂)₃ | CH₂CH(Me)CH₂ | 0 | 2-BozOEt |
| 2-1010 | Pip | (CH₂)₃ | CH₂CH(Me)CH₂ | 0 | 2-(cHxCOO)Et |
| 2-1011 | Pip | (CH₂)₃ | CH₂CH(Me)CH₂ | 0 | 2-HOPr |
| 2-1012 | Pip | (CH₂)₃ | CH₂CH(Me)CH₂ | 0 | 2-AcOPr |
| 2-1013 | Pip | (CH₂)₃ | CH₂CH(Me)CH₂ | 0 | 2-BozOPr |
| 2-1014 | Pip | (CH₂)₃ | CH₂CH(Me)CH₂ | 0 | 2-(cHxCOO)Pr |
| 2-1015 | Pip | (CH₂)₃ | CH₂CH(Me)CH₂ | 0 | 3-HOPr |
| 2-1016 | Pip | (CH₂)₃ | CH₂CH(Me)CH₂ | 0 | 3-AcOPr |
| 2-1017 | Pip | (CH₂)₃ | CH₂CH(Me)CH₂ | 0 | 3-(3-HOOC.PrnO)Pr |
| 2-1018 | Pip | (CH₂)₃ | CH₂CH(Me)CH₂ | 0 | 3-BozOPr |
| 2-1019 | Pip | (CH₂)₃ | CH₂CH(Me)CH₂ | 0 | 3-(cHxCOO)Pr |
| 2-1020 | Pip | (CH₂)₃ | CH₂CH(Me)CH₂ | 0 | 2-HOBu |
| 2-1021 | Pip | (CH₂)₃ | CH₂CH(Me)CH₂ | 0 | 2-AcOBu |
| 2-1022 | Pip | (CH₂)₃ | CH₂CH(Me)CH₂ | 0 | 2-(3-Etc.PrnO)Bu |
| 2-1023 | Pip | (CH₂)₃ | CH₂CH(Me)CH₂ | 0 | 2-(cHxCOO)Bu |
| 2-1024 | Pip | (CH₂)₃ | (CH₂)₅ | 0 | 2-HOEt |
| 2-1025 | Pip | (CH₂)₃ | (CH₂)₅ | 0 | 2-AcOEt |
| 2-1026 | Pip | (CH₂)₃ | (CH₂)₅ | 0 | 2-(3-HOOC.PrnO)Et |
| 2-1027 | Pip | (CH₂)₃ | (CH₂)₅ | 0 | 2-BozOEt |
| 2-1028 | Pip | (CH₂)₃ | (CH₂)₅ | 0 | 2-(cHxCOO)Et |
| 2-1029 | Pip | (CH₂)₃ | (CH₂)₅ | 0 | 2-HOPr |
| 2-1030 | Pip | (CH₂)₃ | (CH₂)₅ | 0 | 2-AcOPr |
| 2-1031 | Pip | (CH₂)₃ | (CH₂)₅ | 0 | 2-(3-HOOC.PrnO)Pr |
| 2-1032 | Pip | (CH₂)₃ | (CH₂)₅ | 0 | 2-BozOPr |
| 2-1033 | Pip | (CH₂)₃ | (CH₂)₅ | 0 | 2-(cHxCOO)Pr |
| 2-1034 | Pip | (CH₂)₃ | (CH₂)₅ | 0 | 3-HOPr |
| 2-1035 | Pip | (CH₂)₃ | (CH₂)₅ | 0 | 3-AcOPr |
| 2-1036 | Pip | (CH₂)₃ | (CH₂)₅ | 0 | 3-(3-HOOC.PrnO)Pr |
| 2-1037 | Pip | (CH₂)₃ | (CH₂)₅ | 0 | 3-BozOPr |
| 2-1038 | Pip | (CH₂)₃ | (CH₂)₅ | 0 | 3-(cHxCOO)Pr |
| 2-1039 | Pip | (CH₂)₃ | (CH₂)₅ | 0 | 2-HOBu |
| 2-1040 | Pip | (CH₂)₃ | (CH₂)₅ | 0 | 2-AcOBu |
| 2-1041 | Pip | (CH₂)₃ | (CH₂)₅ | 0 | 2-(3-HOOC.PrnO)Bu |
| 2-1042 | Pip | (CH₂)₃ | (CH₂)₅ | 0 | 2-(cHxCOO)Bu |
| 2-1043 | Pip | (CH₂)₃ | (CH₂)₆ | 0 | 2-HOEt |
| 2-1044 | Pip | (CH₂)₃ | (CH₂)₆ | 0 | 2-AcOEt |
| 2-1045 | Pip | (CH₂)₃ | (CH₂)₆ | 0 | 2-(3-HOOC.PrnO)Et |
| 2-1046 | Pip | (CH₂)₃ | (CH₂)₆ | 0 | 2-(cHxCOO)Et |
| 2-1047 | Pip | (CH₂)₃ | (CH₂)₆ | 0 | 2-HOPr |
| 2-1048 | Pip | (CH₂)₃ | (CH₂)₆ | 0 | 2-AcOPr |
| 2-1049 | Pip | (CH₂)₃ | (CH₂)₆ | 0 | 2-(3-HOOC.PrnO)Pr |
| 2-1050 | Pip | (CH₂)₃ | (CH₂)₆ | 0 | 2-(cHxCOO)Pr |
| 2-1051 | Pip | (CH₂)₃ | (CH₂)₆ | 0 | 3-HOPr |
| 2-1052 | Pip | (CH₂)₃ | (CH₂)₆ | 0 | 3-AcOPr |
| 2-1053 | Pip | (CH₂)₃ | (CH₂)₆ | 0 | 3-(3-HOOC.PrnO)Pr |
| 2-1054 | Pip | (CH₂)₃ | (CH₂)₆ | 0 | 3-(cHxCOO)Pr |
| 2-1055 | Pip | (CH₂)₃ | (CH₂)₆ | 0 | 2-HOBu |
| 2-1056 | Pip | (CH₂)₃ | (CH₂)₆ | 0 | 2-AcOBu |
| 2-1057 | Pip | (CH₂)₃ | (CH₂)₆ | 0 | 2-(3-HOOC.PrnO)Bu |
| 2-1058 | Pip | (CH₂)₃ | (CH₂)₆ | 0 | 2-(cHxCOO)Bu |
| 2-1059 | Pip | CH₂ | CH₂ | 0 | 2-HOEt |
| 2-1060 | Pip | CH₂ | CH₂ | 0 | 2-FoOEt |
| 2-1061 | Pip | CH₂ | CH₂ | 0 | 2-AcOEt |
| 2-1062 | Pip | CH₂ | CH₂ | 0 | 2-PrnOEt |
| 2-1063 | Pip | CH₂ | CH₂ | 0 | 2-(3-HOOC.PrnO)Et |
| 2-1064 | Pip | CH₂ | CH₂ | 0 | 2-(3-Mec.PrnO)Et |

TABLE 2-continued

| Cpd. No. | R¹ | A | B | m | R⁵ |
|---|---|---|---|---|---|
| 2-1065 | Pip | CH₂ | CH₂ | 0 | 2-(3-Etc.PrnO)Et |
| 2-1066 | Pip | CH₂ | CH₂ | 0 | 2-BozOEt |
| 2-1067 | Pip | CH₂ | CH₂ | 0 | 2-(cPnCOO)Et |
| 2-1068 | Pip | CH₂ | CH₂ | 0 | 2-(cHxCOO)Et |
| 2-1069 | Pip | CH₂ | CH₂ | 0 | 2-HOPr |
| 2-1070 | Pip | CH₂ | CH₂ | 0 | 2-AcOPr |
| 2-1071 | Pip | CH₂ | CH₂ | 0 | 2-(3-HOOC.PrnO)Pr |
| 2-1072 | Pip | CH₂ | CH₂ | 0 | 2-BozOPr |
| 2-1073 | Pip | CH₂ | CH₂ | 0 | 2-(cHxCOO)Pr |
| 2-1074 | Pip | CH₂ | CH₂ | 0 | 3-HOPr |
| 2-1075 | Pip | CH₂ | CH₂ | 0 | 3-FoOPr |
| 2-1076 | Pip | CH₂ | CH₂ | 0 | 3-AcOPr |
| 2-1077 | Pip | CH₂ | CH₂ | 0 | 3-(3-HOOC.PrnO)Pr |
| 2-1078 | Pip | CH₂ | CH₂ | 0 | 3-(3-Mec.PrnO)Pr |
| 2-1079 | Pip | CH₂ | CH₂ | 0 | 3-BozOPr |
| 2-1080 | Pip | CH₂ | CH₂ | 0 | 3-(cHxCOO)Pr |
| 2-1081 | Pip | CH₂ | CH₂ | 0 | 2-HOBu |
| 2-1082 | Pip | CH₂ | CH₂ | 0 | 2-AcOBu |
| 2-1083 | Pip | CH₂ | CH₂CH₂ | 0 | 2-HOEt |
| 2-1084 | Pip | CH₂ | CH₂CH₂ | 0 | 2-AcOEt |
| 2-1085 | Pip | CH₂ | CH₂CH₂ | 0 | 2-(3-HOOC.PrnO)Et |
| 2-1086 | Pip | CH₂ | CH₂CH₂ | 0 | 2-(3-Mec.Prn.O)Et |
| 2-1087 | Pip | CH₂ | CH₂CH₂ | 0 | 2-BozOEt |
| 2-1088 | Pip | CH₂ | CH₂CH₂ | 0 | 2-(cPnCOO)Et |
| 2-1089 | Pip | CH₂ | CH₂CH₂ | 0 | 2-(cHxCOO)Et |
| 2-1090 | Pip | CH₂ | CH₂CH₂ | 0 | 2-HOPr |
| 2-1091 | Pip | CH₂ | CH₂CH₂ | 0 | 2-AcOPr |
| 2-1092 | Pip | CH₂ | CH₂CH₂ | 0 | 2-(3-HOOC.PrnO)Pr |
| 2-1093 | Pip | CH₂ | CH₂CH₂ | 0 | 2-(cHxCOO)Pr |
| 2-1094 | Pip | CH₂ | CH₂CH₂ | 0 | 3-HOPr |
| 2-1095 | Pip | CH₂ | CH₂CH₂ | 0 | 3-AcOPr |
| 2-1096 | Pip | CH₂ | CH₂CH₂ | 0 | 3-(cHxCOO)Pr |
| 2-1097 | Pip | CH₂ | CH₂CH₂ | 0 | 2-HOBu |
| 2-1098 | Pip | CH₂ | CH₂CH₂ | 0 | 2-AcOBu |
| 2-1099 | Pip | CH₂ | (CH₂)₃ | 0 | 2-HOEt |
| 2-1100 | Pip | CH₂ | (CH₂)₃ | 0 | 2-AcOEt |
| 2-1101 | Pip | CH₂ | (CH₂)₃ | 0 | 2-PrnOEt |
| 2-1102 | Pip | CH₂ | (CH₂)₃ | 0 | 2-(3-HOOC.PrnO)Et |
| 2-1103 | Pip | CH₂ | (CH₂)₃ | 0 | 2-BozOEt |
| 2-1104 | Pip | CH₂ | (CH₂)₃ | 0 | 2-(cPnCOO)Et |
| 2-1105 | Pip | CH₂ | (CH₂)₃ | 0 | 2-(cHxCOO)Et |
| 2-1106 | Pip | CH₂ | (CH₂)₃ | 0 | 2-HOPr |
| 2-1107 | Pip | CH₂ | (CH₂)₃ | 0 | 2-AcOPr |
| 2-1108 | Pip | CH₂ | (CH₂)₃ | 0 | 2-BozOPr |
| 2-1109 | Pip | CH₂ | (CH₂)₃ | 0 | 3-HOPr |
| 2-1110 | Pip | CH₂ | (CH₂)₃ | 0 | 3-AcOPr |
| 2-1111 | Pip | CH₂ | (CH₂)₃ | 0 | 3-(3-HOOC.PrnO)Pr |
| 2-1112 | Pip | CH₂ | (CH₂)₃ | 0 | 2-HOBu |
| 2-1113 | Pip | CH₂ | (CH₂)₃ | 0 | 2-AcOBu |
| 2-1114 | Pip | CH₂ | (CH₂)₄ | 0 | 2-HOEt |
| 2-1115 | Pip | CH₂ | (CH₂)₄ | 0 | 2-AcOEt |
| 2-1116 | Pip | CH₂ | (CH₂)₄ | 0 | 2-(3-HOOC.PrnO)Et |
| 2-1117 | Pip | CH₂ | (CH₂)₄ | 0 | 2-(cHxCOO)Et |
| 2-1118 | Pip | CH₂ | (CH₂)₄ | 0 | 2-HOPr |
| 2-1119 | Pip | CH₂ | (CH₂)₄ | 0 | 2-AcOPr |
| 2-1120 | Pip | CH₂ | (CH₂)₄ | 0 | 3-HOPr |
| 2-1121 | Pip | CH₂ | (CH₂)₄ | 0 | 3-AcOPr |
| 2-1122 | Pip | CH₂ | (CH₂)₄ | 0 | 2-HOBu |
| 2-1123 | Pip | CH₂ | (CH₂)₄ | 0 | 2-AcOBu |
| 2-1124 | Pip | CH₂ | CH₂CH(Me)CH₂ | 0 | 2-HOEt |
| 2-1125 | Pip | CH₂ | CH₂CH(Me)CH₂ | 0 | 2-AcOEt |
| 2-1126 | Pip | CH₂ | CH₂CH(Me)CH₂ | 0 | 2-HOPr |
| 2-1127 | Pip | CH₂ | CH₂CH(Me)CH₂ | 0 | 2-AcOPr |
| 2-1128 | Pip | CH₂ | CH₂CH(Me)CH₂ | 0 | 3-HOPr |
| 2-1129 | Pip | CH₂ | CH₂CH(Me)CH₂ | 0 | 3-AcOPr |
| 2-1130 | Pip | CH₂ | CH₂CH(Me)CH₂ | 0 | 2-HOBu |
| 2-1131 | Pip | CH₂ | CH₂CH(Me)CH₂ | 0 | 2-AcOBu |
| 2-1132 | Pip | CH₂ | (CH₂)₅ | 0 | 2-HOEt |
| 2-1133 | Pip | CH₂ | (CH₂)₅ | 0 | 2-AcOEt |
| 2-1134 | Pip | CH₂ | (CH₂)₅ | 0 | 2-HOPr |
| 2-1135 | Pip | CH₂ | (CH₂)₅ | 0 | 2-AcOPr |
| 2-1136 | Pip | CH₂ | (CH₂)₅ | 0 | 2-(cHxCOO)Pr |
| 2-1137 | Pip | CH₂ | (CH₂)₅ | 0 | 3-HOPr |
| 2-1138 | Pip | CH₂ | (CH₂)₅ | 0 | 3-AcOPr |
| 2-1139 | Pip | CH₂ | (CH₂)₅ | 0 | 2-AcOBu |
| 2-1140 | Pip | CH₂ | (CH₂)₆ | 0 | 2-HOEt |

TABLE 2-continued

| Cpd. No. | R¹ | A | B | m | R⁵ |
|---|---|---|---|---|---|
| 2-1141 | Pip | CH₂ | (CH₂)₆ | 0 | 2-AcOEt |
| 2-1142 | Pip | CH₂ | (CH₂)₆ | 0 | 2-HOPr |
| 2-1143 | Pip | CH₂ | (CH₂)₆ | 0 | 2-AcOPr |
| 2-1144 | Pip | CH₂ | (CH₂)₆ | 0 | 3-HOPr |
| 2-1145 | Pip | CH₂ | (CH₂)₆ | 0 | 3-AcOPr |
| 2-1146 | Pip | CH₂ | (CH₂)₆ | 0 | 2-AcOBu |
| 2-1147 | Pip | CH=CH | CH₂ | 0 | 2-(nPnCOO)Et |
| 2-1148 | Pip | CH=CH | CH₂ | 0 | 2-PivOEt |
| 2-1149 | Pip | CH₂ | CH₂ | 0 | 2-(nPnCOO)Et |
| 2-1150 | Pip | CH₂ | CH₂ | 0 | 2-PivOEt |
| 2-1151 | Pyr | CH=CH | CH₂ | 0 | 2-(nPnCOO)Et |
| 2-1152 | Pyr | CH=CH | CH₂ | 0 | 2-PivOEt |

TABLE 3

| Cpd. No. | R¹ | A | B | m | R⁵ |
|---|---|---|---|---|---|
| 3-1 | Pip | CH=CH | CH₂ | 0 | Imdazo-2-yl |
| 3-2 | Pip | CH=CH | CH₂ | 0 | Imdazo-4-yl |
| 3-3 | Pip | CH=CH | CH₂ | 0 | 1-Me-Imdazo-2-yl |
| 3-4 | Pip | CH=CH | CH₂ | 0 | 1,3,4-Oxadiazo-2-yl |
| 3-5 | Pip | CH=CH | CH₂ | 0 | 5-Me-1,3,4-Oxadiazo-2-yl |
| 3-6 | Pip | CH=CH | CH₂ | 0 | 1,3,4-Thiadiazo-2-yl |
| 3-7 | Pip | CH=CH | CH₂ | 0 | 5-Me-1,3,4-Thiadiazo-2-yl |
| 3-8 | Pip | CH=CH | CH₂ | 0 | 1,2,4-Triazo-3-yl |
| 3-9 | Pip | CH=CH | CH₂ | 0 | 1,2,4-Triazo-5-yl |
| 3-10 | Pip | CH=CH | CH₂ | 0 | 1-Me-1,2,4-Triazo-3-yl |
| 3-11 | Pip | CH=CH | CH₂ | 0 | 1-Me-1,2,4-Triazo-5-yl |
| 3-12 | Pip | CH=CH | CH₂ | 0 | 5-Me-1,2,4-Triazo-3-yl |
| 3-13 | Pip | CH=CH | CH₂ | 0 | Tetrazo-5-yl |
| 3-14 | Pip | CH=CH | CH₂ | 0 | 1-Me-Tetrazo-5-yl |
| 3-15 | Pip | CH=CH | CH₂ | 0 | Pyz-2-yl |
| 3-16 | Pip | CH=CH | CH₂ | 0 | Pyz-3-yl |
| 3-17 | Pip | CH=CH | CH₂ | 0 | Pyz-4-yl |
| 3-18 | Pip | CH=CH | CH₂ | 0 | 3-Me-Pyz-2-yl |
| 3-19 | Pip | CH=CH | CH₂ | 0 | 2-Me-Pyz-4-yl |
| 3-20 | Pip | CH=CH | CH₂ | 0 | 3-NH₂-Pyz-2-yl |
| 3-21 | Pip | CH=CH | CH₂ | 0 | 4-NH₂-Pyz-3-yl |
| 3-22 | Pip | CH=CH | CH₂ | 0 | 3-NH₂-Pyz-4-yl |
| 3-23 | Pip | CH=CH | CH₂ | 0 | 3-HO-Pyz-2-yl |
| 3-24 | Pip | CH=CH | CH₂ | 0 | 2-HO-Pyz-4-yl |
| 3-25 | Pip | CH=CH | CH₂ | 0 | Pymz-2-yl |
| 3-26 | Pip | CH=CH | CH₂ | 0 | Pymz-4-yl |
| 3-27 | Pip | CH=CH | CH₂ | 0 | 4-Me-Pymz-2-yl |
| 3-28 | Pip | CH=CH | CH₂ | 0 | 5-Me-Pymz-2-yl |
| 3-29 | Pip | CH=CH | CH₂ | 0 | 2-Me-Pymz-4-yl |
| 3-30 | Pip | CH=CH | CH₂ | 0 | 5-Me-Pymz-4-yl |
| 3-31 | Pip | CH=CH | CH₂ | 0 | 6-Me-Pymz-4-yl |
| 3-32 | Pip | CH=CH | CH₂ | 0 | 2-Me-Pymz-5-yl |
| 3-33 | Pip | CH=CH | CH₂ | 0 | 4-NH₂-Pymz-2-yl |
| 3-34 | Pip | CH=CH | CH₂ | 0 | 5-NH₂-Pymz-2-yl |
| 3-35 | Pip | CH=CH | CH₂ | 0 | 2-NH₂-Pymz-4-yl |
| 3-36 | Pip | CH=CH | CH₂ | 0 | 4-NH₂-5-HO-Pymz-2-yl |
| 3-37 | Pip | CH=CH | CH₂ | 0 | 2-NH₂-5-HO-Pymz-4-yl |
| 3-38 | Pip | CH=CH | CH₂ | 0 | 5-NH₂-2-HO-Pymz-4-yl |
| 3-39 | Pip | CH=CH | CH₂CH₂ | 0 | Imdazo-2-yl |
| 3-40 | Pip | CH=CH | CH₂CH₂ | 0 | Imdazo-4-yl |
| 3-41 | Pip | CH=CH | CH₂CH₂ | 0 | 1-Me-Imdazo-2-yl |
| 3-42 | Pip | CH=CH | CH₂CH₂ | 0 | 1,3,4-Oxadiazo-2-yl |
| 3-43 | Pip | CH=CH | CH₂CH₂ | 0 | 5-Me-1,3,4-Oxadiazo-2-yl |
| 3-44 | Pip | CH=CH | CH₂CH₂ | 0 | 1,3,4-Thiadiazo-2-yl |
| 3-45 | Pip | CH=CH | CH₂CH₂ | 0 | 5-Me-1,3,4-Thiadiazo-2-yl |
| 3-46 | Pip | CH=CH | CH₂CH₂ | 0 | 1,2,4-Triazo-3-yl |
| 3-47 | Pip | CH=CH | CH₂CH₂ | 0 | 1,2,4-Triazo-5-yl |
| 3-48 | Pip | CH=CH | CH₂CH₂ | 0 | 1-Me-1,2,4-Triazo-3-yl |
| 3-49 | Pip | CH=CH | CH₂CH₂ | 0 | 1-Me-1,2,4-Triazo-5-yl |
| 3-50 | Pip | CH=CH | CH₂CH₂ | 0 | 5-Me-1,2,4-Triazo-3-yl |
| 3-51 | Pip | CH=CH | CH₂CH₂ | 0 | Tetrazo-5-yl |
| 3-52 | Pip | CH=CH | CH₂CH₂ | 0 | 1-Me-Tetrazo-5-yl |
| 3-53 | Pip | CH=CH | CH₂CH₂ | 0 | Pyz-2-yl |
| 3-54 | Pip | CH=CH | CH₂CH₂ | 0 | Pyz-3-yl |
| 3-55 | Pip | CH=CH | CH₂CH₂ | 0 | Pyz-4-yl |
| 3-56 | Pip | CH=CH | CH₂CH₂ | 0 | 4-Me-Pyz-2-yl |

TABLE 3-continued

| Cpd. No. | R¹ | A | B | m | R⁵ |
|---|---|---|---|---|---|
| 3-57 | Pip | CH=CH | CH₂CH₂ | 0 | 2-Me-Pyz-4-yl |
| 3-58 | Pip | CH=CH | CH₂CH₂ | 0 | 3-NH₂-Pyz-2-yl |
| 3-59 | Pip | CH=CH | CH₂CH₂ | 0 | 3-NH₂-Pyz-4-yl |
| 3-60 | Pip | CH=CH | CH₂CH₂ | 0 | 3-HO-Pyz-2-yl |
| 3-61 | Pip | CH=CH | CH₂CH₂ | 0 | 2-HO-Pyz-4-yl |
| 3-62 | Pip | CH=CH | CH₂CH₂ | 0 | Pymz-2-yl |
| 3-63 | Pip | CH=CH | CH₂CH₂ | 0 | Pymz-4-yl |
| 3-64 | Pip | CH=CH | CH₂CH₂ | 0 | Pymz-5-yl |
| 3-65 | Pip | CH=CH | CH₂CH₂ | 0 | 4-Me-Pymz-2-yl |
| 3-66 | Pip | CH=CH | CH₂CH₂ | 0 | 5-Me-Pymz-2-yl |
| 3-67 | Pip | CH=CH | CH₂CH₂ | 0 | 2-Me-Pymz-4-yl |
| 3-68 | Pip | CH=CH | CH₂CH₂ | 0 | 5-Me-Pymz-4-yl |
| 3-69 | Pip | CH=CH | CH₂CH₂ | 0 | 6-Me-Pymz-4-yl |
| 3-70 | Pip | CH=CH | CH₂CH₂ | 0 | 4-NH₂-Pymz-2-yl |
| 3-71 | Pip | CH=CH | CH₂CH₂ | 0 | 5-NH₂-Pymz-2-yl |
| 3-72 | Pip | CH=CH | CH₂CH₂ | 0 | 2-NH₂-Pymz-4-yl |
| 3-73 | Pip | CH=CH | CH₂CH₂ | 0 | 4-HO-Pymz-5-yl |
| 3-74 | Pip | CH=CH | CH₂CH₂ | 0 | 4-NH₂-5-HO-Pymz-2-yl |
| 3-75 | Pip | CH=CH | CH₂CH₂ | 0 | 2-NH₂-5-HO-Pymz-4-yl |
| 3-76 | Pip | CH=CH | CH₂CH₂ | 0 | 5-NH₂-2-HO-Pymz-4-yl |
| 3-77 | Pip | CH=CH | (CH₂)₃ | 0 | Imdazo-2-yl |
| 3-78 | Pip | CH=CH | (CH₂)₃ | 0 | Imdazo-4-yl |
| 3-79 | Pip | CH=CH | (CH₂)₃ | 0 | 1-Me-Imdazo-2-yl |
| 3-80 | Pip | CH=CH | (CH₂)₃ | 0 | 2-Me-Imdazo-4-yl |
| 3-81 | Pip | CH=CH | (CH₂)₃ | 0 | 1,3,4-Oxadiazo-2-yl |
| 3-82 | Pip | CH=CH | (CH₂)₃ | 0 | 5-Me-1,3,4-Oxadiazo-2-yl |
| 3-83 | Pip | CH=CH | (CH₂)₃ | 0 | 5-Et-1,3,4-Oxadiazo-2-yl |
| 3-84 | Pip | CH=CH | (CH₂)₃ | 0 | 5-NH₂-1,3,4-Oxadiazo-2-yl |
| 3-85 | Pip | CH=CH | (CH₂)₃ | 0 | 5-AcNH-1,3,4-Oxadiazo-2-yl |
| 3-86 | Pip | CH=CH | (CH₂)₃ | 0 | 1,3,4-Thiadiazo-2-yl |
| 3-87 | Pip | CH=CH | (CH₂)₃ | 0 | 5-Me-1,3,4-Thiadiazo-2-yl |
| 3-88 | Pip | CH=CH | (CH₂)₃ | 0 | 5-NH₂-1,3,4-Thiadiazo-2-yl |
| 3-89 | Pip | CH=CH | (CH₂)₃ | 0 | 1,2,4-Triazo-3-yl |
| 3-90 | Pip | CH=CH | (CH₂)₃ | 0 | 1,2,4-Triazo-5-yl |
| 3-91 | Pip | CH=CH | (CH₂)₃ | 0 | 1-Me-1,2,4-Triazo-3-yl |
| 3-92 | Pip | CH=CH | (CH₂)₃ | 0 | 1-Me-1,2,4-Triazo-5-yl |
| 3-93 | Pip | CH=CH | (CH₂)₃ | 0 | 5-Me-1,2,4-Triazo-3-yl |
| 3-94 | Pip | CH=CH | (CH₂)₃ | 0 | 5-Cl-1,2,4-Triazo-3-yl |
| 3-95 | Pip | CH=CH | (CH₂)₃ | 0 | 5-NH₂-1,2,4-Triazo-3-yl |
| 3-96 | Pip | CH=CH | (CH₂)₃ | 0 | 5-AcNH-1,2,4-Triazo-3-yl |
| 3-97 | Pip | CH=CH | (CH₂)₃ | 0 | Tetrazo-5-yl |
| 3-98 | Pip | CH=CH | (CH₂)₃ | 0 | 1-Me-Tetrazo-5-yl |
| 3-99 | Pip | CH=CH | (CH₂)₃ | 0 | 1-Et-Tetrazo-5-yl |
| 3-100 | Pip | CH=CH | (CH₂)₃ | 0 | 1-(2-HOEt)-Tetrazo-5-yl |
| 3-101 | Pip | CH=CH | (CH₂)₃ | 0 | Pyz-2-yl |
| 3-102 | Pip | CH=CH | (CH₂)₃ | 0 | Pyz-3-yl |
| 3-103 | Pip | CH=CH | (CH₂)₃ | 0 | Pyz-4-yl |
| 3-104 | Pip | CH=CH | (CH₂)₃ | 0 | 3-Me-Pyz-2-yl |
| 3-105 | Pip | CH=CH | (CH₂)₃ | 0 | 5-Me-Pyz-2-yl |
| 3-106 | Pip | CH=CH | (CH₂)₃ | 0 | 2-Me-Pyz-4-yl |
| 3-107 | Pip | CH=CH | (CH₂)₃ | 0 | 3-Me-Pyz-4-yl |
| 3-108 | Pip | CH=CH | (CH₂)₃ | 0 | 3-Cl-Pyz-2-yl |
| 3-109 | Pip | CH=CH | (CH₂)₃ | 0 | 3-Cl-Pyz-4-yl |
| 3-110 | Pip | CH=CH | (CH₂)₃ | 0 | 3-NH₂-Pyz-2-yl |
| 3-111 | Pip | CH=CH | (CH₂)₃ | 0 | 5-NH₂-Pyz-2-yl |
| 3-112 | Pip | CH=CH | (CH₂)₃ | 0 | 4-NH₂-Pyz-3-yl |
| 3-113 | Pip | CH=CH | (CH₂)₃ | 0 | 3-NH₂-Pyz-4-yl |
| 3-114 | Pip | CH=CH | (CH₂)₃ | 0 | 3-HO-Pyz-2-yl |
| 3-115 | Pip | CH=CH | (CH₂)₃ | 0 | 5-HO-Pyz-2-yl |
| 3-116 | Pip | CH=CH | (CH₂)₃ | 0 | 2-HO-Pyz-4-yl |
| 3-117 | Pip | CH=CH | (CH₂)₃ | 0 | 3-HO-Pyz-4-yl |
| 3-118 | Pip | CH=CH | (CH₂)₃ | 0 | Pymz-2-yl |
| 3-119 | Pip | CH=CH | (CH₂)₃ | 0 | Pymz-4-yl |
| 3-120 | Pip | CH=CH | (CH₂)₃ | 0 | Pymz-5-yl |
| 3-121 | Pip | CH=CH | (CH₂)₃ | 0 | 4-Me-Pymz-2-yl |
| 3-122 | Pip | CH=CH | (CH₂)₃ | 0 | 5-Me-Pymz-2-yl |
| 3-123 | Pip | CH=CH | (CH₂)₃ | 0 | 2-Me-Pymz-4-yl |
| 3-124 | Pip | CH=CH | (CH₂)₃ | 0 | 5-Me-Pymz-4-yl |
| 3-125 | Pip | CH=CH | (CH₂)₃ | 0 | 6-Me-Pymz-4-yl |
| 3-126 | Pip | CH=CH | (CH₂)₃ | 0 | 4-Cl-Pymz-2-yl |
| 3-127 | Pip | CH=CH | (CH₂)₃ | 0 | 2-Me-Pymz-4-yl |
| 3-128 | Pip | CH=CH | (CH₂)₃ | 0 | 4-NH₂-Pymz-2-yl |
| 3-129 | Pip | CH=CH | (CH₂)₃ | 0 | 5-NH₂-Pymz-2-yl |
| 3-130 | Pip | CH=CH | (CH₂)₃ | 0 | 2-NH₂-Pymz-4-yl |
| 3-131 | Pip | CH=CH | (CH₂)₃ | 0 | 5-NH₂-Pymz-4-yl |
| 3-132 | Pip | CH=CH | (CH₂)₃ | 0 | 4-AcNH-Pymz-2-yl |

TABLE 3-continued

| Cpd. No. | R¹ | A | B | m | R⁵ |
|---|---|---|---|---|---|
| 3-133 | Pip | CH=CH | (CH₂)₃ | 0 | 2-AcNH-Pymz-4-yl |
| 3-134 | Pip | CH=CH | (CH₂)₃ | 0 | 4-NH₂-5-HO-Pymz-2-yl |
| 3-135 | Pip | CH=CH | (CH₂)₃ | 0 | 2-NH₂-5-HO-Pymz-4-yl |
| 3-136 | Pip | CH=CH | (CH₂)₃ | 0 | 4,6-diNH₂-Pymz-2-yl |
| 3-137 | Pip | CH=CH | (CH₂)₃ | 0 | 2,5-diNH₂-Pymz-4-yl |
| 3-138 | Pip | CH=CH | (CH₂)₄ | 0 | Imdazo-2-yl |
| 3-139 | Pip | CH=CH | (CH₂)₄ | 0 | 1,3,4-Oxadiazo-2-yl |
| 3-140 | Pip | CH=CH | (CH₂)₄ | 0 | 1,3,4-thiadiazo-2-yl |
| 3-141 | Pip | CH=CH | (CH₂)₄ | 0 | 1,2,4-Triazo-3-yl |
| 3-142 | Pip | CH=CH | (CH₂)₄ | 0 | 1,2,4-Triazo-5-yl |
| 3-143 | Pip | CH=CH | (CH₂)₄ | 0 | Tetrazo-5-yl |
| 3-144 | Pip | CH=CH | (CH₂)₄ | 0 | Pyz-2-yl |
| 3-145 | Pip | CH=CH | (CH₂)₄ | 0 | Pyz-3-yl |
| 3-146 | Pip | CH=CH | (CH₂)₄ | 0 | Pyz-4-yl |
| 3-147 | Pip | CH=CH | (CH₂)₄ | 0 | Pymz-2-yl |
| 3-148 | Pip | CH=CH | (CH₂)₄ | 0 | Pymz-4-yl |
| 3-149 | Pip | CH=CH | CH₂CH(Me)CH₂ | 0 | Imdazo-2-yl |
| 3-150 | Pip | CH=CH | CH₂CH(Me)CH₂ | 0 | 1,3,4-Oxadiazo-2-yl |
| 3-151 | Pip | CH=CH | CH₂CH(Me)CH₂ | 0 | 1,3,4-Thiadiazo-2-yl |
| 3-152 | Pip | CH=CH | CH₂CH(Me)CH₂ | 0 | 1,2,4-Triazo-3-yl |
| 3-153 | Pip | CH=CH | CH₂CH(Me)CH₂ | 0 | 1,2,4-Triazo-5-yl |
| 3-154 | Pip | CH=CH | CH₂CH(Me)CH₂ | 0 | Tetrazo-5-yl |
| 3-155 | Pip | CH=CH | CH₂CH(Me)CH₂ | 0 | Pyz-2-yl |
| 3-156 | Pip | CH=CH | CH₂CH(Me)CH₂ | 0 | Pyz-4-yl |
| 3-157 | Pip | CH=CH | CH₂CH(Me)CH₂ | 0 | Pymz-2-yl |
| 3-158 | Pip | CH=CH | CH₂CH(Me)CH₂ | 0 | Pymz-4-yl |
| 3-159 | Pip | CH=CH | (CH₂)₅ | 0 | Imdazo-2-yl |
| 3-160 | Pip | CH=CH | (CH₂)₅ | 0 | 1,3,4-Oxadiazo-2-yl |
| 3-161 | Pip | CH=CH | (CH₂)₅ | 0 | 1,3,4-Thiadiazo-2-yl |
| 3-162 | Pip | CH=CH | (CH₂)₅ | 0 | 1,2,4-Triazo-3-yl |
| 3-163 | Pip | CH=CH | (CH₂)₅ | 0 | 1,2,4-Triazo-5-yl |
| 3-164 | Pip | CH=CH | (CH₂)₅ | 0 | Tetrazo-5-yl |
| 3-165 | Pip | CH=CH | (CH₂)₅ | 0 | Pyz-2-yl |
| 3-166 | Pip | CH=CH | (CH₂)₅ | 0 | Pyz-4-yl |
| 3-167 | Pip | CH=CH | (CH₂)₅ | 0 | Pymz-2-yl |
| 3-168 | Pip | CH=CH | (CH₂)₅ | 0 | Pymz-4-yl |
| 3-169 | Pip | CH=CH | (CH₂)₆ | 0 | Imdazo-2-yl |
| 3-170 | Pip | CH=CH | (CH₂)₆ | 0 | 1,3,4-Oxadiazo,-2-yl |
| 3-171 | Pip | CH=CH | (CH₂)₆ | 0 | 1,3,4-Thiadiazo-2-yl |
| 3-172 | Pip | CH=CH | (CH₂)₆ | 0 | 1,2,4-Triazo-3-yl |
| 3-173 | Pip | CH=CH | (CH₂)₆ | 0 | 1,2,4-Triazo-5-yl |
| 3-174 | Pip | CH=CH | (CH₂)₆ | 0 | Tetrazo-5-yl |
| 3-175 | Pip | CH=CH | (CH₂)₆ | 0 | Pyz-3-yl |
| 3-176 | Pip | CH=CH | (CH₂)₆ | 0 | Pyz-4-yl |
| 3-177 | Pip | CH=CH | (CH₂)₆ | 0 | Pymz-2-yl |
| 3-178 | Pip | CH=CH | (CH₂)₆ | 0 | Pymz-4-yl |
| 3-179 | Pyr | CH=CH | CH₂ | 0 | Imdazo-2-yl |
| 3-180 | Pyr | CH=CH | CH₂ | 0 | Imdazo-4-yl |
| 3-181 | Pyr | CH=CH | CH₂ | 0 | 1,3,4-Oxadiazo-2-yl |
| 3-182 | Pyr | CH=CH | CH₂ | 0 | 1,3,4-Thiadiazo-2-yl |
| 3-183 | Pyr | CH=CH | CH₂ | 0 | 1,2,4-Triazo-3-yl |
| 3-184 | Pyr | CH=CH | CH₂ | 0 | 1,2,4-Triazo-5-yl |
| 3-185 | Pyr | CH=CH | CH₂ | 0 | Tetrazo-5-yl |
| 3-186 | Pye | CH=CH | CH₂ | 0 | Pyz-2-yl |
| 3-187 | Pyr | CH=CH | CH₂ | 0 | Pyz-4-yl |
| 3-188 | Pyr | CH=CH | CH₂ | 0 | 3-Me-Pyz-2-yl |
| 3-189 | Pyr | CH=CH | CH₂ | 0 | 2-Me-Pyz-3-yl |
| 3-190 | Pyr | CH=CH | CH₂ | 0 | 3-NH₂-Pyz-2-yl |
| 3-191 | Pyr | CH=CH | CH₂ | 0 | 2-HO-Pyz-3-yl |
| 3-192 | Pyr | CH=CH | CH₂ | 0 | Pymz-2-yl |
| 3-193 | Pyr | CH=CH | CH₂ | 0 | Pymz-4-yl |
| 3-194 | Pyr | CH=CH | CH₂ | 0 | 4-Me-Pymz-2-yl |
| 3-195 | Pyr | CH=CH | CH₂ | 0 | 5-Me-Pymz-2-yl |
| 3-196 | Pyr | CH=CH | CH₂ | 0 | 2-Me-Pymz-4-yl |
| 3-197 | Pyr | CH=CH | CH₂ | 0 | 6-Me-Pymz-4-yl |
| 3-198 | Pyr | CH=CH | CH₂ | 0 | 4-NH₂-Pymz-2-yl |
| 3-199 | Pyr | CH=CH | CH₂ | 0 | 4-HO-Pymz-2-yl |
| 3-200 | Pyr | CH=CH | CH₂ | 0 | 4-NH₂-5-HO-Pymz-2-yl |
| 3-201 | Pyr | CH=CH | CH₂CH₂ | 0 | Imdazo-2-yl |
| 3-202 | Pyr | CH=CH | CH₂CH₂ | 0 | Imdazo-4-yl |
| 3-203 | Pyr | CH=CH | CH₂CH₂ | 0 | 1,3,4-Oxadiazo-2-yl |
| 3-204 | Pyr | CH=CH | CH₂CH₂ | 0 | 1,3,4-Thiadiazo-2-yl |
| 3-205 | Pyr | CH=CH | CH₂CH₂ | 0 | 1,2,4-Triazo-3-yl |
| 3-206 | Pyr | CH=CH | CH₂CH₂ | 0 | 1,2,4-Triazo-5-yl |
| 3-207 | Pyr | CH=CH | CH₂CH₂ | 0 | Tetrazo-5-yl |
| 3-208 | Pyr | CH=CH | CH₂CH₂ | 0 | Pyz-2-yl |

TABLE 3-continued

| Cpd. No. | R¹ | A | B | m | R⁵ |
|---|---|---|---|---|---|
| 3-209 | Pyr | CH=CH | CH₂CH₂ | 0 | Pyz-4-yl |
| 3-210 | Pyr | CH=CH | CH₂CH₂ | 0 | 3-Me-Pyz-2-yl |
| 3-211 | Pyr | CH=CH | CH₂CH₂ | 0 | 3-NH₂-Pyz-2-yl |
| 3-212 | Pyr | CH=CH | CH₂CH₂ | 0 | 3-HO-Pyz-2-yl |
| 3-213 | Pyr | CH=CH | CH₂CH₂ | 0 | Pymz-2-yl |
| 3-214 | Pyr | CH=CH | CH₂CH₂ | 0 | Pymz-4-yl |
| 3-215 | Pyr | CH=CH | CH₂CH₂ | 0 | Pymz-5-yl |
| 3-216 | Pyr | CH=CH | CH₂CH₂ | 0 | 4-Me-Pymz-2-yl |
| 3-217 | Pyr | CH=CH | CH₂CH₂ | 0 | 5-Me-Pymz-2-yl |
| 3-218 | Pyr | CH=CH | CH₂CH₂ | 0 | 2-Me-Pymz-4-yl |
| 3-219 | Pyr | CH=CH | CH₂CH₂ | 0 | 5-Me-Pymz-4-yl |
| 3-220 | Pyr | CH=CH | CH₂CH₂ | 0 | 4-NH₂-Pymz-2-yl |
| 3-221 | Pyr | CH=CH | CH₂CH₂ | 0 | 2-HO-Pymz-2-yl |
| 3-222 | Pyr | CH=CH | (CH₂)₃ | 0 | Imdazo-2-yl |
| 3-223 | Pyr | CH=CH | (CH₂)₃ | 0 | Imdazo-4-yl |
| 3-224 | Pyr | CH=CH | (CH₂)₃ | 0 | 1,3,4-Oxadiazo-2-yl |
| 3-225 | Pyr | CH=CH | (CH₂)₃ | 0 | 1,3,4-Thiadiazo-2-yl |
| 3-226 | Pyr | CH=CH | (CH₂)₃ | 0 | 1,2,4-Triazo-3-yl |
| 3-227 | Pyr | CH=CH | (CH₂)₃ | 0 | 1,2,4,-Triazo-5-yl |
| 3-228 | Pyr | CH=CH | (CH₂)₃ | 0 | Tetrazo-5-yl |
| 3-229 | Pyr | CH=CH | (CH₂)₃ | 0 | Pyz-2-yl |
| 3-230 | Pyr | CH=CH | (CH₂)₃ | 0 | Pyz-3-yl |
| 3-231 | Pyr | CH=CH | (CH₂)₃ | 0 | Pyz-4-yl |
| 3-232 | Pyr | CH=CH | (CH₂)₃ | 0 | 3-Me-Pyz-2-yl |
| 3-233 | Pyr | CH=CH | (CH₂)₃ | 0 | 2-Me-Pyz-4-yl |
| 3-234 | Pyr | CH=CH | (CH₂)₃ | 0 | 2-Cl-Pyz-3-yl |
| 3-235 | Pyr | CH=CH | (CH₂)₃ | 0 | 3-NH₂-Pyz-2-yl |
| 3-236 | Pyr | CH=CH | (CH₂)₃ | 0 | 3-NH₂-Pyz-4-yl |
| 3-237 | Pyr | CH=CH | (CH₂)₃ | 0 | 3-HO-Pyz-2-yl |
| 3-238 | Pyr | CH=CH | (CH₂)₃ | 0 | Pymz-2-yl |
| 3-239 | Pyr | CH=CH | (CH₂)₃ | 0 | Pymz-4-yl |
| 3-240 | Pyr | CH=CH | (CH₂)₃ | 0 | 4-Me-Pymz-2-yl |
| 3-241 | Pyr | CH=CH | (CH₂)₃ | 0 | 2-Me-Pymz-4-yl |
| 3-242 | Pyr | CH=CH | (CH₂)₃ | 0 | 5-Me-Pymz-4-yl |
| 3-243 | Pyr | CH=CH | (CH₂)₃ | 0 | 4-Me-Pymz-5-yl |
| 3-244 | Pyr | CH=CH | (CH₂)₃ | 0 | 5-NH₂-Pymz-2-yl |
| 3-245 | Pyr | CH=CH | (CH₂)₃ | 0 | 2-NH₂-Pymz-4-yl |
| 3-246 | Pyr | CH=CH | (CH₂)₃ | 0 | 2-HO-Pymz-4-yl |
| 3-247 | Pyr | CH=CH | (CH₂)₃ | 0 | 4-NH₂-5-HO-Pymz-2-yl |
| 3-248 | Pyr | CH=CH | (CH₂)₃ | 0 | 2-NH₂-5-HO-Pymz-4-yl |
| 3-249 | Pyr | CH=CH | (CH₂)₃ | 0 | 4,6-diNH₂-Pymz-2-yl |
| 3-250 | Pyr | CH=CH | (CH₂)₄ | 0 | Imdazo-2-yl |
| 3-251 | Pyr | CH=CH | (CH₂)₄ | 0 | 1,3,4-Oxadiazo-2-yl |
| 3-252 | Pyr | CH=CH | (CH₂)₄ | 0 | 1,3,4-Thiadiazo-2-yl |
| 3-253 | Pyr | CH=CH | (CH₂)₄ | 0 | 1,2,4-Triazo-3-yl |
| 3-254 | Pyr | CH=CH | (CH₂)₄ | 0 | 1,2,4-Triazo-5-yl |
| 3-255 | Pyr | CH=CH | (CH₂)₄ | 0 | Tetrazo-5-yl |
| 3-256 | Pyr | CH=CH | (CH₂)₄ | 0 | Pyz-2-yl |
| 3-257 | Pyr | CH=CH | (CH₂)₄ | 0 | Pyz-3-yl |
| 3-258 | Pyr | CH=CH | (CH₂)₄ | 0 | Pyz-4-yl |
| 3-259 | Pyr | CH=CH | (CH₂)₄ | 0 | Pymz-2-yl |
| 3-260 | Pyr | CH=CH | (CH₂)₄ | 0 | Pymz-4-yl |
| 3-261 | Pyr | CH=CH | (CH₂)₄ | 0 | Pymz-5-yl |
| 3-262 | Pyr | CH=CH | CH₂CH(Me)CH₂ | 0 | Imdazo-2-yl |
| 3-263 | Pyr | CH=CH | CH₂CH(Me)CH₂ | 0 | 1,3,4-Oxadiazo-2-yl |
| 3-264 | Pyr | CH=CH | CH₂CH(Me)CH₂ | 0 | 1,3,4-Thiadiazo-2-yl |
| 3-265 | Pyr | CH=CH | CH₂CH(Me)CH₂ | 0 | 1,2,4-Triazo-3-yl |
| 3-266 | Pyr | CH=CH | CH₂CH(Me)CH₂ | 0 | 1,2,4-Triazo-5-yl |
| 3-267 | Pyr | CH=CH | CH₂CH(Me)CH₂ | 0 | Tetrazo-5-yl |
| 3-268 | Pyr | CH=CH | CH₂CH(Me)CH₂ | 0 | Pyz-2-yl |
| 3-269 | Pyr | CH=CH | CH₂CH(Me)CH₂ | 0 | Pyz-3-yl |
| 3-270 | Pyr | CH=CH | CH₂CH(Me)CH₂ | 0 | Pymz-2-yl |
| 3-271 | Pyr | CH=CH | CH₂CH(Me)CH₂ | 0 | Pymz-4-yl |
| 3-272 | Pyr | CH=CH | (CH₂)₅ | 0 | Imdazo-2-yl |
| 3-273 | Pyr | CH=CH | (CH₂)₅ | 0 | 1,3,4-Oxadiazo-2-yl |
| 3-274 | Pyr | CH=CH | (CH₂)₅ | 0 | 1,3,4-Thiadiazo-2-yl |
| 3-275 | Pyr | CH=CH | (CH₂)₅ | 0 | 1,2,4-Triazo-3-yl |
| 3-276 | Pyr | CH=CH | (CH₂)₅ | 0 | 1,2,4-Triazo-5-yl |
| 3-277 | Pyr | CH=CH | (CH₂)₅ | 0 | Tetrazo-5-yl |
| 3-278 | Pyr | CH=CH | (CH₂)₅ | 0 | Pyz-2-yl |
| 3-279 | Pyr | CH=CH | (CH₂)₅ | 0 | Pyz-3-yl |
| 3-280 | Pyr | CH=CH | (CH₂)₅ | 0 | Pymz-2-yl |
| 3-281 | Pyr | CH=CH | (CH₂)₅ | 0 | Pymz-4-yl |
| 3-282 | Pyr | CH=CH | (CH₂)₆ | 0 | Imdazo-2-yl |
| 3-283 | Pyr | CH=CH | (CH₂)₆ | 0 | 1,3,4-Oxadiazo-2-yl |
| 3-284 | Pyr | CH=CH | (CH₂)₆ | 0 | 1,3,4-Thiadiazo-2-yl |

TABLE 3-continued

| Cpd. No. | R¹ | A | B | m | R⁵ |
|---|---|---|---|---|---|
| 3-285 | Pyr | CH=CH | (CH₂)₆ | 0 | 1,2,4-Triazo-3-yl |
| 3-286 | Pyr | CH=CH | (CH₂)₆ | 0 | 1,2,4-Triazo-5-yl |
| 3-287 | Pyr | CH=CH | (CH₂)₆ | 0 | Tetrazo-5-yl |
| 3-288 | Pyr | CH=CH | (CH₂)₆ | 0 | Pyz-2-yl |
| 3-289 | Pyr | CH=CH | (CH₂)₆ | 0 | Pyz-3-yl |
| 3-290 | Pyr | CH=CH | (CH₂)₆ | 0 | Pymz-2-yl |
| 3-291 | Pyr | CH=CH | (CH₂)₆ | 0 | Pymz-4-yl |
| 3-292 | NMe₂ | CH=CH | CH₂ | 0 | Imdazo-2-yl |
| 3-293 | NMe₂ | CH=CH | CH₂ | 0 | 1,3,4-Oxadiazo-2-yl |
| 3-294 | NMe₂ | CH=CH | CH₂ | 0 | 1,3,4-Thiadiazo-2-yl |
| 3-295 | NMe₂ | CH=CH | CH₂ | 0 | 1,2,4-Triazo-3-yl |
| 3-296 | NMe₂ | CH=CH | CH₂ | 0 | 1,2,4-Triazo-5-yl |
| 3-297 | NMe₂ | CH=CH | CH₂ | 0 | Tetrazo-5-yl |
| 3-298 | NMe₂ | CH=CH | CH₂ | 0 | Pyz-2-yl |
| 3-299 | NMe₂ | CH=CH | CH₂ | 0 | 3-Me-Pyz-2-yl |
| 3-300 | NMe₂ | CH=CH | CH₂ | 0 | Pymz-2-yl |
| 3-301 | NMe₂ | CH=CH | CH₂ | 0 | 4-Me-Pymz-2-yl |
| 3-302 | NMe₂ | CH=CH | CH₂ | 0 | 6-Me-Pymz-4-yl |
| 3-303 | NMe₂ | CH=CH | CH₂CH₂ | 0 | 1,3,4-Oxadiazo-2-yl |
| 3-304 | NMe₂ | CH=CH | CH₂CH₂ | 0 | 1,2,4-Triazo-3-yl |
| 3-305 | NMe₂ | CH=CH | CH₂CH₂ | 0 | 1,2,4-Triazo-5-yl |
| 3-306 | NMe₂ | CH=CH | CH₂CH₂ | 0 | Pyz-2-yl |
| 3-307 | NMe₂ | CH=CH | CH₂CH₂ | 0 | 3-Me-Pyz-2-yl |
| 3-308 | NMe₂ | CH=CH | CH₂CH₂ | 0 | Pymz-2-yl |
| 3-309 | NMe₂ | CH=CH | CH₂CH₂ | 0 | Pymz-4-yl |
| 3-310 | NMe₂ | CH=CH | CH₂CH₂ | 0 | 4-Me-Pymz-2-yl |
| 3-311 | NMe₂ | CH=CH | CH₂CH₂ | 0 | 2-Me-Pymz-4-yl |
| 3-312 | NMe₂ | CH=CH | (CH₂)₃ | 0 | Imdazo-2-yl |
| 3-313 | NMe₂ | CH=CH | (CH₂)₃ | 0 | Imdazo-4-yl |
| 3-314 | NMe₂ | CH=CH | (CH₂)₃ | 0 | 1,3,4-Oxadiazo-2-yl |
| 3-315 | NMe₂ | CH=CH | (CH₂)₃ | 0 | 1,3,4-Thiadiazo-2-yl |
| 3-316 | NMe₂ | CH=CH | (CH₂)₃ | 0 | 1,2,4-Triazo-3-yl |
| 3-317 | NMe₂ | CH=CH | (CH₂)₃ | 0 | 1,2,4-Triazo-5-yl |
| 3-318 | NMe₂ | CH=CH | (CH₂)₃ | 0 | Tetrazo-5-yl |
| 3-319 | NMe₂ | CH=CH | (CH₂)₃ | 0 | Pyz-2-yl |
| 3-320 | NMe₂ | CH=CH | (CH₂)₃ | 0 | Pymz-2-yl |
| 3-321 | NMe₂ | CH=CH | (CH₂)₃ | 0 | Pymz-4-yl |
| 3-322 | NMe₂ | CH=CH | (CH₂)₄ | 0 | 1,3,4-Oxadiazo-2-yl |
| 3-323 | NMe₂ | CH=CH | (CH₂)₄ | 0 | 1,2,4-Triazol-3-yl |
| 3-324 | NMe₂ | CH=CH | (CH₂)₄ | 0 | 1,2,4-Triazo-5-yl |
| 3-325 | NMe₂ | CH=CH | (CH₂)₄ | 0 | Tetrazo-5-yl |
| 3-326 | NMe₂ | CH=CH | (CH₂)₄ | 0 | Pyz-2-yl |
| 3-327 | NMe₂ | CH=CH | (CH₂)₄ | 0 | Pymz-2-yl |
| 3-328 | NMe₂ | CH=CH | (CH₂)₄ | 0 | Pymz-4-yl |
| 3-329 | NMe₂ | CH=CH | CH₂CH(Me)CH₂ | 0 | 1,3,4-Oxadiazo-2-yl |
| 3-330 | NMe₂ | CH=CH | CH₂CH(Me)CH₂ | 0 | 1,2,4-Triazo-3-yl |
| 3-331 | NMe₂ | CH=CH | CH₂CH(Me)CH₂ | 0 | 1,2,4-Triazo-5-yl |
| 3-332 | NMe₂ | CH=CH | CH₂CH(Me)CH₂ | 0 | Pymz-2-yl |
| 3-333 | NMe₂ | CH=CH | CH₂CH(Me)CH₂ | 0 | Pymz-4-yl |
| 3-334 | NMe₂ | CH=CH | (CH₂)₅ | 0 | 1,3,4-Oxadiazo-2-yl |
| 3-335 | NMe₂ | CH=CH | (CH₂)₅ | 0 | 1,2,4-Triazo-3-yl |
| 3-336 | NMe₂ | CH=CH | (CH₂)₅ | 0 | 1,2,4-Triazo-5-yl |
| 3-337 | NMe₂ | CH=CH | (CH₂)₅ | 0 | Pymz-2-yl |
| 3-338 | NMe₂ | CH=CH | (CH₂)₅ | 0 | Pymz-4-yl |
| 3-339 | NMe₂ | CH=CH | (CH₂)₆ | 0 | 1,3,4-Oxadiazo-2-yl |
| 3-340 | NMe₂ | CH=CH | (CH₂)₆ | 0 | 1,2,4-Triazo-3-yl |
| 3-341 | NMe₂ | CH=CH | (CH₂)₆ | 0 | 1,2,4-Triazo-5-yl |
| 3-342 | NMe₂ | CH=CH | (CH₂)₆ | 0 | Pymz-2-yl |
| 3-343 | NMe₂ | CH=CH | (CH₂)₆ | 0 | Pymz-4-yl |
| 3-344 | NEt₂ | CH=CH | CH₂ | 0 | 1,3,4-Oxadiazo-2-yl |
| 3-345 | NEt₂ | CH=CH | CH₂ | 0 | 1,2,4-Triazo-3-yl |
| 3-346 | NEt₂ | CH=CH | CH₂ | 0 | Pymz-2-yl |
| 3-347 | NEt₂ | CH=CH | CH₂CH₂ | 0 | 1,3,4-Oxadiazo-2-yl |
| 3-348 | NEt₂ | CH=CH | CH₂CH₂ | 0 | 1,2,4-Triazo-3-yl |
| 3-349 | NEt₂ | CH=CH | CH₂CH₂ | 0 | Pymz-2-yl |
| 3-350 | NEt₂ | CH=CH | CH₂CH₂ | 0 | Pymz-4-yl |
| 3-351 | NEt₂ | CH=CH | (CH₂)₃ | 0 | Imdazo-2-yl |
| 3-352 | NEt₂ | CH=CH | (CH₂)₃ | 0 | Imdazo-4-yl |
| 3-353 | NEt₂ | CH=CH | (CH₂)₃ | 0 | 1,3,4-Oxadiazo-2-yl |
| 3-354 | NEt₂ | CH=CH | (CH₂)₃ | 0 | 1,3,4-Thiadiazo-2-yl |
| 3-355 | NEt₂ | CH=CH | (CH₂)₃ | 0 | 1,2,4-Triazo-3-yl |
| 3-356 | NEt₂ | CH=CH | (CH₂)₃ | 0 | 1,2,4-Triazo-5-yl |
| 3-357 | NEt₂ | CH=CH | (CH₂)₃ | 0 | Tetrazo-5-yl |
| 3-358 | NEt₂ | CH=CH | (CH₂)₃ | 0 | Pyz-2-yl |
| 3-359 | NEt₂ | CH=CH | (CH₂)₃ | 0 | Pymz-2-yl |
| 3-360 | NEt₂ | CH=CH | (CH₂)₃ | 0 | Pymz-4-yl |

TABLE 3-continued

| Cpd. No. | R¹ | A | B | m | R⁵ |
|---|---|---|---|---|---|
| 3-361 | NEt₂ | CH=CH | (CH₂)₄ | 0 | 1,3,4-Oxadiazo-2-yl |
| 3-362 | NEt₂ | CH=CH | (CH₂)₄ | 0 | 1,2,4-Triazo-3-yl |
| 3-363 | NEt₂ | CH=CH | (CH₂)₄ | 0 | Pymz-2-yl |
| 3-364 | NEt₂ | CH=CH | (CH₂)₄ | 0 | Pymz-4-yl |
| 3-365 | NEt₂ | CH=CH | (CH₂)₅ | 0 | 1,3,4-Oxadiazo-2-yl |
| 3-366 | NEt₂ | CH=CH | (CH₂)₅ | 0 | 1,2,4-Triazo-3-yl |
| 3-367 | NEt₂ | CH=CH | (CH₂)₅ | 0 | Pymz-2-yl |
| 3-368 | NEt₂ | CH=CH | (CH₂)₅ | 0 | Pymz-4-yl |
| 3-369 | NEt₂ | CH=CH | (CH₂)₆ | 0 | 1,3,4-Oxadiazo-2-yl |
| 3-370 | NEt₂ | CH=CH | (CH₂)₆ | 0 | 1,2,4-Triazo-5-yl |
| 3-371 | NEt₂ | CH=CH | (CH₂)₆ | 0 | Pymz-2-yl |
| 3-372 | NEt₂ | CH=CH | (CH₂)₆ | 0 | Pymz-4-yl |
| 3-373 | Azi | CH=CH | (CH₂)₃ | 0 | 1,2,4-Triazo-3-yl |
| 3-374 | Azi | CH=CH | (CH₂)₃ | 0 | Pymz-2-yl |
| 3-375 | Aze | CH=CH | (CH₂)₃ | 0 | 1,2,4-Triazo-3-yl |
| 3-376 | Aze | CH=CH | (CH₂)₃ | 0 | Pymz-2-yl |
| 3-377 | Pip | CH=CH | CH₂ | 1 | Imdazo-2-yl |
| 3-378 | Pip | CH=CH | CH₂ | 1 | 1,3,4-Oxadiazo-2-yl |
| 3-379 | Pip | CH=CH | CH₂ | 1 | 1,3,4-Thiadiazo-2-yl |
| 3-380 | Pip | CH=CH | CH₂ | 1 | 1,2,4-Triazo-3-yl |
| 3-381 | Pip | CH=CH | CH₂ | 1 | 1,2,4-Triazo-5-yl |
| 3-382 | Pip | CH=CH | CH₂ | 1 | Tetrazo-5-yl |
| 3-383 | Pip | CH=CH | CH₂ | 1 | Pyz-2-yl |
| 3-384 | Pip | CH=CH | CH₂ | 1 | 3-Me-Pyz-2-yl |
| 3-385 | Pip | CH=CH | CH₂ | 1 | Pymz-2-yl |
| 3-386 | Pip | CH=CH | CH₂ | 1 | 4-Me-Pymz-2-yl |
| 3-387 | Pip | CH=CH | CH₂ | 1 | 6-Me-Pymz-4-yl |
| 3-388 | Pip | CH=CH | CH₂CH₂ | 1 | 1,3,4-Oxadiazo-2-yl |
| 3-389 | Pip | CH=CH | CH₂CH₂ | 1 | 1,2,4-Triazo-3-yl |
| 3-390 | Pip | CH=CH | CH₂CH₂ | 1 | 1,2,4-Triazo-5-yl |
| 3-391 | Pip | CH=CH | CH₂CH₂ | 1 | Pyz-2-yl |
| 3-392 | Pip | CH=CH | CH₂CH₂ | 1 | 3-Me-Pyz-2-yl |
| 3-393 | Pip | CH=CH | CH₂CH₂ | 1 | Pymz-2-yl |
| 3-394 | Pip | CH=CH | CH₂CH₂ | 1 | Pymz-4-yl |
| 3-395 | Pip | CH=CH | CH₂CH₂ | 1 | 4-Me-Pymz-2-yl |
| 3-396 | Pip | CH=CH | CH₂CH₂ | 2 | 2-Me-Pymz-4-yl |
| 3-397 | Pip | CH=CH | (CH₂)₃ | 1 | Imdazo-2-yl |
| 3-398 | Pip | CH=CH | (CH₂)₃ | 1 | Imdazo-4-yl |
| 3-399 | Pip | CH=CH | (CH₂)₃ | 1 | 1,3,4-Oxadiazo-2-yl |
| 3-400 | Pip | CH=CH | (CH₂)₃ | 1 | 1,3,4-Thiadiazo-2-yl |
| 3-401 | Pip | CH=CH | (CH₂)₃ | 1 | 1,2,4-Triazo-3-yl |
| 3-402 | Pip | CH=CH | (CH₂)₃ | 1 | 1,2,4-Triazo-5-yl |
| 3-403 | Pip | CH=CH | (CH₂)₃ | 1 | Tetrazo-5-yl |
| 3-404 | Pip | CH=CH | (CH₂)₃ | 1 | Pyz-2-yl |
| 3-405 | Pip | CH=CH | (CH₂)₃ | 1 | Pymz-2-yl |
| 3-406 | Pip | CH=CH | (CH₂)₃ | 1 | Pymz-4-yl |
| 3-407 | Pip | CH=CH | (CH₂)₄ | 1 | 1,3,4-Oxadiazo-2-yl |
| 3-408 | Pip | CH=CH | (CH₂)₄ | 1 | 1,2,4-Triazo-3-yl |
| 3-409 | Pip | CH=CH | (CH₂)₄ | 1 | 1,2,4-Triazo-5-yl |
| 3-410 | Pip | CH=CH | (CH₂)₄ | 1 | Tetrazo-5-yl |
| 3-411 | Pip | CH=CH | (CH₂)₄ | 1 | Pyz-2-yl |
| 3-412 | Pip | CH=CH | (CH₂)₄ | 1 | Pymz-2-yl |
| 3-413 | Pip | CH=CH | (CH₂)₄ | 1 | Pymz-4-yl |
| 3-414 | Pip | CH=CH | CH₂CH(Me)CH₂ | 1 | 1,3,4-Oxadiazo-2-yl |
| 3-415 | Pip | CH=CH | CH₂CH(Me)CH₂ | 1 | 1,2,4-Triazo-3-yl |
| 3-416 | Pip | CH=CH | CH₂CH(Me)CH₂ | 1 | 1,2,4-Triazo-5-yl |
| 3-417 | Pip | CH=CH | CH₂CH(Me)CH₂ | 1 | Pymz-2-yl |
| 3-418 | Pip | CH=CH | CH₂CH(Me)CH₂ | 1 | Pymz-4-yl |
| 3-419 | Pip | CH=CH | (CH₂)₅ | 1 | 1,3,4-Oxadiazo-2-yl |
| 3-420 | Pip | CH=CH | (CH₂)₅ | 1 | 1,2,4-Triazo-3-yl |
| 3-421 | Pip | CH=CH | (CH₂)₅ | 1 | 1,2,4-Triazo-5-yl |
| 3-422 | Pip | CH=CH | (CH₂)₅ | 1 | Pymz-2-yl |
| 3-423 | Pip | CH=CH | (CH₂)₅ | 1 | Pymz-4-yl |
| 3-424 | Pip | CH=CH | (CH₂)₆ | 1 | 1,3,4-Oxadiazo-2-yl |
| 3-425 | Pip | CH=CH | (CH₂)₆ | 1 | 1,2,4-Triazo-3-yl |
| 3-426 | Pip | CH=CH | (CH₂)₆ | 1 | 1,2,4-Triazo-5-yl |
| 3-427 | Pip | CH=CH | (CH₂)₆ | 1 | Pymz-2-yl |
| 3-428 | Pip | CH=CH | (CH₂)₆ | 1 | Pymz-4-yl |
| 3-429 | Pip | CH=CH | CH₂ | 2 | 1,3,4-Oxadiazo-2-yl |
| 3-430 | Pip | CH=CH | CH₂ | 2 | 1,2,4-Triazo-3-yl |
| 3-431 | Pip | CH=CH | CH₂ | 2 | Pymz-2-yl |
| 3-432 | Pip | CH=CH | CH₂CH₂ | 2 | 1,3,4-Oxadiazo-2-yl |
| 3-433 | Pip | CH=CH | CH₂CH₂ | 2 | 1,2,4-Triazo-3-yl |
| 3-434 | Pip | CH=CH | CH₂CH₂ | 2 | Pymz-2-yl |
| 3-435 | Pip | CH=CH | CH₂CH₂ | 2 | Pymz-4-yl |
| 3-436 | Pip | CH=CH | (CH₂)₃ | 2 | Imdazo-2-yl |

TABLE 3-continued

| Cpd. No. | R¹ | A | B | m | R⁵ |
|---|---|---|---|---|---|
| 3-437 | Pip | CH=CH | (CH₂)₃ | 2 | Imdazo-4-yl |
| 3-438 | Pip | CH=CH | (CH₂)₃ | 2 | 1,3,4-Oxadiazo-2-yl |
| 3-439 | Pip | CH=CH | (CH₂)₃ | 2 | 1,3,4-Thiadiazo-2-yl |
| 3-440 | Pip | CH=CH | (CH₂)₃ | 2 | 1,2,4-Triazo-3-yl |
| 3-441 | Pip | CH=CH | (CH₂)₃ | 2 | 1,2,4-Triazo-5-yl |
| 3-442 | Pip | CH=CH | (CH₂)₃ | 2 | Tetrazo-5-yl |
| 3-443 | Pip | CH=CH | (CH₂)₃ | 2 | Pyz-2-yl |
| 3-444 | Pip | CH=CH | (CH₂)₃ | 2 | Pymz-2-yl |
| 3-445 | Pip | CH=CH | (CH₂)₃ | 2 | Pymz-4-yl |
| 3-446 | Pip | CH=CH | (CH₂)₄ | 2 | 1,3,4-Oxadiazo-2-yl |
| 3-447 | Pip | CH=CH | (CH₂)₄ | 2 | 1,2,4-Triazo-3-yl |
| 3-448 | Pip | CH=CH | (CH₂)₄ | 2 | Pymz-2-yl |
| 3-449 | Pip | CH=CH | (CH₂)₄ | 2 | Pymz-4-yl |
| 3-450 | Pip | CH=CH | (CH₂)₅ | 2 | 1,3,4-Oxadiazo-2-yl |
| 3-451 | Pip | CH=CH | (CH₂)₅ | 2 | 1,2,4-Triazo-3-yl |
| 3-452 | Pip | CH=CH | (CH₂)₅ | 2 | Pymz-2-yl |
| 3-453 | Pip | CH=CH | (CH₂)₅ | 2 | Pymz-4-yl |
| 3-454 | Pip | CH=CH | (CH₂)₆ | 2 | 1,3,4-Oxadiazo-2-yl |
| 3-455 | Pip | CH=CH | (CH₂)₆ | 2 | 1,2,4-Triazo-5-yl |
| 3-456 | Pip | CH=CH | (CH₂)₆ | 2 | Pymz-2-yl |
| 3-457 | Pip | CH=CH | (CH₂)₆ | 2 | Pymz-4-yl |
| 3-458 | Azi | CH=CH | (CH₂)₃ | 1 | 1,2,4-Triazo-3-yl |
| 3-459 | Azi | CH=CH | (CH₂)₃ | 1 | Pymz-2-yl |
| 3-460 | Aze | CH=CH | (CH₂)₃ | 1 | 1,2,4-Triazo-3-yl |
| 3-461 | Aze | CH=CH | (CH₂)₃ | 1 | Pymz-2-yl |
| 3-462 | Pip | CH₂CH₂ | CH₂ | 0 | Imdazo-2-yl |
| 3-463 | Pip | CH₂CH₂ | CH₂ | 0 | Imdazo-4-yl |
| 3-464 | Pip | CH₂CH₂ | CH₂ | 0 | 1-Me-Imdazo-2-yl |
| 3-465 | Pip | CH₂CH₂ | CH₂ | 0 | 1,3,4-Oxadiazo-2-yl |
| 3-466 | Pip | CH₂CH₂ | CH₂ | 0 | 5-Me-1,3,4-Oxadiazo-2-yl |
| 3-467 | Pip | CH₂CH₂ | CH₂ | 0 | 1,3,4-Thiadiazo-2-yl |
| 3-468 | Pip | CH₂CH₂ | CH₂ | 0 | 5-Me-1,3,4-Thiadiazo-2-yl |
| 3-469 | Pip | CH₂CH₂ | CH₂ | 0 | 1,2,4-Triazo-3-yl |
| 3-470 | Pip | CH₂CH₂ | CH₂ | 0 | 1,2,4-Triazo-5-yl |
| 3-471 | Pip | CH₂CH₂ | CH₂ | 0 | 1-Me-1,2,4-Triazo-3-yl |
| 3-472 | Pip | CH₂CH₂ | CH₂ | 0 | 1-Me-1,2,4-Triazo-5-yl |
| 3-473 | Pip | CH₂CH₂ | CH₂ | 0 | 5-Me-1,2,4-Triazo-3-yl |
| 3-474 | Pip | CH₂CH₂ | CH₂ | 0 | Tetrazo-5-yl |
| 3-475 | Pip | CH₂CH₂ | CH₂ | 0 | 1-Me-Tetrazo-5-yl |
| 3-476 | Pip | CH₂CH₂ | CH₂ | 0 | Pyz-2-yl |
| 3-477 | Pip | CH₂CH₂ | CH₂ | 0 | Pyz-3-yl |
| 3-478 | Pip | CH₂CH₂ | CH₂ | 0 | Pyz-4-yl |
| 3-479 | Pip | CH₂CH₂ | CH₂ | 0 | 3-Me-Pyz-2-yl |
| 3-480 | Pip | CH₂CH₂ | CH₂ | 0 | 2-Me-Pyz-4-yl |
| 3-481 | Pip | CH₂CH₂ | CH₂ | 0 | 3-NH₂-Pyz-2-yl |
| 3-482 | Pip | CH₂CH₂ | CH₂ | 0 | 4-NH₂-Pyz-3-yl |
| 3-483 | Pip | CH₂CH₂ | CH₂ | 0 | 3-NH₂-Pyz-4-yl |
| 3-484 | Pip | CH₂CH₂ | CH₂ | 0 | 3-HO-Pyz-2-yl |
| 3-485 | Pip | CH₂CH₂ | CH₂ | 0 | 2-HO-Pyz-4-yl |
| 3-486 | Pip | CH₂CH₂ | CH₂ | 0 | Pymz-2-yl |
| 3-487 | Pip | CH₂CH₂ | CH₂ | 0 | Pymz-4-yl |
| 3-488 | Pip | CH₂CH₂ | CH₂ | 0 | 4-Me-Pymz-2-yl |
| 3-489 | Pip | CH₂CH₂ | CH₂ | 0 | 5-Me-Pymz-2-yl |
| 3-490 | Pip | CH₂CH₂ | CH₂ | 0 | 2-Me-Pymz-4-yl |
| 3-491 | Pip | CH₂CH₂ | CH₂ | 0 | 5-Me-Pymz-4-yl |
| 3-492 | Pip | CH₂CH₂ | CH₂ | 0 | 6-Me-Pymz-4-yl |
| 3-493 | Pip | CH₂CH₂ | CH₂ | 0 | 2-Me-Pymz-5-yl |
| 3-494 | Pip | CH₂CH₂ | CH₂ | 0 | 4-NH₂-Pymz-2-yl |
| 3-495 | Pip | CH₂CH₂ | CH₂ | 0 | 5-NH₂-Pymz-2-yl |
| 3-496 | Pip | CH₂CH₂ | CH₂ | 0 | 2-NH₂-Pymz-4-yl |
| 3-497 | Pip | CH₂CH₂ | CH₂ | 0 | 4-NH₂-5-HO-Pymz-2-yl |
| 3-498 | Pip | CH₂CH₂ | CH₂ | 0 | 2-NH₂-5-HO-Pymz-4-yl |
| 3-499 | Pip | CH₂CH₂ | CH₂ | 0 | 5-NH₂-2-HO-Pymz-4-yl |
| 3-500 | Pip | CH₂CH₂ | CH₂CH₂ | 0 | Imdazo-2-yl |
| 3-501 | Pip | CH₂CH₂ | CH₂CH₂ | 0 | Imdazo-4-yl |
| 3-502 | Pip | CH₂CH₂ | CH₂CH₂ | 0 | 1-Me-Imdazo-2-yl |
| 3-503 | Pip | CH₂CH₂ | CH₂CH₂ | 0 | 1,3,4-Oxadiazo-2-yl |
| 3-504 | Pip | CH₂CH₂ | CH₂CH₂ | 0 | 5-Me-1,3,4-Oxadiazo-2-yl |
| 3-505 | Pip | CH₂CH₂ | CH₂CH₂ | 0 | 1,3,4-Thiadiazo-2-yl |
| 3-506 | Pip | CH₂CH₂ | CH₂CH₂ | 0 | 5-Me-1,3,4-Thiadiazo-2-yl |
| 3-507 | Pip | CH₂CH₂ | CH₂CH₂ | 0 | 1,2,4-Triazo-3-yl |
| 3-508 | Pip | CH₂CH₂ | CH₂CH₂ | 0 | 1,2,4-Triazo-5-yl |
| 3-509 | Pip | CH₂CH₂ | CH₂CH₂ | 0 | 1-Me-1,2,4-Triazo-3-yl |
| 3-510 | Pip | CH₂CH₂ | CH₂CH₂ | 0 | 1-Me-1,2,4-Triazo-5-yl |
| 3-511 | Pip | CH₂CH₂ | CH₂CH₂ | 0 | 5-Me-1,2,4-Triazo-3-yl |
| 3-512 | Pip | CH₂CH₂ | CH₂CH₂ | 0 | Tetrazo-5-yl |

TABLE 3-continued

| Cpd. No. | R¹ | A | B | m | R⁵ |
|---|---|---|---|---|---|
| 3-513 | Pip | CH₂CH₂ | CH₂CH₂ | 0 | 1-Me-Tetrazo-5-yl |
| 3-514 | Pip | CH₂CH₂ | CH₂CH₂ | 0 | Pyz-2-yl |
| 3-515 | Pip | CH₂CH₂ | CH₂CH₂ | 0 | Pyz-3-yl |
| 3-516 | Pip | CH₂CH₂ | CH₂CH₂ | 0 | Pyz-4-yl |
| 3-517 | Pip | CH₂CH₂ | CH₂CH₂ | 0 | 4-Me-Pyz-2-yl |
| 3-518 | Pip | CH₂CH₂ | CH₂CH₂ | 0 | 2-Me-Pyz-4-yl |
| 3-519 | Pip | CH₂CH₂ | CH₂CH₂ | 0 | 3-NH₂-Pyz-2-yl |
| 3-520 | Pip | CH₂CH₂ | CH₂CH₂ | 0 | 3-NH₂-Pyz-4-yl |
| 3-521 | Pip | CH₂CH₂ | CH₂CH₂ | 0 | 3-HO-Pyz-2-yl |
| 3-522 | Pip | CH₂CH₂ | CH₂CH₂ | 0 | 2-HO-Pyz-4-yl |
| 3-523 | Pip | CH₂CH₂ | CH₂CH₂ | 0 | Pymz-2-yl |
| 3-524 | Pip | CH₂CH₂ | CH₂CH₂ | 0 | Pymz-4-yl |
| 3-525 | Pip | CH₂CH₂ | CH₂CH₂ | 0 | Pymz-5-yl |
| 3-526 | Pip | CH₂CH₂ | CH₂CH₂ | 0 | 4-Me-Pymz-2-yl |
| 3-527 | Pip | CH₂CH₂ | CH₂CH₂ | 0 | 5-Me-Pymz-2-yl |
| 3-528 | Pip | CH₂CH₂ | CH₂CH₂ | 0 | 2-Me-Pymz-4-yl |
| 3-529 | Pip | CH₂CH₂ | CH₂CH₂ | 0 | 5-Me-Pymz-4-yl |
| 3-530 | Pip | CH₂CH₂ | CH₂CH₂ | 0 | 6-Me-Pymz-4-yl |
| 3-531 | Pip | CH₂CH₂ | CH₂CH₂ | 0 | 4-NH₂-Pymz-2-yl |
| 3-532 | Pip | CH₂CH₂ | CH₂CH₂ | 0 | 5-NH₂-Pymz-2-yl |
| 3-533 | Pip | CH₂CH₂ | CH₂CH₂ | 0 | 2-NH₂-Pymz-4-yl |
| 3-534 | Pip | CH₂CH₂ | CH₂CH₂ | 0 | 4-HO-Pymz-5-yl |
| 3-535 | Pip | CH₂CH₂ | CH₂CH₂ | 0 | 4-NH₂-5-HO-Pymz-2-yl |
| 3-536 | Pip | CH₂CH₂ | CH₂CH₂ | 0 | 2-NH₂-5-HO-Pymz-4-yl |
| 3-537 | Pip | CH₂CH₂ | CH₂CH₂ | 0 | 5-NH₂-2-HO-Pymz-4-yl |
| 3-538 | Pip | CH₂CH₂ | (CH₂)₃ | 0 | Imdazo-2-yl |
| 3-539 | Pip | CH₂CH₂ | (CH₂)₃ | 0 | Imdazo-4-yl |
| 3-540 | Pip | CH₂CH₂ | (CH₂)₃ | 0 | 1-Me-Imdazo-2-yl |
| 3-541 | Pip | CH₂CH₂ | (CH₂)₃ | 0 | 2-Me-Imdazo-4-yl |
| 3-542 | Pip | CH₂CH₂ | (CH₂)₃ | 0 | 1,3,4-Oxadiazo-2-yl |
| 3-543 | Pip | CH₂CH₂ | (CH₂)₃ | 0 | 5-Me-1,3,4-Oxadiazo-2-yl |
| 3-544 | Pip | CH₂CH₂ | (CH₂)₃ | 0 | 5-Et-1,3,4-Oxadiazo-2-yl |
| 3-545 | Pip | CH₂CH₂ | (CH₂)₃ | 0 | 5-NH₂-1,3,4-Oxadiazo-2-yl |
| 3-546 | Pip | CH₂CH₂ | (CH₂)₃ | 0 | 5-AcNH-1,3,4-Oxadiazo-2-yl |
| 3-547 | Pip | CH₂CH₂ | (CH₂)₃ | 0 | 1,3,4-Thiadiazo-2-yl |
| 3-548 | Pip | CH₂CH₂ | (CH₂)₃ | 0 | 5-Me-1,3,4-Thiadiazo-2-yl |
| 3-549 | Pip | CH₂CH₂ | (CH₂)₃ | 0 | 5-NH₂-1,3,4-Thiadiazo-2-yl |
| 3-550 | Pip | CH₂CH₂ | (CH₂)₃ | 0 | 1,2,4-Triazo-3-yl |
| 3-551 | Pip | CH₂CH₂ | (CH₂)₃ | 0 | 1,2,4-Triazo-5-yl |
| 3-552 | Pip | CH₂CH₂ | (CH₂)₃ | 0 | 1-Me-1,2,4-Triazo-3-yl |
| 3-553 | Pip | CH₂CH₂ | (CH₂)₃ | 0 | 1-Me-1,2,4-Triazo-5-yl |
| 3-554 | Pip | CH₂CH₂ | (CH₂)₃ | 0 | 5-Me-1,2,4-Triazo-3-yl |
| 3-555 | Pip | CH₂CH₂ | (CH₂)₃ | 0 | 5-Cl-1,2,4-Triazo-3-yl |
| 3-556 | Pip | CH₂CH₂ | (CH₂)₃ | 0 | 5-NH₂-1,2,4-Triazo-3-yl |
| 3-557 | Pip | CH₂CH₂ | (CH₂)₃ | 0 | 5-AcNH-1,2,4-Triazo-3-yl |
| 3-558 | Pip | CH₂CH₂ | (CH₂)₃ | 0 | Tetrazo-5-yl |
| 3-559 | Pip | CH₂CH₂ | (CH₂)₃ | 0 | 1-Me-Tetrazo-5-yl |
| 3-560 | Pip | CH₂CH₂ | (CH₂)₃ | 0 | 1-Et-Tetrazo-5-yl |
| 3-561 | Pip | CH₂CH₂ | (CH₂)₃ | 0 | 1-(2-HOEt)-Tetrazo-5-yl |
| 3-562 | Pip | CH₂CH₂ | (CH₂)₃ | 0 | Pyz-2-yl |
| 3-563 | Pip | CH₂CH₂ | (CH₂)₃ | 0 | Pyz-3-yl |
| 3-564 | Pip | CH₂CH₂ | (CH₂)₃ | 0 | Pyz-4-yl |
| 3-565 | Pip | CH₂CH₂ | (CH₂)₃ | 0 | 3-Me-Pyz-2-yl |
| 3-566 | Pip | CH₂CH₂ | (CH₂)₃ | 0 | 5-Me-Pyz-2-yl |
| 3-567 | Pip | CH₂CH₂ | (CH₂)₃ | 0 | 2-Me-Pyz-4-yl |
| 3-568 | Pip | CH₂CH₂ | (CH₂)₃ | 0 | 3-Me-Pyz-4-yl |
| 3-569 | Pip | CH₂CH₂ | (CH₂)₃ | 0 | 3-Cl-Pyz-2-yl |
| 3-570 | Pip | CH₂CH₂ | (CH₂)₃ | 0 | 3-Cl-Pyz-4-yl |
| 3-571 | Pip | CH₂CH₂ | (CH₂)₃ | 0 | 3-NH₂-Pyz-2-yl |
| 3-572 | Pip | CH₂CH₂ | (CH₂)₃ | 0 | 5-NH₂-Pyz-2-yl |
| 3-573 | Pip | CH₂CH₂ | (CH₂)₃ | 0 | 4-NH₂-Pyz-3-yl |
| 3-574 | Pip | CH₂CH₂ | (CH₂)₃ | 0 | 3-NH₂-Pyz-4-yl |
| 3-575 | Pip | CH₂CH₂ | (CH₂)₃ | 0 | 3-HO-Pyz-2-yl |
| 3-576 | Pip | CH₂CH₂ | (CH₂)₃ | 0 | 5-HO-Pyz-2-yl |
| 3-577 | Pip | CH₂CH₂ | (CH₂)₃ | 0 | 2-HO-Pyz-4-yl |
| 3-578 | Pip | CH₂CH₂ | (CH₂)₃ | 0 | 3-HO-Pyz-4-yl |
| 3-579 | Pip | CH₂CH₂ | (CH₂)₃ | 0 | Pymz-2-yl |
| 3-580 | Pip | CH₂CH₂ | (CH₂)₃ | 0 | Pymz-4-yl |
| 3-581 | Pip | CH₂CH₂ | (CH₂)₃ | 0 | Pymz-5-yl |
| 3-582 | Pip | CH₂CH₂ | (CH₂)₃ | 0 | 4-Me-Pymz-2-yl |
| 3-583 | Pip | CH₂CH₂ | (CH₂)₃ | 0 | 5-Me-Pymz-2-yl |
| 3-584 | Pip | CH₂CH₂ | (CH₂)₃ | 0 | 2-Me-Pymz-4-yl |
| 3-585 | Pip | CH₂CH₂ | (CH₂)₃ | 0 | 5-Me-Pymz-4-yl |
| 3-586 | Pip | CH₂CH₂ | (CH₂)₃ | 0 | 6-Me-Pymz-4-yl |
| 3-587 | Pip | CH₂CH₂ | (CH₂)₃ | 0 | 4-Cl-Pymz-2-yl |
| 3-588 | Pip | CH₂CH₂ | (CH₂)₃ | 0 | 2-Me-Pymz-4-yl |

TABLE 3-continued

| Cpd. No. | R¹ | A | B | m | R⁵ |
|---|---|---|---|---|---|
| 3-589 | Pip | CH₂CH₂ | (CH₂)₃ | 0 | 4-NH₂-Pymz-2-yl |
| 3-590 | Pip | CH₂CH₂ | (CH₂)₃ | 0 | 5-NH₂-Pymz-2-yl |
| 3-591 | Pip | CH₂CH₂ | (CH₂)₃ | 0 | 2-NH₂-Pymz-4-yl |
| 3-592 | Pip | CH₂CH₂ | (CH₂)₃ | 0 | 5-NH₂-Pymz-4-yl |
| 3-593 | Pip | CH₂CH₂ | (CH₂)₃ | 0 | 4-AcNH-Pymz-2-yl |
| 3-594 | Pip | CH₂CH₂ | (CH₂)₃ | 0 | 2-AcNH-Pymz-4-yl |
| 3-595 | Pip | CH₂CH₂ | (CH₂)₃ | 0 | 4-NH₂-5-HO-Pymz-2-yl |
| 3-596 | Pip | CH₂CH₂ | (CH₂)₃ | 0 | 2-NH₂-5-HO-Pymz-4-yl |
| 3-597 | Pip | CH₂CH₂ | (CH₂)₃ | 0 | 4,6-diNH₂-Pymz-2-yl |
| 3-598 | Pip | CH₂CH₂ | (CH₂)₃ | 0 | 2,5-diNH₂-Pymz-4-yl |
| 3-599 | Pip | CH₂CH₂ | (CH₂)₄ | 0 | Imdazo-2-yl |
| 3-600 | Pip | CH₂CH₂ | (CH₂)₄ | 0 | 1,3,4-Oxadiazo-2-yl |
| 3-601 | Pip | CH₂CH₂ | (CH₂)₄ | 0 | 1,3,4-Thiadiazo-2-yl |
| 3-602 | Pip | CH₂CH₂ | (CH₂)₄ | 0 | 1,2,4-Triazo-3-yl |
| 3-603 | Pip | CH₂CH₂ | (CH₂)₄ | 0 | 1,2,4-Triazo-5-yl |
| 3-604 | Pip | CH₂CH₂ | (CH₂)₄ | 0 | Tetrazo-5-yl |
| 3-605 | Pip | CH₂CH₂ | (CH₂)₄ | 0 | Pyz-2-yl |
| 3-606 | Pip | CH₂CH₂ | (CH₂)₄ | 0 | Pyz-3-yl |
| 3-607 | Pip | CH₂CH₂ | (CH₂)₄ | 0 | Pyz-4-yl |
| 3-608 | Pip | CH₂CH₂ | (CH₂)₄ | 0 | Pymz-2-yl |
| 3-609 | Pip | CH₂CH₂ | (CH₂)₄ | 0 | Pymz-4-yl |
| 3-610 | Pip | CH₂CH₂ | CH₂CH(Me)CH₂ | 0 | Imdazo-2-yl |
| 3-611 | Pip | CH₂CH₂ | CH₂CH(Me)CH₂ | 0 | 1,3,4-Oxadiazo-2-yl |
| 3-612 | Pip | CH₂CH₂ | CH₂CH(Me)CH₂ | 0 | 1,3,4-Thiadiazo-2-yl |
| 3-613 | Pip | CH₂CH₂ | CH₂CH(Me)CH₂ | 0 | 1,2,4-Triazo-3-yl |
| 3-614 | Pip | CH₂CH₂ | CH₂CH(Me)CH₂ | 0 | 1,2,4-Triazo-5-yl |
| 3-615 | Pip | CH₂CH₂ | CH₂CH(Me)CH₂ | 0 | Tetrazo-5-yl |
| 3-616 | Pip | CH₂CH₂ | CH₂CH(Me)CH₂ | 0 | Pyz-2-yl |
| 3-617 | Pip | CH₂CH₂ | CH₂CH(Me)CH₂ | 0 | Pyz-4-yl |
| 3-618 | Pip | CH₂CH₂ | CH₂CH(Me)CH₂ | 0 | Pymz-2-yl |
| 3-619 | Pip | CH₂CH₂ | CH₂CH(Me)CH₂ | 0 | Pymz-4-yl |
| 3-620 | Pip | CH₂CH₂ | (CH₂)₅ | 0 | Imdazo-2-yl |
| 3-621 | Pip | CH₂CH₂ | (CH₂)₅ | 0 | 1,3,4-Oxadiazo-2-yl |
| 3-622 | Pip | CH₂CH₂ | (CH₂)₅ | 0 | 1,3,4-Thiadiazo-2-yl |
| 3-623 | Pip | CH₂CH₂ | (CH₂)₅ | 0 | 1,2,4-Triazo-3-yl |
| 3-624 | Pip | CH₂CH₂ | (CH₂)₅ | 0 | 1,2,4-Triazo-5-yl |
| 3-625 | Pip | CH₂CH₂ | (CH₂)₅ | 0 | Tetrazo-5-yl |
| 3-626 | Pip | CH₂CH₂ | (CH₂)₅ | 0 | Pyz-2-yl |
| 3-627 | Pip | CH₂CH₂ | (CH₂)₅ | 0 | Pyz-4-yl |
| 3-628 | Pip | CH₂CH₂ | (CH₂)₅ | 0 | Pymz-2-yl |
| 3-629 | Pip | CH₂CH₂ | (CH₂)₅ | 0 | Pymz-4-yl |
| 3-630 | Pip | CH₂CH₂ | (CH₂)₆ | 0 | Imdazo-2-yl |
| 3-631 | Pip | CH₂CH₂ | (CH₂)₆ | 0 | 1,3,4-Oxadiazo-2-yl |
| 3-632 | Pip | CH₂CH₂ | (CH₂)₆ | 0 | 1,3,4-Thiadiazo-2-yl |
| 3-633 | Pip | CH₂CH₂ | (CH₂)₆ | 0 | 1,2,4-Triazo-3-yl |
| 3-634 | Pip | CH₂CH₂ | (CH₂)₆ | 0 | 1,2,4-Triazo-5-yl |
| 3-635 | Pip | CH₂CH₂ | (CH₂)₆ | 0 | Tetrazo-5-yl |
| 3-636 | Pip | CH₂CH₂ | (CH₂)₆ | 0 | Pyz-3-yl |
| 3-637 | Pip | CH₂CH₂ | (CH₂)₆ | 0 | Pyz-4-yl |
| 3-638 | Pip | CH₂CH₂ | (CH₂)₆ | 0 | Pymz-2-yl |
| 3-639 | Pip | CH₂CH₂ | (CH₂)₆ | 0 | Pymz-4-yl |
| 3-640 | Pyr | CH₂CH₂ | CH₂ | 0 | Imdazo-2-yl |
| 3-641 | Pyr | CH₂CH₂ | CH₂ | 0 | Imdazo-4-yl |
| 3-642 | Pyr | CH₂CH₂ | CH₂ | 0 | 1,3,4-Oxadiazo-2-yl |
| 3-643 | Pyr | CH₂CH₂ | CH₂ | 0 | 1,3,4-Thiadiazo-2-yl |
| 3-644 | Pyr | CH₂CH₂ | CH₂ | 0 | 1,2,4-Triazo-3-yl |
| 3-645 | Pyr | CH₂CH₂ | CH₂ | 0 | 1,2,4-Triazo-5-yl |
| 3-646 | Pyr | CH₂CH₂ | CH₂ | 0 | Tetrazo-5-yl |
| 3-647 | Pyr | CH₂CH₂ | CH₂ | 0 | Pyz-2-yl |
| 3-648 | Pyr | CH₂CH₂ | CH₂ | 0 | Pyz-4-yl |
| 3-649 | Pyr | CH₂CH₂ | CH₂ | 0 | 3-Me-Pyz-2-yl |
| 3-650 | Pyr | CH₂CH₂ | CH₂ | 0 | 2-Me-Pyz-3-yl |
| 3-651 | Pyr | CH₂CH₂ | CH₂ | 0 | 3-NH₂-Pyz-2-yl |
| 3-652 | Pyr | CH₂CH₂ | CH₂ | 0 | 2-HO-Pyz-3-yl |
| 3-653 | Pyr | CH₂CH₂ | CH₂ | 0 | Pymz-2-yl |
| 3-654 | Pyr | CH₂CH₂ | CH₂ | 0 | Pymz-4-yl |
| 3-655 | Pyr | CH₂CH₂ | CH₂ | 0 | 4-Me-Pymz-2-yl |
| 3-656 | Pyr | CH₂CH₂ | CH₂ | 0 | 5-Me-Pymz-2-yl |
| 3-657 | Pyr | CH₂CH₂ | CH₂ | 0 | 2-Me-Pymz-4-yl |
| 3-658 | Pyr | CH₂CH₂ | CH₂ | 0 | 6-Me-Pymz-4-yl |
| 3-659 | Pyr | CH₂CH₂ | CH₂ | 0 | 4-NH₂-Pymz-2-yl |
| 3-660 | Pyr | CH₂CH₂ | CH₂ | 0 | 4-HO-Pymz-2-yl |
| 3-661 | Pyr | CH₂CH₂ | CH₂ | 0 | 4-NH₂-5-HO-Pymz-2-yl |
| 3-662 | Pyr | CH₂CH₂ | CH₂CH₂ | 0 | Imdazo-2-yl |
| 3-663 | Pyr | CH₂CH₂ | CH₂CH₂ | 0 | Imdazo-4-yl |
| 3-664 | Pyr | CH₂CH₂ | CH₂CH₂ | 0 | 1,3,4-Oxadiazo-2-yl |

TABLE 3-continued

| Cpd. No. | R¹ | A | B | m | R⁵ |
|---|---|---|---|---|---|
| 3-665 | Pyr | CH₂CH₂ | CH₂CH₂ | 0 | 1,3,4-Thiadiazo-2-yl |
| 3-666 | Pyr | CH₂CH₂ | CH₂CH₂ | 0 | 1,2,4-Triazo-3-yl |
| 3-667 | Pyr | CH₂CH₂ | CH₂CH₂ | 0 | 1,2,4-Triazo-5-yl |
| 3-668 | Pyr | CH₂CH₂ | CH₂CH₂ | 0 | Tetrazo-5-yl |
| 3-669 | Pyr | CH₂CH₂ | CH₂CH₂ | 0 | Pyz-2-yl |
| 3-670 | Pyr | CH₂CH₂ | CH₂CH₂ | 0 | Pyz-4-yl |
| 3-671 | Pyr | CH₂CH₂ | CH₂CH₂ | 0 | 3-Me-Pyz-2-yl |
| 3-672 | Pyr | CH₂CH₂ | CH₂CH₂ | 0 | 3-NH₂-Pyz-2-yl |
| 3-673 | Pyr | CH₂CH₂ | CH₂CH₂ | 0 | 3-HO-Pyz-2-yl |
| 3-674 | Pyr | CH₂CH₂ | CH₂CH₂ | 0 | Pymz-2-yl |
| 3-675 | Pyr | CH₂CH₂ | CH₂CH₂ | 0 | Pymz-4-yl |
| 3-676 | Pyr | CH₂CH₂ | CH₂CH₂ | 0 | Pymz-5-yl |
| 3-677 | Pyr | CH₂CH₂ | CH₂CH₂ | 0 | 4-Me-Pymz-2-yl |
| 3-678 | Pyr | CH₂CH₂ | CH₂CH₂ | 0 | 5-Me-Pymz-2-yl |
| 3-679 | Pyr | CH₂CH₂ | CH₂CH₂ | 0 | 2-Me-Pymz-4-yl |
| 3-680 | Pyr | CH₂CH₂ | CH₂CH₂ | 0 | 5-Me-Pymz-4-yl |
| 3-681 | Pyr | CH₂CH₂ | CH₂CH₂ | 0 | 4-NH₂-Pymz-2-yl |
| 3-682 | Pyr | CH₂CH₂ | CH₂CH₂ | 0 | 2-HO-Pymz-2-yl |
| 3-683 | Pyr | CH₂CH₂ | (CH₂)₃ | 0 | Imdazo-2-yl |
| 3-684 | Pyr | CH₂CH₂ | (CH₂)₃ | 0 | Imdazo-4-yl |
| 3-685 | Pyr | CH₂CH₂ | (CH₂)₃ | 0 | 1,3,4-Oxadiazo-2-yl |
| 3-686 | Pyr | CH₂CH₂ | (CH₂)₃ | 0 | 1,3,4-Thiadiazo-2-yl |
| 3-687 | Pyr | CH₂CH₂ | (CH₂)₃ | 0 | 1,2,4-Triazo-3-yl |
| 3-688 | Pyr | CH₂CH₂ | (CH₂)₃ | 0 | 1,2,4-Triazo-5-yl |
| 3-689 | Pyr | CH₂CH₂ | (CH₂)₃ | 0 | Tetrazo-5-yl |
| 3-690 | Pyr | CH₂CH₂ | (CH₂)₃ | 0 | Pyz-2-yl |
| 3-691 | Pyr | CH₂CH₂ | (CH₂)₃ | 0 | Pyz-3-yl |
| 3-692 | Pyr | CH₂CH₂ | (CH₂)₃ | 0 | Pyz-4-yl |
| 3-693 | Pyr | CH₂CH₂ | (CH₂)₃ | 0 | 3-Me-Pyz-2-yl |
| 3-694 | Pyr | CH₂CH₂ | (CH₂)₃ | 0 | 2-Me-Pyz-4-yl |
| 3-695 | Pyr | CH₂CH₂ | (CH₂)₃ | 0 | 2-Cl-Pyz-3-yl |
| 3-696 | Pyr | CH₂CH₂ | (CH₂)₃ | 0 | 3-NH₂-Pyz-2-yl |
| 3-697 | Pyr | CH₂CH₂ | (CH₂)₃ | 0 | 3-NH₂-Pyz-4-yl |
| 3-698 | Pyr | CH₂CH₂ | (CH₂)₃ | 0 | 3-HO-Pyz-2-yl |
| 3-699 | Pyr | CH₂CH₂ | (CH₂)₃ | 0 | Pymz-2-yl |
| 3-700 | Pyr | CH₂CH₂ | (CH₂)₃ | 0 | Pymz-4-yl |
| 3-701 | Pyr | CH₂CH₂ | (CH₂)₃ | 0 | 4-Me-Pymz-2-yl |
| 3-702 | Pyr | CH₂CH₂ | (CH₂)₃ | 0 | 2-Me-Pymz-4-yl |
| 3-703 | Pyr | CH₂CH₂ | (CH₂)₃ | 0 | 5-Me-Pymz-4-yl |
| 3-704 | Pyr | CH₂CH₂ | (CH₂)₃ | 0 | 4-Me-Pymz-5-yl |
| 3-705 | Pyr | CH₂CH₂ | (CH₂)₃ | 0 | 5-NH₂-Pymz-2-yl |
| 3-706 | Pyr | CH₂CH₂ | (CH₂)₃ | 0 | 2-NH₂-Pymz-4-yl |
| 3-707 | Pyr | CH₂CH₂ | (CH₂)₃ | 0 | 2-HO-Pymz-4-yl |
| 3-708 | Pyr | CH₂CH₂ | (CH₂)₃ | 0 | 4-NH₂-5-HO-Pymz-2-yl |
| 3-709 | Pyr | CH₂CH₂ | (CH₂)₃ | 0 | 2-NH₂-5-HO-Pymz-4-yl |
| 3-710 | Pyr | CH₂CH₂ | (CH₂)₃ | 0 | 4,6-diNH₂-Pymz-2-yl |
| 3-711 | Pyr | CH₂CH₂ | (CH₂)₄ | 0 | Imdazo-2-yl |
| 3-712 | Pyr | CH₂CH₂ | (CH₂)₄ | 0 | 1,3,4-Oxadiazo-2-yl |
| 3-713 | Pyr | CH₂CH₂ | (CH₂)₄ | 0 | 1,3,4-Thiadiazo-2-yl |
| 3-714 | Pyr | CH₂CH₂ | (CH₂)₄ | 0 | 1,2,4-Triazo-3-yl |
| 3-715 | Pyr | CH₂CH₂ | (CH₂)₄ | 0 | 1,2,4-Triazo-5-yl |
| 3-716 | Pyr | CH₂CH₂ | (CH₂)₄ | 0 | Tetrazo-5-yl |
| 3-717 | Pyr | CH₂CH₂ | (CH₂)₄ | 0 | Pyz-2-yl |
| 3-718 | Pyr | CH₂CH₂ | (CH₂)₄ | 0 | Pyz-3-yl |
| 3-719 | Pyr | CH₂CH₂ | (CH₂)₄ | 0 | Pyz-4-yl |
| 3-720 | Pyr | CH₂CH₂ | (CH₂)₄ | 0 | Pymz-2-yl |
| 3-721 | Pyr | CH₂CH₂ | (CH₂)₄ | 0 | Pymz-4-yl |
| 3-722 | Pyr | CH₂CH₂ | (CH₂)₄ | 0 | Pymz-5-yl |
| 3-723 | Pyr | CH₂CH₂ | CH₂CH(Me)CH₂ | 0 | Imdazo-2-yl |
| 3-724 | Pyr | CH₂CH₂ | CH₂CH(Me)CH₂ | 0 | 1,3,4-Oxadiazo-2-yl |
| 3-725 | Pyr | CH₂CH₂ | CH₂CH(Me)CH₂ | 0 | 1,3,4-Thiadiazo-2-yl |
| 3-726 | Pyr | CH₂CH₂ | CH₂CH(Me)CH₂ | 0 | 1,2,4-Triazo-3-yl |
| 3-727 | Pyr | CH₂CH₂ | CH₂CH(Me)CH₂ | 0 | 1,2,4-Triazo-5-yl |
| 3-728 | Pyr | CH₂CH₂ | CH₂CH(Me)CH₂ | 0 | Tetrazo-5-yl |
| 3-729 | Pyr | CH₂CH₂ | CH₂CH(Me)CH₂ | 0 | Pyz-2-yl |
| 3-730 | Pyr | CH₂CH₂ | CH₂CH(Me)CH₂ | 0 | Pyz-3-yl |
| 3-731 | Pyr | CH₂CH₂ | CH₂CH(Me)CH₂ | 0 | Pymz-2-yl |
| 3-732 | Pyr | CH₂CH₂ | CH₂CH(Me)CH₂ | 0 | Pymz-4-yl |
| 3-733 | Pyr | CH₂CH₂ | (CH₂)₅ | 0 | Imdazo-2-yl |
| 3-734 | Pyr | CH₂CH₂ | (CH₂)₅ | 0 | 1,3,4-Oxadiazo-2-yl |
| 3-735 | Pyr | CH₂CH₂ | (CH₂)₅ | 0 | 1,3,4-Thiadiazo-2-yl |
| 3-736 | Pyr | CH₂CH₂ | (CH₂)₅ | 0 | 1,2,4-Triazo-3-yl |
| 3-737 | Pyr | CH₂CH₂ | (CH₂)₅ | 0 | 1,2,4-Triazo-5-yl |
| 3-738 | Pyr | CH₂CH₂ | (CH₂)₅ | 0 | Tetrazo-5-yl |
| 3-739 | Pyr | CH₂CH₂ | (CH₂)₅ | 0 | Pyz-2-yl |
| 3-740 | Pyr | CH₂CH₂ | (CH₂)₅ | 0 | Pyz-3-yl |

TABLE 3-continued

| Cpd. No. | R¹ | A | B | m | R⁵ |
|---|---|---|---|---|---|
| 3-741 | Pyr | CH₂CH₂ | (CH₂)₅ | 0 | Pymz-2-yl |
| 3-742 | Pyr | CH₂CH₂ | (CH₂)₅ | 0 | Pymz-4-yl |
| 3-743 | Pyr | CH₂CH₂ | (CH₂)₆ | 0 | Imdazo-2-yl |
| 3-744 | Pyr | CH₂CH₂ | (CH₂)₆ | 0 | 1,3,4-Oxadiazo-2-yl |
| 3-745 | Pyr | CH₂CH₂ | (CH₂)₆ | 0 | 1,3,4-Thiadiazo-2-yl |
| 3-746 | Pyr | CH₂CH₂ | (CH₂)₆ | 0 | 1,2,4-Triazo-3-yl |
| 3-747 | Pyr | CH₂CH₂ | (CH₂)₆ | 0 | 1,2,4-Triazo-5-yl |
| 3-748 | Pyr | CH₂CH₂ | (CH₂)₆ | 0 | Tetrazo-5-yl |
| 3-749 | Pyr | CH₂CH₂ | (CH₂)₆ | 0 | Pyz-2-yl |
| 3-750 | Pyr | CH₂CH₂ | (CH₂)₆ | 0 | Pyz-3-yl |
| 3-751 | Pyr | CH₂CH₂ | (CH₂)₆ | 0 | Pymz-2-yl |
| 3-752 | Pyr | CH₂CH₂ | (CH₂)₆ | 0 | Pymz-4-yl |
| 3-753 | NMe₂ | CH₂CH₂ | CH₂ | 0 | Imdazo-2-yl |
| 3-754 | NMe₂ | CH₂CH₂ | CH₂ | 0 | 1,3,4-Oxadiazo-2-yl |
| 3-755 | NMe₂ | CH₂CH₂ | CH₂ | 0 | 1,3,4-Thiadiazo-2-yl |
| 3-756 | NMe₂ | CH₂CH₂ | CH₂ | 0 | 1,2,4-Triazo-3-yl |
| 3-757 | NMe₂ | CH₂CH₂ | CH₂ | 0 | 1,2,4-Triazo-5-yl |
| 3-758 | NMe₂ | CH₂CH₂ | CH₂ | 0 | Tetrazo-5-yl |
| 3-759 | NMe₂ | CH₂CH₂ | CH₂ | 0 | Pyz-2-yl |
| 3-760 | NMe₂ | CH₂CH₂ | CH₂ | 0 | 3-Me-Pyz-2-yl |
| 3-761 | NMe₂ | CH₂CH₂ | CH₂ | 0 | Pymz-2-yl |
| 3-762 | NMe₂ | CH₂CH₂ | CH₂ | 0 | 4-Me-Pymz-2-yl |
| 3-763 | NMe₂ | CH₂CH₂ | CH₂ | 0 | 6-Me-Pymz-4-yl |
| 3-764 | NMe₂ | CH₂CH₂ | CH₂CH₂ | 0 | 1,3,4-Oxadiazo-2-yl |
| 3-765 | NMe₂ | CH₂CH₂ | CH₂CH₂ | 0 | 1,2,4-Triazo-3-yl |
| 3-766 | NMe₂ | CH₂CH₂ | CH₂CH₂ | 0 | 1,2,4-Triazo-5-yl |
| 3-767 | NMe₂ | CH₂CH₂ | CH₂CH₂ | 0 | Pyz-2-yl |
| 3-768 | NMe₂ | CH₂CH₂ | CH₂CH₂ | 0 | 3-Me-Pyz-2-yl |
| 3-769 | NMe₂ | CH₂CH₂ | CH₂CH₂ | 0 | Pymz-2-yl |
| 3-770 | NMe₂ | CH₂CH₂ | CH₂CH₂ | 0 | Pymz-4-yl |
| 3-771 | NMe₂ | CH₂CH₂ | CH₂CH₂ | 0 | 4-Me-Pymz-2-yl |
| 3-772 | NMe₂ | CH₂CH₂ | CH₂CH₂ | 0 | 2-Me-Pymz-4-yl |
| 3-773 | NMe₂ | CH₂CH₂ | (CH₂)₃ | 0 | Imdazo-2-yl |
| 3-774 | NMe₂ | CH₂CH₂ | (CH₂)₃ | 0 | Imdazo-4-yl |
| 3-775 | NMe₂ | CH₂CH₂ | (CH₂)₃ | 0 | 1,3,4-Oxadiazo-2-yl |
| 3-776 | NMe₂ | CH₂CH₂ | (CH₂)₃ | 0 | 1,3,4-Thiadiazo-2-yl |
| 3-777 | NMe₂ | CH₂CH₂ | (CH₂)₃ | 0 | 1,2,4-Triazo-3-yl |
| 3-778 | NMe₂ | CH₂CH₂ | (CH₂)₃ | 0 | 1,2,4-Triazo-5-yl |
| 3-779 | NMe₂ | CH₂CH₂ | (CH₂)₃ | 0 | Tetrazo-5-yl |
| 3-780 | NMe₂ | CH₂CH₂ | (CH₂)₃ | 0 | Pyz-2-yl |
| 3-781 | NMe₂ | CH₂CH₂ | (CH₂)₃ | 0 | Pymz-2-yl |
| 3-782 | NMe₂ | CH₂CH₂ | (CH₂)₃ | 0 | Pymz-4-yl |
| 3-783 | NMe₂ | CH₂CH₂ | (CH₂)₄ | 0 | 1,3,4-Oxadiazo-2-yl |
| 3-784 | NMe₂ | CH₂CH₂ | (CH₂)₄ | 0 | 1,2,4-Triazo-3-yl |
| 3-785 | NMe₂ | CH₂CH₂ | (CH₂)₄ | 0 | 1,2,4-Triazo-5-yl |
| 3-786 | NMe₂ | CH₂CH₂ | (CH₂)₄ | 0 | Tetrazo-5-yl |
| 3-787 | NMe₂ | CH₂CH₂ | (CH₂)₄ | 0 | Pyz-2-yl |
| 3-788 | NMe₂ | CH₂CH₂ | (CH₂)₄ | 0 | Pymz-2-yl |
| 3-789 | NMe₂ | CH₂CH₂ | (CH₂)₄ | 0 | Pymz-4-yl |
| 3-790 | NMe₂ | CH₂CH₂ | CH₂CH(Me)CH₂ | 0 | 1,3,4-Oxadiazo-2-yl |
| 3-791 | NMe₂ | CH₂CH₂ | CH₂CH(Me)CH₂ | 0 | 1,2,4-Triazo-3-yl |
| 3-792 | NMe₂ | CH₂CH₂ | CH₂CH(Me)CH₂ | 0 | 1,2,4-Triazo-5-yl |
| 3-793 | NMe₂ | CH₂CH₂ | CH₂CH(Me)CH₂ | 0 | Pymz-2-yl |
| 3-794 | NMe₂ | CH₂CH₂ | CH₂CH(Me)CH₂ | 0 | Pymz-4-yl |
| 3-795 | NMe₂ | CH₂CH₂ | (CH₂)₅ | 0 | 1,3,4-Oxadiazo-2-yl |
| 3-796 | NMe₂ | CH₂CH₂ | (CH₂)₅ | 0 | 1,2,4-Triazo-3-yl |
| 3-797 | NMe₂ | CH₂CH₂ | (CH₂)₅ | 0 | 1,2,4-Triazo-5-yl |
| 3-798 | NMe₂ | CH₂CH₂ | (CH₂)₅ | 0 | Pymz-2-yl |
| 3-799 | NMe₂ | CH₂CH₂ | (CH₂)₅ | 0 | Pymz-4-yl |
| 3-800 | NMe₂ | CH₂CH₂ | (CH₂)₆ | 0 | 1,3,4-Oxadiazo-2-yl |
| 3-801 | NMe₂ | CH₂CH₂ | (CH₂)₆ | 0 | 1,2,4-Triazo-3-yl |
| 3-802 | NMe₂ | CH₂CH₂ | (CH₂)₆ | 0 | 1,2,4-Triazo-5-yl |
| 3-803 | NMe₂ | CH₂CH₂ | (CH₂)₆ | 0 | Pymz-2-yl |
| 3-804 | NMe₂ | CH=CH | (CH₂)₆ | 0 | Pymz-4-yl |
| 3-805 | Azi | CH₂CH₂ | (CH₂)₃ | 0 | 1,2,4-Triazo-3-yl |
| 3-806 | Azi | CH₂CH₂ | (CH₂)₃ | 0 | Pymz-2-yl |
| 3-807 | Aze | CH₂CH₂ | (CH₂)₃ | 0 | 1,2,4-Triazo-3-yl |
| 3-808 | Aze | CH₂CH₂ | (CH₂)₃ | 0 | Pymz-2-yl |
| 3-809 | Pip | CH₂ | CH₂ | 0 | Imdazo-2-yl |
| 3-810 | Pip | CH₂ | CH₂ | 0 | 1,3,4-Oxadiazo-2-yl |
| 3-811 | Pip | CH₂ | CH₂ | 0 | 1,3,4-Thiadiazo-2-yl |
| 3-812 | Pip | CH₂ | CH₂ | 0 | 1,2,4-Triazo-3-yl |
| 3-813 | Pip | CH₂ | CH₂ | 0 | 1,2,4-Triazo-5-yl |
| 3-814 | Pip | CH₂ | CH₂ | 0 | Tetrazo-5-yl |
| 3-815 | Pip | CH₂ | CH₂ | 0 | Pyz-2-yl |
| 3-816 | Pip | CH₂ | CH₂ | 0 | 3-Me-Pyz-2-yl |

TABLE 3-continued

| Cpd. No. | R¹ | A | B | m | R⁵ |
|---|---|---|---|---|---|
| 3-817 | Pip | CH₂ | CH₂ | 0 | Pymz-2-yl |
| 3-818 | Pip | CH₂ | CH₂ | 0 | 4-Me-Pymz-2-yl |
| 3-819 | Pip | CH₂ | CH₂ | 0 | 6-Me-Pymz-4-yl |
| 3-820 | Pip | CH₂ | CH₂CH₂ | 0 | 1,3,4-Oxadiazo-2-yl |
| 3-821 | Pip | CH₂ | CH₂CH₂ | 0 | 1,2,4-Triazo-3-yl |
| 3-822 | Pip | CH₂ | CH₂CH₂ | 0 | 1,2,4-Triazo-5-yl |
| 3-823 | Pip | CH₂ | CH₂CH₂ | 0 | Pyz-2-yl |
| 3-824 | Pip | CH₂ | CH₂CH₂ | 0 | 3-Me-Pyz-2-yl |
| 3-825 | Pip | CH₂ | CH₂CH₂ | 0 | Pymz-2-yl |
| 3-826 | Pip | CH₂ | CH₂CH₂ | 0 | Pymz-4-yl |
| 3-827 | Pip | CH₂ | CH₂CH₂ | 0 | 4-Me-Pymz-2-yl |
| 3-828 | Pip | CH₂ | CH₂CH₂ | 0 | 2-Me-Pymz-4-yl |
| 3-829 | Pip | CH₂ | (CH₂)₃ | 0 | Imdazo-2-yl |
| 3-830 | Pip | CH₂ | (CH₂)₃ | 0 | Imdazo-4-yl |
| 3-831 | Pip | CH₂ | (CH₂)₃ | 0 | 1,3,4-Oxadiazo-2-yl |
| 3-832 | Pip | CH₂ | (CH₂)₃ | 0 | 1,3,4-Thiadiazo-2-yl |
| 3-833 | Pip | CH₂ | (CH₂)₃ | 0 | 1,2,4-Triazo-3-yl |
| 3-834 | Pip | CH₂ | (CH₂)₃ | 0 | 1,2,4-Triazo-5-yl |
| 3-835 | Pip | CH₂ | (CH₂)₃ | 0 | Tetrazo-5-yl |
| 3-836 | Pip | CH₂ | (CH₂)₃ | 0 | Pyz-2-yl |
| 3-837 | Pip | CH₂ | (CH₂)₃ | 0 | Pymz-2-yl |
| 3-838 | Pip | CH₂ | (CH₂)₃ | 0 | Pymz-4-yl |
| 3-839 | Pip | CH₂ | (CH₂)₄ | 0 | 1,3,4-Oxadiazo-2-yl |
| 3-840 | Pip | CH₂ | (CH₂)₄ | 0 | 1,2,4-Triazo-3-yl |
| 3-841 | Pip | CH₂ | (CH₂)₄ | 0 | 1,2,4-Triazo-5-yl |
| 3-842 | Pip | CH₂ | (CH₂)₄ | 0 | Tetrazo-5-yl |
| 3-843 | Pip | CH₂ | (CH₂)₄ | 0 | Pyz-2-yl |
| 3-844 | Pip | CH₂ | (CH₂)₄ | 0 | Pymz-2-yl |
| 3-845 | Pip | CH₂ | (CH₂)₄ | 0 | Pymz-4-yl |
| 3-846 | Pip | CH₂ | CH₂CH(Me)CH₂ | 0 | 1,3,4-Oxadiazo-2-yl |
| 3-847 | Pip | CH₂ | CH₂CH(Me)CH₂ | 0 | 1,2,4-Triazo-3-yl |
| 3-848 | Pip | CH₂ | CH₂CH(Me)CH₂ | 0 | 1,2,4-Triazo-5-yl |
| 3-849 | Pip | CH₂ | CH₂CH(Me)CH₂ | 0 | Pymz-2-yl |
| 3-850 | Pip | CH₂ | CH₂CH(Me)CH₂ | 0 | Pymz-4-yl |
| 3-851 | Pip | CH₂ | (CH₂)₅ | 0 | 1,3,4-Oxadiazo-2-yl |
| 3-852 | Pip | CH₂ | (CH₂)₅ | 0 | 1,2,4-Triazo-3-yl |
| 3-853 | Pip | CH₂ | (CH₂)₅ | 0 | 1,2,4-Triazo-5-yl |
| 3-854 | Pip | CH₂ | (CH₂)₅ | 0 | Pymz-2-yl |
| 3-855 | Pip | CH₂ | (CH₂)₅ | 0 | Pymz-4-yl |
| 3-856 | Pip | CH₂ | (CH₂)₆ | 0 | 1,3,4-Oxadiazo-2-yl |
| 3-857 | Pip | CH₂ | (CH₂)₆ | 0 | 1,2,4-Triazo-3-yl |
| 3-858 | Pip | CH₂ | (CH₂)₆ | 0 | 1,2,4-Triazo-5-yl |
| 3-859 | Pip | CH₂ | (CH₂)₆ | 0 | Pymz-2-yl |
| 3-860 | Pip | CH₂ | (CH₂)₆ | 0 | Pymz-4-yl |
| 3-861 | Pip | (CH₂)₃ | CH₂ | 0 | 1,3,4-Oxadiazo-2-yl |
| 3-862 | Pip | (CH₂)₃ | CH₂ | 0 | 1,2,4-Triazo-3-yl |
| 3-863 | Pip | (CH₂)₃ | CH₂ | 0 | Pymz-2-yl |
| 3-864 | Pip | (CH₂)₃ | CH₂CH₂ | 0 | 1,3,4-Oxadiazo-2-yl |
| 3-865 | Pip | (CH₂)₃ | CH₂CH₂ | 0 | 1,2,4-Triazo-3-yl |
| 3-866 | Pip | (CH₂)₃ | CH₂CH₂ | 0 | Pymz-2-yl |
| 3-867 | Pip | (CH₂)₃ | CH₂CH₂ | 0 | Pymz-4-yl |
| 3-868 | Pip | (CH₂)₃ | (CH₂)₃ | 0 | Imdazo-2-yl |
| 3-869 | Pip | (CH₂)₃ | (CH₂)₃ | 0 | Imdazo-4-yl |
| 3-870 | Pip | (CH₂)₃ | (CH₂)₃ | 0 | 1,3,4-Oxadiazo-2-yl |
| 3-871 | Pip | (CH₂)₃ | (CH₂)₃ | 0 | 1,3,4-Thiadiazo-2-yl |
| 3-872 | Pip | (CH₂)₃ | (CH₂)₃ | 0 | 1,2,4-Triazo-3-yl |
| 3-873 | Pip | (CH₂)₃ | (CH₂)₃ | 0 | 1,2,4-Triazo-5-yl |
| 3-874 | Pip | (CH₂)₃ | (CH₂)₃ | 0 | Tetrazo-5-yl |
| 3-875 | Pip | (CH₂)₃ | (CH₂)₃ | 0 | Pyz-2-yl |
| 3-876 | Pip | (CH₂)₃ | (CH₂)₃ | 0 | Pymz-2-yl |
| 3-877 | Pip | (CH₂)₃ | (CH₂)₃ | 0 | Pymz-4-yl |
| 3-878 | Pip | (CH₂)₃ | (CH₂)₄ | 0 | 1,3,4-Oxadiazo-2-yl |
| 3-879 | Pip | (CH₂)₃ | (CH₂)₄ | 0 | 1,2,4-Triazo-3-yl |
| 3-880 | Pip | (CH₂)₃ | (CH₂)₄ | 0 | Pymz-2-yl |
| 3-881 | Pip | (CH₂)₃ | (CH₂)₄ | 0 | Pymz-4-yl |
| 3-882 | Pip | (CH₂)₃ | (CH₂)₅ | 0 | 1,3,4-Oxadiazo-2-yl |
| 3-883 | Pip | (CH₂)₃ | (CH₂)₅ | 0 | 1,2,4-Triazo-3-yl |
| 3-884 | Pip | (CH₂)₃ | (CH₂)₅ | 0 | Pymz-2-yl |
| 3-885 | Pip | (CH₂)₃ | (CH₂)₅ | 0 | Pymz-4-yl |
| 3-886 | Pip | (CH₂)₃ | (CH₂)₆ | 0 | 1,3,4-Oxadiazo-2-yl |
| 3-887 | Pip | (CH₂)₃ | (CH₂)₆ | 0 | 1,2,4-Triazo-5-yl |
| 3-888 | Pip | (CH₂)₃ | (CH₂)₆ | 0 | Pymz-2-yl |
| 3-889 | Pip | (CH₂)₃ | (CH₂)₆ | 0 | Pymz-4-yl |
| 3-890 | Pyr | CH₂ | (CH₂)₃ | 0 | 1,2,4-Triazo-3-yl |
| 3-891 | Pyr | CH₂ | (CH₂)₃ | 0 | Pymz-2-yl |

TABLE 3-continued

| Cpd. No. | R¹ | A | B | m | R⁵ |
|---|---|---|---|---|---|
| 3-892 | Azi | CH₂ | (CH₂)₃ | 0 | 1,2,4-Triazo-3-yl |
| 3-893 | Aze | CH₂ | (CH₂)₃ | 0 | Pymz-2-yl |

Of the compounds listed above, the following are preferred, that is to say Compounds No. 1-1, 1-5, 1-16, 1-17, 1-19, 1-28, 1-31, 1-45, 1-46, 1-47, 1-61, 1-82, 1-87, 1-92, 1-115, 1-116, 1-125, 1-137, 1-166, 1-185, 1-216, 1-260, 1-350, 1-462, 1-591, 1-612, 1-951, 1-974, 1-975, 1-976, 1-977, 1-981, 1-985, 1-1004, 1-1016, 1-1018, 1-1019, 1-1020, 1-1021, 1-1022, 1-1023, 1-1065, 1-1124, 1-1168, 1-1169, 1-1274, 2-2, 2-4, 2-5, 2-6, 2-7, 2-8, 2-9, 2-10, 2-12, 2-20, 2-27, 2-28, 2-42, 2-44, 2-57, 2-59, 2-96, 2-98, 2-123, 2-209, 2-211, 2-212, 2-216, 2-217, 2-218, 2-297, 2-298, 2-390, 2-391, 2-392, 2-461, 2-482, 2-483, 2-493, 2-494, 2-506, 2-508, 2-509, 2-852, 2-854, 2-1059, 2-1061, 2-1147, 2-1148, 3-8, 3-14, 3-25, 3-79, 3-82, 3-86, 3-87, 3-89, 3-98, 3-100, 3-101, 3-103, 3-118, 3-119, 3-121, 3-136, 3-238, 3-405 and 3-579. More preferred compounds are Compounds No. 1-46, 1-116, 1-137, 1-591, 1-612, 1-974, 1-1019, 2-2, 2-4, 2-5, 2-6, 2-7, 2-9, 2-10, 2-12, 2-20, 2-27, 2-28, 2-209, 2-211, 2-212, 2-216, 2-217, 2-218, 2-390, 2-392, 2-1147, 2-1148, 3-118, 3-238 and 3-579.

The most preferred compounds of the present invention are Compounds No.:

1-116. N-[4-(4-piperidinomethyl-2-pyridyloxy)-cis-2-butenyl]pyrazole-4-carboxamide;
1-137. 3-amino-N-[4-(4-piperidinomethyl-2-pyridyloxy)-cis-2-butenyl]pyrazole-4-carboxamide;
2-2. N-[4-(4-piperidinomethyl-2-pyridyloxy)-cis-2-butenyl]-2-(2-hydroxyethylthio)acetamide;
2-4. N-[4-(4-piperidinomethyl-2-pyridyloxy)-cis-2-butenyl]-2-(2-acetoxyethylthio)acetamide;
2-5. N-[4-(4-piperidinomethyl-2-pyridyloxy)-cis-2-butenyl]-2-(2-propionyloxyethylthio)acetamide;
2-6. N-[4-(4-piperidinomethyl-2-pyridyloxy)-cis-2-butenyl]-2-(2-butyryloxyethylthio)acetamide;
2-7. N-[4-(4-piperidinomethyl-2-pyridyloxy)-cis-2-butenyl]-2-(2-isobutyryloxyethylthio)acetamide;
2-9. N-[4-(4-piperidinomethyl-2-pyridyloxy)-cis-2-butenyl]-2-(2-isovaleryloxyethylthio)acetamide;
2-10. N-[4-(4-piperidinomethyl-2-pyridyloxy)-cis-2-butenyl]-2-(2-phenylacetoxyethylthio)acetamide;
2-12. 2-{-N-[4-(4-piperidinomethyl-2-pyridyloxy)-cis-2-butenyl]carbamoylmethylthio}ethyl hydrogen succinate;
2-20. N-[4-(4-piperidinomethyl-2-pyridyloxy)-cis-2-butenyl]-2-(2-benzoyloxyethylthio)acetamide;
2-27. N-[4-(4-piperidinomethyl-2-pyridyloxy)-cis-2-butenyl]-2-(2-cyclopentylcarbonyloxyethylthio)acetamide;
2-28. N-[4-(4-piperidinomethyl-2-pyridyloxy)-cis-2-butenyl]-2-(2-cyclohexylcarbonyloxyethylthio)acetamide;
2-390. N-[4-(4-piperidinomethyl-2-pyridyloxy)-cis-2-butenyl]-2-(2-hydroxyethylsulfinyl)acetamide;
2-392. N-[4-(4-piperidinomethyl-2-pyridyloxy)-cis-2-butenyl]-2-(2-propionyloxyethylsulfinyl)acetamide;
2-1147. -N-[4-(4-piperidinomethyl-2-pyridyloxy)-cis-2-butenyl]-2-[2-(3,3-dimethylbutyryloxy)ethylthio]acetamide;
2-1148. N-[4-(4-piperidinomethyl-2-pyridyloxy)-cis-2-butenyl]-2-[2-(2,2-dimethylpropionyloxy)ethylthio]acetamide;
3-118. N-[4-(4-piperidinomethyl-2-pyridyloxy)-cis-2-butenyl]-4-(2-pyrimidinylthio)butyramide;

and pharmaceutically acceptable salts thereof.

The compounds of the present invention may be prepared by a variety of methods well known in the art for the preparation of compounds of this type. For example, they may be prepared by the following Reactions A to G:

Reaction A:

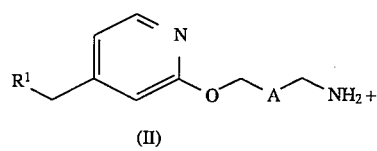

(II)

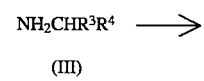

(III)

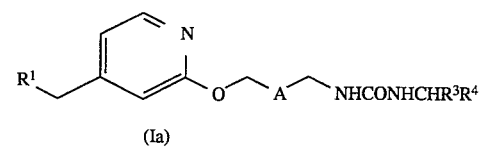

(Ia)

Reaction B:

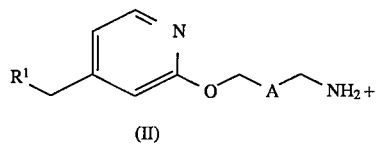

(II)

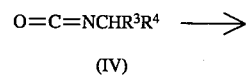

(IV)

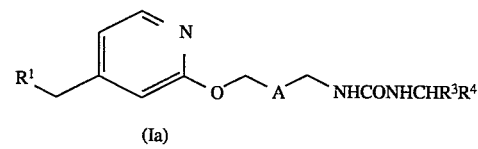

(Ia)

Reaction C:

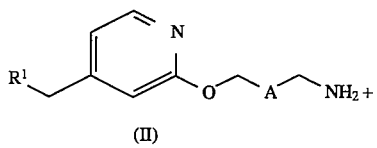

(II)

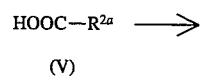

(V)

-continued

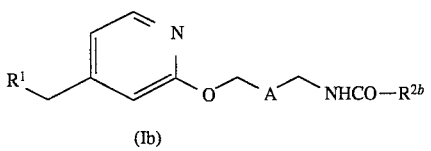
(Ib)

Reaction D:

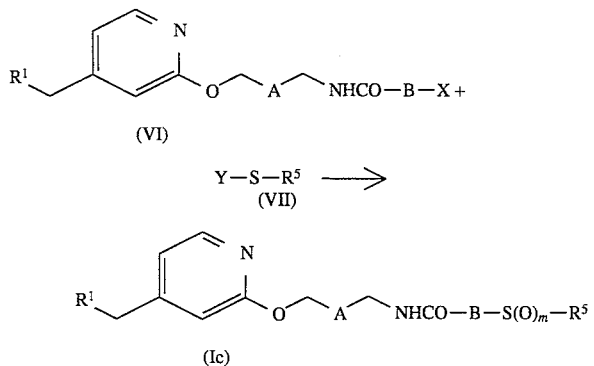

Reaction E:

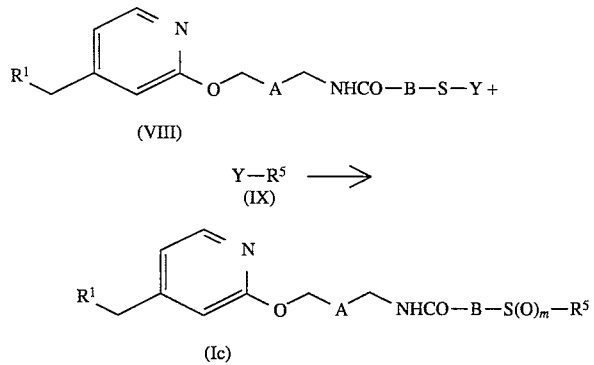

Reaction F:

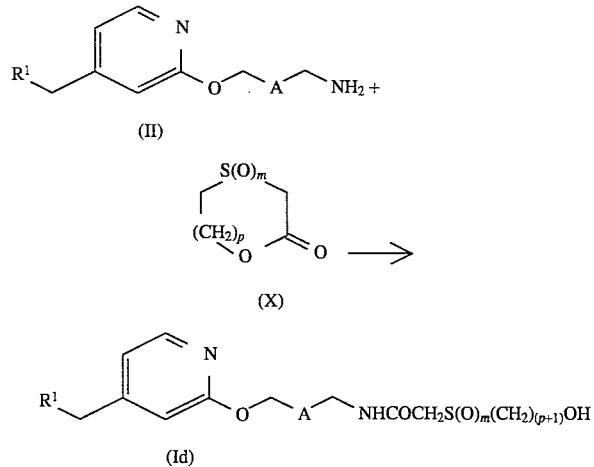

Reaction G:

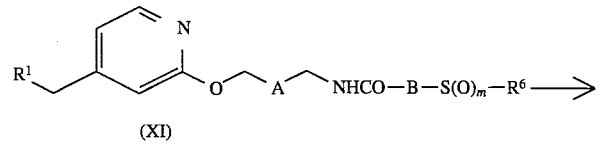

-continued

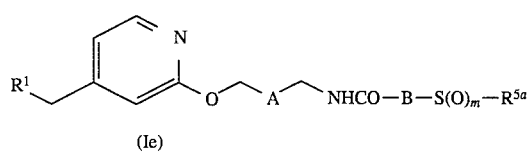
(Ie)

In the above formulae:

$R^1$, $R^2$, $R^3$, $R^4$, $R^5$, A, B and m are as defined above;

$R^{2a}$ represents any of the groups defined above for $R^2$, except the groups of formula —NHCHR$^3$R$^4$ (wherein $R^3$ and $R^4$ are as defined above) and provided that any hydroxy group in the group represented by $R^2$ is protected;

$R^{2b}$ represents any of the groups defined above for $R^2$, except the groups of formula —NHCHR$^3$R$^4$ (wherein $R^3$ and $R^4$ are as defined above);

$R^{5a}$ represents a hydroxyalkyl group having from 2 to 4 carbon atoms (with the proviso that the group must include a moiety having the formula —CH$_2$OH);

$R^6$ represents an alkyl group having from 1 to 3 carbon atoms and substituted with a carboxy or alkoxycarbonyl group having from 1 to 6 carbon atoms in the alkoxy moiety;

X represents a halogen atom, preferably a chlorine, bromine or iodine atom;

Y represents a hydrogen atom or an alkali metal atom, such as a lithium, sodium or potassium atom; and p is an integer from 1 to 3.

Where a hydroxy-protecting group is present, there is no particular limitation upon the nature of this group, and any such group well known in the field of organic chemistry may equally be used here. Typical examples of such groups include: cyclic ether groups, such as the tetrahydropyranyl, tetrahydrofuranyl and tetrahydrothiopyranyl groups; tri(C$_1$–C$_4$alkyl)silyl or di(C$_1$–C$_4$alkyl)arylsilyl groups, such as the trimethylsilyl, triethylsilyl, t-butyldimethylsilyl and methyldiphenylsilyl groups; methyl groups substituted with a methoxy, methylthio or trihaloethoxy group, such as the methoxymethyl, methylthiomethyl and 2,2,2-trichloroethoxymethyl groups; and aralkyl groups, such as the benzyl and diphenylmethyl groups. Of these, we particularly prefer the cyclic ether groups (particularly a tetrahydropyranyl group), the substituted silyl groups (particularly a trimethylsilyl or t-butyldimethylsilyl group) and the methoxymethyl group.

In Reaction A, a compound of formula (Ia), i.e. a compound of formula (I) in which $R^2$ represents a group of formula —NHCHR$^3$R$^4$ (wherein $R^3$ and $R^4$ are as defined above) is prepared by reacting a compound of formula (II) with a compound of formula (III) in the presence of carbonyldiimidazole in an inert solvent.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene or xylene; halogenated hydrocarbons, especially halogenated aliphatic hydrocarbons, such as methylene chloride or chloroform; ethers, such as diethyl ether, tetrahydrofuran or dioxane; amides, such as dimethylformamide, diethylformamide or dimethylacetamide; nitriles, such as acetonitrile; and sulfoxides, such as dimethyl sulfoxide. Of these, we prefer the halogenated hydrocarbons.

The reaction can take place over a wide range of temperatures, and the precise reaction temperature is not critical to the invention. In general, we find it convenient to carry out the reaction at a temperature of from −20° C. to 100° C. (more preferably from 0° C. to 50° C.). The time required for the reaction may also vary widely, depending on many factors, notably the reaction temperature and the nature of the reagents and solvent employed. However, provided that the reaction is effected under the preferred conditions outlined above, a period of from 30 minutes to 10 hours (more preferably from 1 to 5 hours) will usually suffice.

After completion of the reaction, the desired compound can be recovered from the reaction mixture by conventional means. For example, one such recovery method comprises: distilling off the solvent from the reaction mixture or pouring the reaction mixture into water; extracting the mixture with a water-immiscible organic solvent; and distilling off the organic solvent, to leave the desired product as a residue. If necessary, the resulting product can be further purified by conventional means, such as recrystallization, reprecipitation or the various chromatography techniques, notably column chromatography.

Reaction B comprises another method for preparing a compound of formula (Ia). In this reaction, a compound of formula (Ia) is prepared by reacting a compound of formula (II) with a compound of formula (IV) in an inert solvent.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene or xylene; halogenated hydrocarbons, especially halogenated aliphatic hydrocarbons, such as methylene chloride or chloroform; ethers, such as diethyl ether, tetrahydrofuran or dioxane; alcohols, such as methanol, ethanol or isopropanol; and nitriles, such as acetonitrile. Of these, we prefer the aromatic hydrocarbons or the halogenated hydrocarbons.

The reaction can take place over a wide range of temperatures, and the precise reaction temperature is not critical to the invention. In general, we find it convenient to carry out the reaction at a temperature of from −20° C. to 100° C. (more preferably from 0° C. to 50° C.). The time required for the reaction may also vary widely, depending on many factors, notably the reaction temperature and the nature of the reagents and solvent employed. However, provided that the reaction is effected under the preferred conditions outlined above, a period of from 30 minutes to 10 hours (more preferably from 1 to 5 hours) will usually suffice.

After completion of the reaction, the desired compound can be recovered from the reaction mixture by conventional means. For example, one such recovery method comprises: distilling off the solvent from the reaction mixture or pouring the reaction mixture into water; extracting the mixture with a water-immiscible organic solvent; and distilling off the organic solvent, to leave the desired product as a residue. If necessary, the resulting product can be further purified by conventional means, such as recrystallization, reprecipitation or the various chromatography techniques, notably column chromatography.

In Reaction C, a compound of formula (Ib), that is a compound of formula (I) wherein $R^2$ represents $R^{2b}$ ($R^{2b}$ is as defined above) is prepared by reacting an amine derivative of formula (II) with a carboxylic acid compound of formula (V) or with a reactive derivative of the carboxylic acid, and, if desired, removing any hydroxy-protecting group.

The reaction of the amine of formula (II) with the carboxylic acid of formula (V) may be carried out in the presence or absence of a base and preferably in the presence of a condensing agent and of in an inert solvent.

There is no particular limitation upon the nature of the condensing agent used for the reaction, and any reagent capable of producing an amide bond from a carboxylic acid and an amine may be used. Examples of the preferred condensing agents which may be used include: dicyclohexylcarbodiimide (DCC); diethyl cyanophosphonate (DEPC); carbonyldiimidazole; diphenylphosphoryl azide (DPPA); 1-hydroxybenzotriazole in admixture with dicyclohexylcarbodiimide; or diethyl azodicarboxylate in admixture with triphenyl phosphine, Of these, we prefer either 1-hydroxybenzotriazole in admixture with dicyclohexylcarbodiimide or diethyl cyanophosphonate.

Examples of preferred bases which may be used include organic amines, such as trimethylamine, triethylamine, pyridine, dimethylaniline, N-methylmorpholine or 4-(N,N-dimethylamino)pyridine. Of these, we prefer triethylamine or N-methylmorpholine.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene or xylene; halogenated hydrocarbons, especially halogenated aliphatic hydrocarbons, such as methylene chloride, dichloroethane or chloroform; ethers, such as diethyl ether, tetrahydrofuran or dioxane; esters, such as ethyl acetate or propyl acetate; amides, such as dimethylformamide, dimethylacetamide or hexamethylphosphoric triamide; and nitriles, such as acetonitrile. Of these, we prefer the ethers (particularly tetrahydrofuran), halogenated hydrocarbons (particularly methylene chloride), amides (particularly dimethylformamide) and esters (particularly ethyl acetate).

The reaction can take place over a wide range of temperatures, and the precise reaction temperature is not critical to the invention. In general, we find it convenient to carry out the reaction at a temperature of from −10° C. to 50° C. (more preferably from 0° C. to 30° C.). The time required for the reaction may also vary widely, depending on many factors, notably the reaction temperature and the nature of the reagents and solvent employed. However, provided that the reaction is effected under the preferred conditions outlined above, a period of from 30 minutes to 24 hours (more preferably from 1 to 15 hours) will usually suffice.

Alternatively, the compound of formula (Ib) can be prepared by converting a carboxylic acid of formula (V) to a reactive derivative thereof, and reacting an amine of formula (II) with the reactive derivative.

Examples of reactive derivatives of the carboxylic acid compound include: acid halides, such as the acid chloride or acid bromide; acid azides; reactive esters, such as esters with N-hydroxybenzotriazole or N-hydroxysuccinimide; acid anhydrides of the carboxylic acid used; and mixed acid anhydrides comprising monoalkyl carbonates in which the alkyl group has from 1 to 4 carbon atoms (such as monomethyl carbonate, monoethyl carbonate or monoisobutyl carbonate) or monoaryl carbonates (such as monophenyl carbonate or monotolyl carbonate). Of these, we prefer the mixed acid anhydrides with an alkyl carbonate. The reactive derivative of the carboxylic acid, typically an acid halide or an acid anhydride, can be prepared by conventional means. For example, they may be prepared by reacting a carboxylic acid of formula (V) with an appropriate halide (for example, thionyl chloride, thionyl bromide, acid chloride or acid bromide of the desired carboxylic acid, methyl chloroformate, ethyl chloroformate, isobutyl chloroformate, phenyl chloroformate or tolyl chloroformate) in an inert solvent (for example, methylene chloride, benzene or tetrahydrofuran) and, if necessary, in the presence of a base (for example, pyridine, triethylamine or dimethylaniline) in the temperature range from 20° C. to 100° C. for a period of from 1 to 20 hours. Other reactive derivatives, such as the acid amide or the reactive ester, can be prepared by reacting the carboxylic acid of formula (V) with an appropriate compound (for example, hydrogen azide, N-hydroxybenzotriazole or N-hydroxysuccinimide) in the same manner as described above in Reaction C for producing an amide bond, using a carboxylic acid of formula (V) and an amine of formula (II).

The reaction of the amine of formula (II) and the reactive derivative of the carboxylic acid of formula (V) is preferably carried out in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene or xylene; halogenated hydrocarbons, especially halogenated aliphatic hydrocarbons, such as methylene chloride, dichloroethane or chloroform; ethers, such as diethyl ether, tetrahydrofuran or dioxane; and esters, such as ethyl acetate. Of these, we prefer the aromatic hydrocarbons or ethers.

The reaction can take place over a wide range of temperatures, and the precise reaction temperature is not critical to the invention. In general, we find it convenient to carry out the reaction at a temperature of from −10° C. to 50° C. (more preferably from 0° C. to 25° C.). The time required for the reaction may also vary widely, depending on many factors, notably the reaction temperature and the nature of the reagents and solvent employed. However, provided that the reaction is effected under the preferred conditions outlined above, a period of from 5 minutes to 20 hours (more preferably from 30 minutes to 10 hours) will usually suffice.

The reaction employed to remove the hydroxy-protecting group will, of course, vary depending upon the nature of the protecting group, but its removal may be achieved by conventional means well known in the field of organic chemistry.

For example, where the protecting group is a silyl group, it can be removed by reacting the corresponding compound with a base (for example, an alkali metal carbonate, such as sodium carbonate or potassium carbonate), an acid (for example, a mineral acid, such as hydrochloric acid or sulfuric acid, or an organic carboxylic acid, such as acetic acid or citric acid) or a fluoride (for example, an ammonium fluoride compound, such as tributylammonium fluoride) in an inert solvent. The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: ethers, such as diethyl ether, tetrahydrofuran or dioxane; and alcohols, such as methanol or ethanol. Of these, we prefer the alcohols.

The reaction can take place over a wide range of temperatures, and the precise reaction temperature is not critical to the invention. In general, we find it convenient to carry out the reaction at a temperature of from −20° C. to 50° C. (preferably from 0° C. to 30° C.). The time required for the reaction may also vary widely, depending on many factors, notably the reaction temperature and the nature of the reagents and solvent employed. However, provided that the reaction is effected under the preferred conditions outlined above, a period of from 5 minutes to 2 hours (more preferably from 20 minutes to 1 hour) will usually suffice.

Where the protecting group is a cyclic ether or a substituted methyl group, it can be removed by reacting the corresponding compound with an acid in an inert solvent. Examples of acids which may be used for this reaction include: mineral acids, such as hydrochloric acid, hydrobromic acid or sulfuric acid; and organic sulfonic acids, such as methanesulfonic acid, benzenesulfonic acid or toluenesulfonic acid. Of these, we prefer hydrochloric acid or toluenesulfonic acid.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene or xylene; halogenated hydrocarbons, especially halogenated aliphatic hydrocarbons, such as methylene chloride, dichloroethane or chloroform; ethers, such as diethyl ether, tetrahydrofuran or dioxane; alcohols, such as methanol or ethanol; esters, such as ethyl acetate or propyl acetate; amides, such as dimethylformamide, dimethylacetamide or hexamethylphosphoric triamide; and nitriles, such as acetonitrile. Of these, we prefer the halogenated hydrocarbons or esters.

The reaction can take place over a wide range of temperatures, and the precise reaction temperature is not critical to the invention. In general, we find it convenient to carry out the reaction at a temperature of from −20° C. to 100° C. (more preferably from 20° C. to 70° C.). The time required for the reaction may also vary widely, depending on many factors, notably the reaction temperature and the nature of the reagents and solvent employed. However, provided that the reaction is effected under the preferred conditions outlined above, a period of from 15 minutes to 5 hours (more preferably from 30 minutes to 2 hours) will usually suffice.

Where the protecting group is an aralkyl group, it can be removed by reacting the corresponding compound with hydrogen in an inert solvent in the presence of a catalyst for reduction. Examples of catalysts which may be used for reduction include: platinum oxide, platinum black, palladium-on-charcoal, and rhodium-on-charcoal. Of these, we prefer palladium-on-charcoal.

The hydrogen pressure used is normally in the range of from atmospheric pressure to 3 atmospheres pressure.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene or xylene; halogenated hydrocarbons, especially halogenated aliphatic hydrocarbons, such as methylene chloride, dichloroethane or chloroform; ethers, such as diethyl ether, tetrahydrofuran or dioxane; alcohols, such as methanol or ethanol; esters, such as ethyl acetate or propyl acetate; amides, such as dimethylformamide, dimethylacetamide or hexamethylphosphoric triamide; and nitriles, such as acetonitrile. Of these, we prefer the alcohols.

The reaction can take place over a wide range of temperatures, and the precise reaction temperature is not critical to the invention. In general, we find it convenient to carry out the reaction at a temperature of from −20° C. to 100° C. (more preferably from 10° C. to 50° C.). The time required for the reaction may also vary widely, depending on many factors, notably the reaction temperature and the nature of the reagents and solvent employed. However, provided that the reaction is effected under the preferred conditions outlined above, a period of from 15 minutes to 5 hours (more preferably from 30 minutes to 2 hours) will usually suffice.

After completion of the reaction, the desired compound from each reaction can be recovered from the reaction mixture by conventional means. For example, one such method comprises: neutralizing properly the reaction mixture; distilling off the solvent from the reaction mixture; or if necessary, after distilling off the solvent, pouring the reaction mixture into water; extracting the mixture with a water-immiscible organic solvent; and distilling off the solvent from the extract, to leave the desired product as a residue. If necessary, the resulting product can be further purified by conventional means, such as recrystallization, reprecipitation or the various chromatography techniques, notably column chromatography.

In Reaction D, a compound of formula (Ic), that is a compound of formula (I) wherein $R^2$ represents a group of formula —B—S(O)$_m$—R$^5$ (wherein $R^5$, B and m are as defined above), is prepared by reacting a compound of formula (VI) with a compound of formula (VII), normally in an inert solvent in the presence of a base and then, if desired, oxidizing the resulting thioether compound.

There is no particular restriction on the nature of the base employed in this reaction, and any base may be used, provided that it has no adverse effect on any part of the molecule of the reagents. Examples of bases which may be used for the reaction include: alkali metal hydroxides, such as sodium hydroxide or potassium hydroxide; alkali metal carbonates, such as sodium carbonate or potassium carbonate; alkali metal hydrogencarbonates, such as sodium hydrogencarbonate or potassium hydrogencarbonate; and organic amines, such as trimethylamine, triethylamine, pyridine, dimethylaniline, N-methylmorpholine or 4-(N,N-dimethylamino)pyridine. Of these, we prefer the alkali metal hydroxides.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene or xylene; halogenated hydrocarbons, especially halogenated aliphatic hydrocarbons, such as methylene chloride or chloroform; ethers, such as diethyl ether, tetrahydrofuran or dioxane; alcohols, such as methanol, ethanol or isopropanol; amides, such as dimethylformamide diethylformamide or dimethylacetamide; nitriles, such as acetonitrile; and sulfoxides, such as dimethyl sulfoxide. Of these, we prefer the alcohols.

The reaction can take place over a wide range of temperatures, and the precise reaction temperature is not critical to the invention. In general, we find it convenient to carry out the reaction at a temperature of from −20° C. to 100° C. (more preferably from 0° C. to 50° C.). The time required for the reaction may also vary widely, depending on many factors, notably the reaction temperature and the nature of the reagents and solvent employed. However, provided that the reaction is effected under the preferred conditions outlined above, a period of from 10 minutes to 5 hours (more preferably from 30 minutes to 2 hours) will usually suffice.

Oxidation can be conducted by oxidizing the corresponding thioether compound with an oxidizing reagent in an inert solvent. Examples of oxidizing reagents which may be used for this reaction include: inorganic peroxides, such as hydrogen peroxide or periodic acid; peroxyaliphatic acids, such as peracetic acid or perpropionic acid; peroxyarylic acids, such as perbenzoic acid or m-chloroperbenzoic acid; and metal salts of peroxyphthalic acids, such as magnesium monoperoxyphthalate. Of these, we prefer the peroxyarylic acids.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene or xylene; halogenated hydrocarbons, especially halogenated aliphatic hydrocarbons, such as methylene chloride, dichloroethane or chloroform; and ethers, such as diethyl ether, tetrahydrofuran or dioxane. Of these, we prefer the halogenated hydrocarbons.

The reaction can take place over a wide range of temperatures, and the precise reaction temperature is not critical to the invention. In general, we find it convenient to carry out the reaction at a temperature of from −30° C. to 50° C. (more preferably from −20° C. to room temperature). The time required for the reaction may also vary widely, depending on many factors, notably the reaction temperature and the nature of the reagents and solvent employed. However, provided that the reaction is effected under the preferred conditions outlined above, a period of from 10 minutes to 5 hours (more preferably from 30 minutes to 2 hours) will usually suffice.

In this reaction, a sulfinyl compound may be obtained by using about an equimolar of the oxidizing reagent per mole of the thioether compound, and a sulfonyl compound may be obtained by using more than two moles of the oxidizing reagent per mole of the thioether compound.

The corresponding thioether compounds of formula (Ib), (Id) or (Ie) can be subjected to oxidation in a similar manner to that described above to afford the corresponding sulfinyl and sulfonyl compounds.

In the compounds of formula (Ic) where $R^5$ represents a hydroxyalkyl group, if desired, the corresponding acyloxyalkyl compound can be prepared by acylating the hydroxy group.

Specifically, compounds of formula (Ic), wherein $R^5$ represents: a $C_1$–$C_5$ alkanoyloxy group; a $C_2$–$C_5$ alkanoyloxy group substituted with a $C_2$–$C_5$ alkoxycarbonyl, $C_7$–$C_{11}$ aryloxycarbonyl or $C_6$–$C_{10}$ aryl group; a $C_7$–$C_{11}$ arylcarbonyloxy group; or an alkyl group substituted with a $C_3$–$C_6$ cycloalkylcarbonyloxy group, can be prepared by reacting a hydroxy compound with the corresponding carboxylic acid compound or with a reactive derivative thereof.

The reaction conditions used in the reaction of the hydroxy compound with the carboxylic acid compound are similar to those used, in the presence of a condensing agent, in Reaction C, described above.

Reaction of the hydroxy compound with a reactive derivative of the carboxylic acid compound is preferably conducted in an inert solvent in the presence or absence of a base.

There is no particular limitation upon the nature of the reactive derivative of the carboxylic acid used, provided that it is a compound capable of producing an ester compound by reaction with an alcohol compound, and it will, of course, depend on the nature of the group which it is desired to introduce. Examples of reactive derivatives which may be used for the reaction include: acid halides, such as acetyl chloride, propionyl chloride, valeryl chloride, valeryl bromide, isovaleryl chloride, methyl chloroformylacetate, ethyl 3-chloroformylpropionate, ethyl 4-chloroformylbutyrate, ethyl 5-chloroformylvalerate, phenylacetyl chloride, phenylpropionyl chloride, benzoyl chloride, toluoyl chloride, naphthoyl chloride, cyclopropanecarbonyl chloride, cyclobutanecarbonyl chloride, cyclopentanecarbonyl chloride, and cyclohexanecarbonyl chloride; acid anhydrides, such as acetic formic anhydride, acetic anhydride, propionic anhydride or benzoic anhydride; and mixed acid anhydrides of monoalkyl carbonates (in which the alkyl part has from 1 to 4 carbon atoms), such as monomethyl carbonate, monoethyl carbonate or monoisobutyl carbonate, or monoaryl carbonates, such as monophenyl carbonate or mono(methylphenyl) carbonate, and of the corresponding acids, such as acetic acid, propionic acid, phenylacetic acid, benzoic acid, cyclopentanecarboxylic acid or cyclohexanecarbonylic acid. Of these, we prefer the acid chlorides, acid anhydrides or mixed acid anhydrides comprising alkyl carbonates. These reactive derivatives of carboxylic acids can be prepared in the same manner as those of carboxylic acids described in Reaction C, described above.

There is no particular restriction on the nature of the base employed in this reaction, and any base may be used, provided that it has no adverse effect on any part of the molecule of the reagents. Examples of preferred bases which may be used for this reaction include: organic amines, such as trimethylamine, triethylamine, pyridine, dimethylaniline, N-methylmorpholine or 4-(N,N-dimethylamino)pyridine; and particularly preferably triethylamine or N-methylmorpholine. An excess of the organic amine can also serve as a solvent.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene or xylene; halogenated hydrocarbons, especially halogenated aliphatic hydrocarbons, such as methylene chloride, dichloroethane or chloroform; ethers, such as diethyl ether, tetrahydrofuran or dioxane; esters, such as ethyl acetate or propyl acetate; amides, such as dimethylformamide, dimethylacetamide or hexamethylphosphoric triamide; and nitriles, such as acetonitrile. Of these, we prefer the ethers (particularly tetrahydrofuran) or esters (particularly ethyl acetate).

The reaction can take place over a wide range of temperatures, and the precise reaction temperature is not critical to the invention. In general, we find it convenient to carry out the reaction at a temperature of from −10° C. to 50° C. (more preferably from 0° C. to 30° C.). The time required for the reaction may also vary widely, depending on many factors, notably the reaction temperature and the nature of the reagents and solvent employed. However, provided that the reaction is effected under the preferred conditions outlined above, a period of from 30 minutes to 24 hours will usually suffice.

Where $R^5$ represents an alkyl group substituted with a carboxyl group, the corresponding compounds of formula (Ic) can be prepared by reacting a hydroxy compound with a cyclic carboxylic acid anhydride, such as succinic anhydride, glutaric anhydride or adipic anhydride (preferably succinic anhydride or glutaric anhydride).

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene or xylene; halogenated hydrocarbons, especially halogenated aliphatic hydrocarbons, such as methylene chloride or chloroform; ethers, such as diethyl ether, tetrahydrofuran or dioxane; ketones, such as acetone or methyl ethyl ketone; amides, such as dimethylformamide, diethylformamide or dimethylacetamide; nitriles, such as acetonitrile; and sulfoxides, such as dimethyl sulfoxide. Of these, we prefer the ketones.

The reaction can take place over a wide range of temperatures, and the precise reaction temperature is not critical to the invention. In general, we find it convenient to carry out the reaction at a temperature of from −20° C. to 100° C. (more preferably from 0° C. to 50° C.). The time required for the reaction may also vary widely, depending on many factors, notably the reaction temperature and the nature of the reagents and solvent employed. However, provided that the reaction is effected under the preferred conditions outlined above, a period of from 30 minutes to 8 hours (more preferably from 1 to 5 hours) will usually suffice.

The carboxylic acid compounds obtained above may be converted to the corresponding ester compounds by conventional esterification procedures, including reacting the carboxylic acid compound with a diazo compound, such as diazomethane, diazoethane, diazopropane, diazobutane or trimethylsilyldiazomethane in an inert solvent (preferably an ether, such as diethyl ether, tetrahydrofuran or dioxane), at about room temperature for a period of from 10 minutes to 2 hours.

After completion of the reaction, the desired compound prepared in this step can be recovered from the reaction mixture by conventional means. For example, one such technique comprises: neutralizing properly the reaction mixture; distilling off the solvent from the reaction mixture or, if necessary, after distilling off the solvent from the reaction mixture, pouring the reaction mixture into water; extracting the mixture with a water-immiscible organic solvent; and finally distilling off the solvent from the extract. Further, if necessary, the product can be purified by conventional means, for example, recrystallization, reprecipitation or the various chromatography techniques, notably column chromatography.

Reaction E comprises an alternative method for preparing a compound of formula (Ic). In this reaction, a compound of formula (Ic) is prepared by reacting a compound of formula (VIII) with a compound of formula (IX) and, if desired, oxidizing the thioether compound thus obtained. This step is carried out in a similar manner as those described above in Reactions C and D.

In Reaction F, a compound of formula (Id), that is, a compound of formula (I) wherein $R^2$ represents a group of formula —$CH_2S(O)_m(CH_2)_{p+1}OH$ (wherein m and p are as defined as above), is prepared by reacting a compound of formula (II) with a compound of formula (X), normally in an inert solvent.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene or xylene; ethers, such as diethyl ether, tetrahydrofuran or dioxane; halogenated hydrocarbons, especially halogenated aliphatic hydrocarbons, such as methylene chloride or chloroform; and alcohols, such as methanol, ethanol or isopropanol. The reaction may also be carried out in the absence of a solvent.

The reaction can take place over a wide range of temperatures, and the precise reaction temperature is not critical to the invention. In general, we find it convenient to carry out the reaction at a temperature of from −20° C. to 130° C. (more preferably from 50° C. to 100° C.). The time required for the reaction may also vary widely, depending on many factors, notably the reaction temperature and the nature of the reagents and solvent employed. However, provided that the reaction is effected under the preferred conditions outlined above, a period of from 30 minutes to 5 hours (more preferably from 1 to 2 hours) will usually suffice.

After completion of the reaction, the desired compound prepared in this step can be recovered from the reaction mixture by conventional means. For example, one such technique comprises: neutralizing properly the reaction mixture; distilling off the solvent from the reaction mixture or, if necessary, after distilling off the solvent from the reaction mixture, pouring the reaction mixture into water; extracting the mixture with a water-immiscible organic solvent; and finally distilling off the solvent from the extract. Further, if necessary, the product can be purified by conventional means, for example, recrystallization, reprecipitation or the various chromatography techniques, notably column chromatography.

In Reaction G, a compound of formula (Ie), that is, a compound of formula (I) wherein $R^2$ represents a group of formula $-B-S(O)_m-R^{5a}$ (wherein $R^{5a}$, B and m are as defined above), can be prepared by reacting a compound of formula (XI) with a reducing reagent in an inert solvent.

Examples of reducing reagents which may be used include: borohydride compounds, such as lithium borohydride, sodium borohydride, calcium borohydride or sodium cyanoborohydride. Of these, we prefer sodium borohydride.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: ethers, such as diethyl ether, tetrahydrofuran or dioxane; alcohols, such as methanol or ethanol; water; or a mixture of any two or more of these solvents. Of these, we prefer a mixture of an alcohol and an ether.

The reaction can take place over a wide range of temperatures, and the precise reaction temperature is not critical to the invention. In general, we find it convenient to carry out the reaction at a temperature of from −20° C. to 100° C. (more preferably from 0° C. to 30° C.). The time required for the reaction may also vary widely, depending on many factors, notably the reaction temperature and the nature of the reagents and solvent employed. However, provided that the reaction is effected under the preferred conditions outlined above, a period of from 1 to 24 hours (more preferably from 3 to 10 hours) will usually suffice.

After completion of the reaction, the desired compound prepared in this step can be recovered from the reaction mixture by conventional means. For example, one such technique comprises: neutralizing properly the reaction mixture; distilling off the solvent from the reaction mixture or, if necessary, after distilling off the solvent from the reaction mixture, pouring the reaction mixture into water; extracting the mixture with a water-immiscible organic solvent; and finally distilling off the solvent from the extract. Further, if necessary, the product can be purified by conventional means, for example, recrystallization, reprecipitation or the various chromatography techniques, notably column chromatography.

The starting materials of formula (II) are known or can be prepared by any of several known methods (for example, as described Japanese Patent Kokai Application No. Sho 61-85365 or in an analogous manner).

The starting compounds of formulae (VI), (VIII) and (XI) can be prepared by reacting a compound of formula (II) with a compound of formula HOCO—B—X, HOCO—B—SY' or HOCO—B—SR$^6$, in which: R$^6$, B and X are as defined above; and Y' represents a hydrogen atom, an alkali metal, a $C_2$-$C_5$ alkanoyl group (such as an acetyl, propionyl, butyryl or valeryl group, preferably an acetyl or propionyl group) or an aromatic acyl group in which the aromatic part has from 6 to 10 ring carbon atoms (such as a benzoyl, toluoyl or naphthoyl group, preferably a benzoyl group). These reactions may be carried out in a similar manner to those described in Reaction C described above. Where Y' represents an acyl group, the compound produced may, if desired, be subjected to hydrolysis using a base (for example, an alkali metal alkoxide, such as sodium methoxide or sodium ethoxide, or an alkali metal hydroxide, such as sodium hydroxide or potassium hydroxide) at a temperature of from −20° C. to 80° C. (more preferably from 0° C. to 50° C.) in an inert solvent (for example, an alcohol, such as methanol or ethanol) for a suitable period, for example from 5 minutes to 10 hours (more preferably from 10 minutes to 5 hours) to give a compound in which Y' is a hydrogen atom.

The pyridyloxy derivatives of the present invention have excellent histamine-$H_2$ receptor antagonist activity, and are therefore useful for the prevention and therapy of peptic diseases resulting from undesirable peptic secretion, such as gastric ulcers, duodenal ulcers, gastritis, esophagistis, gastric dispepsia and Zollinger-Ellison syndrome; they are also useful for the prophylaxis or treatment of gastric disease before surgery.

The compounds of the present invention may be administered in any conventional form known for use with compounds having this type of activity, the precise form depending on the patient and the preferred route of administration, as is well known in the art. For example, for oral administration they may be formulated as tablets, capsules, granules, powders or syrups; and for parentheral administration they may be formulated as injections. Depending on the formulation, the compounds of the present invention may be administered by themselves or in admixture with conventional additives, such as vehicles (for example lactose, mannitol, corn starch or crystalline cellulose), binders (for example cellulose derivatives, gum arabic or gelatin), disintegrating agents (for example calcium carboxymethylcelulose), lubricants (for example talc or magnesium stearate), stabilizers, corrigents, solvents for preparing injections (for example water, ethanol or glycerin). The dosage may vary depending on the age, condition and symptoms of the patient, as well as the nature and severity of the disorder being treated, however, the usual daily dosage for an adult human patient would be from 1 mg to 1000 mg (preferably from 10 mg to 500 mg), per day, which may be administered as a single dose or divided into several doses.

BIOLOGICAL ACTIVITY

The activity of the compounds of the present invention is illustrated by the following Test Examples. In these, the compounds of the invention are identified by the number of the subsequent Example in which its preparation is illustrated. The prior art compounds A, B and C are as identified in the introductory portion of this specification.

TEST EXAMPLE 1

Atrial Test in Guinea Pigs

The guinea pig right atrium in a spontaneous palpitation was excised, suspended in 40 ml of Krebs-Henselite solution, and a tension of 1 g was loaded between the atrium preparation and a transducer. The solution was aerated at a fixed rate at 37° C. $10^{-5}$M histamine was added, and the heart rate was recorded as control. A test compound was added to a concentration of 1 μg/ml and then, after 3 minutes, $10^{-5}$M histamine was added, and the heart rate was again recorded. The inhibitory rate (R %) compared to the control group was calculated according to the following equation:

$$R=(1-B/A)\times100$$

where:

A: The heart rate of the control group

B: The heart rate of the group to which the drug was administered

The results are shown in the following Table 4.

TABLE 4

| Compound of Example No. | % Inhibition |
|---|---|
| 1 | 86 |
| 2 | 90 |
| 6 | 86 |
| 13 | 84 |
| 17 | 83 |
| 26 | 80 |
| 34 | 94 |
| 37 | 99 |
| 41 | 85 |
| 48 | 81 |
| A | 68 |
| B | 99 |
| C | 45 |

TEST EXAMPLE 2

Inhibition of Gastric Secretions

This test was carried out according to Shay's method [H. Shay: Gastroenterology 5, 43 (1945)] using male SD rats (5 weeks old). The rats were divided into groups, each group containing 5 rats. The animals were fasted for 24 hours before the beginning of the experiment. They were then anesthetized with ether, the abdominal region was opened, and the pylorus was ligated. A test compound suspended in a 0.5% w/v aqueous carboxymethylcellulose (CMC) solution was administered intraduodenally. After 4 hours, the rat was sacrificed by deep anesthesia with ether, and the stomach was excised. The gastric juice was removed, centrifuged for 15 minutes at 2500 rpm, and then 0.1 ml of the supernatant was taken out and titrated until the end point of neutralization with a 0.01N aqueous solution of sodium hydroxide, to determine the total gastric acidity. The amount of gastric acid secreted per hour (μEq/hr) was calculated, and the inhibition rate (R %) to the control group was calculated according to the following equation.

$$R=(1-B/A)\times100$$

where

A: The gastric acid output of the control group (μEq/hr)

B: The amount of gastric acid output of the drug administered group (μEq/hr)

The results are shown in Table 5.

TABLE 5

| Compound of Example No. | Dose (mg/kg) | % Inhibition |
|---|---|---|
| 1 | 50 | 63 |
| 2 | 50 | 52 |
| 6 | 50 | 73 |
| 7 | 25 | 63 |
| 7 | 12.5 | 51 |
| 13 | 50 | 80 |
| 13 | 25 | 62 |
| 17 | 50 | 71 |
| 17 | 25 | 73 |
| 34 | 25 | 86 |
| 34 | 12.5 | 61 |
| 37 | 50 | 74 |
| 41 | 50 | 76 |
| 41 | 25 | 61 |
| 48 | 50 | 71 |
| 58 | 50 | 56 |
| A | 50 | −67 |
| B | 50 | −40 |
| C | 50 | 56 |

TEST EXAMPLE 3

HCl-Ethanol-Induced Ulcer Test in Rats

Male SD rats (6 to 8 weeks old) were fasted for 24 hours before the beginning of the experiment. Each was then administered orally with 1 ml of a 60% ethanol solution containing 150 mM of hydrogen chloride. After 1 hour, the stomach was excised. Into the stomach was injected 10 ml of a 0.5% formaldehyde solution, and the stomach was fixed for 20 minutes. The injured area ($mm^2$) occuring on the surface of the gastric mucosa was measured, and the total injured area per rat was regarded as the injury index.

Test compounds and 0.5% CMC, as the control, were orally administered each at a dose of 0.1 ml/100 g, 60 minutes before treatment with the HCl-ethanol solution.

The ulcer formation inhibitory rate (R %) was calculated by the following equation.

$$R=(1-B/A)\times100$$

where

A: The injury index of the control group ($mm^2$)

B: The injury index of the drug administered group ($mm^2$)

The results are shown in the following Table 6.

TABLE 6

| Compound of Example No. | % Inhibition[*] |
|---|---|
| 2 | 100 |
| 7 | 61 |
| 13 | 87 |
| 34 | 79 |
| 48 | 78 |

TABLE 6-continued

| Compound of Example No. | % Inhibition*) |
|---|---|
| A | 39 |
| B | 97 |
| C | 56 |

*)Dose: 50 mg/kg.

From these results, it can be seen that the compounds of the present invention strongly inhibit ulcer formation in our HCl-ethanol-induced ulcer model, and have a defense factor potentiating activity.

The invention is further illustrated by the following Examples, which illustrate the preparation of certain of the compounds of the present invention, and the subsequent Preparations, which illustrate the preparation of certain starting materials used in these Examples.

EXAMPLE 1

N-[4-(4-Piperidinomethyl-2-pyridyloxy)-cis-2-butenyl]-2-(2-hydroxyethylthio)acetamide 0.20 ml of 2-mercaptoethanol was added to a solution of 0.24 g of 85% potassium hydroxide (i.e. potassium hydroxide of 85% purity) and 0.94 g of N-[4-(4-piperidinomethyl-2-pyridyloxy)-cis-2-butenyl]-2-chloroacetamide (prepared as described in Preparation 1) in 20 ml of methanol, and the resulting mixture was stirred at room temperature for 1 hour. At the end of this time, the reaction mixture was concentrated by evaporation under reduced pressure. The concentrate was diluted with water, after which it was extracted with chloroform. The extract was concentrated by evaporation under reduced pressure, and the residue thus obtained was purified by column chromatography through silica gel, using a 1:9 by volume mixture of ethanol and chloroform as the eluent, to give 0.95 g (yield 90%) of the title compound as an oil.

Nuclear Magnetic Resonance. Spectrum (CDCl$_3$), δ ppm: 1.32–1.52 (2H, multiplet); 1.52–1.70 (4H, multiplet); 2.25–2.55 (4H, multiplet); 2.77 (2H, triplet, J=6.3 Hz); 3.25–3.50 (1H, broad); 3.27 (2H, singlet); 3.44 (2H, singlet); 3.80 (2H, triplet, J=6.3 Hz); 4.05 (2H, triplet, J=6.1 Hz); 4.93 (2H, doublet, J=6.8 Hz); 5.68–5.80 (1H, multiplet); 5.80–5.95 (1H, multiplet); 6.79 (1H, singlet); 6.90 (1H, doublet, J=5.4 Hz); 7.08–7.28 (1H, broad); 8.06 (1H, doublet, J=5.4 Hz).

Infrared Absorption Spectrum (CHCl$_3$), ν$_{max}$ cm$^{-1}$: 3360, 2920, 1650, 1610, 1415, 1400, 1295, 1285, 1030.

EXAMPLE 2

N-[4-(4-Piperidinomethyl-2-pyridyloxy)-cis-2-butenyl]-2-(2-acetoxyethylthio)acetamide 0.50 g of N-[4-(4-piperidinomethyl-2-pyridyloxy)-cis-2-butenyl]-2-(2-hydroxyethylthio)acetamide (prepared as described in Example 1) was added to a mixture of 0.47 ml of acetic anhydride and 0.39 g of pyridine, and the resulting mixture was heated at 60° C. for 2 hours. At the end of this time, the reaction mixture was poured into ice-water, after which a saturated aqueous solution of sodium hydrogencarbonate was added. The aqueous mixture was then extracted with chloroform. The extract was concentrated by evaporation under reduced pressure, and the residue was purified by column chromatography through silica gel, using a 1:19 by volume mixture of methanol and methylene chloride as the eluent, to give 0.51 g (yield 91%) of the title compound as an oil.

Nuclear Magnetic Resonance Spectrum (CDCl$_3$), δ ppm: 1.38–1.50 (2H, multiplet); 1.50–1.70 (4H, multiplet); 2.06 (3H, singlet); 2.30–2.45 (4H, multiplet); 2.79 (2H, triplet, J=6.3 Hz); 3.28 (2H, singlet); 3.41 (2H, singlet); 4.08 (2H, triplet, J=6.3 Hz); 4.23 (2H, triplet, J=6.3 Hz); 4.94 (2H, doublet, J=6.8 Hz); 5.62–5.74 (1H, multiplet); 5.82–5.95 (1H, multiplet); 6.74 (1H, singlet); 6.88 (1H, doublet, J=5.4 Hz); 6.90–7.05 (1H, broad); 8.06 (1H, doublet, J=5.4 Hz).

Infrared Absorption Spectrum (CHCl$_3$), ν$_{max}$ cm$^{-1}$: 3370, 2920, 1735, 1660, 1610, 1515, 1415, 1400, 1295, 1285, 1025.

The hydrochloride of the title compound, melting at 198°–208° C., was prepared by dissolving the compound obtained above in ethyl acetate, after which it was treated with an excess of a 4N ethyl acetate solution of hydrogen chloride.

The oxalate of the title compound, melting at 127°–133° C., was prepared by dissolving the title compound, obtained as described above, in acetone, after which an equimolar amount of oxalic acid was added, and crystals of the oxalate, which precipitated, were collected by filtration.

EXAMPLE 3

N-[4-(4-Piperidinomethyl-2-pyridyloxy)-cis-2-butenyl]-4-(2-hydroxyethylthio)butyramide Following a procedure similar to that described in Example 1, but using N-[4-(4-piperidinomethyl-2-pyridyloxy)-cis-2-butenyl]-4-chlorobutyramide (prepared as described in Preparation 2) and 2-mercaptoethanol as starting materials, in relative proportions similar to those used in that Example, and carrying out the reaction at 80° C. for 5 hours, the title compound was obtained in a 66% yield.

Nuclear Magnetic Resonance Spectrum (CDCl$_3$) δ ppm: 1.35–1.50 (2H, multiplet); 1.50–1.75 (4H, multiplet); 1.80–2.02 (2H, multiplet); 2.30–2.50 (4H, multiplet); 2.32 (2H, triplet, J=7.0 Hz); 2.50–2.65 (1H, singlet); 2.59 (2H, triplet, J=7.0 Hz); 2.72 (2H, triplet, J=6.7 Hz); 3.44 (2H, singlet); 3.68–3.80 (2H, multiplet); 4.03 (2H, triplet, J=6.8 Hz); 4.93 (2H, doublet, J=6.8 Hz); 5.60–5.75 (1H, multiplet); 5.75–5.90 (1H, multiplet); 6.10–6.30 (1H, broad); 6.76 (1H, singlet); 6.90 (1H, doublet, J=5.4 Hz); 8.05 (1H, doublet, J=5.4 Hz).

Infrared Absorption Spectrum (CHCl$_3$), ν$_{max}$ cm$^{-1}$: 3440, 2930, 1660, 1610, 1415, 1400, 1295, 1285, 1030.

EXAMPLE 4

N-[4-(4-Piperidinomethyl-2-pyridyloxy)-cis-2-butenyl]-2-(2-hydroxypropylthio)acetamide Following a procedure similar to that described in Example 1, but using N-[4-(4-piperidinomethyl-2-pyridyloxy)-cis-2-butenyl]-2-chloroacetamide (prepared as described in Preparation 1) and 1-mercapto-2-propanol as starting materials, in relative proportions similar to those used in that Example, the title compound was obtained in an 89% yield.

Nuclear Magnetic Resonance Spectrum (CDCl$_3$), δ ppm: 1.25 (3H, doublet, J=6.4 Hz); 1.30–1.86 (1H, broad); 1.38–1.49 (2H, multiplet); 1.53–1.65 (4H, multiplet); 2.31–2.43 (4H, multiplet); 2.54 (1H, doublet of doublets, J=8.3 & 13.9 Hz); 2.74 (1H, doublet of doublets, J=3.4 & 13.9 Hz); 3.25 (1H, doublet, J=16.1 Hz); 3.29 (1H, doublet, J=16.1 Hz); 3.41 (2H, singlet); 3.87–4.01 (1H, multiplet); 4.06 (2H, doublet, J=6.1 Hz); 4.93 (2H, doublet, J=6.8 Hz); 5.65–5.77 (1H, multiplet); 5.83–5.93 (1H, multiplet); 6.75 (1H, singlet); 6.89 (1H, doublet, J=5.4 Hz); 7.03–7.21 (1H, broad); 8.05 (1H, doublet, J=5.4 Hz).

Infrared Absorption Spectrum (liquid film), $v_{max}$ cm$^{-1}$: 3293, 2935, 1648, 1613, 1560, 1421, 1403, 1301, 1290, 1039.

EXAMPLE 5

N-[4-(4-Piperidinomethyl-2-pyridyloxy)-cis -2-butenyl]-4-(2-hydroxypropylthio)butyramide Following a procedure similar to that described in Example 1, but using N-[4-(4-piperidinomethyl-2-pyridyloxy) -cis-2-butenyl]-4-chlorobutyramide (prepared as described in Preparation 2) and 1-mercapto-2-propanol as starting materials, in relative proportions similar to those used in that Example, the title compound was obtained in a 58% yield.

Nuclear Magnetic Resonance Spectrum (CDCl$_3$), δ ppm: 1.24 (3H, doublet, J=6.6 Hz); 1.38–1.50 (2H, multiplet); 1.52–1.64 (4H, multiplet); 1.84–2.04 (2H, multiplet); 2.27–2.46 (6H, multiplet); 2.46 (1H, doublet of doublets, J=5.3 & 13.9 Hz); 2.59 (2H, triplet, J=6.9 Hz); 2.71 (1H, doublet of doublets, J=3.3 & 13.9 Hz); 3.41 (2H, singlet); 3.81–3.92 (1H, multiplet); 4.03 (2H, triplet, J=5.9 Hz); 4.93 (2H, doublet, J=6.6 Hz); 5.78–5.91 (1H, multiplet); 5.63–5.76 (1H, multiplet); 6.06–6.22 (1H, broad); 6.74 (1H, singlet); 6.89 (1H, doublet, J=5.3 Hz); 8.04 (1H, doublet, J=5.3 Hz).

Infrared Absorption Spectrum (liquid film), $v_{max}$ cm$^{-1}$: 3298, 2935, 1647, 1613, 1560, 1421, 1403, 1311, 1301, 1289, 1070.

EXAMPLE 6

N-[4-(4-Piperidinomethyl-2-pyridyloxy)-cis-2-butenyl]-4-(2-acetoxyethylthio)butyramide Following a procedure similar to that described in Example 2, but using N-[4-(4-piperidinomethyl-2-pyridyloxy) -cis-2-butenyl]-4-(2-hydroxyethylthio)butyramide (prepared as described in Example 3) and acetic anhydride as starting materials, in relative proportions similar to those used in that Example, the title compound, melting at 36°–40° C., was obtained in an 80% yield.

Nuclear Magnetic Resonance Spectrum (CDCl$_3$), δ ppm: 1.30–1.60 (2H, multiplet); 1.60–1.80 (4H, multiplet); 1.80–2.02 (2H, multiplet); 2.06 (3H, singlet); 2.32 (2H, triplet, J=7.0 Hz); 2.30–2.55 (4H, multiplet); 2.62 (2H, triplet, J=7.0 Hz); 2.73 (2H, triplet, J=6.8 Hz); 3.46 (2H, singlet); 4.04 (2H, triplet, J=6.1 Hz); 4.20 (2H, triplet, J=6.8 Hz); 4.93 (2H, doublet, J=6.8 Hz); 5.60–5.75 (1H, multiplet); 5.77–5.90 (1H, multiplet); 6.00–6.20 (1H, broad); 6.75 (1H, singlet); 6.92 (1H, doublet, J=5.4 Hz); 8.06 (1H, doublet, J=5.4 Hz).

Infrared Absorption Spectrum (CHCl$_3$) $v_{max}$ cm$^{-1}$: 3450, 2930, 1735, 1665, 1610, 1415, 1400, 1295, 1285, 1030.

EXAMPLE 7

N-[4-(4-Piperidinomethyl-2-pyridyloxy)-cis-2-butenyl]-2-(2-propionyloxyethylthio)acetamide 0.09 ml of propionyl chloride was added to a mixture of 0.40 g of N-[4-(4-piperidinomethyl-2-pyridyloxy) -cis-2-butenyl]-2-(2-hydroxyethylthio)acetamide (prepared as described in Example 1) and 1.02 ml of pyridine, and the resulting mixture was allowed to stand at room temperature for 2 hours. At the end of this time, the reaction mixture was poured into ice-water, and a saturated aqueous solution of sodium hydrogencarbonate was added to the resulting mixture, after which it was extracted with chloroform. The extract was concentrated by evaporation under reduced pressure and the residue was purified by column chromatography through silica gel, using a 1:19 by volume mixture of methanol and ethyl acetate as the eluent, to give 0.39 g (yield 85%) of the title compound as an oil.

Nuclear Magnetic Resonance Spectrum (CDCl$_3$), δ ppm: 1.14 (3H, triplet, J=7.5 Hz); 1.35–1.75 (6H, multiplet); 2.30–2.60 (4H, multiplet); 2.34 (2H, quartet, J=7.5 Hz); 2.79 (2H, triplet, J=6.6 Hz); 3.28 (2H, singlet); 3.41 (2H, singlet); 4.08 (2H, triplet, J=6.6 Hz); 4.25 (2H, triplet, J=6.3 Hz); 4.93 (2H, doublet, J=6.6 Hz); 5.63–5.69 (1H, multiplet); 5.72–5.93 (1H, multiplet); 6.73 (1H, singlet); 6.88 (1H, doublet, J=5.3 Hz); 6.95–7.10 (1H, broad); 8.06 (1H, doublet, J=5.3 Hz).

Infrared Absorption Spectrum (CHCl$_3$), $v_{max}$ cm$^{-1}$: 3380, 2940, 1735, 1665, 1615, 1420, 1405, 1300, 1290, 1180.

The hydrochloride of the title compound, melting at 99°–106° C., was prepared by dissolving the title compound, prepared as described above, in diethyl ether, after which the resulting solution was treated with an equimolar amount of a 4N ethyl acetate solution of hydrogen chloride.

Nuclear Magnetic Resonance Spectrum (CDCl$_3$+ CD$_3$OD), δ ppm: 1.10 (3H, triplet, J=7.6 Hz); 1.58–1.76 (2H, multiplet); 1.76–1.94 (4H, multiplet); 2.35 (2H, quartet, J=7.6 Hz); 2.84 (2H, triplet, J=6.6 Hz); 3.03–3.38 (4H, multiplet); 3.24 (2H, singlet); 3.99 (2H, triplet, J=6.6 Hz); 4.24 (2H, triplet, J=6.6 Hz); 4.26 (2H, singlet); 4.99 (2H, doublet, J=6.6 Hz); 5.59–5.70 (1H, multiplet); 5.76–5.86 (1H, multiplet); 7.00 (1H, singlet); 7.10 (1H, doublet, J=5.0 Hz); 8.25 (1H, doublet, J=5.0 Hz).

The dihydrochloride of the title compound, melting at 235°–255° C., was prepared by dissolving the title compound, prepared as described above, in ethyl acetate, after which the resulting solution was treated with a molar excess of a 4N ethyl acetate solution of hydrogen chloride.

Nuclear Magnetic Resonance Spectrum (CDCl$_3$+ CD$_3$OD), δ ppm: 1.10 (3H, triplet, J=7.6 Hz); 1.44–1.69 (2H, multiplet); 1.75–2.05 (4H, multiplet); 2.35 (2H, quartet, J=7.6 Hz); 2.84 (2H, triplet, J=6.6 Hz); 2.98–3.19 (2H, multiplet); 4.00 (2H, triplet, J=5.9 Hz); 4.24 (2H, triplet, J=6.6 Hz); 4.49 (2H, singlet); 5.18 (2H, doublet, J=5.9 Hz); 5.66–5.88 (2H, multiplet); 7.48 (1H, doublet, J=5.3 Hz); 7.66 (1H, singlet); 8.39 (1H, doublet, J=5.3 Hz).

EXAMPLE 8

2-{N-[4-(4-piperidinomethyl-2-pyridyloxy)-cis-2-butenyl]carbamoylmethylthio}ethyl hydrogen succinate 0.11 g of succinic anhydride was added to a solution of 0.4 g of N-[4-(4-piperidinomethyl-2-pyridyloxy) -cis-2-butenyl]-2-(2-hydroxyethylthio)acetamide (prepared as described in Example 1) in 10 ml of acetone, and the resulting mixture was stirred at room temperature for 3 hours. At the end of this time, the reaction mixture was concentrated by evaporation under reduced pressure, and the concentrate was purified by column chromatography through silica gel, using a 100:5:2 by volume mixture of methylene chloride, triethylamine and methanol as the eluent, to give 0.49 g of the triethylamine salt of the title compound in an 80% yield.

Nuclear Magnetic Resonance Spectrum (CDCl$_3$), δ ppm: 1.18 (9H, triplet, J=7.3 Hz); 1.40–1.55 (2H, multiplet); 1.55–1.80 (4H, multiplet); 2.40–2.60 (2H, multiplet); 2.50–2.68 (4H, multiplet); 2.78 (2H, triplet, J=6.3 Hz); 2.82 (6H, quartet, J=7.3 Hz); 3.50 (2H, singlet); 4.08 (2H, triplet, J=6.3 Hz); 4.26 (2H, triplet, J=6.3 Hz); 4.40–5.10 (1H, broad); 4.93 (2H, doublet, J=7.2 Hz); 5.66–5.75 (1H, multiplet); 5.82–5.95 (1H, multiplet); 6.79 (1H, singlet); 6.87 (1H, doublet, J=5.2 Hz); 8.08 (1H, doublet, J=5.2 Hz).

Infrared Absorption Spectrum (CHCl$_3$), ν$_{max}$ cm$^{-1}$: 3380, 1735, 1660, 1610, 1415, 1400, 1295, 1285, 1160, 1030.

EXAMPLE 9

N-[4-(4-piperidinomethyl-2-pyridyloxy)-cis-2-butenyl]-2-(2-benzoyloxyethylthio)acetamide 0.24 ml of benzoyl chloride was added, whilst ice-cooling, to a mixture of 0.40 g of N-[4-(4-piperidinomethyl-2-pyridyloxy)-cis-2-butenyl]-2-(2-hydroxyethylthio)acetamide (prepared as described in Example 1) and 1.02 ml of pyridine, and the resulting mixture was stirred at room temperature for 2 hours. At the end of this time, the mixture was concentrated by evaporation under reduced pressure. The concentrate was diluted with water and made alkaline by the addition of an aqueous ammonia solution, after which it was extracted with ethyl acetate. The extract was concentrated by evaporation under reduced pressure, and the concentrate was purified by column chromatography through silica gel, using a 1:40 by volume mixture of methanol and ethyl acetate as the eluent, to give 0.31 g of the title compound in a 61% yield.

Nuclear Magnetic Resonance Spectrum (CDCl$_3$), δ ppm: 1.35–1.50 (2H, multiplet); 1.50–1.75 (4H, multiplet); 2.25–2.45 (4H, multiplet); 2.94 (2H, triplet, J=6.3 Hz); 3.40 (2H, singlet); 3.32 (2H, singlet); 4.07 (2H, triplet, J=6.3 Hz); 4.49 (2H, triplet, J=6.6 Hz); 4.92 (2H, doublet, J=6.6 Hz); 5.62–5.71 (1H, multiplet); 5.81–5.88 (1H, multiplet); 6.73 (1H, singlet); 6.87 (1H, doublet, J=5.3 Hz); 7.40–7.62 (4H, multiplet); 8.02–8.07 (3H, multiplet).

Infrared Absorption Spectrum (CHCl$_3$), ν$_{max}$ cm$^{-1}$: 3390, 2940, 1720, 1665, 1615, 1275, 1170.

The dihydrochloride of the title compound, melting at 185°–195° C., was prepared by dissolving the compound obtained above in ethyl acetate, after which the resulting solution was treated with a molar excess of a 4N ethyl acetate solution of hydrogen chloride.

EXAMPLE 10

N-[4-(4-Piperidinomethyl-2-pyridyloxy)-cis-2-butenyl]-2-(2-cyclohexylcarbonyloxyethylthio)acetamide 0.10 ml of ethyl chloroformate was added, whilst ice-cooling, to a solution of 0.13 ml of cyclohexanecarboxylic acid in 18 ml of ethyl acetate, and the resulting mixture was stirred at room temperature for 1 hour. At the end of this time, a solution of 0.40 g of N-[4-(4-piperidinomethyl-2-pyridyloxy)-cis-2-butenyl]-2-(2-hydroxyethylthio)acetamide (prepared as described in Example 1) in 4 ml of ethyl acetate was added to the reaction mixture, whilst ice-cooling. The reaction mixture was then stirred at room temperature for 1 hour, after which it was heated under reflux for 16 hours. At the end of this time, it was concentrated by evaporation under reduced pressure. The concentrate was purified by column chromatography through silica gel, using a 1:9 by volume mixture of methanol and ethyl acetate as the eluent, to give 0.18 g of the title compound in a 35% yield.

Nuclear Magnetic Resonance Spectrum (CDCl$_3$), δ ppm: 1.17–2.09 (16H, multiplet); 2.23–2.47 (5H, multiplet); 2.79 (2H, triplet, J=6.3 Hz); 3.28 (2H, singlet); 3.42 (2H, singlet); 4.08 (2H, triplet, J=6.3 Hz); 4.23 (2H, triplet, J=6.3 Hz); 4.94 (2H, doublet, J=6.6 Hz); 5.81–5.94 (1H, multiplet); 5.62–5.74 (1H, multiplet); 6.74 (1H, singlet); 6.85–7.05 (1H, broad); 6.89 (1H, doublet, J=5.3 Hz); 8.06 (1H, doublet, J=5.3 Hz).

Infrared Absorption Spectrum (CHCl$_3$), ν$_{max}$ cm$^{-1}$: 3380, 2940, 1730, 1665, 1610, 1310, 1165.

EXAMPLE 11

N-[4-(4-Piperidinomethyl-2-pyridyloxy)-cis-2-butenyl]-3-(2-hydroxyethylthio)propionamide 105 mg of sodium hydride (as a 55% w/w dispersion in mineral oil) were added, whilst ice-cooling and in an atmosphere of nitrogen, to a solution of 0.76 g of N-[4-(4-piperidinomethyl-2-pyridyloxy)-cis-2-butenyl]-3-mercaptopropionamide (prepared as described in Preparation 3) in 24 ml of dimethylformamide, and the resulting mixture was stirred at room temperature for 30 minutes. At the end of this time, 0.16 ml of ethylene chlorohydrin were added to the reaction mixture, whilst ice-cooling. The reaction mixture was stirred at room temperature for 15 minutes, after which it was poured into ice-water and extracted with ethyl acetate. The extract was concentrated by evaporation under reduced pressure, and the residue thus obtained was purified by column chromatography through silica gel, using a 1:9 by volume mixture of methanol and methylene chloride as the eluent, to give 0.56 g of the title compound as an oil in a 65% yield.

Nuclear Magnetic Resonance Spectrum (CDCl$_3$), δ ppm: 1.38–1.50 (2H, multiplet); 1.50–1.64 (4H, multiplet); 1.55–2.10 (1H, broad); 2.30–2.43 (4H, multiplet); 2.49 (2H, triplet, J=6.9 Hz); 2.74 (2H, triplet, J=5.9 Hz); 2.88 (2H, triplet, J=6.9 Hz); 3.41 (2H, singlet); 3.76 (2H, doublet of triplets, J=5.3 & 5.9 Hz); 4.05 (2H, triplet, J=6.3 Hz); 4.93 (2H, doublet, J=6.6 Hz); 5.63–5.78 (1H, multiplet); 5.78–5.90 (1H, multiplet); 6.75 (1H, singlet); 6.89 (1H, doublet, J=5.3 Hz); 8.04 (1H, doublet, J=5.3 Hz).

Infrared Absorption Spectrum (CHCl$_3$), ν$_{max}$ cm$^{-1}$: 3450, 2930, 1665, 1612, 1418, 1400, 1300, 1290, 1035.

EXAMPLE 12

N-[4-(4-piperidinomethyl-2-pyridyloxy)-cis-2-butenyl]-3-(2-acetoxyethylthio)propionamide Following a procedure similar to that described in Example 2, but using N-[4-(4-piperidinomethyl-2-pyridyloxy)-cis-2-butenyl]-3-(2-hydroxyethylthio)propionamide (prepared as described in Example 11) and acetic anhydride as starting materials, in relative proportions similar to those used in that Example, the title compound was obtained in an 87% yield.

Nuclear Magnetic Resonance Spectrum (CDCl$_3$), δ ppm: 1.36–1.50 (2H, multiplet); 1.50–1.63 (4H, multiplet); 2.07 (3H, singlet); 2.28–2.43 (4H, multiplet); 2.48 (3H, triplet, J=7.3 Hz); 2.77 (2H, triplet, J=6.9 Hz); 3.41 (2H, singlet); 4.05 (2H, triplet, J=6.3 Hz); 4.22 (2H, triplet, J=6.9 Hz); 4.93 (2H, doublet, J=6.6 Hz); 5.62–5.76 (1H, multiplet); 5.79–5.90 (1H, multiplet); 6.17–6.40 (1H, broad); 6.74 (1H, singlet); 6.89 (1H, doublet, J=5.3 Hz); 8.04 (1H, doublet, J=5.3 Hz).

Infrared Absorption Spectrum (CHCl$_3$) $v_{max}$ cm$^{-1}$: 3450, 2930, 1735, 1665, 1610, 1415, 1400, 1298, 1288, 1028.

EXAMPLE 13

N-[4-(4-piperidinomethyl-2-pyridyloxy)-cis-2-butenyl]pyrazole-4-carboxamide

A solution of 2.39 g of 4-(4-piperidinomethyl-2-pyridyloxy)-cis-2-butenylamine and 1.08 g of 4-pyrazolecarboxylic acid in 40 ml of dry dimethylformamide was stirred for 5 minutes, whilst ice-cooling. 1.89 g of diethyl cyanophosphonate and 1.65 ml of triethylamine were added to the mixture, and the resulting mixture was stirred at room temperature for 3 hours. At the end of this time, the reaction mixture was diluted with water and extracted with ethyl acetate. The extract was washed with a saturated aqueous solution of sodium hydrogencarbonate and then with a saturated aqueous solution of sodium chloride, after which it was dried over anhydrous magnesium sulfate. The solvent was then removed by distillation under reduced pressure, and the residue was purified by column chromatography through silica gel, using a 1:9 by volume mixture of methanol and chloroform as the eluent, to give 1.65 g (yield 51%) of the title compound as a white powder, melting at 121°–123° C.

Nuclear Magnetic Resonance Spectrum (CDCl$_3$), δ ppm: 1.38–1.52 (2H, multiplet); 1.52–1.66 (4H, multiplet); 2.32–2.48 (4H, multiplet); 3.42 (2H, singlet); 4.16 (2H, triplet, J=5.6 Hz); 4.95 (2H, doublet, J=5.9 Hz); 5.72–5.96 (2H, multiplet); 6.74 (1H, singlet); 6.81 (1H, broad triplet, J=5.6 Hz); 6.87 (1H, doublet, J=5.3 Hz); 7.99 (2H, singlet); 8.03 (1H, doublet, J=5.3 Hz).

Infrared Absorption Spectrum (KBr), $v_{max}$ cm$^{-1}$: 2933, 1629, 1611, 1566, 1530, 1408, 1342, 1299.

EXAMPLE 14

N-[4-(4-piperidinomethyl-2 -pyridyloxy)-cis-2-butenyl]thiophene-2-carboxamide 240 mg of 2-thiophenecarboxylic acid, 390 mg of N,N'-dicyclohexylcarbodiimide and 275 mg of 1-hydroxybenzotriazole were added to a solution of 485 mg of 4-(4-piperidinomethyl-2-pyridyloxy)-cis-2-butenylamine in 10 ml of dry dimethylformamide, and the resulting mixture was stirred at room temperature for 17 hours. At the end of this time, the reaction mixture was mixed with ethyl acetate, and the urea which precipitated was removed by filtration. The filtrate was diluted with water and extracted with ethyl acetate. The extract was washed with a saturated aqueous solution of sodium hydrogencarbonate and then with a saturated aqueous solution of sodium chloride, after which it was dried over anhydrous magnesium sulfate. The solvent was then removed by distillation under reduced pressure, and the residue was purified by column chromatography through silica gel, using a 1:19 by volume mixture of methanol and methylene chloride as the eluent, to give 499 mg (yield 73%) of the title compound as an oil.

Nuclear Magnetic Resonance Spectrum (CDCl$_3$), δ ppm: 1.37–1.52 (2H, multiplet); 1.52–1.65 (4H, multiplet); 2.28–2.46 (4H, multiplet); 3.41 (2H, singlet); 4.22 (2H, triplet, J=6.3 Hz); 4.98 (2H, doublet, J=6.6 Hz); 5.73–5.85 (1H, multiplet); 5.85–5.97 (1H, multiplet); 6.56 (1H, broad singlet); 6.74 (1H, singlet); 6.89 (1H, doublet, J=5.3 Hz); 7.02–7.09 (1H, multiplet); 7.46 (1H, doublet, J=5.3 Hz); 7.51 (1H, doublet, J=4.0 Hz); 8.03 (1H, doublet, J=5.3 Hz).

Infrared Absorption Spectrum (CHCl$_3$), $v_{max}$ cm$^{-1}$: 2920, 1665, 1640, 1610, 1565, 1530, 1500, 1415, 1400, 1295, 1285.

The hydrochloride of the title compound, melting at 180°–183° C., was prepared by dissolving the title compound obtained above in ethyl acetate, after which it was treated with an equimolar amount of an ethyl acetate solution of hydrogen chloride.

EXAMPLE 15

N-[4-(4-piperidinomethyl-2-pyridyloxy)-cis-2-butenyl]pyrrole-2-carboxamide

Following a procedure similar to that described in Example 13, but using 4-(4-piperidinomethyl-2-pyridyloxy)-cis-2-butenylamine and 2-pyrrolecarboxylic acid as starting materials, in relative proportions similar to those used in that Example, the title compound was obtained as colorless prisms, melting at 136°–137° C., in an 80% yield.

Nuclear Magnetic Resonance Spectrum (CDCl$_3$), δ ppm: 1.39–1.51 (2H, multiplet); 1.51–1.65 (4H, multiplet); 2.33–2.48 (4H, multiplet); 3.42 (2H, singlet); 4.21 (2H, triplet, J=6.4 Hz); 4.98 (2H, doublet, J=6.3 Hz); 5.70–5.79 (1H, multiplet); 5.83–5.92 (1H, multiplet); 6.20–6.23 (1H, multiplet); 6.25–6.36 (1H, broad); 6.52–6.55 (1H, multiplet); 6.75 (1H, singlet); 6.88–6.93 (2H, multiplet); 8.06 (1H, doublet, J=4.9 Hz); 9.51–9.75 (1H, broad).

Infrared Absorption Spectrum (KBr), $v_{max}$ cm$^{-1}$: 3242, 1641, 1561, 1524.

EXAMPLE 16

1,3,5-Trimethyl-N-[4-(4-piperidinomethyl-2-pyridyloxy) -cis-2-butenyl]pyrazole-4-carboxamide Following a procedure similar to that described in Example 13, but using 4-(4-piperidinomethyl-2-pyridyloxy) -cis-2-butenylamine and 1,3,5-trimethyl-4-pyrazolecarboxylic acid as starting materials, in relative proportions similar to those used in that Example, the title compound was obtained as a white powder, melting at 75°–77° C., in a 69% yield.

Nuclear Magnetic Resonance Spectrum (CDCl$_3$), δ ppm: 1.37–1.52 (2H, multiplet); 1.52–1.69 (4H, multiplet); 2.36 (3H, singlet); 2.30–2.49 (4H, multiplet); 2.46 (3H, singlet); 3.44 (2H, singlet); 3.71 (3H, singlet); 4.19 (2H, triplet, J=6.1 Hz); 4.96 (2H, doublet, J=6.4 Hz); 5.75–5.91 (3H, multiplet); 6.74 (1H, singlet); 6.89 (1H, doublet, J=4.9 Hz); 8.00 (1H, doublet, J=4.9 Hz).

Infrared Absorption Spectrum (KBr), $v_{max}$ cm$^{-1}$: 3344, 2930, 1617, 1561, 1410.

EXAMPLE 17

3-Amino-N-[4-(4-piperidinomethyl-2-pyridyloxy) -cis-2-butenyl]pyrazole-4-carboxamide Following a procedure similar to that described in Example 13, but using 4-(4-piperidinomethyl-2-pyridyloxy) -cis-2-butenylamine and 3-amino-4-pyrazolecarboxylic acid as starting materials, in relative proportions similar to those used in that Example, the title compound was obtained as a white powder, melting at 172°–174° C., in a 38% yield.

Nuclear Magnetic Resonance Spectrum (hexadeuterated dimethyl sulfoxide), δ ppm: 1.32–1.45 (2H, multiplet); 1.45–1.57 (4H, multiplet); 2.26–2.44 (4H, multiplet); 3.42 (2H, singlet); 3.92 (2H, triplet, J=5.9 Hz); 4.92 (2H, doublet, J=5.9 Hz); 5.52–5.78 (2H, multiplet); 6.72 (1H, singlet); 6.92 (1H, doublet, J=5.4 Hz); 7.67–7.79 (1H, broad); 7.88 (1H, broad triplet, J=5.4 Hz); 8.08 (1H, doublet, J=5.4 Hz).

Infrared Absorption Spectrum (KBr), $v_{max}$ cm$^{-1}$: 3229, 2934, 1616, 1529, 1399.

EXAMPLE 18

N-[4-(4-Piperidinomethyl-2-pyridyloxy)-cis-2-butenyl]pyrazole-3-carboxamide

Following a procedure similar to that described in Example 13, but using 4-(4-piperidinomethyl-2-pyridyloxy)-cis-2-butenylamine and 3-pyrazolecarboxylic acid as starting materials, in relative proportions similar to those used in that Example, the title compound was obtained as an oil in a 57% yield.

Nuclear Magnetic Resonance Spectrum (CDCl$_3$), δ ppm: 1.38–1.52 (2H, multiplet); 1.52–1.65 (4H, multiplet); 2.31–2.50 (4H, multiplet); 3.43 (2H, singlet); 4.21 (2H, triplet, J=6.3 Hz); 4.96 (2H, doublet, J=6.6 Hz); 5.77–5.99 (2H, multiplet); 6.80–6.89 (3H, multiplet); 7.21–7.31 (1H, broad); 7.57 (1H, doublet, J=2.0 Hz); 8.08 (1H, doublet, J=5.3 Hz).

Infrared Absorption Spectrum (CHCl$_3$), $v_{max}$ cm$^{-1}$: 2925, 1655, 1610, 1560 (shoulder), 1540.

EXAMPLE 19

5-Methyl-N-[4-(piperidinomethyl-2-pyridyloxy)-cis-2-butenyl]pyrazole-3-carboxamide Following a procedure similar to that described in Example 13, but using 4-(4-piperidinomethyl-2-pyridyloxy)-cis-2-butenylamine and 5-methyl-3-pyrazolecarboxylic acid as starting materials, in relative proportions similar to those used in that Example, the title compound was obtained as a white powder, melting at 93°–95° C., in a 52% yield.

Nuclear Magnetic Resonance Spectrum (CDCl$_3$), δ ppm: 1.38–1.52 (2H, multiplet); 1.52–1.66 (4H, multiplet); 2.33 (3H, singlet); 2.31–2.48 (4H, multiplet); 3.42 (2H, singlet); 4.20 (2H, triplet, J=6.4 Hz); 4.96 (2H, doublet, J=6.8 Hz); 5.72–5.81 (1H, multiplet); 5.83–5.93 (1H, multiplet); 6.55 (1H, singlet); 6.76 (1H, singlet); 6.87 (1H, doublet, J=5.4 Hz); 7.06–7.20 (1H, broad); 8.08 (1H, doublet, J=5.4 Hz); 10.37–10.93 (1H, broad).

Infrared Absorption Spectrum (KBr), $v_{max}$ cm$^{-1}$: 3195, 2931, 1645, 1612, 1558.

EXAMPLE 20

N-[4-(4-Piperidinomethyl-2-pyridyloxy)-cis-2-butenyl]furan-2-carboxamide

Following a procedure similar to that described in Example 13, but using 4-(4-piperidinomethyl-2-pyridyloxy)-cis-2-butenylamine and 2-furancarboxylic acid as starting materials, in relative proportions similar to those used in that Example, the title compound was obtained as an oil in an 82% yield.

Nuclear Magnetic Resonance Spectrum (CDCl$_3$), δ ppm: 1.35–1.53 (2H, multiplet); 1.53–1.80 (4H, multiplet); 2.25–2.60 (4H, multiplet); 3.48 (2H, singlet); 4.22 (2H, triplet, J=6.4 Hz); 4.98 (2H, doublet, J=6.8 Hz); 5.70–5.82 (1H, multiplet); 5.84–5.96 (1H, multiplet); 6.49 (1H, doublet of doublets, J=3.4 & 2.0 Hz); 6.58–6.72 (1H, multiplet); 6.77 (1H, singlet); 6.85–7.03 (1H, multiplet); 7.11 (1H, doublet of doublets, J=3.4 & 1.0 Hz); 7.43 (1H, triplet, J=1.0 Hz); 8.10 (1H, doublet, J=5.3 Hz).

Infrared Absorption Spectrum (CHCl$_3$) $v_{max}$ cm$^{-1}$: 3430, 2930, 1655, 1610, 1595, 1518, 1475, 1415, 1400, 1295, 1285.

EXAMPLE 21

5-Methyl-N-[4-(4-piperidinomethyl-2-pyridyloxy)-cis-2-butenyl]thiophene-2-carboxamide Following a procedure similar to that described in Example 13, but using 4-(4-piperidinomethyl-2-pyridyloxy)-cis-2-butenylamine and 5-methyl-2-thiophenecarboxylic acid as starting materials, in relative proportions similar to those used in that Example, the title compound, melting at 71°–73° C., was obtained in a yield.

Nuclear Magnetic Resonance Spectrum (CDCl$_3$), δ ppm: 1.45–1.55 (2H, multiplet); 1.55–1.80 (4H, multiplet); 2.30–2.60 (4H, multiplet); 3.48 (2H, singlet); 4.20 (2H, triplet, J=6.3 Hz); 4.97 (2H, doublet, J=6.3 Hz); 5.78–5.82 (1H, multiplet); 5.82–5.93 (1H, multiplet); 6.20–6.35 (1H, broad); 6.72 (1H, doublet, J=3.5 Hz); 6.78 (1H, singlet); 6.87–7.03 (1H, multiplet); 7.31 (1H, doublet, J=3.5 Hz); 8.07 (1H, doublet, J=5.4 Hz).

Infrared Absorption Spectrum (CHCl$_3$) $v_{max}$ cm$^{-1}$: 3430, 2920, 1640, 1505, 1415, 1400, 1295, 1285, 1032.

EXAMPLE 22

3-Amino-N-[4-(4-piperidinomethyl-2-pyridyloxy)-cis-2-butenyl]thiophene-2-carboxamide Following a procedure similar to that described in Example 13, but using 4-(4-piperidinomethyl-2-pyridyloxy)-cis-2-butenylamine and 3-amino-2-thiophenecarboxylic acid as starting materials, in relative proportions similar to those used in that Example, the title compound was obtained as colorless needles, melting at 138°–140° C., in a 40% yield.

Nuclear Magnetic Resonance Spectrum (CDCl$_3$), δ ppm: 1.40–1.52 (2H, multiplet); 1.52–1.65 (4H, multiplet); 2.28–2.44 (4H, multiplet); 3.41 (2H, singlet); 4.17 (2H, triplet, J=5.9 Hz); 4.96 (2H, doublet, J=5.9 Hz); 5.60 (2H, broad singlet); 5.67–5.94 (3H, multiplet); 6.55 (1H, doublet, J=5.3 Hz); 6.74 (1H, singlet); 6.89 (1H, doublet, J=5.3 Hz); 7.12 (1H, doublet, J=5.3 Hz); 8.08 (1H, doublet, J=5.3 Hz).

Infrared Absorption Spectrum (KBr), $v_{max}$ cm$^{-1}$: 3300, 2935, 1617, 1560, 1525, 1402, 1313, 1299, 1291.

EXAMPLE 23

N-[4-(4-piperidinomethyl-2-pyridyloxy)-cis-2-butenyl]thiophene-3-carboxamide

Following a procedure similar to that described in Example 13, but using 4-(4-piperidinomethyl-2-pyridyloxy)-cis-2-butenylamine and 3-thiophenecarboxylic acid as starting materials, in relative proportions similar to those used in that Example, the title compound was obtained as an oil in a 90% yield.

Nuclear Magnetic Resonance Spectrum (CDCl$_3$), δ ppm: 1.38–1.52 (2H, multiplet); 1.52–1.65 (4H, multiplet); 2.30–2.45 (4H, multiplet); 3.41 (1H, singlet); 4.22 (2H, triplet, J=6.1 Hz); 4.98 (2H, doublet, J=6.4 Hz); 5.73–5.93 (2H, multiplet); 6.40–6.60 (1H, broad); 6.74 (1H, singlet); 6.87 (1H, doublet, J=5.4 Hz); 7.32 (1H, doublet of doublets, J=5.2 & 2.9 Hz); 7.39 (1H, doublet, J=5.2 Hz); 7.85 (1H, doublet, J=2.9 Hz); 8.01 (1H, doublet, J=5.4 Hz).

Infrared Absorption Spectrum (CHCl$_3$), ν$_{max}$ cm$^{-1}$: 2930, 1655 (shoulder), 1645, 1610, 1560, 1535, 1500, 1415, 1400, 1285.

EXAMPLE 24

5-Chloro-N-[4-(4-piperidinomethyl-2-pyridyloxy) -cis-2-butenyl]thiophene-2-carboxamide Following a procedure similar to that described in Example 13, but using 4-(4-piperidinomethyl-2-pyridyloxy) -cis-2-butenylamine and 5-chloro-3-thiophenecarboxylic acid as starting materials, in relative proportions similar to those used in that Example, the title compound was obtained as colorless prisms, melting at 75°–77° C., in a 54% yield.

Nuclear Magnetic Resonance Spectrum (CDCl$_3$), δ ppm: 1.38–1.52 (2H, multiplet); 1.52–1.68 (4H, multiplet); 2.30–2.42 (4H, multiplet); 3.41 (2H, singlet); 4.19 (2H, triplet, J=6.1 Hz); 4.97 (2H, doublet, J=6.8 Hz); 5.70–5.84 (1H, multiplet); 5.84–5.95 (1H, multiplet); 6.41–6.53 (1H, broad); 6.74 (1H, singlet); 6.88 (1H, doublet, J=5.4 Hz); 7.19 (1H, doublet, J=2.0 Hz); 7.62 (1H, doublet, J=2.0 Hz); 7.99 (1H, doublet, J=5.4 Hz).

Infrared Absorption Spectrum (CHCl$_3$), ν$_{max}$ cm$^{-1}$: 3450, 2930, 1655, 1610, 1415, 1400, 1298, 1285, 1032.

EXAMPLE 25

5-Phenyl-N-[4-(4-piperidinomethyl-2-pyridyloxy) -cis-2-butenyl]isoxazole-3-carboxamide Following a procedure similar to that described in Example 13, but using 4-(4-piperidinomethyl-2-pyridyloxy) -cis-2-butenylamine and 5-phenyl-3-isoxazolecarboxylic acid as starting materials, in relative proportions similar to those used in that Example, the title compound, melting at 105°–106° C., was obtained as colorless prisms in a 50% yield.

Nuclear Magnetic Resonance Spectrum (CDCl$_3$), δ ppm: 1.36–1.51 (2H, multiplet); 1.51–1.67 (4H, multiplet); 2.29–2.46 (4H, multiplet); 3.43 (2H, singlet); 4.27 (2H, triplet, J=6.3 Hz); 4.99 (2H, doublet, J=6.6 Hz); 5.72–5.82 (1H, multiplet); 5.88–5.97 (1H, multiplet); 6.75 (1H, singlet); 6.91 (1H, doublet, J=5.4 Hz); 6.97 (1H, singlet); 7.13–7.27 (1H, broad); 7.44–7.55 (3H, multiplet); 7.75–7.84 (2H, multiplet); 8.12 (1H, doublet, J=5.4 Hz).

Infrared Absorption Spectrum (KBr), ν$_{max}$ cm$^{-1}$: 3322, 2936, 1668, 1613, 1561, 1448.

EXAMPLE 26

N-[4-(4-Piperidinomethyl-2-pyridyloxy) -cis-2-butenyl]thiazole-4-carboxamide

Following a procedure similar to that described in Example 13, but using 4-(4-piperidinomethyl-2-pyridyloxy) -cis-2-butenylamine and 4-thiazolecarboxylic acid as starting materials, in relative proportions similar to those used in that Example, the title compound was obtained as an oil in a 68% yield.

Nuclear Magnetic Resonance Spectrum (CDCl$_3$), δ ppm: 1.36–1.52 (2H, multiplet); 1.52–1.67 (4H, multiplet); 2.24–2.53 (4H, multiplet); 3.43 (2H, singlet); 4.26 (2H, triplet, J=6.4 Hz); 4.98 (2H, doublet, J=6.4 Hz); 5.72–5.81 (1H, multiplet); 5.86–5.96 (1H, multiplet); 6.75 (1H, singlet); 6.90 (1H, doublet, J=5.4 Hz); 7.40–7.58 (1H, broad); 8.11 (1H, doublet, J=5.4 Hz); 8.18 (1H, doublet, J=2.4 Hz); 8.75 (1H, doublet, J=2.4 Hz).

Infrared Absorption Spectrum (liquid film), ν$_{max}$ cm$^{-1}$: 2936, 1664, 1611, 1560, 1540, 1481, 1420, 1403, 1313, 1288.

EXAMPLE 27

N-[4-(4-piperidinomethyl-2-pyridyloxy) -cis-2-butenyl]-1,2,3-thiadiazole-4-carboxamide Following a procedure similar to that described in Example 13, but using 4-(4-piperidinomethyl-2-pyridyloxy) -cis-2-butenylamine and 1,2,3-thiadiazole-4-carboxylic acid as starting materials, in relative proportions similar to those used in that Example, the title compound was obtained as colorless needles, melting at 70°–72° C., in a 52% yield.

Nuclear Magnetic Resonance Spectrum (CDCl$_3$), δ ppm: 1.28–1.53 (2H, multiplet); 1.53–1.82 (4H, multiplet); 2.24–2.55 (4H, multiplet); 3.46 (2H, singlet); 4.35 (2H, triplet, J=6.3 Hz); 5.01 (2H, doublet, J=6.3 Hz); 5.75–5.87 (1H, multiplet); 5.87–6.00 (1H, multiplet); 6.77 (1H, singlet); 6.85–7.00 (1H, multiplet); 7.72–7.90 (1H, broad); 8.13 (1H, doublet, J=5.4 Hz); 9.23 (1H, singlet).

Infrared Absorption Spectrum (CHCl$_3$), ν$_{max}$ cm$^{-1}$: 3425, 2940, 1675, 1612, 1540, 1420, 1402, 1300, 1290, 1260, 1035.

EXAMPLE 28

N-{4-[4-(1-Pyrrolidinylmethyl)-2-pyridyloxy]-cis-2-butenyl}pyrazole-4-carboxamide Following a procedure similar to that described in Example 13, but using 4-[4-(1-pyrrolidinylmethyl)-2-pyridyloxy]-cis-2-butenylamine and 4-pyrazolecarboxylic acid as starting materials, in relative proportions similar to those used in that Example, the title compound was obtained as a white powder, melting at 57°–61° C., in a 34% yield.

Nuclear Magnetic Resonance Spectrum (CDCl$_3$), δ ppm: 1.75–1.90 (4H, multiplet); 2.50–2.67 (4H, multiplet); 3.61 (2H, singlet); 4.17 (2H, triplet, J=5.9 Hz); 4.95 (2H, doublet, J=6.4 Hz); 5.69–5.92 (2H, multiplet); 6.72 (1H, broad triplet, J=5.4 Hz); 6.77 (1H, singlet); 6.90 (1H, doublet, J=5.4 Hz); 7.96 (2H, singlet); 8.04 (1H, doublet, J=5.4 Hz).

Infrared Absorption Spectrum (KBr), ν$_{max}$ cm$^{-1}$: 2962, 1626, 1610, 1568, 1539, 1421, 1410, 1400.

EXAMPLE 29

N-{4-[4-(1-Pyrrolidinylmethyl)-2-pyridyloxy]-cis-2-butenyl}pyrrole-2-carboxamide Following a procedure similar to that described in Example 13, but using 4-[4-(1-pyrrolidinylmethyl)-2-pyridyloxy]-cis-2-butenylamine and 2-pyrrolecarboxylic acid as starting materials, in relative proportions similar to those used in that Example, the title compound was obtained as a white powder, melting at 124°–127° C., in a 64% yield.

Nuclear Magnetic Resonance Spectrum (CDCl$_3$), δ ppm: 1.71–1.88 (4H, multiplet); 2.43–2.61 (4H, multiplet); 3.57 (2H, singlet); 4.21 (2H, triplet, J=6.3 Hz); 4.97 (2H, doublet, J=6.6 Hz); 5.70–5.80 (1H, multiplet); 5.83–5.94 (1H, multiplet); 6.16–6.25 (1H, multiplet); 6.30–6.42 (1H, broad); 6.53–6.59 (1H, multiplet); 6.88–6.96 (2H, multiplet); 8.07 (1H, doublet, J=5.3 Hz); 9.67–9.92 (1H, broad).

Infrared Absorption Spectrum (KBr), $v_{max}$ cm$^{-1}$: 3252, 1637, 1617, 1561, 1528, 1428, 1423, 1401, 1307, 1029.

EXAMPLE 30

4-Hydroxy-N-[4-(4-piperidinomethyl-2-pyridyloxy) -cis-2-butenyl]isoxazole-3-carboxamide 375 mg of ethyl 4-hydroxy-3-isoxazolecarboxylate (prepared as described in Preparation 4) were added to a solution of 520 mg of 4-(4-piperidinomethyl-2-pyridyloxy) -cis-2-butenylamine in 10 ml of toluene, and the resulting mixture was heated under reflux for 6 hours. At the end of this time, the solvent was removed by distillation under reduced pressure, and the residue was dissolved in ethyl acetate. The resulting solution was washed with a saturated aqueous solution of sodium hydrogencarbonate and then with a saturated aqueous solution of sodium chloride, after which it was dried over anhydrous magnesium sulfate. The solvent was then removed by distillation under reduced pressure, and the residue was purified by column chromatography through silica gel, using a 1:19 by volume mixture of methanol and ethyl acetate as the eluent, to give 228 mg (yield 31%) of the title compound as an oil.

Nuclear Magnetic Resonance Spectrum (CDCl$_3$), δ ppm: 1.33–1.50 (2H, multiplet); 1.50–1.65 (4H, multiplet); 2.25–2.46 (4H, multiplet); 3.42 (2H, singlet); 4.26 (2H, triplet, J=6.6 Hz); 4.98 (2H, doublet, J=6.6 Hz); 5.67–5.82 (1H, multiplet); 5.88–6.00 (1H, multiplet); 6.75 (1H, singlet); 6.90 (1H, doublet, J=5.3 Hz); 7.25–7.42 (1H, broad); 8.13 (1H, doublet, J=5.3 Hz); 8.22 (1H, singlet).

Infrared Absorption Spectrum (CHCl$_3$), $v_{max}$ cm$^{-1}$: 2930, 1680, 1610, 1560 (shoulder), 1550.

EXAMPLE 31

1-Methyl-N-[4-(4-piperidinomethyl-2-pyridyloxy) -cis-2-butenyl]pyrrole-2-carboxamide Following a procedure similar to that described in Example 13, but using 4-(4-piperidinomethyl-2-pyridyloxy) -cis-2-butenylamine and 1-methyl-2-pyrrolecarboxylic acid as starting materials, in relative proportions similar to those used in that Example, the title compound was obtained as an oil in a 76% yield.

Nuclear Magnetic Resonance Spectrum (CDCl$_3$), δ ppm: 1.38–1.51 (2H, multiplet); 1.51–1.65 (4H, multiplet); 2.33–2.43 (4H, multiplet); 3.42 (2H, singlet); 3.94 (3H, singlet); 4.16 (2H, triplet, J=6.1 Hz); 4.97 (2H, doublet, J=6.8 Hz); 5.71–5.83 (1H, multiplet); 5.83–5.94 (1H, multiplet); 6.06 (1H, doublet of doublets, J=3.9 & 2.2 Hz); 6.14–6.24 (1H, broad); 6.53 (1H, doublet of doublets, J=7.8 & 2.2 Hz); 6.69–6.73 (1H, multiplet); 6.74 (1H, singlet); 6.89 (1H, doublet, J=5.2 Hz); 8.04 (1H, doublet, J=5.2 Hz).

Infrared Absorption Spectrum (CHCl$_3$), $v_{max}$ cm$^{-1}$: 2935, 1655 (shoulder), 1645, 1610, 1560, 1535, 1500, 1475, 1415, 1400.

The hydrochloride of the title compound, melting at 136°–137° C., was prepared by dissolving the title compound, obtained as described above, in ethyl acetate, after which an ethyl acetate solution containing an equimolar amount of hydrogen chloride was added to the resulting solution.

EXAMPLE 32

N-[4-(4-Piperidinomethyl-2-pyridyloxy) -cis-2-butenyl]pyrrole-3-carboxamide

Following a procedure similar to that described in Example 13, but using 4-(4-piperidinomethyl-2-pyridyloxy) -cis-2-butenylamine and 3-pyrrolecarboxylic acid as starting materials, in relative proportions similar to those used in that Example, the title compound was obtained as an oil in a 74% yield.

Nuclear Magnetic Resonance Spectrum (CDCl$_3$), δ ppm: 1.33–1.51 (2H, multiplet); 1.51–1.67 (4H, multiplet); 2.27–2.49 (4H, multiplet); 3.41 (2H, singlet); 4.18 (2H, triplet, J=6.3 Hz); 4.96 (2H, doublet, J=5.9 Hz); 5.69–5.94 (2H, multiplet); 6.17–6.33 (1H, broad); 6.42 (1H, broad singlet); 6.73 (2H, broad singlet); 6.87 (1H, doublet, J=4.9 Hz); 7.33 (1H, broad singlet); 8.05 (1H, doublet, J=4.9 Hz); 9.31–9.54 (1H, broad).

Infrared Absorption Spectrum (CHCl$_3$), $v_{max}$ cm$^{-1}$: 3470, 2930, 1635, 1610, 1560, 1510, 1415, 1400, 1310, 1295.

EXAMPLE 33

N-[4-(4-Piperidinomethyl-2-pyridyloxy) -cis-2-butenyl]-2-(2-pyrimidinylthio)acetamide 163 mg of 2-mercaptopyrimidine were added to a solution of 116 mg of 85% potassium hydroxide and 484 mg of N-[4-(4-piperidinomethyl-2-pyridyl-cis-2-butenyl]-2-chloroacetamide (prepared as described in Preparation 1) in 10 ml of methanol, and the resulting mixture was stirred at room temperature for 7 hours. At the end of this time, the reaction mixture was concentrated by evaporation under reduced pressure, and the concentrate was mixed with water, after which it was extracted with ethyl acetate. The extract was freed from the solvent by distillation under reduced pressure. The residue thus obtained was recrystallized from ethyl acetate, to give 474 mg (yield 80%) of the title compound as a white powder, melting at 103°–106° C.

Nuclear Magnetic Resonance Spectrum (CDCl$_3$), δ ppm: 1.37–1.50 (2H, multiplet); 1.52–1.64 (4H, multiplet); 2.30–2.43 (4H, multiplet); 3.40 (2H, singlet); 3.82 (2H, singlet); 4.29 (2H, triplet, J=6.3 Hz); 4.87 (2H, doublet, J=5.9 Hz); 5.52–5.65 (1H, multiplet); 5.75–5.86 (1H, multiplet); 6.70 (1H, singlet); 6.87 (1H, doublet, J=5.4 Hz); 7.00–7.11 (1H, broad); 7.02 (1H, doublet, J=4.9 Hz); 8.03 (1H, doublet, J=5.4 Hz); 8.53 (2H, doublet, J=4.9 Hz).

Infrared Absorption Spectrum (KBr), $v_{max}$ cm$^{-1}$: 3333, 2940, 2920, 1643, 1560, 1552, 1524, 1397, 1316.

EXAMPLE 34

N-[4-(4-Piperidinomethyl-2-pyridyloxy) -cis-2-butenyl]-4-(2-pyrimidinylthio) butyramide 2.78 g of 2-mercaptopyrimidine were added to a solution of 1.95 g of 85% potassium hydroxide and 9.03 g of N-[4-(4-piperidinomethyl-2-pyridyloxy)-cis-2-butenyl]-4-chlorobutyramide (prepared as described in Preparation 2) in 140 ml of methanol, and the resulting mixture was heated under reflux for 15 hours. At the end of this time, the reaction mixture was cooled, and the solvent was removed by distillation under reduced pressure. The resulting residue was mixed with water, and the aqueous mixture was extracted with ethyl acetate. The extract was concentrated by evaporation under reduced pressure, and the concentrate was purified by column chromatography through silica gel, using a 9:1 by volume mixture of ethyl acetate and methanol as the eluent, to give 10.1 g (yield 92%) of the title compound as an oil.

Nuclear Magnetic Resonance Spectrum (CDCl$_3$), δ ppm: 1.38–1.50 (2H, multiplet); 1.53–1.67 (4H, multiplet); 2.11 (2H, quintet, J=7.2 Hz); 2.30–2.49 (6H, multiplet); 3.20 (2H, triplet, J=7.2 Hz); 3.41 (2H, singlet); 4.06 (2H, doublet, J=5.9 Hz); 4.93 (2H, doublet, J=6.3 Hz); 5.64–5.73 (1H, multiplet); 5.80–5.89 (1H, multiplet); 6.27–6.41 (1H, broad); 6.73 (1H, singlet); 6.88 (1H, doublet, J=5.1 Hz); 6.94 (1H, triplet, J=4.9 Hz); 8.03 (1H, doublet, J=5.1 Hz); 8.49 (2H, doublet, J=4.9 Hz).

Infrared Absorption Spectrum (liquid film), $v_{max}$ cm$^{-1}$: 3295, 2936, 1646, 1611, 1564, 1548, 1420, 1403, 1382, 1312, 1300, 1289.

The compound obtained as described above was dissolved in ethyl acetate, and an ethyl acetate solution containing an equimolar amount of hydrogen chloride was added to the resulting solution. The mixture was stirred at room temperature for 10 minutes, and then the solvent was removed by distillation under reduced pressure, to give the hydrochloride of the title compound, melting at 123°–125° C.

EXAMPLE 35

N-[4-(4-Piperidinomethyl-2-pyridyloxy)-cis-2-butenyl]-4-(4-methyl-2-pyrimidinylthio)butyramide Following a procedure similar to that described in Example 34, but using N-[4-(4-piperidinomethyl-2-pyridyloxy) -cis-2-butenyl]-4-chlorobutyramide (prepared as described in Preparation 2) and 2-mercapto-4-methylpyrimidine as starting materials, in relative proportions similar to those used in that Example, the title compound was obtained as an oil in a 70% yield.

Nuclear Magnetic Resonance Spectrum (CDCl$_3$), δ ppm: 1.40–1.56 (2H, multiplet); 1.60–1.81 (4H, multiplet); 2.10 (2H, quintet, J=7.1 Hz); 2.39 (2H, triplet, J=7.1 Hz); 2.44 (3H, singlet); 2.35–2.70 (4H, multiplet); 3.20 (2H, triplet, J=7.1 Hz); 3.55 (2H, singlet); 4.05 (2H, triplet, J=6.1 Hz); 4.93 (2H, doublet, J=6.3 Hz); 5.64–5.73 (1H, multiplet); 5.78–5.87 (1H, multiplet); 6.25–6.37 (1H, broad); 6.76–6.81 (2H, multiplet); 6.98 (1H, singlet); 8.08 (1H, triplet, J=5.4 Hz); 8.34 (1H, doublet, J=5.4 Hz).

Infrared Absorption Spectrum (CHCl$_3$), $v_{max}$ cm$^{-1}$: 2930, 1660, 1610, 1570, 1560, 1540, 1415, 1325.

EXAMPLE 36

N-[4-(4-Piperidinomethyl-2-pyridyloxy)-cis-2-butenyl]-4-(1-methylimidazol-2-ylthio)butyramide Following a procedure similar to that described in Example 34, but using N-[4-(4-piperidinomethyl-2-pyridyloxy) -cis-2-butenyl]-4-chlorobutyramide (prepared as described in Preparation 2) and 2-mercapto-1-methylimidazole as starting materials, in relative proportions similar to those used in that Example, the title compound was obtained as an oil in a 49% yield.

Nuclear Magnetic Resonance Spectrum (CDCl$_3$), δ ppm: 1.36–1.50 (2H, multiplet); 1.50–1.62 (4H, multiplet); 2.03 (2H, quintet, J=6.8 Hz); 2.30–2.46 (6H, multiplet); 3.08 (2H, triplet, J=6.8 Hz); 3.41 (2H, singlet); 3.60 (3H, singlet); 4.04 (2H, triplet, J=6.1 Hz); 4.93 (2H, doublet, J=5.9 Hz); 5.63–5.73 (1H, multiplet); 5.76–5.91 (1H, multiplet); 6.72 (1H, singlet); 6.89 (1H, doublet, J=5.4 Hz); 6.90 (1H, singlet); 7.01 (1H, singlet); 7.24–7.38 (1H, broad); 8.04 (1H, doublet, J=5.4 Hz).

Infrared Absorption Spectrum (CHCl$_3$), $v_{max}$ cm$^{-1}$: 3250, 2940, 1660, 1610, 1560, 1420, 1290.

EXAMPLE 37

N-[4-(4-Piperidinomethyl-2-pyridyloxy)-cis-2-butenyl]-4-(5-methyl-1,3,4-oxadiazol-2-ylthio)butyramide Following a procedure similar to that described in Example 34, but using N-[4-(4-piperidinomethyl-2-pyridyloxy) -cis-2-butenyl]-4-chlorobutyramide (prepared as described in Preparation 2) and 2-mercapto-5-methyl -1,3, 4-oxadiazole as starting materials, in relative proportions similar to those used in that Example, the title compound was obtained as an oil in a 79% yield.

Nuclear Magnetic Resonance Spectrum (CDCl$_3$), δ ppm: 1.37–1.50 (2H, multiplet); 1.50–1.65 (4H, multiplet); 2.17 (2H, quintet, J=7.3 Hz); 2.31–2.41 (6H, multiplet); 2.51 (3H, singlet); 3.28 (2H, triplet, J=7.3 Hz); 3.41 (2H, singlet); 4.04 (2H, triplet, J=5.9 Hz); 4.93 (2H, doublet, J=6.6 Hz); 5.64–5.75 (1H, multiplet); 5.79–5.90 (1H, multiplet); 6.39–6.54 (1H, broad); 6.73 (1H, singlet); 6.89 (1H, doublet, J=5.3 Hz); 8.04 (1H, doublet, J=5.3 Hz).

Infrared Absorption Spectrum (CHCl$_3$), $v_{max}$ cm$^{-1}$: 3440, 2930, 1660, 1610, 1560, 1510, 1480, 1420.

EXAMPLE 38

N-[4-(4-Piperidinomethyl-2-pyridyloxy)-cis-2-butenyl]-4-(1,3,4-thiadiazol-2-ylthio)butyramide Following a procedure similar to that described in Example 34, but using N-[4-(4-piperidinomethyl-2-pyridyloxy) -cis-2-butenyl]-4-chlorobutyramide (prepared as described in Preparation 2) and 2-mercapto-1,3,4-thiadiazole as starting materials, in relative proportions similar to those used in that Example, the title compound was obtained as an oil in an 84% yield.

Nuclear Magnetic Resonance Spectrum (CDCl$_3$), δ ppm: 1.36–1.51 (2H, multiplet); 1.51–1.68 (4H, multiplet); 2.20 (2H, quintet, J=7.3 Hz); 2.27–2.45 (6H, multiplet); 3.41 (2H, singlet); 3.43 (2H, triplet, J=7.3 Hz); 5.63–5.73 (1H, multiplet); 5.78–5.89 (1H, multiplet); 6.34–6.51 (1H, broad); 6.73 (1H, singlet); 6.89 (1H, doublet, J=5.3 Hz); 8.04 (1H, doublet, J=5.3 Hz); 9.00 (1H, singlet).

Infrared Absorption Spectrum (CHCl$_3$) $v_{max}$ cm$^{-1}$: 3350, 3300, 2940, 1660, 1610, 1560, 1510, 1420.

EXAMPLE 39

N-[4-(4-Piperidinomethyl-2-pyridyloxy)-cis-2-butenyl]-4-(5-methyl-1,3,4-thiadiazol-2-ylthio)butyramide Following a procedure similar to that described in Example 34, but using N-[4-(4-piperidinomethyl-2-pyridyloxy) -cis-2-butenyl]-4-chlorobutyramide (prepared as described in Preparation 2) and 2-mercapto-5-methyl -1,3, 4-thiadiazole as starting materials, in relative proportions similar to those used in that Example, the title compound was obtained as a white powder, melting at 65°–68° C., in a 78% yield.

Nuclear Magnetic Resonance Spectrum (CDCl$_3$), δ ppm: 1.37–1.51 (2H, multiplet); 1.51–1.68 (4H, multiplet); 2.16 (2H, quintet, J=6.9 Hz); 2.31–2.44 (6H, multiplet); 2.71 (3H, singlet); 3.35 (2H, triplet, J=6.9 Hz); 3.41 (2H, singlet); 4.04 (2H, triplet, J=5.9 Hz); 4.94 (2H, doublet, J=6.6 Hz); 5.65–5.76 (1H, multiplet); 5.77–5.90 (1H, multiplet); 6.37–6.50 (1H, broad); 6.73 (1H, singlet); 6.89 (1H, doublet, J=5.3 Hz); 8.04 (1H, doublet, J=5.3 Hz).

Infrared Absorption Spectrum (CHCl$_3$), ν$_{max}$ cm$^{-1}$: 3450, 3300, 2940, 1660, 1610, 1560, 1510, 1420, 1300.

EXAMPLE 40

N-[4-(4-Piperidinomethyl-2-pyridyloxy)-cis-2-butenyl]-2-(1,2,4-triazol-3-ylthio)acetamide Following a procedure similar to that described in Example 33, but using N-[4-(4-piperidinomethyl-2-pyridyloxy) -cis-2-butenyl]-2-chloroacetamide (prepared as described in Preparation 1) and 3-mercapto-1,2,4-triazole as starting materials, in relative proportions similar to those used in that Example, the title compound was obtained as a white powder, melting at 65°–67° C., in a 91% yield.

Nuclear Magnetic Resonance Spectrum (CDCl$_3$), δ ppm: 1.41–1.55 (2H, multiplet); 1.55–1.67 (4H, multiplet); 2.42–2.55 (4H, multiplet); 3.47 (2H, singlet); 3.77 (2H, singlet); 4.00 (2H, triplet, J=6.3 Hz); 4.83 (2H, doublet, J=6.8 Hz); 5.71–5.80 (1H, multiplet); 5.85–5.94 (1H, multiplet); 6.73 (1H, singlet); 6.85 (1H, doublet, J=5.1 Hz); 7.32–7.44 (1H, broad); 8.06 (1H, doublet, J=5.1 Hz); 8.07 (1H, singlet).

Infrared Absorption Spectrum (liquid film), ν$_{max}$ cm$^{-1}$: 2935, 1652, 1612, 1560, 1421, 1403, 1301, 1288.

EXAMPLE 41

N-[4-(4-Piperidinomethyl-2-pyridyloxy)-cis-2-butenyl]-4-(1,2,4-triazol-3-ylthio)butyramide Following a procedure similar to that described in Example 34, but using N-[4-(4-piperidinomethyl-2-pyridyloxy) -cis-2-butenyl]-4-chlorobutyramide (prepared as described in Preparation 2) and 3-mercapto-1,2,4-triazole as starting materials, in relative proportions similar to those used in that Example, the title compound was obtained as a white powder, melting at 87°–89° C., in a 56% yield.

Nuclear Magnetic Resonance Spectrum (CDCl$_3$), δ ppm: 1.39–1.51 (2H, multiplet); 1.54–1.65 (4H, multiplet); 2.09 (2H, quintet, J=7.0 Hz); 2.33–2.50 (6H, multiplet); 3.13 (2H, triplet, J=7.0 Hz); 3.44 (2H, singlet); 4.06 (2H, triplet, J=6.1 Hz); 4.93 (2H, doublet, J=6.4 Hz); 5.69–5.82 (1H, multiplet); 5.82–5.9 3 (1H, multiplet); 6.75 (1H, singlet); 6.89 (1H, doublet, J=5.4 Hz); 6.92–7.0 3 (1H, broad); 8.03 (1H, singlet); 8.04 (1H, doublet, J=5.4 Hz).

Infrared Absorption Spectrum (KBr), ν$_{max}$ cm$^{-1}$: 2942, 2915, 1625, 1614, 1564, 1293, 1250, 1238.

EXAMPLE 42

N-[4-(4-Piperidinomethyl-2-pyridyloxy)-cis-2-butenyl]-2-(1-methyltetrazol-5-ylthio)acetamide Following a procedure similar to that described in Example 33, but using N-[4-(4-piperidinomethyl-2-pyridyloxy) -cis-2-butenyl]-2-chloroacetamide (prepared as described in Preparation 1) and 1-methyl-5-mercaptotetrazole as starting materials, in relative proportions similar to those used in that Example, the title compound was obtained as a white powder, melting at 58°–62° C., in an 87% yield.

Nuclear Magnetic Resonance Spectrum (CDCl$_3$), δ ppm: 1.35–1.50 (2H, multiplet); 1.50–1.63 (4H, multiplet); 2.27–2.44 (4H, multiplet); 3.41 (2H, singlet); 3.95 (3H, singlet); 3.96 (2H, singlet); 4.04 (2H, triplet, J=5.9 Hz); 4.90 (2H, doublet, J=5.9 Hz); 5.54–5.68 (1H, multiplet); 5.78–5.89 (1H, multiplet); 6.73 (1H, singlet); 6.88 (1H, doublet, J=5.9 Hz); 8.05 (1H, doublet, J=5.9 Hz).

Infrared Absorption Spectrum (CHCl$_3$), ν$_{max}$ cm$^{-1}$: 3300, 2950, 1730, 1670, 1610, 1560, 1400, 1290.

EXAMPLE 43

N-[4-(4-Piperidinomethyl-2-pyridyloxy)-cis-2-butenyl]-4-(1-methyltetrazol-5-ylthio)butyramide Following a procedure similar to that described in Example 34, but using N-[4-(4-piperidinomethyl-2-pyridyloxy) -cis-2-butenyl]-4-chlorobutyramide (prepared as described in Preparation 2) and 1-methyl-5-mercaptotetrazole as starting materials, in relative proportions similar to those used in that Example, the title compound was obtained as an oil in a 70% yield.

Nuclear Magnetic Resonance Spectrum (CDCl$_3$), δ ppm: 1.38–1.50 (2H, multiplet); 1.50–1.63 (4H, multiplet); 2.13–2.24 (2H, quintet, J=7.3 Hz); 2.26–2.47 (6H, multiplet); 3.40 (2H, triplet, J=7.3 Hz); 3.41 (2H, singlet); 3.91 (3H, singlet); 4.05 (2H, triplet, J=5.3 Hz); 4.94 (2H, doublet, J=6.6 Hz); 5.66–5.75 (1H, multiplet); 5.80–5.89 (1H, multiplet); 6.39–6.50 (1H, broad); 6.73 (1H, singlet); 6.89 (1H, doublet, J=5.2 Hz); 8.03 (1H, doublet, J=5.2 Hz).

Infrared Absorption Spectrum (CHCl$_3$), ν$_{max}$ cm$^{-1}$: 3450, 2925, 1660, 1610, 1560, 1510, 1410, 1290.

EXAMPLE 44

N-[4-(4-Piperidinomethyl-2-pyridyloxy)-cis-2-butenyl]-4-[1-(2-hydroxyethyl)tetrazol-5-ylthio]butyramide Following a procedure similar to that described in Example 34, but using N-[4-(4-piperidinomethyl-2-pyridyloxy) -cis-2-butenyl]-4-chlorobutyramide (prepared as described in Preparation 2) and 1-(2-hydroxyethyl)-5-mercaptotetrazole as starting materials, in relative proportions similar to those used in that Example, the title compound was obtained as an oil in a 63% yield.

Nuclear Magnetic Resonance Spectrum (CDCl$_3$), δ ppm: 1.38–1.50 (2H, multiplet); 1.50–1.63 (4H, multiplet); 2.17 (2H, quintet, J=6.8 Hz); 2.33–2.60 (6H, multiplet); 3.38 (2H, triplet, J=6.8 Hz); 3.49 (2H, singlet); 4.01 (2H, triplet, J=6.1 Hz); 4.08–4.11 (2H, multiplet); 4.34–4.38 (2H, multiplet); 4.92 (2H, doublet, J=6.4 Hz); 5.67–5.87 (2H, multiplet); 6.49–6.65 (1H, broad); 6.79 (1H, singlet); 6.93 (1H, doublet, J=4.9 Hz); 8.05 (1H, doublet, J=4.9 Hz).

Infrared Absorption Spectrum (CHCl$_3$) ν$_{max}$ cm$^{-1}$: 3300, 2940, 1660, 1610, 1560, 1510, 1420, 1400.

EXAMPLE 45

N-[4-(4-Piperidinomethyl-2-pyridyloxy)-cis-2-butenyl]-4-(2-pyridylthio)butyramide Following a procedure similar to that described in Example 34, but using N-[4-(4-piperidinomethyl-2-pyridyloxy) -cis-2-butenyl]-4-chlorobutyramide (prepared as described in Preparation 2) and 2-mercaptopyridine as starting materials, in relative proportions similar to those used in that Example, the title compound was obtained as an oil in a 53% yield.

Nuclear Magnetic Resonance Spectrum (CDCl$_3$), δ ppm: 1.40–1.53 (2H, multiplet); 1.59–1.75 (4H, multiplet); 2.07 (2H, quintet, J=7.1 Hz); 2.39 (2H, triplet, J=7.1 Hz); 2.33–2.60 (4H, broad); 3.21 (2H, triplet, J=7.1 Hz); 3.51 (2H, singlet); 4.07 (2H, triplet, J=6.2 Hz); 4.94 (2H, doublet, J=6.3 Hz); 5.63–5.75 (1H, multiplet); 5.80–5.88 (1H, multiplet); 6.58–6.69 (1H, broad); 6.77 (1H, singlet); 6.92–7.00 (2H, multiplet); 7.17 (1H, triplet of doublets, J=8.3 & 1.0 Hz); 7.46 (1H, doublet of triplets, J=8.3 & 2.0 Hz); 8.07 (1H, doublet, J=5.4 Hz); 8.39 (1H, triplet of doublets, J=4.9 & 1.0 Hz).

Infrared Absorption Spectrum (CHCl$_3$), ν$_{max}$ cm$^{-1}$: 2945, 1660, 1655 (shoulder), 1610, 1580, 1560, 1415.

EXAMPLE 46

N-[4-(4-Piperidinomethyl-2-pyridyloxy)-cis-2-butenyl]-4-(4-pyridylthio)butyramide Following a procedure similar to that described in Example 34, but using N-[4-(4-piperidinomethyl-2-pyridyloxy) -cis-2-butenyl]-4-chlorobutyramide (prepared as described in Preparation 2) and 4-mercaptopyridine as starting materials, in relative proportions similar to those used in that Example, the title compound was obtained as an oil in a 33% yield.

Nuclear Magnetic Resonance Spectrum (CDCl$_3$), δ ppm: 1.37–1.48 (2H, multiplet); 1.54–1.63 (4H, multiplet); 2.07 (2H, quintet, J=7.2 Hz); 2.25–2.39 (6H, multiplet); 3.05 (2H, triplet, J=7.2 Hz); 3.41 (2H, singlet); 4.04 (2H, triplet, J=5.9 Hz); 4.92 (2H, doublet, J=6.6 Hz); 5.63–5.75 (1H, multiplet); 5.78–5.96 (1H, multiplet); 6.15–6.27 (1H, broad); 6.73 (1H, singlet); 6.88 (1H, doublet, J=5.3 Hz); 7.13 (2H, doublet, J=4.6 Hz); 8.02 (1H, doublet, J=5.3 Hz); 8.37 (2H, doublet, J=4.6 Hz).

Infrared Absorption Spectrum (CHCl$_3$), ν$_{max}$ cm$^{-1}$: 2945, 1660, 1655 (shoulder), 1610, 1580, 1560, 1415, 1405, 1310, 1300, 1290.

EXAMPLE 47

N-[4-(4-Piperidinomethyl-2-pyridyloxy)-cis-2-butenyl]-4-(4,6-diamino-2-pyrimidinylthio)butyramide Following a procedure similar to that described in Example 34, but using N-[4-(4-piperidinomethyl-2-pyridyloxy) -cis-2-butenyl]-4-chlorobutyramide (prepared as described in Preparation 2) and 4,6-diamino-2-mercaptopyrimidine as starting materials, in relative proportions similar to those used in that Example, the title compound was obtained as an oil in a 48% yield.

Nuclear Magnetic Resonance Spectrum (CDCl$_3$), δ ppm: 1.39–1.50 (2H, multiplet); 1.55–1.67 (4H, multiplet); 1.83–2.14 (4H, multiplet); 2.30–2.47 (6H, multiplet); 3.10 (2H, triplet, J=6.8 Hz); 3.45 (2H, singlet); 3.99–4.09 (2H, multiplet); 4.61 (2H, broad singlet); 4.92 (2H, doublet, J=6.8 Hz); 5.24 (1H, singlet); 5.63–5.72 (1H, multiplet); 5.78–5.87 (1H, multiplet); 6.12–6.23 (1H, broad); 6.72–6.79 (1H, multiplet); 6.91 (1H, doublet, J=4.4 Hz); 8.05 (1H, doublet, J=4.4 Hz).

Infrared Absorption Spectrum (CHCl$_3$) ν$_{max}$ cm$^{-1}$: 2940, 1655, 1610, 1580, 1555, 1310.

EXAMPLE 48

N-[4-(4-piperidinomethyl-2-pyridyloxy) -cis-2-butenyl]-N'-isopropylurea

A solution of 0.113 g of isopropylamine in 2 ml of methylene chloride was added to a solution of 0.31 g of carbonyldiimidazole in 5 ml of methylene chloride, and the resulting mixture was cooled with ice, after which a solution of 0.500 g of 4-(4-piperidinomethyl-2-pyridyloxy) -cis-2-butenylamine in 5 ml of methylene chloride was added. The reaction mixture was stirred at room temperature for 2 hours, after which it was poured into ice-water and extracted with methylene chloride. The extract was dried over anhydrous magnesium sulfate, and the solvent was removed by distillation under reduced pressure. The residue was purified by column chromatography through silica gel, using a 1:20 by volume mixture of methanol and ethyl acetate as the eluent, to give 0.41 g (yield 62%) of the title compound as a white powder, melting at 90°–92° C.

Nuclear Magnetic Resonance Spectrum (CDCl$_3$), δ ppm: 1.13 (6H, doublet, J=6.4 Hz); 1.40–1.55 (2H, multiplet); 1.55–1.90 (6H, multiplet); 2.30–2.57 (4H, multiplet); 3.49 (2H, singlet); 3.80–3.90 (1H, multiplet); 3.95 (2H, triplet, J=5.9 Hz); 4.10–4.30 (1H, broad); 4.52–4.67 (1H, broad); 4.91 (2H, doublet, J=6.3 Hz); 5.67–5.88 (2H, multiplet); 6.80 (1H, singlet); 6.92 (1H, doublet, J=5.9 Hz); 8.07 (1H, doublet, J=5.9 Hz).

Infrared Absorption Spectrum (CHCl$_3$), ν$_{max}$ cm$^{-1}$: 3430, 2920, 1655, 1605, 1555, 1520, 1410.

EXAMPLE 49

N-Diphenylmethyl-N'-[4-(47piperidinomethyl)-2-pyridyloxy) -cis-2-butenyl]urea

Following a procedure similar to that described in Example 48, but using 4-(4-piperidinomethyl-2-pyridyloxy) -cis-2-butenylamine and diphenylmethylamine as starting materials, in relative proportions similar to those used in that Example, the title compound was obtained as an oil in a 69% yield.

Nuclear Magnetic Resonance Spectrum (CDCl$_3$), δ ppm: 1.37–1.42 (2H, multiplet); 1.42–1.70 (4H, multiplet); 2.28–2.57 (4H, multiplet); 3.44 (2H, singlet); 3.94 (2H, triplet, J=5.9 Hz); 4.86 (2H, doublet, J=6.3 Hz); 4.87 (1H, singlet); 5.10–5.24 (1H, broad); 5.58–5.70 (1H, multiplet); 5.72–5.83 (1H, multiplet); 5.97 (1H, doublet, J=7.3 Hz); 6.74 (1H, singlet); 6.87 (1H, doublet, J=5.4 Hz); 7.13–7.42 (10H, multiplet); 8.00 (1H, doublet, J=5.4 Hz).

Infrared Absorption Spectrum (CHCl$_3$, ν$_{max}$ cm$^{-1}$: 3430, 2980, 2930, 1660, 1610, 1560, 1520, 1415, 1400, 1298, 1285.

EXAMPLE 50

N-(1-Methylpropyl)-N'-[4-(4-piperidinomethyl-2-pyridyloxy) -cis-2-butenyl]urea

Following a procedure similar to that described in Example 48, but using 4-(4-piperidinomethyl-2-pyridyloxy) -cis-2-butenylamine and 1-methylpropylamine as starting materials, in relative proportions similar to those used in that Example, the title compound was obtained as a white powder, melting at 72°–74° C., in an 80% yield.

Nuclear Magnetic Resonance Spectrum (CDCl$_3$), δ ppm: 0.90 (3H, triplet, J=7.5 Hz); 1.11 (3H, doublet, J=6.4 Hz); 1.35–1.80 (6H, multiplet); 2.33–2.60 (4H, multiplet); 3.51 (2H, singlet); 3.60–3.77 (1H, multiplet); 3.95 (2H, triplet, J=5.9 Hz); 4.13–4.28 (1H, broad); 4.54–4.69 (1H, broad); 4.92 (2H, doublet, J=6.5 Hz); 6.67–6.88 (2H, multiplet); 6.81 (1H, singlet); 6.93 (1H, doublet, J=5.4 Hz); 8.07 (1H, doublet, J=5.4 Hz).

Infrared Absorption Spectrum (CHCl$_3$) ν$_{max}$ cm$^{-1}$: 3430, 3350, 2920, 1655, 1610, 1558, 1525, 1415, 1400, 1340, 1298, 1285.

EXAMPLE 51

N-(1-Methylbutyl)-N'-[4-(4-piperidinomethyl-2-pyridyloxy)-cis-2-butenyl]urea

Following a procedure similar to that described in Example 48, but using 4-(4-piperidinomethyl-2-pyridyloxy)-cis-2-butenylamine and 1-methylbutylamine as starting materials, in relative proportions similar to those used in that Example, the title compound was obtained as an oil in a 66% yield.

Nuclear Magnetic Resonance Spectrum (CDCl$_3$), δ ppm: 0.89 (3H, triplet, J=7.1 Hz); 1.10 (3H, doublet, J=6.4 Hz); 1.22–1.50 (6H, multiplet); 1.50–1.64 (4H, multiplet); 2.30–2.43 (4H, multiplet); 3.41 (2H, singlet); 3.67–3.82 (1H, multiplet); 3.95 (2H, triplet, J=5.9 Hz); 4.17 (1H, broad doublet, J=7.8 Hz); 4.58–4.68 (1H, broad); 4.91 (2H, doublet, J=6.8 Hz); 5.66–5.76 (1H, multiplet); 5.76–5.88 (1H, multiplet); 6.73 (1H, singlet); 6.80 (1H, doublet, J=5.9 Hz); 8.04 (1H, doublet, J=5.9 Hz).

Infrared Absorption Spectrum (CHCl$_3$), ν$_{max}$ cm$^{-1}$: 3430, 3350, 2930, 1650, 1610, 1558, 1525, 1415, 1400, 1310, 1295, 1285.

EXAMPLE 52

N-(1-Methylhexyl)-N'-[4-(4-piperidinomethyl-2-pyridyloxy)-cis-2-butenyl]urea

Following a procedure similar to that described in Example 48, but using 4-(4-piperidinomethyl-2-pyridyloxy)-cis-2-butenylamine and 1-methylhexylamine as starting materials, in relative proportions similar to those used in that Example, the title compound was obtained as an oil in a 65% yield.

Nuclear Magnetic Resonance Spectrum (CDCl$_3$), δ ppm: 0.87 (3H, triplet, J=6.6 Hz); 1.10 (3H, doublet, J=6.4 Hz); 1.20–1.50 (10H, multiplet); 1.50–1.67 (4H, multiplet); 2.30–2.47 (4H, multiplet); 3.42 (2H, singlet); 3.64–3.80 (1H, multiplet); 3.95 (2H, triplet, J=6.1 Hz); 4.07–4.20 (1H, broad doublet, J=7.7 Hz); 4.25–4.65 (1H, broad); 4.92 (2H, doublet, J=6.3 Hz); 5.63–5.88 (2H, multiplet); 6.74 (1H, singlet); 6.89 (1H, doublet, J=5.3 Hz); 8.05 (1H, doublet, J=5.3 Hz).

Infrared Absorption Spectrum (CHCl$_3$), ν$_{max}$ cm$^{-1}$: 3430, 3350, 2930, 2850, 1655, 1610, 1560, 1528, 1415, 1400, 1310, 1298, 1285.

EXAMPLE 53

N-(1-Phenylethyl)-N'-[4-(4-piperidinomethyl-2-pyridyloxy)-cis-2-butenyl]urea

Following a procedure similar to that described in Example 48, but using 4-(4-piperidinomethyl-2-pyridyloxy)-cis-2-butenylamine and 1-phenylethylamine as starting materials, in relative proportions similar to those used in that Example, the title compound was obtained as an oil in a 62% yield.

Nuclear Magnetic Resonance Spectrum (CDCl$_3$), δ ppm: 1.45 (3H, doublet, J=6.8 Hz); 1.50–1.74 (6H, multiplet); 2.30–2.43 (4H, multiplet); 3.41 (2H, singlet); 3.92 (2H, triplet, J=5.6 Hz); 4.50–4.70 (2H, broad); 4.86 (2H, doublet, J=6.3 Hz); 5.57–5.68 (1H, multiplet); 5.72–5.84 (1H, multiplet); 6.71 (1H, singlet); 6.86 (2H, doublet, J=5.4 Hz); 7.19–7.37 (5H, multiplet); 8.01 (1H, doublet, J=5.4 Hz).

Infrared Absorption Spectrum (CHCl$_3$) ν$_{max}$ cm$^{-1}$: 3440, 2980, 2930, 1660, 1610, 1558, 1525, 1415, 1400, 1298, 1285.

EXAMPLE 54

N-(1-Ethylpropyl)-N'-[4-(4-piperidinomethyl-2-pyridyloxy)-cis-2-butenyl]urea

Following a procedure similar to that described in Example 48, but using 4-(4-piperidinomethyl-2-pyridyloxy)-cis-2-butenylamine and 1-ethylpropylamine as starting materials, in relative proportions similar to those used in that Example, the title compound was obtained as a white powder, melting at 82°–84° C., in a 77% yield.

Nuclear Magnetic Resonance Spectrum (CDCl$_3$), δ ppm: 0.89 (6H, triplet, J=7.3 Hz); 1.22–1.78 (10H, multiplet); 2.30–2.56 (4H, multiplet); 3.49 (2H, singlet); 3.96 (2H, triplet, J=6.1 Hz); 4.05–4.20 (1H, broad); 4.57–4.68 (1H, broad); 4.92 (2H, doublet, J=6.3 Hz); 5.65–5.88 (2H, multiplet); 6.80 (1H, singlet); 6.92 (1H, doublet, J=5.3 Hz); 8.07 (1H, doublet, J=5.3 Hz).

Infrared Absorption Spectrum (CHCl$_3$), ν$_{max}$ cm$^{-1}$: 3440, 3370, 2960, 2930, 1655, 1622, 1540, 1528, 1418, 1400, 1300, 1285.

EXAMPLE 55

N-(1,2-Dimethylpropyl)-N'-[4-(4-piperidinomethyl-2-pyridyloxy)-cis-2-butenyl]urea Following a procedure similar to that described in Example 48, but using 4-(4-piperidinomethyl-2-pyridyloxy)-cis-2-butenylamine and 1,2-dimethylpropylamine as starting materials, in relative proportions similar to those used in that Example, the title compound was obtained as an oil in a 73% yield.

Nuclear Magnetic Resonance Spectrum (CDCl$_3$), δ ppm: 0.87 (3H, triplet, J=6.8 Hz); 0.88 (3H, doublet, J=6.8 Hz); 1.05 (3H, doublet, J=5.8 Hz); 1.37–1.51 (2H, multiplet); 1.51–1.82 (5H, multiplet); 2.30–2.42 (4H, multiplet); 3.56 (2H, singlet); 3.56–3.71 (1H, multiplet); 3.95 (2H, triplet, J=6.1 Hz); 4.20 (1H, broad doublet, J=8.8 Hz); 4.58–4.70 (1H, broad); 4.92 (2H, doublet, J=6.3 Hz); 5.65–5.77 (1H, multiplet); 5.77–5.88 (1H, multiplet); 6.73 (1H, sin91et); 6.88 (1H, doublet, J=5.4 Hz); 8.04 (1H, doublet, J=5.4 Hz).

Infrared Absorption Spectrum (CHCl$_3$), ν$_{max}$ cm$^{-1}$: 3440, 2930, 1660, 1610, 1560, 1525, 1415, 1400, 1308, 1300, 1285.

EXAMPLE 56

N-(1,2-Diphenylethyl)-N'-[4-(4-piperidinomethyl-2-pyridyloxy)-cis-2-butenyl]urea Following a procedure similar to that described in Example 48, but using 4-(4-piperidinomethyl-2-pyridyloxy)-cis-2-butenylamine and 1,2-diphenylethylamine as starting materials, in relative proportions similar to those used in that Example, the title compound was obtained as an oil in an 80% yield.

Nuclear Magnetic Resonance Spectrum (CDCl$_3$), δ ppm: 1.37–1.54 (2H, multiplet); 1.54–1.84 (4H, multiplet); 2.32–2.62 (4H, multiplet); 3.05 (2H, doublet, J=6.8 Hz); 3.52 (2H, singlet); 3.85 (2H, triplet, J=5.9 Hz); 4.63–4.78 (1H, broad); 4.83 (2H, doublet, J=6.8 Hz); 4.90–5.02 (1H, multiplet); 5.52–5.62 (1H, multiplet); 5.68–5.79 (1H, multiplet); 6.74–6.87 (1H, broad); 6.91 (1H, doublet, J=5.3 Hz); 7.00–7.08 (2H, multiplet); 7.12–7.39 (8H, multiplet); 8.02 (1H, doublet, J=5.3 Hz).

Infrared Absorption Spectrum (CHCl$_3$), ν$_{max}$ cm$^{-1}$: 3450, 3010, 2950, 1668, 1615, 1560, 1528, 1420, 1408, 1300, 1290.

EXAMPLE 57

N-Cyclopropyl-N'-[4-(4-piperidinomethyl-2-pyridyloxy) -cis-2-butenyl]urea

Following a procedure similar to that described in Example 48, but using 4-(4-piperidinomethyl-2-pyridyloxy) -cis-2-butenylamine and cyclopropylamine as starting materials, in relative proportions similar to those used in that Example, the title compound was obtained as a white powder, melting at 102°–104° C., in a 60% yield.

Nuclear Magnetic Resonance Spectrum (CDCl$_3$), δ ppm: 1.51–1.59 (2H, multiplet); 1.67–1.77 (2H, multiplet); 1.36–1.82 (6H, multiplet); 2.30–2.60 (4H, multiplet); 3.49 (2H, singlet); 4.04 (2H, triplet, J=6.1 Hz); 4.62–4.78 (1H, broad); 4.94 (2H, doublet, J=6.4 Hz); 5.02–5.17 (1H, broad); 5.67–5.90 (2H, multiplet); 6.78 (1H, singlet); 6.93 (1H, doublet, J=5.4 Hz); 8.07 (1H, doublet, J=5.4 Hz).

Infrared Absorption Spectrum (CHCl$_3$), ν$_{max}$ cm$^{-1}$: 3430, 2990, 2930, 1642, 1610, 1560, 1528, 1415, 1400, 1298, 1285.

EXAMPLE 58

N-Cyclobutyl-N'-[4-(4-piperidinomethyl-2-pyridyloxy) -cis-2-butenyl]urea

Following a procedure similar to that described in Example 48, but using 4-(4-piperidinomethyl-2-pyridyloxy) -cis-2-butenylamine and cyclobutylamine as starting materials, in relative proportions similar to those used in that Example, the title compound was obtained as a white powder, melting at 130°–132° C., in a 66% yield.

Nuclear Magnetic Resonance Spectrum (CDCl$_3$), δ ppm: 1.37–1.49 (2H, multiplet); 1.52–1.88 (8H, multiplet); 2.23–2.42 (6H, multiplet); 3.41 (2H, singlet); 3.95 (2H, triplet, J=5.8 Hz); 4.03–4.21 (1H, multiplet); 4.50–4.68 (2H, multiplet); 4.91 (2H, doublet, J=6.4 Hz); 5.62–5.74 (1H, multiplet); 5.76–5.89 (1H, multiplet); 6.74 (1H, singlet); 6.88 (1H, doublet, J=5.4 Hz); 8.05 (1H, doublet, J=5.4 Hz).

Infrared Absorption Spectrum (CHCl$_3$), ν$_{max}$ cm$^{-1}$: 3440, 2980, 2940, 1660, 1612, 1560, 1528, 1415, 1400, 1300, 1288, 1248.

EXAMPLE 59

N-Cyclopentyl-N'-[4-(4-piperidinomethyl-2-pyridyloxy) -cis-2-butenyl]urea

Following a procedure similar to that described in Example 48, but using 4-(4-piperidinomethyl-2-pyridyloxy) -cis-2-butenylamine and cyclopentylamine as starting materials, in relative proportions similar to those used in that Example, the title compound was obtained as a white powder, melting at 121°–124° C., in a 77% yield.

Nuclear Magnetic Resonance Spectrum (hexadeuterated dimethyl sulfoxide), δ ppm: 1.14–1.67 (12H, multiplet); 1.67–1.82 (2H, multiplet); 2.20–2.43 (4H, multiplet); 3.45 (2H, singlet); 3.72 (2H, triplet, J=5.8 Hz); 3.75–3.91 (1H, multiplet); 4.86 (2H, doublet, J=6.4 Hz); 5.49–5.72 (2H, multiplet); 5.77 (1H, triplet, J=5.9 Hz); 5.84 (2H, doublet, J=7.3 Hz); 6.71 (1H, singlet); 6.92 (1H, doublet of doublets, J=5.4 & 1.0 Hz); 8.07 (1H, doublet, J=5.4 Hz).

Infrared Absorption Spectrum (KBr), ν$_{max}$ cm$^{-1}$: 3318, 2935, 1618, 1584, 1561, 1426, 1409, 1301, 1041.

EXAMPLE 60

N-Cyclohexyl -N'-[4-(4-piperidinomethyl-2-pyridyloxy) -cis-2-butenyl]urea

Following a procedure similar to that described in Example 48, but using 4-(4-piperidinomethyl-2-pyridyloxy)-cis-2-butenylamine and cyclohexylamine as starting materials, in relative proportions similar to those used in that Example, the title compound was obtained as a white powder, melting at 131°–132° C., in a 72% yield.

Nuclear Magnetic Resonance Spectrum (CDCl$_3$) δ ppm: 0.99–1.21 (2H, multiplet); 1.25–1.50 (4H, multiplet); 1.52–1.75 (8H, multiplet); 1.85–1.97 (2H, multiplet); 2.30–2.42 (4H, multiplet); 3.40 (2H, singlet); 3.42–3.58 (1H, multiplet); 3.95 (2H, triplet, J=5.8 Hz); 4.25 (1H, broad doublet, J=7.8 Hz); 4.61 (1H, broad triplet, J=5.9 Hz); 4.92 (2H, doublet, J=6.8 Hz); 5.64–5.76 (1H, multiplet); 5.76–5.87 (1H, multiplet); 6.73 (1H, singlet); 6.87 (1H, doublet, J=5.4 Hz); 8.04 (1H, doublet, J=5.4 Hz). Infrared Absorption Spectrum (CHCl$_3$), ν$_{max}$ cm$^{-1}$: 3430, 3350, 2980, 2920, 2850, 1655, 1610, 1558, 1528, 1415, 1400, 1310, 1300, 1288.

EXAMPLE 61

N-Cycloheptyl-N'-[4-(4-iperidinomethyl-2-pyridyloxy)-cis-2-butenyl]urea

Following a procedure similar to that described in Example 48, but using 4-(4-piperidinomethyl-2-pyridyloxy)-cis-2-butenylamine and cycloheptylamine as starting materials, in relative proportions similar to those used in that Example, the title compound was obtained as a white powder, melting at 89°–91° C., in a 60% yield.

Nuclear Magnetic Resonance Spectrum (CDCl$_3$), δ ppm: 1.32–1.80 (16H, multiplet); 1.82–2.00 (2H, multiplet); 2.25–2.50 (4H, multiplet); 3.43 (2H, singlet); 3.64–3.80 (1H, multiplet); 3.95 (2H, triplet, J=5.9 Hz); 4.29 (1H, broad doublet, J=7.3 Hz); 4.56 (1H, broad triplet, J=5.4 Hz); 4.92 (2H, doublet, J=6.3 Hz); 5.64–5.77 (1H, multiplet); 5.77–5.88 (1H, multiplet); 6.75 (1H, singlet); 6.88 (1H, doublet, J=5.4 Hz); 8.05 (1H, doublet, J=5.4 Hz). Infrared Absorption Spectrum (CHCl$_3$), ν$_{max}$ cm$^{-1}$: 3430, 2920, 1655, 1610, 1558, 1520, 1413, 1400, 1308, 1298, 1285.

EXAMPLE 62

N-Cyclooctyl-N'-[4-(4-piperidinomethyl-2-pyridyloxy)-cis-2-butenyl]urea

Following a procedure similar to that described in Example 48, but using 4-(4-piperidinomethyl-2-pyridyloxy)-cis-2-butenylamine and cyclooctylamine as starting materials, in relative proportions similar to those used in that Example, the title compound was obtained as an oil in a 59% yield.

Nuclear Magnetic Resonance Spectrum (CDCl$_3$), δ ppm: 1.32–1.93 (20H, multiplet); 2.30–2.70 (4H, multiplet); 3.49 (2H, singlet); 3.68–3.86 (1H, multiplet); 3.94 (2H, triplet, J=5.9 Hz); 4.27–4.43 (1H, broad); 4.52–4.67 (1H, broad); 4.91 (2H, doublet, J=6.3 Hz); 5.65–5.88 (2H, multiplet); 6.80 (1H, singlet); 6.92 (1H, doublet, J=5.3 Hz); 8.07 (1H, doublet, J=5.3 Hz). Infrared Absorption Spectrum (CHCl$_3$) $v_{max}$ cm$^{-1}$: 3440, 2930, 1655, 1610, 1560, 1525, 1415, 1400, 1310, 1300, 1288.

EXAMPLE 63

N-Isopropyl-N'-[3-(4-piperidinomethyl-2-pyridyloxy)propyl]urea

Following a procedure similar to that described in Example 48, but using 3-(4-piperidinomethyl-2-pyridyloxy)propylamine and isopropylamine as starting materials, in relative proportions similar to those used in that Example, the title compound was obtained as a white powder, melting at 58°–60° C., in a 50% yield.

Nuclear Magnetic Resonance Spectrum (CDCl$_3$), δ ppm: 1.14 (6H, doublet, J=6.3 Hz); 1.38–1.50 (2H, multiplet); 1.52–1.64 (4H, multiplet); 1.90–2.05 (2H, multiplet); 2.37 (4H, triplet, J=5.1 Hz); 3.34 (2H, triplet of doublets, J=6.3 & 5.8 Hz); 3.41 (2H, singlet); 3.74–3.92 (1H, multiplet); 4.19 (1H, broad doublet, J=7.8 Hz); 4.38 (2H, triplet, J=5.8 Hz); 4.70–4.82 (1H, broad); 6.72 (1H, singlet); 6.86 (1H, doublet, J=5.4 Hz); 8.04 (1H, doublet, J=5.4 Hz). Infrared Absorption Spectrum (CHCl$_3$), $v_{max}$ cm$^{-1}$: 3420, 3320, 2920, 1650, 1608, 1555, 1530, 1412.

EXAMPLE 64

N-[3-(4-Piperidinomethyl-2-pyridyloxy)propyl]-pyrazole-4-carboxamide

A solution of 1.0 g of 3-(4-piperidinomethyl-2-pyridyloxy)propylamine and 0.45 g of 4-pyrazolecarboxylic acid dissolved in 15 ml of dimethylformamide was stirred for 5 minutes, whilst ice-cooling, after which 734 mg of diethyl cyanophosphonate and 0.68 ml of triethylamine were added to the resulting mixture. The mixture was then stirred at room temperature for 3 hours, after which it was diluted with water, and the aqueous mixture was extracted with ethyl acetate. The extract was washed with a saturated aqueous solution of sodium hydrogencarbonate and then with a saturated aqueous solution of sodium chloride, and dried over anhydrous magnesium sulfate. The solvent was then removed by distillation under reduced pressure, and the resulting residue was purified by column chromatography through silica gel, using a 1:9 by volume mixture of methanol and chloroform as the eluent, to give 1.2 g (yield 85%) of the title compound as a white powder, melting at 117°–119° C.

Nuclear Magnetic Resonance Spectrum (CDCl$_3$), δ ppm: 1.39–1.47 (2H, multiplet); 1.50–1.62 (4H, multiplet); 1.99–2.11 (2H, multiplet); 2.34–2.44 (4H, multiplet); 3.41 (2H, singlet); 3.55 (2H, quartet, J=5.9 Hz); 4.42 (2H, triplet, J=5.9 Hz); 6.72 (1H, singlet); 6.88 (1H, doublet, J=5.3 Hz); 7.16 (2H, broad triplet, J=5.9 Hz); 7.99–8.05 (2H, multiplet); 8.05 (1H, doublet, J=5.3 Hz). Infrared Absorption Spectrum (KBr), $v_{max}$ cm$^{-1}$: 3250, 2935, 1631, 1607, 1566, 1421, 1386, 1302, 1212.

EXAMPLE 65

N-[4-(4-Piperidinomethyl-2-pyridyloxy)butyl]-pyrazole-4-carboxamide

Following a procedure similar to that described in Example 64, but using 4-(4-piperidinomethyl-2-pyridyloxy)butylamine and 4-pyrazolecarboxylic acid as starting materials, in relative proportions similar to those used in that Example, the title compound was obtained as a white powder, melting at 145°–147° C., in a 71% yield.

Nuclear Magnetic Resonance Spectrum (CDCl$_3$), δ ppm. 1.39–1.50 (2H, multiplet); 1.53–1.62 (4H, multiplet); 1.71–1.92 (4H, multiplet); 2.31–2.42 (4H, multiplet); 3.41 (2H, singlet); 3.49 (2H, doublet of doublets, J=12.5 & 6.6 Hz); 4.29 (2H, doublet of doublets, J=11.2 & 6.1 Hz); 6.36–6.42 (1H, broad); 6.71 (1H, singlet); 6.85 (1H, doublet, J=5.3 Hz); 7.96 (2H, singlet); 8.05 (1H, doublet, J=5.3 Hz). Infrared Absorption Spectrum (KBr), $v_{max}$ cm$^{-1}$: 3335, 2940, 1628, 1619, 1560, 1426, 1366, 1299, 992.

EXAMPLE 66

N-[5-(4-Piperidinomethyl-2-pyridyloxy)pentyl]pyrazole-4-carboxamide

Following a procedure similar to that described in Example 64, but using 5-(4-piperidinomethyl-2-pyridyloxy)pentylamine and 4-pyrazolecarboxylic acid as starting materials, in relative proportions similar to those used in that Example, the title compound was obtained as a white powder, melting at 105°–106° C., in a yield.

Nuclear Magnetic Resonance Spectrum (CDCl$_3$), δ ppm: 1.42–1.60 (4H, multiplet); 1.60–1.74 (6H, multiplet); 1.76–1.88 (2H, multiplet); 2.40–2.63 (4H, multiplet); 3.43 (2H, quartet, J=6.7 Hz); 3.51 (2H, singlet); 4.27 (2H, triplet, J=6.3 Hz); 6.15–6.25 (1H, broad); 6.75 (1H, singlet); 6.88 (1H, doublet, J=5.3 Hz); 7.96 (2H, singlet); 8.07 (1H, doublet, J=5.3 Hz). Infrared Absorption Spectrum (CHCl$_3$), $v_{max}$ cm$^{-1}$: 3460, 2930, 1640, 1610, 1570, 1418, 1320.

EXAMPLE 67

N-[3-(4-Piperidinomethyl-2-pyridyloxy)propyl]-2-(2-acetoxyethylthio)acetamide

67(a) N-[3-(4-Piperidinomethyl-2-pyridyloxy)propyl]-2-chloroacetamide 1.68 ml of triethylamine were added to a solution of 3.00 g of 3-(4-piperidinomethyl-2-pyridyloxy)propylamine in 60 ml of ethyl acetate, and the resulting mixture was cooled with ice, after which 0.96 ml of 2-chloroacetyl chloride was added. The reaction mixture was then stirred at room temperature for 1 hour, after which it was mixed with water and the aqueous mixture was extracted with ethyl acetate. The extract was concentrated by evaporation under reduced pressure, and the concentrate was purified by column chromatography through silica gel, using a 1:9 by volume mixture of methanol and ethyl acetate as the eluent, to give 3.40 g (yield 87%) of the title compound as an oil.

Nuclear Magnetic Resonance Spectrum (CDCl$_3$), δ ppm: 1.39–1.52 (2H, multiplet); 1.52–1.66 (4H, multiplet); 2.94–3.07 (2H, multiplet); 2.33–2.44 (4H, multiplet); 3.43 (2H, singlet); 3.48 (2H, triplet of doublets, J=6.6 & 5.9 Hz); 4.07 (2H, singlet); 4.44 (2H, triplet, J=5.9 Hz); 6.76 (1H, singlet); 6.89 (1H, doublet, J=5.3 Hz); 7.36–7.58 (1H, broad); 8.06 (1H, doublet, J=5.3 Hz). Infrared Absorption Spectrum (CHCl$_3$), $v_{max}$ cm$^{-1}$: 3425, 2925, 1730, 1660, 1610, 1530, 1420.

67(b) N-[3-(4-Piperidinomethyl-2-pyridyloxy)propyl]-2-(2-hydroxyethylthio)acetamide 0.12 ml of 2-mercaptoethanol was added to a solution of 0.13 g of 85% potassium hydroxide and 0.50 g of N-[3-(4-piperidinomethyl-2-pyridyloxy)propyl]-2-chloroacetamide [prepared as described in step (a) above] in 10 ml methanol, and the resulting mixture was stirred at room temperature for 1 hour. At the end of this time, the reaction mixture was concentrated by evaporation under reduced pressure, the concentrate was mixed with water, and the resulting aqueous mixture was extracted with chloroform. The extract was concentrated by evaporation under reduced pressure, and the residue was purified by column chromatography through silica gel, using a 1:9 by volume mixture of ethanol and chloroform as the eluent, to give 0.43 g (yield 77%) of the title compound as an oil.

Nuclear Magnetic Resonance Spectrum (CDCl$_3$), δ ppm: 1.38–1.52 (2H, multiplet); 1.52–1.66 (4H, multiplet); 1.95–2.09 (2H, multiplet); 2.31–2.85 (4H, multiplet); 2.79 (2H, triplet, J=5.6 Hz); 3.30 (2H, singlet); 3.42 (2H, singlet); 3.49 (2H, triplet of doublets, J=6.6 & 5.9 Hz); 3.82 (2H, triplet, J=5.6 Hz); 4.42 (2H, triplet, J=5.9 Hz); 6.77 (1H, singlet); 6.88 (1H, doublet, J=5.3 Hz); 7.48–7.66 (1H, broad); 8.06 (1H, doublet, J=5.3 Hz). Infrared Absorption Spectrum (CHCl$_3$) $v_{max}$ cm$^{-1}$: 3350, 2925, 1650, 1610, 1560, 1520, 1420.

67(c) N-[3-(4-Piperidinomethyl-2-pyridyloxy)propyl]-2-(2-acetoxyethylthio)acetamide 0.49 g of N-[3-(4-piperidinomethyl-2-pyridyloxy)propyl]-2-(2-hydroxyethylthio)acetamide [prepared as described in step (b) above] was added to a mixture of 0.48 ml of acetic anhydride and 0.43 ml of pyridine, and the resulting mixture was warmed at 60° C. for 2 hours. At the end of this time, the reaction mixture was poured into ice-water and a saturated aqueous solution of sodium hydrogencarbonate was added to it. The resulting aqueous mixture was extracted with ethyl acetate. The extract was concentrated by evaporation under reduced pressure, and the concentrate was purified by column chromatography through silica gel, using a 1:9 by volume mixture of methanol and ethyl acetate as the eluent, to give 0.41 g (yield 75%) of the title compound as an oil.

Nuclear Magnetic Resonance Spectrum (CDCl$_3$), δ ppm: 1.37–1.51 (2H, multiplet); 1.51–1.67 (4H, multiplet); 1.93–2.09 (2H, multiplet); 2.05 (3H, singlet); 2.31–2.43 (4H, multiplet); 2.80 (2H, triplet, J=5.9 Hz); 3.30 (2H, singlet); 3.42 (2H, singlet); 3.46 (2H, triplet of doublets, J=6.6 & 5.9 Hz); 4.24 (2H, triplet, J=6.6 Hz); 4.42 (2H, triplet, J=5.9 Hz); 6.77 (1H, singlet); 6.88 (1H, doublet, J=5.3 Hz); 7.38–7.54 (1H, broad); 8.06 (1H, doublet, J=5.3 Hz). Infrared Absorption Spectrum (CHCl$_3$), $v_{max}$ cm$^{-1}$: 3375, 2925, 1740, 1660, 1610, 1520, 1420, 1220.

The title compound, prepared as described above, was dissolved in ethyl acetate, and a 4N ethyl acetate solution of hydrogen chloride was added to the solution. The crystals which precipitated were collected by filtration, to give the hydrochloride of the title compound, melting at 121°–128° C.

EXAMPLE 68

N-[3-(4-Piperidinomethyl-2-pyridyloxy)propyl]-2-(2-hydroxyethylthio)acetamide

A mixture of 0.38 g of 3-(4-piperidinomethyl-2-pyridyloxy)propylamine and 0.18 g of 1,4-oxathian-2-one was added to 10 ml of ethanol, and the resulting mixture was heated under reflux for 2 hours. At the end of this time, the reaction mixture was concentrated by evaporation under reduced pressure. The concentrate was mixed with water, and the resulting aqueous mixture was extracted with ethyl acetate. The extract was concentrated by evaporation under reduced pressure, and the concentrate was purified by column chromatography through silica gel, using a 1:9 by volume mixture of methanol and methylene chloride as the eluent, to give 0.49 g (yield 88%) of the title compound as an oil.

Nuclear Magnetic Resonance Spectrum (CDCl$_3$), δ ppm: 1.38–1.52 (2H, multiplet); 1.52–1.66 (4H, multiplet); 1.95–2.09 (2H, multiplet); 2.31–2.85 (4H, multiplet); 2.79 (2H, triplet, J=5.6 Hz); 3.30 (2H, singlet); 3.42 (2H, singlet); 3.49 (2H, triplet of doublets, J=6.6 & 5.9 Hz); 3.82 (2H, triplet, J=5.6 Hz); 4.42 (2H, triplet, J=5.9 Hz); 6.77 (1H, singlet); 6.88 (1H, doublet, J=5.3 Hz); 7.48–7.66 (1H, broad); 8.06 (1H, doublet, J=5.3 Hz). Infrared Absorption Spectrum (CHCl$_3$), $v_{max}$ cm$^{-1}$: 3350, 2925, 1650, 1610, 1560, 1520, 1420.

EXAMPLE 69

N-[4-(4-Piperidinomethyl-2-pyridyloxy)butyl]-2-(2-acetoxyethylthio)acetamide

69(a) N-[4-(4-Piperidinomethyl-2-pyridyloxy)butyl]-2-chloroacetamide

Following a procedure similar to that described in Example 67(a), but using 4-(4-piperidinomethyl-2-pyridyloxy)butylamine and 2-chloroacetyl chloride as starting materials, in relative proportions similar to those used in that Example, the title compound was obtained as a white powder, melting at 59°–63° C., in an 80% yield.

Nuclear Magnetic Resonance Spectrum (CDCl$_3$), δ ppm: 1.39–1.51 (2H, multiplet); 1.51–1.66 (4H, multiplet); 1.66–1.91 (4H, multiplet); 2.31–2.44 (4H, multiplet); 3.35–3.47 (2H, multiplet); 3.41 (2H, singlet); 4.05 (2H, singlet); 4.31 (2H, triplet, J=5.9 Hz); 6.63–6.81 (1H, broad); 6.71 (1H, singlet); 6.87 (1H, triplet, J=5.3 Hz); 8.05 (1H, doublet, J=5.3 Hz). Infrared Absorption Spectrum (CHCl$_3$) $v_{max}$ cm$^{-1}$: 3325, 2925, 1670, 1610, 1530, 1420.

69(b) N-[4-(4-Piperidinomethyl-2-pyridyloxy)butyl]-2-(2-hydroxyethylthio)acetamide Following a procedure similar to that described in Example 67(b), but using 4-(4-piperidinomethyl-2-pyridyloxy)butyl-2-chloroacetamide [prepared as described in step (a) above] and 2-mercaptoethanol as starting materials, in relative proportions similar to those used in that Example, the title compound was obtained as an oil in a quantitative yield.

Nuclear Magnetic Resonance Spectrum (CDCl$_3$), δ ppm: 1.38–1.50 (2H, multiplet); 1.59–1.64 (4H, multiplet); 1.64–1.91 (5H, multiplet); 2.31–2.44 (4H, multiplet); 2.77 (2H, triplet, J=5.9 Hz); 3.27 (2H, singlet); 3.31–3.45 (2H, multiplet); 3.41 (2H, singlet); 3.81 (2H, triplet, J=5.9 Hz); 4.30 (2H, triplet, J=5.9 Hz); 6.74 (1H, singlet); 6.86 (1H, doublet, J=5.3 Hz); 6.86–7.14 (1H, broad); 8.04 (1H, doublet, J=5.3 Hz). Infrared Absorption Spectrum (CHCl$_3$), $v_{max}$ cm$^{-1}$: 3350, 2925, 1660, 1610, 1540, 1520, 1420, 1300.

69(c) N-[4-(4-Piperidinomethyl-2-pyridyloxy)butyl]-2-(2-acetoxyethylthio)acetamide Following a procedure similar to that described in Example 67(c), but using N-[4-(4-piperidinomethyl-2-pyridyloxy)butyl]-2-(2-hydroxyethylthio)acetamide [prepared as described in step (b) above] and acetic anhydride as starting materials, in relative proportions similar to those used in that Example, the title compound was obtained as an oil in an 84% yield.

Nuclear Magnetic Resonance Spectrum (CDCl$_3$), δ ppm: 1.38–1.51 (2H, multiplet); 1.51–1.64 (4H, multiplet); 1.64–1.89 (4H, multiplet); 2.07 (3H, singlet); 2.31–2.44 (4H, multiplet); 2.79 (2H, triplet, J=6.6 Hz); 3.27 (2H, singlet); 3.32–3.43 (2H, multiplet); 3.41 (2H, singlet); 4.24 (2H, triplet, J=6.6 Hz); 4.31 (2H, triplet, J=5.9 Hz); 6.70 (1H, singlet); 6.81–6.94 (1H, broad); 6.87 (2H, doublet, J=5.3 Hz); 8.05 (1H, doublet, J=5.3 Hz). Infrared Absorption Spectrum (CHCl$_3$), ν$_{max}$ cm$^{-1}$: 3375, 2925, 1740, 1660, 1610, 1560, 1520, 1420.

The title compound, prepared as described above, was dissolved in ethyl acetate, and a 4N ethyl acetate solution of hydrogen chloride was added to the solution. The crystals which precipitated were collected by filtration, to give the hydrochloride of the title compound, melting at 91°–98° C.

EXAMPLE 70

N-[5-(4-Piperidinomethyl-2-pyridyloxy)pentyl]-2-(2-acetoxyethylthio)acetamide

70(a) N-[5-(4-Piperidinomethyl-2-pyridyloxy)pentyl]-2-(2-hydroxyethylthio)acetamide Following a procedure similar to that described in Example 68, but using 5-(4-piperidinomethyl-2-pyridyloxy)pentylamine and 1,4-oxathian-2-one as starting materials, in relative proportions similar to those used in that Example, the title compound was obtained as an oil in a 78% yield.

Nuclear Magnetic Resonance Spectrum (CDCl$_3$), δ ppm: 1.37–2.00 (13H, multiplet); 2.31–2.43 (4H, multiplet); 2.77 (2H, triplet, J=5.9 Hz); 3.26 (2H, singlet); 3.33 (2H, triplet of doublets, J=6.6 & 5.9 Hz); 3.40 (2H, singlet); 3.81 (2H, triplet, J=5.9 Hz); 4.26 (2H, triplet, J=5.9 Hz); 6.74 (1H, singlet); 6.78–6.95 (1H, broad); 6.84 (1H, triplet, J=5.3 Hz); 8.04 (1H, doublet, J=5.3 Hz). Infrared Absorption Spectrum (CHCl$_3$), ν$_{max}$ cm$^{-1}$: 3375, 2925, 1660, 1610, 1560, 1520, 1420.

70(b) N-[5-(4-Piperidinomethyl-2-pyridyloxy)pentyl]-2-(2-acetoxyethylthio)acetamide Following a procedure similar to that described in Example 67(c), but using N-[5-(4-piperidinomethyl-2-pyridyloxy)pentyl]-2-(2-hydroxyethylthio)acetamide [prepared as described in step (a) above] and acetic anhydride as starting materials, in relative proportions similar to those used in that Example, the title compound was obtained as an oil in a 90% yield.

Nuclear Magnetic Resonance Spectrum (CDCl$_3$), δ ppm: 1.36–1.64 (10H, multiplet); 1.72–1.86 (2H, multiplet); 2.07 (3H, singlet); 2.31–2.41 (4H, multiplet); 2.79 (2H, triplet, J=6.6 Hz); 3.27 (2H, singlet); 3.32 (2H, quartet, J=6.6 Hz); 4.19–4.31 (4H, multiplet); 6.69 (1H, singlet); 6.69–6.88 (1H, broad); 6.85 (1H, doublet, J=5.3 Hz); 8.05 (1H, doublet, J=5.3 Hz). Infrared Absorption Spectrum (CHCl$_3$), ν$_{max}$ cm$^{-1}$: 3375, 2925, 1740, 1660, 1610, 1520, 1420.

EXAMPLE 71

N-[4-(4-Piperidinomethyl-2-pyridyloxy)butyl]-2-(2-propionyloxyethylthio)acetamide Following a procedure similar to that described in Example 67(c), but using N-[4-(4-piperidinomethyl-2-pyridyloxy)butyl]-2-(2-hydroxyethylthio)acetamide [prepared as described in Example 69(b)] and propionic anhydride as starting materials, in relative proportions similar to those used in that Example, the title compound was obtained as an oil in an 80% yield.

Nuclear Magnetic Resonance Spectrum (CDCl$_3$), δ ppm: 1.14 (3H, triplet, J=7.3 Hz); 1.35–1.88 (10H, multiplet); 2.26–2.42 (4H, multiplet); 2.35 (2H, quartet, J=7.3 Hz); 2.79 (2H, triplet, J=6.3 Hz); 3.27 (2H, singlet); 3.32–3.43 (2H, multiplet); 3.41 (2H, singlet); 4.25 (2H, triplet, J=6.3 Hz); 4.30 (2H, triplet, J=6.6 Hz); 6.70 (1H, singlet); 6.75–6.98 (1H, broad); 6.86 (1H, doublet, J=5.3 Hz); 8.04 (1H, doublet, J=5.3 Hz). Infrared Absorption Spectrum (CHCl$_3$), ν$_{max}$ cm$^{-1}$: 3375, 2925, 1730, 1660, 1610, 1560, 1520, 1420.

EXAMPLE 72

N-[4-(4-Piperidinomethyl-2-pyridyloxy)-cis-2-butenyl]-5-(2-acetoxyethylthio)pentanamide

72(a) N-[4-(4-Piperidinomethyl-2-pyridyloxy)-cis-2-butenyl]-5-chloropentanamide Following a procedure similar to that described in Example 67(a), but using 4-(4-piperidinomethyl-2-pyridyloxy)-cis-2-butenylamine and 5-chlorovaleryl chloride as starting materials, in relative proportions similar to those used in that Example, the title compound was obtained as an oil in a 93% yield.

Nuclear Magnetic Resonance Spectrum (CDCl$_3$), δ ppm: 1.36–1.50 (2H, multiplet); 1.50–1.63 (4H, multiplet); 1.74–1.86 (4H, multiplet); 2.18–2.28 (2H, multiplet); 2.28–2.42 (4H, multiplet); 3.41 (2H, singlet); 3.50–3.59 (2H, multiplet); 4.04 (2H, triplet, J=5.9 Hz); 4.93 (2H, doublet, J=6.6 Hz); 5.62–5.74 (1H, multiplet); 5.77–5.90 (1H, multiplet); 5.92–6.20 (1H, broad); 6.73 (1H, singlet); 6.89 (1H, doublet, J=5.3 Hz); 8.03 (1H, doublet, J=5.3 Hz). Infrared Absorption Spectrum (CHCl$_3$), ν$_{max}$ cm$^{-1}$: 3450, 2950, 1660, 1610, 1560, 1510, 1400.

72(b) N-[4-(4-Piperidinomethyl-2-pyridyloxy)-cis-2-butenyl]-5-(methoxycarbonylmethylthio)pentanamide 344 mg of sodium hydride (as a 55% w/w dispersion in mineral oil) were added, whilst ice-cooling and in an atmosphere of nitrogen, to a solution of 0.35 ml of methyl thioglycolate in 90 ml of tetrahydrofuran, and the resulting mixute was stirred at room temperature for 30 minutes. At the end of this time, it was cooled with ice, and a solution of 2.94 g of N-[4-(4-piperidinomethyl-2-pyridyloxy)-cis-2-butenyl]-5-chloropentanamide [prepared as described in step (a) above] in 30 ml of tetrahydrofuran was added dropwise to the mixture. The reaction mixture was then stirred at room temperature for 2 hours, after which the solvent was removed by distillation under reduced pressure. The residue was mixed with water, and the resulting aqueous mixture was extracted with ethyl acetate. The extract was concentrated by evaporation under reduced pressure, and the residue was purified by column chromatography through silica gel, using a 1:19 by volume mixture of methanol and ethyl acetate as the eluent, to give 2.84 g (yield 89%) of the title compound as an oil.

Nuclear Magnetic Resonance Spectrum (CDCl$_3$), δ ppm: 1.38–1.48 (2H, multiplet); 1.48–1.87 (8H, multiplet); 2.23 (2H, triplet, J=7.3 Hz); 2.32–2.46 (4H, multiplet); 2.66 (2H, triplet, J=7.3 Hz); 3.23 (2H, singlet); 3.42 (2H, singlet); 3.75 (3H, singlet); 4.05 (2H, triplet, J=5.9 Hz); 4.94 (2H, doublet, J=6.6 Hz); 5.63–5.76 (1H, multiplet); 5.79–5.92 (1H, multiplet); 5.95–6.18 (1H, broad); 6.75 (1H, singlet); 6.91 (1H, doublet, J=5.3 Hz); 8.05 (1H, doublet, J=5.3 Hz). Infrared Absorption Spectrum (CHCl$_3$), ν$_{max}$ cm$^{-1}$: 3450, 2925, 1730, 1660, 1610, 1560, 1510, 1400.

72(c) N-[4-(4-Piperidinomethyl-2-pyridyloxy)-cis-2butenyl]-5-(2-hydroxyethylthio)pentanamide 0.21 g of sodium borohydride was added to a solution of 1.98 g of N-[4-(4-piperidinomethyl-2-pyridyloxy)-cis-2-butenyl]-5-(methoxycarbonylmethylthio)pentanamide [prepared as described in step (b) above] in 40 ml of tetrahydrofuran, and 8 ml of methanol were added dropwise to the mixture, whilst ice-cooling; it was then stirred at room temperature for 3 hours. At the end of this time, the reaction mixture was concentrated by evaporation under reduced pressure, and the residue was mixed with water. The resulting aqueous mixture was extracted with ethyl acetate, and the extract was freed from the solvent by distillation under reduced pressure. The residue was purified by column chromatography through silica gel, using a 1:9 by volume mixture of methanol and methylene chloride as the eluent, to give 1.51 g (yield 63%) of the title compound as an oil.

Nuclear Magnetic Resonance Spectrum (CDCl$_3$), δ ppm: 1.38–2.09 (11H, multiplet); 2.22 (2H, triplet, J=7.3 Hz); 2.26–2.47 (4H, multiplet); 2.54 (2H, triplet, J=7.3 Hz); 2.72 (2H, triplet, J=5.9 Hz); 3.41 (2H, singlet); 3.72 (2H, triplet, J=5.9 Hz); 4.04 (2H, triplet, J=5.9 Hz); 4.93 (2H, doublet, J=6.6 Hz); 5.62–5.75 (1H, multiplet); 5.78–5.90 (1H, multiplet); 5.97–6.19 (1H, broad); 6.74 (1H, singlet); 6.90 (1H, doublet, J=5.3 Hz); 8.04 (1H, doublet, J=5.3 Hz). Infrared Absorption Spectrum (CHCl$_3$), ν$_{max}$ cm$^{-1}$: 3450, 2925, 1660, 1610, 1560, 1510, 1420.

72(d) N-[4-(4-Piperidinomethyl-2-pyridyloxy)-cis-2-butenyl]-5-(2-acetoxyethylthio)pentanamide Following a procedure similar to that described in Example 67(c), but using N-[4-(4-piperidinomethyl-2-pyridyloxy)-cis-2-butenyl]-5-(2-hydroxyethylthio)pentanamide [prepared as described in step (c) above] and acetic anhydride as starting materials, in relative proportions similar to those used in that Example, the title compound was obtained as an oil in a 92% yield.

Nuclear Magnetic Resonance Spectrum (CDCl$_3$), δ ppm: 1.36–1.86 (10H, multiplet); 2.07 (3H, singlet); 2.21 (2H, triplet, J=7.3 Hz); 2.30–2.47 (4H, multiplet); 2.57 (2H, triplet, J=7.3 Hz); 2.73 (2H, doublet of doublets, J=7.3 & 6.6 Hz); 3.41 (2H, singlet); 4.03 (2H, triplet, J=5.8 Hz); 4.20 (2H, doublet of doublets, J=7.3 & 6.6 Hz); 4.93 (2H, doublet, J=6.6 Hz); 5.58–5.76 (1H, multiplet); 5.78–5.90 (1H, multiplet); 5.95–6.16 (1H, broad); 6.73 (1H, singlet); 6.89 (1H, doublet, J=5.3 Hz); 8.04 (1H, doublet, J=5.3 Hz). Infrared Absorption Spectrum (CHCl$_3$), ν$_{max}$ cm$^{-1}$: 3375, 2950, 1660, 1610, 1560, 1520, 1420.

EXAMPLE 73

N-[4-(4-Piperidinomethyl-2-pyridyloxy)-cis-2-butenyl]-6-(2-acetoxyethylthio)hexanamide

73(a) N-[4-(4-Piperidinomethyl-2-pyridyloxy)-cis-2-butenyl]-6-bromohexanamide Following a procedure similar to that described in Example 67(a), but using N-[4-(4-piperidinomethyl-2-pyridyloxy)-cis-2-butenylamine] and 6-bromohexanoyl bromide as starting materials, in relative proportions similar to those used in that Example, the title compound was obtained as an oil in an 86% yield.

Nuclear Magnetic Resonance Spectrum (CDCl$_3$), δ ppm: 1.37–1.77 (10H, multiplet); 1.82–1.95 (2H, multiplet); 2.20 (2H, triplet, J=7.3 Hz); 2.28–2.43 (4H, multiplet); 3.41 (2H, triplet, J=5.3 Hz); 4.04 (2H, triplet, J=5.9 Hz); 4.93 (2H, doublet, J=6.6 Hz); 5.62–5.76 (1H, multiplet); 5.78–5.90 (1H, multiplet); 5.92–6.11 (1H, broad); 6.73 (1H, singlet); 6.89 (1H, doublet, J=5.3 Hz); 8.03 (1H, doublet, J=5.3 Hz). Infrared Absorption Spectrum (CHCl$_3$), ν$_{max}$ cm$^{-1}$: 3350, 2925, 1660, 1610, 1560, 1510, 1420, 1300.

73(b) N-[4-(4-Piperidinomethyl-2-pyridyloxy)-cis-2-butenyl]-6-(2-hydroxyethylthio)hexanamide Following a procedure similar to that described in Example 67(b), but using N-[4-(4-piperidinomethyl-2-pyridyloxy)-cis-2-butenyl]-6-bromohexanamide [prepared as described in step (a) above] and 2-mercaptoethanol as starting materials, in relative proportions similar to those used in that Example, the title compound was obtained in a 94% yield.

Nuclear Magnetic Resonance Spectrum (CDCl$_3$), δ ppm: 1.36–1.74 (12H, multiplet); 1.63–2.19 (1H, broad); 2.19 (2H, triplet, J=7.3 Hz); 2.29–2.45 (4H, multiplet); 2.53 (2H, triplet, J=7.3 Hz); 2.71 (2H, triplet, J=5.9 Hz); 3.41 (2H, singlet); 3.72 (2H, triplet, J=5.9 Hz); 4.03 (2H, doublet of doublets, J=6.6 & 5.9 Hz); 4.92 (2H, doublet, J=6.6 Hz); 5.61–5.74 (1H, multiplet); 5.77–5.89 (1H, multiplet); 5.93–6.13 (1H, broad); 6.73 (1H, singlet); 6.89 (1H, doublet, J=5.3 Hz); 8.03 (1H, doublet, J=5.3 Hz). Infrared Absorption Spectrum (CHCl$_3$), ν$_{max}$ cm$^{-1}$: 3450, 2925, 1660, 1610, 1560, 1510, 1420.

73(c) N-[4-(4-Piperidinomethyl-2-pyridyloxy)-cis-2-butenyl]-6-(2-acetoxyethylthio)hexanamide Following a procedure similar to that described in Example 67(c), but using N-[4-(4-piperidinomethyl-2-pyridyloxy)-cis-2-butenyl]-6-(2-hydroxyethylthio)hexanamide [prepared as described in step (b) above] and acetic anhydride as starting materials, in relative proportions similar to those used in that Example, the title compound was obtained in an 87% yield.

Nuclear Magnetic Resonance Spectrum (CDCl$_3$), δ ppm: 1.37–1.74 (12H, multiplet); 2.07 (3H, singlet); 2.19 (2H, triplet, J=7.3 Hz); 2.31–2.44 (4H, multiplet); 2.56 (2H, triplet, J=7.3 Hz); 2.72 (2H, triplet, J=7.3 Hz); 3.41 (2H, singlet); 4.03 (2H, doublet of doublets, J=6.6 & 5.9 Hz); 4.20 (2H, triplet, J=7.3 Hz); 4.92 (2H, doublet, J=6.6 Hz); 5.62–5.74 (1H, multiplet); 5.78–5.90 (1H, multiplet); 5.92–6.12 (1H, broad); 6.73 (1H, singlet); 6.89 (1H, doublet, J=5.3 Hz); 8.03 (1H, doublet, J=5.3 Hz). Infrared Absorption Spectrum (CHCl$_3$), ν$_{max}$ cm$^{-1}$: 3450, 2925, 1740, 1660, 1610, 1560, 1510, 1420.

EXAMPLE 74

N-[4-(4-Piperidinomethyl-2-pyridyloxy)-cis-2-butenyl]-2-(3-acetoxyethylthio)acetamide

74 (a) N-[4-(4-Piperidinomethyl-2-pyridyloxy)-cis-2-butenyl]-2-chloroacetamide 0.54 ml of triethylamine was added to a solution of 1.00 g of 4-(4-piperidinomethyl-2-pyridyloxy)-cis-2-butenylamine in 20 ml of ethyl acetate, and the resulting mixture was cooled. 0.31 ml of 2-chloroacetyl chloride were then added to the mixture. The reaction mixture was then stirred at room temperature for 1 hour, after which it was mixed with water, and the aqueous mixture was extracted with ethyl acetate. The extract was concentrated by evaporation under reduced pressure, and the residue was purified by column chromatography through silica gel, using a 1:19 by volume mixture of methanol and ethyl acetate as the eluent, to give 0.94 g (yield 73%) of the title compound as an oil.

Nuclear Magnetic Resonance Spectrum (CDCl$_3$), δ ppm: 1.37–1.50 (2H, multiplet); 1.50–1.64 (4H, multiplet); 2.30–2.43 (2H, multiplet); 2.30–2.43 (4H, multiplet); 3.41 (2H, singlet); 4.06 (2H, singlet); 4.11 (2H, triplet, J=6.6 Hz); 4.94 (2H, doublet, J=6.6 Hz); 5.62–5.75 (1H, multiplet); 5.84–5.97 (1H, multiplet); 6.69–6.92 (1H, broad); 6.74 (1H, singlet); 6.88 (1H, doublet, J=4.6 Hz); 8.06 (1H, doublet, J=4.6 Hz). Infrared Absorption Spectrum (CHCl$_3$), ν$_{max}$ cm$^{-1}$: 3420, 2920, 1665, 1610, 1525, 1400, 1285.

74(b) N-[4-(4-Piperidinomethyl-2-pyridyloxy)-cis-2-butenyl]-2-(acetylthio)acetamide A solution of 0.47 ml of thioacetic acid in 20 ml of tetrahydrofuran was added dropwise, whilst ice-cooling and in an atmosphere of nitrogen, to a suspension of 0.29 g of sodium hydride (as a 55% w/w dispersion in mineral oil) in 20 ml of tetrahydrofuran, and the resulting mixture was stirred at room temperature for 30 minutes. At the end of this time, a solution of 2.00 g of N-[4-(4-piperidinomethyl-2-pyridyloxy)-cis-2-butenyl]-2-chloroacetamide [prepared as described in step (a) above] in 20 ml of tetrahydrofuran was added dropwise to the mixture, whilst ice-cooling, after which it was stirred at room temperature for 30 minutes. The reaction mixture was then concentrated by evaporation under reduced pressure, the residue was mixed with water, and the resulting aqueous mixture was extracted with ethyl acetate. The extract was concentrated by evaporation under reduced pressure, and the concentrate was purified by column chromatography through silica gel, using a 1:19 by volume mixture of methanol and ethyl acetate as the eluent, to give 1.72 g (yield 77%) of the title compound as an oil.

Nuclear Magnetic Resonance Spectrum (CDCl$_3$), δ ppm: 1.39–1.50 (2H, multiplet); 1.50–1.67 (4H, multiplet); 2.32–2.43 (4H, multiplet); 2.41 (3H, singlet); 3.42 (2H, singlet); 3.57 (2H, singlet); 4.04 (2H, triplet, J=5.9 Hz); 4.93 (2H, triplet, J=6.6 Hz); 5.57–5.71 (1H, multiplet); 5.81–5.91 (1H, multiplet); 6.35–6.66 (1H, broad); 6.75 (1H, singlet); 6.90 (1H, doublet, J=5.3 Hz); 8.08 (1H, doublet, J=5.3 Hz). Infrared Absorption Spectrum (CHCl$_3$), ν$_{max}$ cm$^{-1}$: 3400, 2925, 1680, 1610, 1560, 1520, 1400.

74(c) N-[4-(4-Piperidinomethyl-2-pyridyloxy)-cis-2-butenyl]-2-(3-hydroxypropylthio)acetamide 5 ml of a methanolic solution containing 0.26 g of a 28% w/v sodium methoxide solution were added, whilst ice-cooling, to a solution of 0.50 g of N-[4-(4-piperidinomethyl-2-pyridyloxy)-cis-2-butenyl]-2-(acetylthio)acetamide [prepared as described in step (b) above] in 5 ml of methanol, and the resulting solution was stirred for 20 minutes. At the end of this time, a solution of 0.11 ml of 3-chloro-1-propanol in 5 ml of methanol, was added, and the reaction mixture was heated under reflux for 5 hours. The solvent was then removed by distillation under reduced pressure. The residue thus obtained was mixed with water, and the aqueous mixture was extracted with ethyl acetate. The extract was concentrated by evaporation under reduced pressure, and the residue was purified by column chromatography through silica gel, using a 1:9 by volume mixture of methanol and methylene chloride as the eluent, to give 0.42 g (yield 81%) of the title compound as an oil.

Nuclear Magnetic Resonance Spectrum (CDCl$_3$), δ ppm: 1.39–1.51 (2H, multiplet); 1.51–1.66 (4H, multiplet); 1.54–2.02 (4H, broad); 1.84 (2H, triplet of doublets, J=7.3 & 5.9 Hz); 2.32–2.45 (4H, multiplet); 2.68 (2H, triplet, J=7.3 Hz); 3.24 (2H, singlet); 3.41 (2H, singlet); 3.73 (2H, triplet, J=5.9 Hz); 4.07 (2H, doublet of doublets, J=6.6 & 5.9 Hz); 4.93 (2H, doublet, J=6.6 Hz); 5.61–5.78 (1H, multiplet); 5.82–5.94 (1H, multiplet); 6.76 (1H, singlet); 6.89 (1H, doublet, J=5.3 Hz); 7.70–7.25 (1H, broad); 8.06 (1H, doublet, J=5.3 Hz). Infrared Absorption Spectrum (CHCl$_3$), ν$_{max}$ cm$^{-1}$: 3375, 2950, 1660, 1610, 1560, 1520, 1420.

74(d) N-[4-(4-Piperidinomethyl-2-pyridyloxy)-cis-2-butenyl]-2-(3-acetoxypropylthio)acetamide Following a procedure similar to that described in Example 67(c), but using N-[4-(4-piperidinomethyl-2-pyridyloxy)-cis-2-butenyl]-2-(3-hydroxypropylthio)acetamide [prepared as described in step (c) above] and acetic anhydride as starting materials, in relative proportions similar to those used in that Example, the title compound was obtained in an 87% yield.

Nuclear Magnetic Resonance Spectrum (CDCl$_3$), δ ppm: 1.38–1.51 (2H, multiplet); 1.51–1.66 (4H, multiplet); 1.91 (2H, triplet of doublets, J=7.3 & 5.9 Hz); 2.05 (3H, singlet); 2.31–2.43 (4H, multiplet); 2.61 (2H, triplet, J=7.3 Hz); 3.23 (2H, singlet); 3.41 (2H, singlet); 4.03–4.20 (4H, multiplet); 4.94 (2H, doublet, J=6.6 Hz); 5.60–5.77 (1H, multiplet); 5.81–5.94 (1H, multiplet); 6.74 (1H, singlet); 6.89 (1H, doublet, J=5.3 Hz); 6.92–7.10 (1H, broad); 8.06 (1H, doublet, J=5.3 Hz). Infrared Absorption Spectrum (CHCl$_3$), ν$_{max}$ cm$^{-1}$: 3375, 2950, 1715, 1660, 1610, 1560, 1520, 1420.

The title compound, prepared as described above, was dissolved in ethyl acetate, and a 4N ethyl acetate solution of hydrogen chloride was added to the resulting solution. The crystals which precipitated were collected by filtration, to give the hydrochloride of the title compound, melting at 110°–124° C.

EXAMPLE 75

N-[4-(4-Dimethylaminomethyl-2-pyridyloxy)-cis-2-butenyl]-2-(2-acetoxyethylthio)acetamide

75(a) N-[4-(4-Dimethylaminomethyl-2-pyridyloxy)-cis-2-butenyl]-2-(2-hydroxyethylthio)acetamide Following a procedure similar to that described in Example 68, but using 4-(4-dimethylaminomethyl-2-pyridyloxy)-cis-2-butenylamine and 1,4-oxathian-2-one as starting materials, in relative proportions similar to those used in that Example, the title compound was obtained in a 53% yield.

Nuclear Magnetic Resonance Spectrum (CDCl$_3$), δ ppm: 1.61–2.27 (1H, broad singlet); 2.26 (6H, singlet); 2.77 (2H, triplet, J=5.9 Hz); 3.29 (2H, singlet); 3.40 (2H, singlet); 4.07 (2H, doublet of doublets, J=6.6 & 5.9 Hz); 4.95 (2H, doublet, J=6.6 Hz); 5.61–5.73 (1H, multiplet); 5.76–5.87 (1H, multiplet); 6.76 (1H, singlet); 6.89 (1H, doublet, J=5.3 Hz); 7.07–7.26 (1H, broad); 8.08 (1H, doublet, J=5.3 Hz). Infrared Absorption Spectrum (CHCl$_3$), $\nu_{max}$ cm$^{-1}$: 3400, 2975, 1660, 1610, 1560, 1520, 1420.

75(b) N-[4-(4-Dimethylaminomethyl-2-pyridyloxy)-cis-2-butenyl]-2-(2-acetoxyethylthio)acetamide Following a procedure similar to that described in Example 67(c), but using N-[4-(4-dimethylaminomethyl-2-pyridyloxy)-cis-2-butenyl]-2-(2-hydroxyethylthio)acetamide [prepared as described in step (a) above] and acetic anhydride as starting materials, in relative proportions similar to those used in that Example, the title compound was obtained in a 58% yield.

Nuclear Magnetic Resonance Spectrum (CDCl$_3$), δ ppm: 2.09 (3H, singlet); 2.26 (6H, singlet); 2.81 (2H, triplet, J=6.6 Hz); 3.30 (2H, singlet); 3.40 (2H, singlet); 4.10 (2H, doublet of doublets, J=6.6 & 5.9 Hz); 4.26 (2H, triplet, J=6.6 Hz); 4.96 (2H, doublet, J=6.6 Hz); 5.62–5.75 (1H, multiplet); 5.82–5.96 (1H, multiplet); 6.73 (1H, singlet); 6.89 (1H, doublet, J=5.3 Hz); 6.90–7.13 (1H, broad); 8.10 (1H, doublet, J=5.3 Hz). Infrared Absorption Spectrum (CHCl$_3$), $\nu_{max}$ cm$^{-1}$: 3375, 2950, 2800, 1740, 1660, 1610, 1560, 1510, 1400.

EXAMPLE 76

N-{4-[4-(1-Pyrrolidinylmethyl)-2-pyridyloxy]-cis-2-butenyl}-2-(2-acetoxyethylthio)acetamide Following a procedure similar to that described in Example 68, but using 4-[4-(1-pyrrolidinylmethyl)-2-pyridyloxy]-cis-2-butenylamine and 1,4-oxathian-2-one as starting materials, in relative proportions similar to those used in that Example, N-{4-[4-(1-pyrrolidinylmethyl)-2-pyridyloxy]-cis-2-butenyl}-2-(2-hydroxyethylthio)acetamide was obtained. This product was reacted with acetic anhydride in the same manner and same relative proportions as described in Example 67(c), to give the title compound in a 42% yield.

Nuclear Magnetic Resonance Spectrum (CDCl$_3$), δ ppm: 1.71–1.84 (4H, multiplet); 2.07 (3H, singlet); 2.46–2.57 (4H, multiplet); 2.79 (2H, triplet, J=6.3 Hz); 3.28 (2H, singlet); 3.58 (2H, singlet); 4.08 (2H, triplet, J=6.6 Hz); 4.24 (2H, triplet, J=6.3 Hz); 4.94 (2H, doublet, J=6.6 Hz); 5.61–5.73 (1H, multiplet); 5.81–5.94 (1H, multiplet); 6.74 (1H, singlet); 6.90 (1H, doublet, J=5.3 Hz); 6.90–7.09 (1H, broad); 8.07 (1H, doublet, J=5.3 Hz). Infrared Absorption Spectrum (CHCl$_3$), $\nu_{max}$ cm$^{-1}$: 3400, 2950, 2800, 1740, 1660, 1610, 1560, 1520, 1420.

EXAMPLE 77

N-[4-(4-Piperidinomethyl-2-pyridyloxy)-cis-2-butenyl]-2-(2-acetoxyethylsulfinyl)acetamide 77 µl of methanesulfonic acid was added to a solution of 0.50 g of N-[4-(4-piperidinomethyl-2-pyridyloxy)-cis-2-butenyl]-2-(2-acetoxyethylthio)acetamide (prepared as described in Example 2) in 5.5 ml of 1,2-dichloroethane, and the resulting mixture was cooled to −10° C. 0.28 g of 3-chloroperoxybenzoic acid (purity: 80%) was then added, and the reaction mixture was stirred, whilst keeping the temperature in the range from −10° C. to −5° C., for 2 hours. At the end of this time, it was washed with a 10% w/v aqueous solution of sodium hydrogensulfite, with a saturated aqueous solution of sodium hydrogencarbonate and with a saturated aqueous solution of sodium chloride, in that order. The solvent was then removed by distillation under reduced pressure, and the resulting residue was purified by column chromatography through silica gel, using a 1:9 by volume mixture of ethanol and chloroform as the eluent, to give 0.38 g (yield 73%) of the title compound as an oil.

Nuclear Magnetic Resonance Spectrum (CDCl$_3$), δ ppm: 1.37–1.49 (2H, multiplet); 1.49–1.64 (4H, multiplet); 2.09 (3H, singlet); 2.31–2.42 (4H, multiplet); 3.12–3.18 (2H, multiplet); 3.39 (1H, doublet, J=13.2 Hz); 3.41 (2H, singlet); 3.73 (1H, doublet, J=13.2 Hz); 4.10 (2H, triplet, J=5.9 Hz); 4.38–4.60 (2H, multiplet); 4.93 (2H, doublet, J=5.3 Hz); 5.61–5.73 (1H, multiplet); 5.79–5.90 (1H, multiplet); 6.73 (1H, singlet); 6.88 (1H, doublet, J=5.3 Hz); 7.05–7.24 (1H, broad); 8.06 (1H, doublet, J=5.3 Hz). Infrared Absorption Spectrum (CHCl$_3$), $\nu_{max}$ cm$^{-1}$: 3400, 2950, 1740, 1670, 1610, 1560, 1410, 1310, 1220.

EXAMPLE 78

N-[4-(4-Piperidinomethyl-2-pyridyloxy)-cis-2-butenyl]-2-(2-acetoxyethylsulfonyl)acetamide 72 µl of methanesulfonic acid were added to a solution of 0.47 g of N-[4-(4-piperidinomethyl-2-pyridyloxy)-cis-2-butenyl]-2-(2-acetoxyethylthio)acetamide (prepared as described in Example 2) in 5.5 ml of 1,2-dichloroethane. The resulting mixture was cooled to −10° C. 0.51 g of 3-chloroperoxybenzoic acid (purity: was added to the reaction mixture, which was then stirred at a temperature in the range from −10° C. to −5° C. for 2 hours. At the end of this time, the reaction mixture was washed with a 10% w/v aqueous solution of sodium hydrogensulfite, with a saturated aqueous solution of sodium hydrogencarbonate and with a saturated aqueous solution of sodium chloride, in that order, and then the solvent was removed by distillation under reduced pressure. The residue was purified by column chromatography through silica gel, using a 1:9 by volume mixture of ethanol and chloroform as the eluent, to give 0.40 g (yield 40%) of the title compound as an oil.

Nuclear Magnetic Resonance Spectrum (CDCl$_3$), δ ppm: 1.37–1.50 (2H, multiplet); 1.50–1.70 (4H, multiplet); 2.11 (3H, singlet); 2.30–2.41 (4H, multiplet); 3.41 (2H, singlet); 3.55 (2H, triplet, J=5.6 Hz); 3.93 (2H, singlet); 4.09 (2H, triplet, J=5,6 Hz); 4.93 (2H, doublet, J=5.9 Hz); 5.61–5.73 (1H, multiplet); 5.80–5.93 (1H, multiplet); 6.75 (1H, singlet); 6.90 (1H, doublet, J=5.3 Hz); 7.32–7.43 (1H, broad); 8.06 (1H, doublet, J=5.3 Hz). Infrared Absorption Spectrum (CHCl$_3$) $\nu_{max}$ cm$^{-1}$: 3300, 2950, 1740, 1680, 1610, 1560, 1400, 1320.

EXAMPLE 79

N-[4-(4-Piperidinomethyl-2-pyridyloxy)-cis-2-butenyl]-2-[2-(3,3-dimethylbutyryloxy)ethylthio]acetamide Following a procedure similar to that described in Example 7, but using N-[4-(4-piperidinomethyl-2-pyridyloxy)-cis-2-butenyl]-2-(2-hydroxyethylthio)acetamide (prepared as described in Example 1) and 3,3-dimethylbutyryl chloride as starting materials, in relative proportions similar to those used in that Example, the title compound was obtained in an 83% yield.

Nuclear Magnetic Resonance Spectrum (CDCl$_3$), δ ppm: 1.02 (9H, singlet); 1.37–1.50 (2H, multiplet); 1.50–1.65 (4H, multiplet); 2.21 (2H, singlet); 2.31–2.43 (4H, multiplet); 2.79 (2H, triplet, J=6.6 Hz); 3.28 (2H, singlet); 3.41 (2H, singlet); 4.08 (2H, triplet, J=5.9 Hz); 4.23 (2H, triplet, J=6.6 Hz); 4.94 (2H, doublet, J=5.9 Hz); 5.60–5.72 (1H, multiplet); 5.81–5.93 (1H, multiplet); 6.73 (1H, singlet); 6.88 (1H, doublet, J=5.3 Hz); 6.92–7.10 (1H, broad); 8.06 (1H, doublet, J=5.3 Hz). Infrared Absorption Spectrum (CHCl$_3$), $\nu_{max}$ cm$^{-1}$: 3375, 2925, 1730, 1660, 1610, 1560, 1520, 1400.

The title compound, prepared as described above, was dissolved in ethyl acetate and treated with an equivalent amount of a 4N solution of hydrogen chloride in ethyl acetate to give the hydrochloride of the title compound, melting at 106°–109° C.

EXAMPLE 80

N-[4-(4-Piperidinomethyl-2-pyridyloxy)-cis-2-butenyl]-2-[2-(2-methylpropionyloxy)ethylthio]acetamide Following a procedure similar to that described in Example 7, but using N-[4-(4-piperidinomethyl-2-pyridyloxy)-cis-2-butenyl]-2-(2-hydroxyethylthio)acetamide (prepared as described in Example 1) and 2-methylpropionyl chloride as starting materials, in relative proportions similar to those used in that Example, the title compound was obtained in a 73% yield.

Nuclear Magnetic Resonance Spectrum (CDCl$_3$), δ ppm: 1.17 (6H, doublet, J=7.3 Hz); 1.37–1.52 (2H, multiplet); 1.50–1.66 (4H, multiplet); 2.31–2.44 (4H, multiplet); 2.56 (1H, septet, J=7.3 Hz); 2.79 (2H, triplet, J=6.6 Hz); 3.28 (2H, singlet); 3.42 (2H, singlet); 4.08 (2H, triplet, J=6.3 Hz); 4.24 (2H, triplet, J=6.6 Hz); 4.94 (2H, doublet, J=6.6 Hz); 5.60–5.74 (1H, multiplet); 5.81–5.93 (1H, multiplet); 6.73 (1H, singlet); 6.88 (1H, doublet, J=5.3 Hz); 6.93–7.07 (1H, broad); 8.06 (1H, doublet, J=5.3 Hz). Infrared Absorption Spectrum (CHCl$_3$), $\nu_{max}$ cm$^{-1}$: 3375, 2925, 1730, 1660, 1610, 1560, 1520, 1400.

The title compound, prepared as described above, was dissolved in ethyl acetate and treated with an equimolar amount of a 4N solution of hydrogen chloride in ethyl acetate to give the hydrochloride of the title compound, melting at 93°–96° C.

EXAMPLE 81

N-[4-(4-Piperidinomethyl-2-pyridyloxy)-cis-2-butenyl]-2-[2-(2,2-dimethylpropionyloxy)ethylthio]acetamide Following a procedure similar to that described in Example 7, but using N-[4-(4-piperidinomethyl-2-pyridyloxy)-cis-2-butenyl]-2-(2-hydroxyethylthio)acetamide (prepared as described in Example 1) and 2,2-dimethylpropionyl chloride as starting materials, in relative proportions similar to those used in that Example, the title compound was obtained in a 63% yield.

Nuclear Magnetic Resonance Spectrum (CDCl$_3$), δ ppm: 1.20 (9H, singlet); 1.38–1.52 (2H, multiplet); 1.52–1.69 (4H, multiplet); 2.28–2.53 (4H, multiplet); 2.79 (2H, triplet, J=6.6 Hz); 3.28 (2H, singlet); 3.45 (2H, singlet); 4.09 (2H, triplet, J=6.6 Hz); 4.22 (2H, triplet, J=6.6 Hz); 4.94 (2H, doublet, J=6.6 Hz); 5.64–5.73 (1H, multiplet); 5.82–5.93 (1H, multiplet); 6.75 (1H, singlet); 6.91 (1H, doublet, J=5.1 Hz); 6.93–7.09 (1H, broad); 8.07 (1H, doublet, J=5.1 Hz). Infrared Absorption Spectrum (CHCl$_3$), $\nu_{max}$ cm$^{-1}$: 3375, 2925, 1720, 1660, 1610, 1540, 1520, 1480, 1400.

The title compound, prepared as described above, was dissolved in ethyl acetate and treated with an equimolar amount of a 4N solution of hydrogen chloride in ethyl acetate to give the hydrochloride of the title compound, melting at 93°–97° C.

EXAMPLE 82

N-[4-(4-Piperidinomethyl-2-pyridyloxy)-cis-2-butenyl]-2-(2-butyryloxyethylthio)acetamide Following a procedure similar to that described in Example 7, but using N-[4-(4-piperidinomethyl-2-pyridyloxy)-cis-2-butenyl]-2-(2-hydroxyethylthio)acetamide (prepared as described in Example 1) and butyryl chloride as starting materials, in relative proportions similar to those used in that Example, the title compound was obtained in an 88% yield.

Nuclear Magnetic Resonance Spectrum (CDCl$_3$), δ ppm: 0.94 (3H, triplet, J=7.3 Hz); 1.34–1.78 (8H, multiplet); 2.29–2.39 (4H, multiplet); 2.30 (2H, triplet, J=7.3 Hz); 2.79 (2H, triplet, J=6.6 Hz); 3.28 (2H, singlet); 3.41 (2H, singlet); 4.08 (2H, doublet of doublets, J=7.3 & 6.6 Hz); 4.24 (2H, triplet, J=6.6 Hz); 4.93 (2H, doublet, J=7.9 Hz); 5.60–5.78 (1H, multiplet); 5.81–5.94 (1H, multiplet); 6.73 (1H, singlet); 6.89 (1H, doublet, J=5.3 Hz); 6.92–7.10 (1H, broad); 8.07 (1H, doublet, J=5.3 Hz). Infrared Absorption Spectrum (CHCl$_3$), $\nu_{max}$ cm$^{-1}$: 3400, 2950, 1740, 1660, 1610, 1560, 1520, 1420.

EXAMPLE 83

N-[4-(4-Piperidinomethyl-2-pyridyloxy)-cis-2-butenyl]-2-(2-hydroxyethylsulfinyl)acetamide Following a procedure similar to that described in Example 77, but using N-[4-(4-piperidinomethyl-2-pyridyloxy)-cis-2-butenyl]-2-(2-hydroxyethylthio)acetamide (prepared as described in Example 1) as a starting material, in a relative proportion similar to that used in that Example, the title compound was obtained in a 63% yield.

Nuclear Magnetic Resonance Spectrum (CDCl$_3$), δ ppm: 1.34–1.50 (2H, multiplet); 1.50–1.64 (4H, multiplet); 1.76–1.98 (1H, broad); 2.28–2.45 (4H, multiplet); 3.10 (2H, triplet, J=5.9 Hz); 3.41 (2H, singlet); 3.52 (2H, doublet, J=13.9 Hz); 3.79 (1H, doublet, J=13.9 Hz); 4.04–4.16 (4H, multiplet); 4.92 (2H, doublet, J=6.6 Hz); 5.65–5.77 (1H, multiplet); 5.82–5.93 (1H, multiplet); 6.75 (1H, singlet); 6.88 (1H, doublet, J=5.3 Hz); 7.15–7.34 (1H, broad); 8.06 (1H, doublet, J=5.3 Hz). Infrared Absorption Spectrum (CHCl$_3$), $\nu_{max}$ cm$^{-1}$: 3300, 2925, 1730, 1670, 1610, 1560, 1420, 1400.

The title compound, prepared as described above, was dissolved in ethyl acetate and treated with an equimolar amount of a 4N solution of hydrogen chloride in ethyl acetate to give the hydrochloride of the title compound, melting at 111°–114° C.

EXAMPLE 84

N-[4-(4-Piperidinomethyl-2-pyridyloxy)-cis-2-butenyl]-2-(2-propionyloxyethylsulfinyl)acetamide Following a procedure similar to that described in Example 77, but using N-[4-(4-piperidinomethyl-2-pyridyloxy)-cis-2-butenyl]-2-(2-propionyloxyethylthio)acetamide (prepared as described in Example 7) as a starting material, in a relative proportion similar to that used in that Example, the title compound was obtained in a 73% yield.

Nuclear Magnetic Resonance Spectrum (CDCl$_3$), δ ppm: 1.15 (3H, triplet, J=7.3 Hz); 1.34–1.50 (2H, multiplet); 1.50–1.62 (4H, multiplet); 2.28–2.42 (4H, multiplet); 2.37 (2H, quartet, J=7.3 Hz); 3.15 (2H, triplet, J=6.6 Hz); 3.38 (1H, doublet, J=14.2 Hz); 3.41 (2H, singlet); 3.73 (1H, doublet, J=14.2 Hz); 4.10 (2H, triplet, J=6.6 Hz); 4.39–4.61 (2H, multiplet); 4.93 (2H, doublet, J=6.6 Hz); 5.60–5.72 (1H, multiplet); 5.78–5.91 (1H, multiplet); 6.73 (1H, singlet); 6.88 (1H, doublet, J=5.3 Hz); 7.04–7.23 (1H, broad); 8.06 (1H, doublet, J=5.3 Hz). Infrared Absorption Spectrum (CHCl$_3$), $v_{max}$ cm$^{-1}$: 3300, 2925, 1740, 1670, 1610, 1560, 1420, 1400.

The title compound, prepared as described above, was dissolved in ethyl acetate and treated with an equimolar amount of a 4N solution of hydrogen chloride in ethyl acetate to give the hydrochloride of the title compound, melting at 77°–83° C.

EXAMPLE 85

N-[4-(4-Piperidinomethyl-2-pyridyloxy)-cis-2-butenyl]-4-(4-pyrimidinylthio)butyramide

85(a) N-[4-(4-Piperidinomethyl-2-pyridyloxy)-cis-2-butenyl]-4-(acetylthio)butyramide 0.50 g of sodium hydride (as a 55% w/w dispersion in mineral oil) was added to 80 ml of dimethylformamide under an atmosphere of nitrogen gas, and then 10 ml of a dimethylformamide solution containing 0.81 ml of thioacetic acid was added to the resulting mixture. The mixture was then stirred at room temperature for 30 minutes. At the end of this time, 30 ml of a dimethylformamide solution containing 3.79 g of N-[4-(4-piperidinomethyl-2-pyridyloxy)-cis-2-butenyl]-4-chlorobutyramide (prepared as described in Preparation 2) were added to the mixture, and the mixture was stirred at room temperature for 2 hours. Ethyl acetate was then added to the reaction mixture, which was then washed with a saturated aqueous solution of sodium hydrogencarbonate and water. The solvent was removed by distillation under reduced pressure, and the residue was purified by column chromatography through silica gel, using a 1:19 by volume mixture of methanol and ethyl acetate as the eluent, to give 5.04 g (a quantitative yield) of the title compound as an oil.

Nuclear Magnetic Resonance Spectrum (CDCl$_3$), δ ppm: 1.37–1.50 (2H, multiplet); 1.50 1.63 (4H, multiplet); 1.93 (2H, quintet, J=7.3 Hz); 2.26 (2H, triplet, J=7.3 Hz); 2.29–2.42 (4H, multiplet); 2.91 (2H, triplet, J=7.3 Hz); 3.41 (2H, singlet); 4.03 (2H, triplet, J=5,9 Hz); 4.93 (2H, triplet, J=5.9 Hz); 5.61–5.75 (1H, multiplet); 5.78–5.89 (1H, multiplet); 6.09–6.34 (1H, broad); 6.73 (1H, singlet); 6.89 (1H, doublet, J=5.3 Hz); 8.04 (1H, doublet, J=5.3 Hz). Infrared Absorption Spectrum (CHCl$_3$) $v_{max}$ cm$^{-1}$: 3450, 3350, 2925, 2800, 1670, 1610, 1560, 1520, 1480, 1420, 1400.

85(b) N-[4-(4-Piperidinomethyl-2-pyridyloxy)-cis-2-butenyl]-4-(4-pyrimidinylthio)butyramide A solution of 1.00 g of N-[4-(4-piperidinomethyl-2-pyridyloxy)-cis-2-butenyl]-4-(acetylthio)butyramide [prepared as described in step (a) above] in 10 ml of methanol was added to a mixture of 0.48 g of 28% w/v methanolic sodium methoxide and 5 ml of methanol, whilst ice-cooling, and the mixture was stirred at the same temperature for 20 minutes. At the end of this time, 0.28 g of 4-chloropyrimidine was added to the mixture and the mixture was heated under reflux for 2 hours. The solvent was then removed by evaporation under reduced pressure, and water was added to the resulting residue, which was then extracted with ethyl acetate. The solvent was removed from the extract by distillation under reduced pressure, and the residue was purified by column chromatography through silica gel, using a 1:9 by volume mixture of ethanol and chloroform as the eluent, to give 0.65 g (yield 60%) of the title compound as an oil.

Nuclear Magnetic Resonance Spectrum (CDCl$_3$), δ ppm: 1.36–1.50 (2H, multiplet); 1.50–1.65 (4H, multiplet); 2.06 (2H, quintet, J=7.3 Hz); 2.29–2.43 (4H, multiplet); 2.37 (2H, triplet, J=7.3 Hz); 3.24 (2H, triplet, J=7.3 Hz); 3.41 (2H, singlet); 4.05 (2H, triplet, J=5,9 Hz); 4.93 (2H, doublet, J=6.6 Hz); 5.61–5.76 (1H, multiplet); 5.78–5.90 (1H, multiplet); 6.22–6.44 (1H, broad); 6.73 (1H, singlet); 6.88 (1H, doublet, J=5.3 Hz); 7.17 (2H, doublet, J=5.3 Hz); 8.03 (1H, doublet, J=5.3 Hz); 8.32 (1H, doublet, J=5.3 Hz); 8.91 (1H, singlet). Infrared Absorption Spectrum (CHCl$_3$), $v_{max}$ cm$^{-}$: 3450, 3300, 2925, 1660, 1610, 1570, 1520, 1440, 1420, 1380.

EXAMPLE 86

N-[4-(4-Dimethylaminomethyl-2-pyridyloxy)-cis-2-butenyl]pyrazole-2-carboxamide

Following a procedure similar to that described in Example 13, but using 4-(4-dimethylaminomethyl-2-pyridyloxy)-cis-2-butenylamine and 4-pyrazolecarboxylic acid as starting materials, in relative proportions similar to those used in that Example, the title compound was obtained as an oil in a 65% yield.

Nuclear Magnetic Resonance Spectrum (CDCl$_3$), δ ppm: 2.27 (6H, singlet); 3.40 (2H, singlet); 4.22 (2H, triplet, J=5.9 Hz); 4.99 (2H, doublet, J=6.6 Hz); 5.71–5.94 (2H, multiplet); 6.47 (1H, broad singlet); 6.74 (1H, singlet); 6.89 (1H, doublet, J=5.3 Hz); 7.97 (2H, singlet); 8.07 (1H, doublet, J=5.3 Hz). Infrared Absorption Spectrum (CHCl$_3$), $v_{max}$ cm$^{-1}$: 3450, 3170, 2980, 2940, 1640, 1615, 1565, 1510, 1415, 1400, 1290.

EXAMPLE 87

N-[4-(4-Piperidinomethyl-2-pyridyloxy)-cis-2-butenyl]-3,5-dimethylpyrrole-2-carboxamide Following a procedure similar to that described in Example 13, but using 4-(4-piperidinomethyl-2-pyridyloxy)-cis-2-butenylamine and 3,5-dimethylpyrrole-2-carboxylic acid as starting materials, in relative proportions similar to those used in that Example, the title compound was obtained as crystals, melting 140°–141° C., in a 58% yield.

Nuclear Magnetic Resonance Spectrum (CDCl$_3$), δ ppm: 1.37–1.48 (2H, multiplet); 1.50–1.61 (4H, multiplet); 2.23 (3H, singlet); 2.26 (2H, singlet); 2.30–2.42 (4H, multiplet);

3.40 (2H, singlet); 4.22 (2H, triplet, J=5.6 Hz); 4.96 (2H, doublet, J=6.6 Hz); 5.66–5.79 (3H, multiplet); 5.82–5.92 (1H, multiplet); 6.73 (1H, singlet); 6.87 (1H, doublet, J=5.3 Hz); 8.04 (1H, doublet, J=5.3 Hz); 9.13–9.27 (1H, broad). Infrared Absorption Spectrum (KBr), $v_{max}$ cm$^{-1}$: 3249, 1612, 1525, 1410, 1272, 1035, 826.

EXAMPLE 88

N-[4-(4-Piperidinomethyl-2-pyridyloxy)-cis-2-butenyl]-2-methylfuran-3-carboxamide Following a procedure similar to that described in Example 13, but using 4-(4-piperidinomethyl-2-pyridyloxy)-cis-2-butenylamine and 2-methylfuran-3-carboxylic acid as starting materials, in relative proportions similar to those used in that Example, the title compound was obtained as an oil in a 77% yield.

Nuclear Magnetic Resonance Spectrum (CDCl$_3$), δ ppm: 1.39–1.51 (2H, multiplet); 1.53–1.66 (4H, multiplet); 2.31–2.45 (4H, multiplet); 2.58 (3H, singlet); 3.42 (2H, singlet); 4.17 (2H, triplet, J=6.4 Hz); 4.97 (2H, doublet, J=6.4 Hz); 5.71–5.81 (1H, multiplet); 5.83–5.93 (1H, multiplet); 6.01–6.18 (1H, broad); 6.41 (1H, doublet, J=2.2 Hz); 6.75 (1H, singlet); 6.90 (1H, doublet, J=5.4 Hz); 7.23 (1H, doublet, J=2.2 Hz); 8.03 (1H, doublet, J=5.4 Hz). Infrared Absorption Spectrum (liquid film), $v_{max}$ cm$^{-1}$: 3325, 2936, 1636, 1611, 1561, 1523, 1420, 1402, 1301, 1290, 1039.

The title compound, prepared as described above, was dissolved in ethyl acetate and treated with an equimolar amount of a 4N solution of hydrogen chloride in ethyl acetate to give the hydrochloride of the title compound, melting at 258°–261° C. (with decomposition).

EXAMPLE 89

N-[4-(4-Piperidinomethyl-2-pyridyloxy)-cis-2-butenyl]-4-(2-pyrimidinylsulfinyl)butyramide Following a procedure similar to that described in Example 77, but using N-[4-(4-piperidinomethyl-2-pyridyloxy)-cis-2-butenyl]-4-(2-pyrimidinylthio)butyramide (prepared as described in Example 34) as a starting material, in a relative proportion similar to that used in that Example, the title compound was obtained as an oil in a 55% yield.

Nuclear Magnetic Resonance Spectrum (CDCl$_3$), δ ppm: 1.37–1.50 (2H, multiplet); 1.52–1.63 (4H, multiplet); 1.99–2.12 (1H, multiplet); 2.20–2.45 (7H, multiplet); 3.10–3.32 (2H, multiplet); 3.41 (2H, singlet); 4.01 (2H, doublet, J=6.3 Hz); 4.91 (2H, doublet, J=6.6 Hz); 5.61–5.71 (1H, multiplet); 5.78–5.87 (1H, multiplet); 6.32 (1H, broad singlet); 6.73 (1H, singlet); 6.89 (1H, doublet, J=5.3 Hz); 7.41 (1H, triplet, J=4.6 Hz); 8.03 (1H, doublet, J=5.3 Hz); 8.89 (2H, doublet, J=4.6 Hz). Infrared Absorption Spectrum (liquid film), $v_{max}$ cm$^{-1}$: 3302, 2936, 1657, 1612, 1561, 1420, 1403, 1384, 1312, 1300, 1289, 1062, 1040, 753.

EXAMPLE 90

N-[4-(4-Piperidinomethyl-2-pyridyloxy)-cis-2-butenyl]-2-(2-propionyloxyethylthio)acetamide Following a procedure similar to that described in Example 2, but using N-[4-(4-piperidinomethyl-2-pyridyloxy)-cis-2-butenyl]-2-(2-hydroxyethylthio)acetamide (prepared as described in Example 1) and propionic anhydride as starting materials, in relative proportions similar to those used in that Example, the title compound was obtained in a 90% yield.

The nuclear magnetic resonance spectrum and the infrared spectrum of the title compound are identical with those of the compound prepared as described in Example 7.

PREPARATION 1

N-[4-(4-Piperidinomethyl-2-pyridyloxy)-cis-2-butenyl]-2-chloroacetamide 1.00 g of 4-(4-piperidinomethyl-2-pyridyloxy)-cis-2-butenylamine was dissolved in 20 ml of ethyl acetate. 0.54 ml of triethylamine was added to the solution, and the resulting mixture was cooled in an ice bath. 0.31 ml of 2-chloroacetyl chloride was added, and the mixture was stirred for 1 hour at room temperature. At the end of this time, water was added, and the reaction mixture was extracted with ethyl acetate. The extract was condensed by evaporation under reduced pressure, and the residue was purified by silica gel chromatography, eluted with a 1:19 by volume mixture of methanol and ethyl acetate, to give 0.94 g (yield 73%) of the title compound as an oil.

Nuclear Magnetic Resonance Spectrum (CDCl$_3$), δ ppm: 1.37–1.50 (2H, multiplet); 1.50–1.64 (4H, multiplet); 2.30–2.43 (2H, multiplet); 3.41 (2H, singlet); 4.06 (2H, singlet); 4.11 (2H, triplet, J=6.6 Hz); 4.94 (2H, doublet, J=6.6 Hz); 5.62–5.75 (1H, multiplet); 5.84–5.97 (1H, multiplet); 6.69–6.92 (1H, broad); 6.74 (1H, singlet); 6.88 (1H, doublet, J=4.6 Hz); 8.06 (1H, doublet, J=4.6 Hz). Infrared Absorption Spectrum (CHCl$_3$), $v_{max}$ cm$^{-1}$: 3420, 2920, 1665, 1610, 1525, 1400, 1285.

PREPARATION 2

N-[4-(4-Piperidinomethyl-2-pyridyloxy)-cis-2-butenyl]-4-chlorobutyramide

Following a procedure similar to that described in Preparation 1, but using 4-(4-piperidinomethyl-2-pyridyloxy)-cis-2-butenylamine and 4-chlorobutyryl chloride as starting materials, in relative proportions similar to those used in that Preparation, the title compound was obtained at a yield of 73%.

Nuclear Magnetic Resonance Spectrum (CDCl$_3$), δ ppm: 1.35–1.53 (2H, multiplet); 1.53–1.78 (4H, multiplet); 2.06–2.17 (2H, multiplet); 2.33–2.41 (2H, multiplet); 2.41–2.52 (4H, multiplet); 3.50 (2H, singlet); 3.61 (2H, triplet, J=6.1 Hz); 4.04 (2H, triplet, J=6.1 Hz); 4.93 (2H, doublet, J=6.8 Hz); 5.62–5.73 (1H, multiplet); 5.77–5.89 (1H, multiplet); 6.07 (1H, doublet, J=4.9 Hz); 6.08–6.26 (1H, broad); 6.78 (1H, singlet); 6.95 (1H, doublet, J=4.9 Hz). Infrared Absorption Spectrum (CHCl$_3$), $v_{max}$ cm$^{-1}$: 3440, 2920, 1660, 1610, 1415, 1295.

PREPARATION 3

N-[4-(4-Piperidinomethyl-2-pyridyloxy)-cis-2-butenyl]-3-mercaptopropionamide

3(a) N-[4-(4-Piperidinomethyl-2-pyridyloxy]-cis-2-butenyl]-3-(acetylthio)propionamide 1.00 g of 3-(acetylthio)propionic acid, 1.39 g of dicyclohexyl carbodiimide, 1.05 g of 1-hydroxybenzotriazole and 1.76 g of 4-(4-piperidinomethyl-2-pyridyloxy)-cis-2-butenylamine were added to 45 ml of dimethylformamide, and the solution was stirred for 5 hours at room temperature. At the end of this time, ethyl acetate was added to the reaction mixture, insoluble matter was filtered off, and the filtrate was washed with a saturated aqueous solution of sodium hydrogencarbonate and then with water. The reaction mixture was then condensed by evaporation under reduced pressure, and the resulting residue was subjected to silica gel chromatography, eluted with a 1:19 by volume mixture of methanol and ethyl acetate, to give 1.27 g (yield 48%) of the title compound as an oil.

Nuclear Magnetic Resonance Spectrum (CDCl$_3$), δ ppm: 1.30–1.50 (2H, multiplet); 1.50–1.70 (4H, multiplet); 2.28–2.44 (4H, multiplet); 2.32 (3H, singlet); 2.50 (2H, triplet, J=6.9 Hz); 3.16 (2H, triplet, J=6.9 Hz); 3.41 (2H, singlet); 4.04 (2H, triplet, J=6.3 Hz); 4.93 (2H, doublet, J=6.6 Hz); 5.62–5.74 (1H, multiplet); 5.78–5.90 (1H, multiplet); 6.73 (1H, singlet); 6.89 (1H, doublet, J=5.3 Hz); 8.03 (1H, doublet, J=5.3 Hz). Infrared Absorption Spectrum (CHCl$_3$), ν$_{max}$ cm$^{-1}$: 3440, 2930, 1675, 1610, 1415, 1400, 1310, 1295, 1285, 1140.

3(b) N-[4-(4-Piperidinomethyl-2-pyridyloxy)-cis-2-butenyl]3-(mercapto)propionamide 1.0 g of N-[4-(4-piperidinomethyl-2-pyridyloxy)-cis-2-butenyl]-3-(acetylthio)propionamide [prepared as described in step (a) above] and 0.49 g of a 28% w/v methanolic solution of sodium methoxide were added to 20 ml of methanol, whilst ice-cooling, and the mixture was stirred at the same temperature for 20 minutes. At the end of this time, 0.15 ml of acetic acid was added, and the solvent was removed by distillation under reduced pressure. The residue was dissolved in ethyl acetate, washed with water and condensed by evaporation under reduced pressure, to obtain 0.76 g (yield 85%) of the title compound as an oil.

Nuclear Magnetic Resonance Spectrum (CDCl$_3$), δ ppm: 1.37–1.50 (2H, multiplet); 1.46–1.96 (1H, broad); 1.50–1.65 (4H, multiplet); 2.27–2.43 (4H, multiplet); 2.51 (2H, triplet, J=6.9 Hz); 2.83 (2H, doublet of triplets, J=6.9 & 7.9 Hz); 3.41 (2H, singlet); 4.06 (2H, triplet, J=5.9 Hz); 4.94 (2H, doublet, J=6.6 Hz); 5.63–5.77 (1H, multiplet); 5.79–5.90 (1H, multiplet); 6.74 (1H, singlet); 6.89 (1H, doublet, J=5.3 Hz); 8.04 (1H, doublet, J=5.3 Hz). Infrared Absorption Spectrum (CHCl$_3$), ν$_{max}$ cm$^{-1}$: 3450, 2940, 1665, 1612, 1418, 1400, 1300, 1290.

PREPARATION 4

Ethyl 4-Hydroxy-3-isoxazolecarboxylate 144 g of urea were added to 1 liter of a dimethylformamide solution containing 72 g of ethyl 4-bromo-2-hydroxyimino-3-oxobutyrate. The reaction solution was heated for 15 minutes at 100° C. and then cooled, after which water was added to the reaction solution, and the mixture was extracted with ethyl acetate. The extract was washed with dilute aqueous hydrochloric acid and with a saturated aqueous solution of sodium chloride, in that order, after which it was dried over anhydrous sodium sulfate. The solvent was then removed by distillation under reduced pressure, and a 1:1 by volume mixture of ethyl acetate and hexane was added to the residue, to remove insoluble materials. The solution thus obtained was purified by silica gel chromatography, eluted with a 1:4 by volume mixture of ethyl acetate and hexane, to give 19 g of the title compound, melting at 59°–60° C. (after recrystallization from a mixture of ethyl acetate and hexane).

Nuclear Magnetic Resonance Spectrum (CDCl$_3$), δ ppm: 1.42 (3H, triplet, J=8.0 Hz); 4.48 (2H, quartet, J=8.0 Hz); 6.72 (1H, broad); 8.32 (1H, singlet). Infrared Absorption Spectrum (KBr), ν$_{max}$ cm$^{-1}$: 3420, 1718, 1140.

We claim:

1. A compound of formula (I):

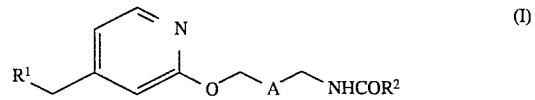

wherein:

R$^1$ represents
  a cyclic amino group having from 3 to 7 ring atoms, of which from 1 to 3 are nitrogen atoms, 0 or 1 is an oxygen atom or a sulfur atom, and the remainder are carbon atoms, or
  a dialkylamino group in which each alkyl group is independently selected from the group consisting of alkyl groups having from 1 to 4 carbon atoms;

R$^2$ represents
  a group of formula —NHCHR$^3$R$^4$, wherein
    R$^3$ and R$^4$ are independently selected from the group consisting of alkyl groups having from 1 to 6 carbon atoms, aryl groups as defined below and aralkyl groups as defined below, or R$^3$ and R$^4$ together with the carbon atom to which they are attached, represent a cycloalkyl group having from 3 to 8 ring carbon atoms, which group is unsubstituted or is substituted by at least one substituent selected from the group consisting of substituents α,
  an aromatic heterocyclic group having 5 ring atoms, of which from 1 to 3 are hetero-atoms selected from the group consisting of nitrogen, oxygen and sulfur hetero-atoms, said group being unsubstituted or having at least one substituent selected, in the case of substituents on carbon atoms, from the group consisting of substituents α and, in the case of substituents on nitrogen atoms, from the group consisting of substituents β,
  or a group of formula —B—S(O)$_m$—R$^5$, wherein
    R$^5$ represents: a substituted alkyl group which has from 1 to 4 carbon atoms and which is substituted by at least one substituent selected from the group consisting of substituents γ; or an aromatic heterocyclic group which has 5 or 6 ring atoms of which from 1 to 4 are hetero-atoms selected from the group consisting of nitrogen, oxygen and sulfur hetero-atoms, said group being unsubstituted or having at least one substituent selected, in the case of substituents on carbon atoms, from the group consisting of substituents α and, in the case of substituents on nitrogen atoms, from the group consisting of substituents ε,
    B represents an alkylene or alkylidene group having from 1 to 6 carbon atoms,
    and m is 0, 1 or 2;

A represents a group of formula —CH═CH— or —(CH$_2$)$_n$—, where n is 1, 2 or 3;

said aryl groups are carbocyclic aromatic groups having from 6 to 10 ring carbon atoms which are unsubstituted or which are substituted by at least one substituent selected from the group consisting of substituents ζ;

said aralkyl groups are alkyl groups which have from 1 to 4 carbon atoms and which are substituted by from 1 to 3 aryl groups as defined above;

said substituents α are selected from the group consisting of: alkyl groups having from 1 to 4 carbon atoms; alkoxy groups having from 1 to 4 carbon atoms; hydroxy groups; halogen atoms; amino groups; monoalkylamino groups in which the alkyl part has from 1 to 4 carbon atoms; dialkylamino groups in which each alkyl part is independently selected from the group consisting of alkyl groups having from 1 to 4 carbon atoms; alkanoylamino groups having from 1 to 5 carbon atoms; arylcarbonylamino groups in which the aryl part is as defined above; and aryl groups as defined above;

said substituents β are selected from the group consisting of alkyl groups having from 1 to 4 carbon atoms;

said substituents γ are selected from the group consisting of: hydroxy groups; alkanoyloxy groups having from 1 to 5 carbon atoms; substituted alkanoyloxy groups which have from 2 to 5 carbon atoms and which are substituted by at least one substituent selected from the group consisting of substituents δ; arylcarbonyloxy groups in which the aryl part is as defined above; and cycloalkylcarbonyloxy groups in which the cycloalkyl part has from 3 to 6 ring carbon atoms and is unsubstituted or is substituted by at least one substituent selected from the group consisting of substituents α;

said substituents δ are selected from the group consisting of: carboxy groups; alkoxycarbonyl groups in which the alkoxy part has from 1 to 4 carbon atoms; aryloxycarbonyl groups in which the aryl part is as defined above; and aryl groups as defined above;

said substituents ε are selected from the group consisting of: alkyl groups having from 1 to 4 carbon atoms; and hydroxyalkyl groups having from 2 to 4 carbon atoms;

said substituents ζ are selected from the group consisting of substituents α, provided that any aryl group in said substituents α is not further substituted by an aryl group;

PROVIDED THAT, when m is 1, $R^5$ represents: said substituted alkyl group having from 1 to 4 carbon atoms; an aromatic heterocyclic group which has 5 ring atoms of which from 2 to 4 are hetero-atoms selected from the group consisting of nitrogen, oxygen and sulfur hetero-atoms, said group being unsubstituted as defined above or an aromatic heterocyclic group which has 6 ring atoms of which from 1 to 4 are hetero-atoms selected from the group consisting of nitrogen, oxygen and sulfur hetero-atoms, said group being unsubstituted as defined above;

and pharmaceutically acceptable salts thereof.

2. The compound of claim 1, wherein $R^1$ represents a cyclic amino group having from 3 to 7 ring atoms, of which 1 is a nitrogen atom and the remainder are carbon atoms, or said dialkylamino group.

3. The compound of claim 2, wherein $R^1$ represents a cyclic amino group having 5 or 6 ring atoms, of which 1 is a nitrogen atom and the remainder are carbon atoms, or said dialkylamino group.

4. The compound of claim 3, wherein $R^1$ represents a 1-pyrrolidinyl, piperidino, dimethylamino or diethylamino group.

5. The compound of claim 1, wherein $R^2$ represents a group of formula —NHCHR³R⁴, wherein $R^3$ and $R^4$ are independently selected from the group consisting of:

alkyl groups having from 1 to 4 carbon atoms, phenyl groups which are unsubstituted or have at least one substituent selected from the group consisting of substituents ζ, defined in claim 1, and benzyl and phenethyl groups;

or $R^3$ and $R^4$ together with the carbon atom to which they are attached, represent a cycloalkyl group having from 3 to 6 ring carbon atoms.

6. The compound of claim 1, wherein $R^2$ represents an aromatic heterocyclic group having 5 ring atoms, of which 1 is a hetero-atom selected from the group consisting of nitrogen, oxygen and sulfur hetero-atoms, there are 0, 1 or 2 additional nitrogen hetero-atoms, and the remaining ring atoms are carbon atoms, said group being unsubstituted or having at least one substituent selected, in the case of substituents on carbon atoms, from the group consisting of substituents α and, in the case of substituents on nitrogen atoms, from the group consisting of substituents β, as defined in claim 1.

7. The compound of claim 6, wherein said aromatic heterocyclic group is selected from the group consisting of furyl, thienyl, pyrrolyl, oxazolyl, isoxazolyl, thiazolyl, isothiazolyl, pyrazolyl, imidazolyl, oxadiazolyl and thiadiazolyl groups, which are unsubstituted or are substituted as defined in claim 6.

8. The compound of claim 1, wherein $R^2$ represents a group of formula —B—S(O)$_m$—R⁵, wherein:

B represents an alkylene or alkylidene group having from 1 to 3 carbon atoms;

m is 0, 1 or 2; and $R^5$ represents: a substituted alkyl group which has from 2 to 4 carbon atoms and which is substituted at its 2-position by at least one substituent selected from the group consisting of substituents γ; or an aromatic heterocyclic group which has 5 or 6 ring atoms of which 1 is a hetero-atom selected from the group consisting of nitrogen, oxygen and sulfur hetero-atoms, there are 0, 1, 2 or 3 additional nitrogen hetero-atoms, and the remaining ring atoms are carbon atoms, said group being unsubstituted or having at least one substituent selected, in the case of substituents on carbon atoms, from the group consisting of substituents α and, in the case of substituents on nitrogen atoms, from the group consisting of substituents ε, as defined in claim 1.

9. The compound of claim 1, wherein A represents a group of formula —CH=CH— or —(CH₂)$_n$—, where n is 1 or 2.

10. The compound of claim 1, wherein:

$R^1$ represents a 1-pyrrolidinyl, piperidino, dimethylamino or diethylamino group;

$R^2$ represents a group of formula —NHCHR³R⁴, wherein $R^3$ and $R^4$ are independently selected from the group consisting of alkyl groups having from 1 to 4 carbon atoms, benzyl groups, phenethyl groups and phenyl groups which are unsubstituted or which are substituted by at least one substituent selected from the group consisting of methyl, methoxy, fluorine atoms and chlorine atoms, or $R^3$ and $R^4$ together with the carbon atom to which they are attached, represent a cycloalkyl group having from 3 to 6 ring carbon atoms, a furyl, thienyl, pyrrolyl, oxazolyl, isoxazolyl, thiazolyl, pyrazolyl, imidazolyl or thiadiazolyl group, which is unsubstituted or is substituted by at least one substituent selected, in the case of substituents on carbon atoms, from the group consisting of substituents $\alpha^1$ and, in the case of substituents on nitrogen atoms, from the group consisting of methyl and ethyl groups, or a group of formula —B—S(O)$_m$—R$^5$, wherein
  R$^5$ represents: a substituted ethyl or propyl group which is substituted at its 2-position by at least one substituent selected from the group consisting of substituents $\gamma^1$; or an imidazolyl, 1,2,4-triazolyl, 1,3,4-oxadiazolyl, 1,3,4-thiadiazolyl, tetrazolyl, pyridyl or pyrimidinyl group which is unsubstituted or has at least one substituent selected, in the case of substituents on carbon atoms, from the group consisting of substituents $\alpha^1$ and, in the case of substituents on nitrogen atoms, from the group consisting of substituents $\epsilon^1$,
  B represents an alkylene or alkylidene group having from 1 to 3 carbon atoms,
  and m is 0, 1 or 2;

A represents a group of formula —CH=CH— or —(CH$_2$)$_n$—, where n is 1 or 2;

said substituents $\alpha^1$ are selected from the group consisting of: methyl groups, ethyl groups, methoxy groups, ethoxy groups, hydroxy groups, chlorine atoms, amino groups; methylamino groups, ethylamino groups, dimethylamino groups, diethylamino groups, alkanoylamino groups having from 1 to 3 carbon atoms, phenyl groups, and substituted phenyl groups in which the substituent is selected from the group consisting of methyl groups, methoxy groups, chlorine atoms and fluorine atoms;

said substituents $\gamma^1$ are selected from the group consisting of: hydroxy groups; alkanoyloxy groups having from 1 to 5 carbon atoms; substituted alkanoyloxy groups which have 3 or 4 carbon atoms and which are substituted by at least one substituent selected from the group consisting of carboxy, methoxycarbonyl and ethoxycarbonyl groups; phenylacetoxy groups; benzoyloxy groups; and cycloalkylcarbonyloxy groups in which the cycloalkyl part has from 3 to 6 ring carbon atoms;

said substituents $\epsilon^1$ are selected from the group consisting of: methyl groups, ethyl groups, and hydroxyalkyl groups having from 2 to 4 carbon atoms.

11. The compound of claim 1, wherein:
R$^1$ represents a 1-pyrrolidinyl or piperidino group;
R$^2$ represents
  a group of formula —NHCHR$^3$R$^4$, wherein
    R$^3$ and R$^4$ are independently selected from the group consisting of methyl, ethyl, phenyl and benzyl groups, or R$^3$ and R$^4$ together with the carbon atom to which they are attached, represent a cycloalkyl group having from 3 to 5 ring carbon atoms,
a furyl, thienyl, pyrrolyl, oxazolyl, isoxazolyl, thiazolyl, pyrazolyl or 1,2,3-thiadiazolyl group, which is unsubstituted or is substituted by at least one substituent selected, in the case of substituents on carbon atoms, from the group consisting of substituents $\alpha^2$ and, in the case of substituents on nitrogen atoms, from the group consisting of methyl and ethyl groups, or a group of formula —B—S(O)$_m$—R$^5$, wherein
  R$^5$ represents: a substituted ethyl or propyl group which is substituted at its 2-position by at least one substituent selected from the group consisting of substituents $\gamma^2$; or a 1,2,4-triazolyl, 1,3,4-oxadiazolyl or pyrimidinyl group which is unsubstituted or has at least one substituent selected, in the case of substituents on carbon atoms, from the group consisting of substituents $\alpha^3$ and, in the case of substituents on nitrogen atoms, from the group consisting of methyl and ethyl groups,
  B represents an alkylene or alkylidene group having from 1 to 3 carbon atoms,
  and m is 0 or 1;

A represents a group of formula —CH=CH— or —(CH$_2$)$_2$—;

said substituents $\alpha^2$ are selected from the group consisting of: methyl groups, ethyl groups, methoxy groups, ethoxy groups, hydroxy groups, chlorine atoms, amino groups, acetamido groups and phenyl groups;

said substituents $\alpha^3$ are selected from the group consisting of: methyl groups, ethyl groups, methoxy groups, ethoxy groups, hydroxy groups, chlorine atoms, amino groups, and acetamido groups;

said substituents $\gamma^2$ are selected from the group consisting of: hydroxy groups; acetoxy groups; propionyloxy groups; substituted alkanoyloxy groups which have 3 or 4 carbon atoms and which are substituted by at least one substituent selected from the group consisting of carboxy, methoxycarbonyl and ethoxycarbonyl groups; phenylacetoxy groups; benzoyloxy groups; and cycloalkylcarbonyloxy groups in which the cycloalkyl part has from 3 to 6 ring carbon atoms.

12. The compound of claim 1, wherein:
R$^1$ represents a piperidino group;
R$^2$ represents
  a group of formula —NHCHR$^3$R$^4$, wherein
    R$^3$ and R$^4$ are independently selected from the group consisting of methyl, ethyl, phenyl and benzyl groups, or R$^3$ and R$^4$ together with the carbon atom to which they are attached, represent a cycloalkyl group having 3 or 4 ring carbon atoms,
a thienyl, pyrrolyl, thiazolyl, pyrazolyl or 1,2,3-thiadiazolyl group, which is unsubstituted or is substituted by at least one substituent selected, in the case of substituents on carbon atoms, from the group consisting of substituents $\alpha^4$ and, in the case of substituents on nitrogen atoms, from methyl groups,
or a group of formula —B—S(O)$_m$—R$^5$, wherein
  B represents a methylene group and R$^5$ represents: a substituted ethyl or propyl group which is substituted at its 2-position by at least one substituent selected from the group consisting of substituents $\gamma^3$;

or

B represents a trimethylene group and R$^5$ represents: a 1,2,4-triazolyl, 1,3,4-oxadiazolyl or pyrimidinyl group which is unsubstituted or has at least one substituent selected, in the case of substituents on carbon atoms, from the group consisting of methyl, hydroxy and amino groups, and, in the case of substituents on nitrogen atoms, from methyl groups, and m is 0;

A represents a group of formula —CH=CH—;

said substituents $\alpha^4$ are selected from the group consisting of: methyl groups, methoxy groups, hydroxy groups, chlorine atoms and amino groups;

said substituents $\gamma^3$ are selected from the group consisting of: hydroxy groups; acetoxy groups; propionyloxy groups; substituted propionoyloxy groups which are substituted by at least one substituent selected from the group consisting of carboxy, methoxycarbonyl and ethoxycarbonyl groups; benzoyloxy groups; and cycloalkylcarbonyloxy groups in which the cycloalkyl part has 5 or 6 ring carbon atoms.

13. The compound of claim 1, wherein:

$R^1$ represents a piperidino group;

$R^2$ represents:

a pyrazolyl group, which is unsubstituted or is substituted on a carbon atom by at least one amino substituent, or a group of formula —B—S(O)$_m$—R$^5$, wherein B represents a methylene group and R$^5$ represents: a substituted ethyl group which is substituted at its 2-position by at least one substituent selected from the group consisting of substituents hydroxy, acetoxy, propionyloxy, benzoyloxy, cyclopentylcarbonyloxy and cyclohexylcarbonyloxy groups;

or

B represents a trimethylene group and R$^5$ represents: a 2-pyrimidinyl group;

and m is 0;

A represents a group of formula —CH=CH—.

14. The compound of claim 1, selected from the group consisting of N-[4-(4-piperidinomethyl-2-pyridyloxy)-cis-2-butenyl]pyrazole-4-carboxamide and pharmaceutically acceptable salts thereof.

15. The compound of claim 1, selected from the group consisting of 3-amino-N-[4-(4-piperidinomethyl-2-pyridyloxy)-cis-2-butenyl]pyrazole-4-carboxamide and pharmaceutically acceptable salts thereof.

16. The compound of claim 1, selected from the group consisting of N-[4-(4-piperidinomethyl-2-pyridyloxy)-cis-2-butenyl]-2-(2-hydroxyethylthio)acetamide and pharmaceutically acceptable salts thereof.

17. The compound of claim 1, selected from the group consisting of N-[4-(4-piperidinomethyl-2-pyridyloxy)-cis-2-butenyl]-2-(2-acetoxyethylthio)acetamide and pharmaceutically acceptable salts thereof.

18. The compound of claim 1, selected from the group consisting of N-[4-(4-piperidinomethyl-2-pyridyloxy)-cis-2-butenyl]-2-(2-propionyloxyethylthio)acetamide and pharmaceutically acceptable salts thereof.

19. The compound of claim 1, selected from the group consisting of N-[4-(4-piperidinomethyl-2-pyridyloxy)-cis-2-butenyl]-2-(2-butyryloxyethylthio)acetamide and pharmaceutically acceptable salts thereof.

20. The compound of claim 1, selected from the group consisting of N-[4-(4-piperidinomethyl-2-pyridyloxy)-cis-2-butenyl]-2-(2-isobutyryloxyethylthio)acetamide and pharmaceutically acceptable salts thereof.

21. The compound of claim 1, selected from the group consisting of N-[4-(4-piperidinomethyl-2-pyridyloxy)-cis-2-butenyl]-2-(2-isovaleryloxyethylthio)acetamide and pharmaceutically acceptable salts thereof.

22. The compound of claim 1, selected from the group consisting of N-[4-(4-piperidinomethyl-2-pyridyloxy)-cis-2-butenyl]-2-(2-phenylacetoxyethylthio)acetamide and pharmaceutically acceptable salts thereof.

23. The compound of claim 1, selected from the group consisting of 2-{N-[4-(4-piperidinomethyl-2-pyridyloxy)-cis-2-butenyl]carbamoylmethylthio}ethyl hydrogen succinate and pharmaceutically acceptable salts thereof.

24. The compound of claim 1, selected from the group consisting of N-[4-(4-piperidinomethyl-2-pyridyloxy)-cis-2-butenyl]-2-(2-benzoyloxyethylthio)acetamide and pharmaceutically acceptable salts thereof.

25. The compound of claim 1, selected from the group consisting of N-[4-(4-piperidinomethyl-2-pyridyloxy)-cis-2-butenyl]-2-(2-cyclopentylcarbonyloxyethylthio)acetamide and pharmaceutically acceptable salts thereof.

26. The compound of claim 1, selected from the group consisting of N-[4-(4-piperidinomethyl-2-pyridyloxy)-cis-2-butenyl]-2-(2-cyclohexylcarbonyloxyethylthio)acetamide and pharmaceutically acceptable salts thereof.

27. The compound of claim 1, selected from the group consisting of N-[4-(4-piperidinomethyl-2-pyridyloxy)-cis-2-butenyl]-2-(2-hydroxyethylsulfinyl)acetamide and pharmaceutically acceptable salts thereof.

28. The compound of claim 1, selected from the group consisting of N-[4-(4-piperidinomethyl-2-pyridyloxy)-cis-2-butenyl]-2-(2-propionyloxyethylsulfinyl)acetamide and pharmaceutically acceptable salts thereof.

29. The compound of claim 1, selected from the group consisting of N-[4-(4-piperidinomethyl-2-pyridyloxy)-cis-2-butenyl]-2-[2-(3,3-dimethylbutyryloxy)ethylthio]acetamide and pharmaceutically acceptable salts thereof.

30. The compound of claim 1, selected from the group consisting of N-[4-(4-piperidinomethyl-2-pyridyloxy)-cis-2-butenyl]-2-[2-(2,2-dimethylpropionyloxy)ethylthio]acetamide and pharmaceutically acceptable salts thereof.

31. The compound of claim 1, selected from the group consisting of N-[4-(4-piperidinomethyl-2-pyridyloxy)-cis-2-butenyl]-4-(2-pyrimidinylthio)butyramide and pharmaceutically acceptable salts thereof.

32. A pharmaceutical composition for the treatment and prophylaxis of ulcerous conditions, which comprises an anti-ulcer compound in admixture with a pharmaceutically acceptable carrier or diluent, wherein the anti-ulcer compound is selected from the group consisting of compounds of formula (I) and pharmaceutically acceptable salts thereof, as claimed in claim 1.

33. The composition of claim 32, wherein:

$R^1$ represents a piperidino group;

$R^2$ represents a group of formula —NHCHR$^3$R$^4$, wherein

R$^3$ and R$^4$ are independently selected from the group consisting of methyl, ethyl, phenyl and benzyl groups, or R$^3$ and R$^4$, together with the carbon atom to which they are attached, represent a cycloalkyl group having 3 or 4 ring carbon atoms, a thienyl, pyrrolyl, thiazolyl, pyrazolyl or 1,2,3-thiadiazolyl group, which is unsubstituted or is substituted by at least one substituent selected, in the case of substituents on carbon atoms, from the group consisting of substituents α⁴ and, in the case of substituents on nitrogen atoms, from methyl groups, or a group of formula —B—S(O)$_m$—R⁵, wherein B represents a methylene group and R⁵ represents: a substituted ethyl or propyl group which is substituted at its 2-position by at least one substituent selected from the group consisting of substituents γ³;

or

B represents a trimethylene group and R⁵ represents: a 1,2,4-triazolyl, 1,3,4-oxadiazolyl or pyrimidinyl group which is unsubstituted or has at least one substituent selected, in the case of substituents on carbon atoms, from the group consisting of methyl, hydroxy and amino groups, and, in the case of substituents on nitrogen atoms, from methyl groups, and m is 0;

A represents a group of formula —CH=CH—;

said substituents α⁴ are selected from the group consisting of: methyl groups, methoxy groups, hydroxy groups, chlorine atoms and amino groups;

said substituents γ³ are selected from the group consisting of: hydroxy groups; acetoxy groups; propionyloxy groups; substituted propionoyloxy groups which are substituted by at least one substituent selected from the group consisting of carboxy, methoxycarbonyl and ethoxycarbonyl groups; benzoyloxy groups; and cycloalkylcarbonyloxy groups in which the cycloalkyl part has 5 or 6 ring carbon atoms.

34. The composition of claim 32, wherein:

R¹ represents a piperidino group;

R² represents:

a pyrazolyl group, which is unsubstituted or is substituted on a carbon atom by at least one amino substituent, or a group of formula —B—S(O)$_m$—R⁵, wherein B represents a methylene group and R⁵ represents: a substituted ethyl group which is substituted at its 2-position by at least one substituent selected from the group consisting of substituents hydroxy, acetoxy, propionyloxy, benzoyloxy, cyclopentylcarbonyloxy and cyclohexylcarbonyloxy groups;

or

B represents a trimethylene group and R represents: a 2-pyrimidinyl group;

and m is 0;

A represents a group of formula —CH=CH—.

35. The composition of claim 32, wherein said anti-ulcer compound is selected from the group consisting of:

N-[4-(4-piperidinomethyl-2-pyridyloxy)-cis-2-butenyl]-pyrazole-4-carboxamide;

3-amino-N-[4-(4-piperidinomethyl-2-pyridyloxy)-cis-2-butenyl]pyrazole-4-carboxamide;

N-[4-(4-piperidinomethyl-2-pyridyloxy)-cis-2-butenyl]-2-(2-hydroxyethylthio)acetamide;

N-[4-(4-piperidinomethyl-2-pyridyloxy)-cis-2-butenyl]-2-(2-acetoxyethylthio)acetamide;

N-[4-(4-piperidinomethyl-2-pyridyloxy)-cis-2-butenyl]-2-(2-propionyloxyethylthio)acetamide;

N-[4-(4-piperidinomethyl-2-pyridyloxy)-cis-2-butenyl]-2-(2-butyryloxyethylthio)acetamide;

N-[4-(4-piperidinomethyl-2-pyridyloxy)-cis-2-butenyl]-2-(2-isobutyryloxyethylthio)acetamide;

N-[4-(4-piperidinomethyl-2-pyridyloxy)-cis-2-butenyl]-2-(2-isovaleryloxyethylthio)acetamide;

N-[4-(4-piperidinomethyl-2-pyridyloxy)-cis-2-butenyl]-2-(2-phenylacetoxyethylthio)acetamide;

2-{N-[4-(4-piperidinomethyl-2-pyridyloxy)-cis-2-butenyl]carbamoylmethylthio}ethyl hydrogen succinate;

N-[4-(4-piperidinomethyl-2-pyridyloxy)-cis-2-butenyl]-2-(2-benzoyloxyethylthio)acetamide;

N-[4-(4-piperidinomethyl-2-pyridyloxy)-cis-2-butenyl]-2-(2-cyclopentylcarbonyloxyethylthio)acetamide;

N-[4-(4-piperidinomethyl-2-pyridyloxy)-cis-2-butenyl]-2-(2-cyclohexylcarbonyloxyethylthio)acetamide;

N-[4-(4-piperidinomethyl-2-pyridyloxy)-cis-2-butenyl]-2-(2-hydroxyethylsulfinyl)acetamide;

N-[4-(4-piperidinomethyl-2-pyridyloxy)-cis-2-butenyl]-2-(2-propionyloxyethylsulfinyl)acetamide;

N-[4-(4-piperidinomethyl-2-pyridyloxy)-cis-2-butenyl]-2-[2-(3,3-dimethylbutyryloxy)ethylthio]acetamide;

N-[4-(4-piperidinomethyl-2-pyridyloxy)-cis-2-butenyl]-2-[2-(2,2-dimethylpropionyloxy)ethylthio]acetamide;

N-[4-(4-piperidinomethyl-2-pyridyloxy)-cis-2-butenyl]-4-(2-pyrimidinylthio)butyramide;

and pharmaceutically acceptable salts thereof.

36. A method for the treatment and prophylaxis of ulcerous conditions, which comprises administering an effective amount of an anti-ulcer compound to a mammal, wherein the anti-ulcer compound is selected from the group consisting of compounds of formula (I) and pharmaceutically acceptable salts thereof, as claimed in claim 1.

37. The method of claim 36, wherein:

R¹ represents a piperidino group;

R² represents a group of formula —NHCHR³R⁴, wherein

R³ and R⁴ are independently selected from the group consisting of methyl, ethyl, phenyl and benzyl groups, or R³ and R⁴ together with the carbon atom to which they are attached, represent a cycloalkyl group having 3 or 4 ring carbon atoms, a thienyl, pyrrolyl, thiazolyl, pyrazolyl or 1,2,3-thiadiazolyl group, which is unsubstituted or is substituted by at least one substituent selected, in the case of substituents on carbon atoms, from the group consisting of substituents α⁴ and, in the case of substituents on nitrogen atoms, from methyl groups, or a group of formula —B—S(O)$_m$—R⁵, wherein B represents a methylene group and R⁵ represents: a substituted ethyl or propyl group which is substituted at its 2-position by at least one substituent selected from the group consisting of substituents γ³;

or

B represents a trimethylene group and R⁵ represents: a 1,2,4-triazolyl, 1,3,4-oxadiazolyl or pyrimidinyl group which is unsubstituted or has at least one substituent selected, in the case of substituents on carbon atoms, from the group consisting of methyl, hydroxy and amino groups, and, in the case of substituents on nitrogen atoms, from methyl groups,
and m is 0;

A represents a group of formula —CH=CH—;

said substituents $\alpha^4$ are selected from the group consisting of: methyl groups, methoxy groups, hydroxy groups, chlorine atoms and amino groups;

said substituents $\gamma^3$ are selected from the group consisting of: hydroxy groups; acetoxy groups; propionyloxy groups; substituted propionoyloxy groups which are substituted by at least one substituent selected from the group consisting of carboxy, methoxycarbonyl and ethoxycarbonyl groups; benzoyloxy groups; and cycloalkylcarbonyloxy groups in which the cycloalkyl part has 5 or 6 ring carbon atoms.

38. The method of claim 36, wherein:

$R^1$ represents a piperidino group;

$R^2$ represents:

a pyrazolyl group, which is unsubstituted or is substituted on a carbon atom by at least one amino substituent, or a group of formula —B—S(O)$_m$—R$^5$, wherein B represents a methylene group and R$^5$ represents: a substituted ethyl group which is substituted at its 2-position by at least one substituent selected from the group consisting of substituents hydroxy, acetoxy, propionyloxy, benzoyloxy, cyclopentylcarbonyloxy and cyclohexylcarbonyloxy groups;

or

B represents a trimethylene group and R$^5$ represents:
a 2-pyrimidinyl group;
and m is 0;

A represents a group of formula —CH=CH—.

39. The method of claim 36, wherein said anti-ulcer compound is selected from the group consisting of:

N-[4-(4-piperidinomethyl-2-pyridyloxy)-cis-2-butenyl]-pyrazole-4-carboxamide;

3-amino-N-[4-(4-piperidinomethyl-2-pyridyloxy)-cis-2-butenyl]pyrazole-4-carboxamide;

N-[4-(4-piperidinomethyl-2-pyridyloxy)-cis-2-butenyl]-2-(2-hydroxyethylthio)acetamide;

N-[4-(4-piperidinomethyl-2-pyridyloxy)-cis-2-butenyl]-2-(2-acetoxyethylthio)acetamide;

N-[4-(4-piperidinomethyl-2-pyridyloxy)-cis-2-butenyl]-2-(2-propionyloxyethylthio)acetamide;

N-[4-(4-piperidinomethyl-2-pyridyloxy)-cis-2-butenyl]-2-(2-butyryloxyethylthio)acetamide;

N-[4-(4-piperidinomethyl-2-pyridyloxy)-cis-2-butenyl]-2-(2-isobutyryloxyethylthio)acetamide;

N-[4-(4-piperidinomethyl-2-pyridyloxy)-cis-2-butenyl]-2-(2-isovaleryloxyethylthio)acetamide;

N-[4-(4-piperidinomethyl-2-pyridyloxy)-cis-2-butenyl]-2-(2-phenylacetoxyethylthio)acetamide;

2-{N-[4-(4-piperidinomethyl-2-pyridyloxy)-cis-2-butenyl]-2-(2-carbamoylmethylthio}ethyl hydrogen succinate;

N-[4-(4-piperidinomethyl-2-pyridyloxy)-cis-2-butenyl]-2-(2-benzoyloxyethylthio)acetamide;

N-[4-(4-piperidinomethyl-2-pyridyloxy)-cis-2-butenyl]-2-(2-cyclopentylcarbonyloxyethylthio)acetamide;

N-[4-(4-piperidinomethyl-2-pyridyloxy)-cis-2-butenyl]-2-(2-cyclohexylcarbonyloxyethylthio)acetamide;

N-[4-(4-piperidinomethyl-2-pyridyloxy)-cis-2-butenyl]-2-(2-hydroxyethylsulfinyl)acetamide;

N-[4-(4-piperidinomethyl-2-pyridyloxy)-cis-2-butenyl]-2-(2-propionyloxyethylsulfinyl)acetamide;

N-[4-(4-piperidinomethyl-2-pyridyloxy)-cis-2-butenyl]-2-[2-(3,3-dimethylbutyryloxy)ethylthio]acetamide;

N-[4-(4-piperidinomethyl-2-pyridyloxy)-cis-2-butenyl]-2-[2-(2,2-dimethylpropionyloxy)ethylthio]acetamide;

N-[4-(4-piperidinomethyl-2-pyridyloxy)-cis-2-butenyl]-4-(2-pyrimidinylthio)butyramide;

and pharmaceutically acceptable salts thereof.

* * * * *